(12) United States Patent
Wang et al.

(10) Patent No.: US 6,900,205 B2
(45) Date of Patent: May 31, 2005

(54) 1,8-NAPHTHYRIDINE DERIVATIVES AND THEIR USE TO TREAT DIABETES AND RELATED DISORDERS

(75) Inventors: Yamin Wang, Sandy Hook, CT (US); William H. Bullock, Easton, CT (US); David E. Gunn, Hamden, CT (US); Qingjie Liu, Milford, CT (US); Sidney X. Liang, Bethany, CT (US); Donglei Liu, West Haven, CT (US); Steven R. Magnuson, Wallingford, CT (US); Tindy Li, West Haven, CT (US); Eric S. Mull, Guilford, CT (US); Jill E. Wood, North Haven, CT (US); Ning Qi, Hamden, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 55 days.

(21) Appl. No.: 10/253,104

(22) Filed: Sep. 23, 2002

(65) Prior Publication Data

US 2004/0014751 A1 Jan. 22, 2004

Related U.S. Application Data

(60) Provisional application No. 60/324,511, filed on Sep. 26, 2001.

(51) Int. Cl.$^7$ .................. A61K 31/5375; C07D 413/14
(52) U.S. Cl. .................. 514/235.2; 544/127; 544/362; 546/183; 514/253.04; 514/299
(58) Field of Search ................. 544/127, 362; 514/235.2, 253.04, 299; 546/183

(56) References Cited

U.S. PATENT DOCUMENTS

| | | | |
|---|---|---|---|
| 4,284,629 A | 8/1981 | Grohe et al. | 424/246 |
| 4,616,019 A | 10/1986 | Chu | 514/254 |
| 4,810,708 A | 3/1989 | Ganguly et al. | 514/278 |
| 4,840,954 A | 6/1989 | Petersen et al. | 514/254 |
| 4,881,969 A | 11/1989 | Saupe et al. | 71/94 |
| 5,116,840 A | 5/1992 | Ganguly et al. | 514/250 |
| 5,126,352 A | 6/1992 | Ganguly et al. | 514/293 |
| 5,245,037 A | 9/1993 | Kuramoto et al. | 546/156 |
| 5,658,924 A | 8/1997 | Matsuura et al. | 514/300 |
| 5,817,669 A | 10/1998 | Tomita et al. | 514/300 |
| 5,817,670 A | 10/1998 | Takayama et al. | 514/300 |
| 5,891,878 A | 4/1999 | Beasley et al. | 514/247 |
| 6,297,248 B1 | 10/2001 | Shimamoto et al. | 514/255.5 |
| 6,331,548 B1 | 12/2001 | Shimamoto et al. | 514/300 |

Primary Examiner—Deborah C. Lambkin
Assistant Examiner—Golam M M Shameem
(74) Attorney, Agent, or Firm—Susan M. Pellegrino

(57) ABSTRACT

The invention relates generally to naphthyridine derivatives of the formula

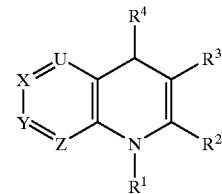

wherein one of U, X, Y and Z is nitrogen and the others are C—R, where R is hydrogen or a substituent. More specifically, the invention relates to 1,8-naphthyridine derivatives and pharmaceutical compositions containing such derivatives. Methods of the invention comprise administration of a naphthyridine derivative of the invention for the treatment of diabetes and related disorders.

36 Claims, No Drawings

1,8-NAPHTHYRIDINE DERIVATIVES AND THEIR USE TO TREAT DIABETES AND RELATED DISORDERS

FIELD OF THE INVENTION

The present invention relates to 1,8-naphthyridine derivatives, pharmaceutical compositions containing them, and their use for treating diabetes and related disorders in a subject.

DESCRIPTION OF THE RELATED ART

Diabetes is characterized by impaired glucose metabolism manifesting itself among other things by an elevated blood glucose level in the diabetic patient. Underlying defects lead to a classification of diabetes into two major groups: type 1 diabetes, or insulin dependent diabetes mellitus (IDDM), arises when patients lack insulin-producing beta-cells in their pancreatic glands. Type 2 diabetes, or non-insulin dependent diabetes mellitus (NIDDM), occurs in patients with impaired beta-cell function and alterations in insulin action.

The current treatment for type 1 diabetic patients is the injection of insulin, while the majority of type 2 diabetic patients are treated with agents that stimulate beta-cell function or with agents that enhance the tissue sensitivity of the patients towards insulin. The drugs presently used to treat type 2 diabetes include alpha-glucosidase inhibitors, insulin sensitizers, insulin secretagogues, and metformin.

Over time almost one-half of type 2 diabetic subjects lose their response to these agents. Insulin treatment is instituted after diet, exercise, and oral medications have failed to adequately control blood glucose. The drawbacks of insulin treatment are the need for drug injection, the potential for hypoglycemia, and weight gain.

Because of the problems with current treatments, new therapies to treat type 2 diabetes are needed. In particular, new treatments to retain normal (glucose-dependent) insulin secretion are needed. Such new drugs should have the following characteristics: dependency on glucose for promoting insulin secretion, i.e., compounds that stimulate insulin secretion only in the presence of elevated blood glucose; low primary and secondary failure rates; and preservation of islet cell function. The strategy to develop the new therapy disclosed herein is based on the cyclic adenosine monophosphate (cAMP) signaling mechanism and its effects on insulin secretion.

Metabolism of glucose promotes the closure of ATP-dependent K+ channels, which leads to cell depolarization and subsequent opening of Ca++ channels. This in turn results in the exocytosis of insulin granules. cAMP is a major regulator of glucose-stimulated insulin secretion However, it has little if any effects on insulin secretion in the absence of or at low glucose concentrations (Weinhaus, A., et al., *Diabetes* 47: 1426–1435 (1998)). The effects of cAMP on insulin secretion are thought to be mediated by a protein kinase A pathway.

Endogenous secretagogues like pituitary adenylate cyclase activating peptide (PACAP), VIP, and GLP-1 use the cAMP system to regulate insulin secretion in a glucose-dependent fashion (Komatsu, M., et al., *Diabetes* 46: 1928–1938, (1997)). Also, phosphodiesterases (PDEs) are known to be involved in the regulation of the cAMP system.

PACAP is a potent stimulator of glucose-dependent insulin secretion from pancreatic beta cells. Three different PACAP receptor types (R1, R2, and R3) have been described (Harmar, A., et al., *Pharmacol. Reviews* 50: 265–270 (1998)). The insulinotropic action of PACAP is mediated by the GTP binding protein Gs. Accumulation of intracellular cAMP in turn activates nonselective cation channels in beta cells increasing [Ca++]i, and promoting the exocytosis of insulin-containing secretory granules.

Vasoactive intestinal peptide (VIP) is a 28 amino acid peptide that was first isolated from hog upper small intestine (Said and Mutt, *Science* 169: 1217–1218, 1970; U.S. Pat. No. 3,879,371). This peptide belongs to a family of structurally related, small polypeptides that includes helodermin, secretin, the somatostatins, and glucagon. The biological effects of VIP are mediated by the activation of membrane-bound receptor proteins that are coupled to the intracellular cAMP signaling system. These receptors were originally known as VIP-R1 and VIP-R2, however, they were later found to be the same receptors as PACAP-R2 and PACAP-R3.

GLP-1 is released from the intestinal L-cell after a meal and functions as an incretin hormone (i.e., it potentiates glucose-induced insulin release from the pancreatic beta cell). It is a 37-amino acid peptide that is differentially expressed by the glucagon gene, depending upon tissue type. The clinical data that support the beneficial effect of raising cAMP levels in β-cells have been collected with GLP-1. Infusions of GLP-1 in poorly controlled type 2 diabetics normalized their fasting blood glucose levels (Gutniak, M., et al., *New Eng. J. Med.* 326:1316–1322, (1992)) and with longer infusions improved the beta cell function to those of normal subjects (Rachman, J. et al., *Diabetes* 45: 1524–1530, (1996)). A recent report has shown that GLP-1 improves the ability of β-cells to respond to glucose in subjects with impaired glucose tolerance (Byrne M., et al., *Diabetes* 47: 1259–1265 (1998)). All of these effects, however, are short-lived because of the short half-life of the peptide.

SUMMARY OF THE INVENTION

The invention provides compounds, pharmaceutical compositions, and methods of using the same for treating diabetes and related disorders. Compounds of the invention include compounds of formula (I)

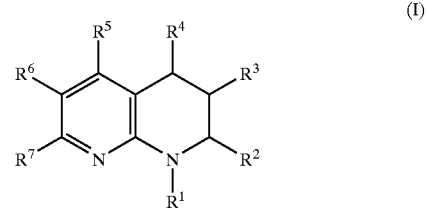

wherein $R^1$ is selected from alkyl of 1–8 carbon atoms, alkenyl of 2–8 carbon atoms, alkynyl of 2–8 carbon atoms, and A—$R^9$, or $R^1$ is selected from aryl of 6–10 carbon atoms, heteroaryl of 2–9 carbon atoms and 1–4 heteroatoms selected from N, $S(=O)_{0-2}$ and O, cycloalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, wherein said heterocycloalkyl and said heterocycloalkenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, all of which may be substituted with 1–3 of $R^{10}$;

is $R^{10}$ is selected from nitro, nitrile, hydroxy, halogen, acyl of 1–6 carbon atoms, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms, cycloalkoxy of 3–6 carbon atoms, aryl of 6–10 carbon atoms, heteroaryl of 2–9 carbon atoms and 1–4 heteroatoms selected from N, $S(=O)_{0-2}$ and O, $NR^{11}R^{12}$, $C(=O)OR^{11}$, $C(=O)NHR^{11}$, $NHC(=O)R^{13}$, $NHS(=O)_2R^{13}$, $S(=O)_{0-2}R^{13}$, $S(=O)_2NHR^{11}$, cycyloalkyl of 3–6 carbon atoms, cycloalkenyl of 3–6 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$;

$R^{13}$ is selected from alkyl of 1–6 carbon atoms, alkenyl of 2–6 carbon atoms, alkynyl of 2–6 carbon atoms, haloalkyl of 1–6 carbon atoms, cycloalkyl of 3–6 carbon atoms, and cycloalkenyl of 4–6 carbon atoms;

$R^{11}$ and $R^{12}$ are independently selected from hydrogen, alkyl of 1–6 carbon atoms, alkenyl of 2–6 carbon atoms, alkynyl of 2–6 carbon atoms, haloalkyl of 1–6 carbon atoms, cycloalkyl of 3–6 carbon atoms, and cycloalkenyl of 4–6 carbon atoms;

A is selected from alkyl of 1–8 carbon atoms, alkenyl of 2–8 carbon atoms, alkynyl of 2–8 carbon atoms, and haloalkyl of 1–8 carbon atoms;

$R^9$ is selected from hydroxy, alkoxy of 1–6 carbon atoms, cycloalkoxy of 3–6 carbon atoms, $O—A—R^{14}$, $NR^{11}R^{12}$; or $R^9$ is selected from aryl of 6–10 carbon atoms, heteroaryl of 2–9 carbon atoms and 1–4 heteroatoms selected from N, $S(=O)_{0-2}$ and O, cylcoalkyl of 3–8 carbon atoms, cycloalkenyl of 5–8 carbon atoms, all of which may be substituted with 1–3 of $R^{10}$, or $R^9$ is selected from 5–7 membered heterocycloalkyl of 3–6 carbon atoms and 1–2 heteroatoms selected from N, $S(=O)_{0-2}$ and O and 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{14}$ is selected from cylcoalkyl of 3–8 carbon atoms, cycloalkenyl of 5–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$;

$R^2$ is selected from $NR^{15}R^{16}$, $S(O)_{0-2}R^{17}$, and $OR^{17}$;

$R^{15}$ is selected from hydrogen, alkyl of 1–6 carbon atoms, alkenyl of 2–6 carbon atoms, alkynyl of 2–6 carbon atoms, cylcoalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, 5–7 membered heterocycloalkenyl of 3–6 carbon atoms and 1–2 heteroatoms selected from N, $S(=O)_{0-2}$ and O, $A—R^9$, $C(=O)R^{18}$, $C(=O)NHR^{18}$, $S(=O)_2NHR^{18}$;

$R^{18}$ is selected from aryl of 6–10 carbon atoms, heteroaryl of 2–9 carbon atoms and 1–4 heteroatoms selected from N, $S(=O)_{0-2}$ and O, cylcoalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$, or $R^{18}$ is selected from alkyl of 1–6 carbon atoms, alkenyl of 2–6 carbon atoms, and alkynyl of 2–6 carbon atoms, all of which may be substituted with 1–3 of halogen or alkoxy of 1–6 carbon atoms, or $R^8$ is $A—R^9$;

$R^{16}$ is selected from alkyl of 1–8 carbon atoms, alkenyl of 2–8 carbon atoms, alkynyl of 2–8 carbon atoms, and $A—R^9$, or $R^{16}$ is selected from aryl of 6–10 carbon atoms, heteroaryl of 2–9 carbon atoms and 1–4 heteroatoms selected from N, $S(=O)_{0-2}$ and O, cycloalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$, or $R^{15}$ and $R^{16}$ combine, together with the nitrogen atom to which they are attached, to form a heteroaryl of 2–9 carbon atoms and 1–4 heteroatoms selected from N, $S(=O)_{0-2}$ and O, or a 5–7 membered heterocycloalkyl of 3–6 carbon atoms and 1–2 heteroatoms selected from N, $S(=O)_{0-2}$ and O, 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, all of which may be substituted with 1–3 of $R^{10}$;

$R^{17}$ is selected from alkyl of 1–8 carbon atoms, alkenyl of 2–8 carbon atoms, and alkynyl of 2–8 carbon atoms, haloalkyl of 1–8 carbon atoms, $A—R^9$, or $R^{17}$ is selected from aryl of 6–10 carbon atoms, heteroaryl of 2–9 carbon atoms and 1–4 heteroatoms selected from N, $S(=O)_{0-2}$ and O, cylcoalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$;

$R^3$ is selected from aryl of 6–10 carbon atoms, beteroaryl of 2–9 carbon atoms and 1–4 heteroatoms selected from N, $S(=O)_{0-2}$ and O, cylcoalkyl of 3–8 carbon atoms, heterocycloalkyl of 3–6 carbon atoms and 1–2 heteroatoms selected from N, $S(O)_{0-2}$, and O, cycloalkenyl of 4–8 carbon atoms, and heterocycloalkenyl of 3–6 carbon atoms and 1–2 heteroatoms selected from N, S(O)$_{0-2}$ and O, all of which may be substituted with 1–3 of R$^{10}$, or R$^3$ is selected from alkyl of 1–6 carbon atoms, alkenyl of 2–6 carbon atoms, alkynyl of 2–6 carbon atoms, haloalkyl of 1–6 carbon atoms, hydrogen, nitro, halogen, NR$^{19}$R$^{20}$, A—OR$^{19}$, A—NR$^{19}$R$^{20}$, and A—R$^{20}$;

R$^{19}$ and R$^{20}$ are independently selected from hydrogen, alkyl of 1–6 carbon atoms, alkenyl of 2–6 carbon atoms, alkynyl of 2–6 carbon atoms, haloalkyl of 1–6 carbon atoms, and A—R$^9$, or R$^{19}$ and R$^{20}$ are independently selected from aryl of 6–10 carbon atoms, heteroaryl of 2–9 carbon atoms and 1–4 heteroatoms selected from N, S(O)$_{0-2}$ and O, cylcoalkyl of 3–8 carbon atoms, cycloalkenyl of 5–8 carbon atoms, 5–7 membered heterocycloalkyl of 3–6 carbon atoms and 1–2 heteroatoms selected from N, S(O)$_{0-2}$ and O, 5–7 membered heterocycloalkenyl of 3–6 carbon atoms and 1–2 heteroatoms selected from N, S(O)$_{0-2}$ and O, wherein said heterocycloalkyl and said heterocycloakenyl may further be fused with phenyl or a 5–6 membered heteroaryl of 2–5 carbon atoms and 1–3 heteroatoms selected from N, S(=O)$_{0-2}$ and O, and/or wherein one or more of the carbon atoms in said heterocycloalkyl or heterocycloalkenyl may be oxidized to C(=O), all of which may be substituted with 1–3 of R$^{10}$;

R$^4$ is selected from =O, =S, and OR$^{21}$;

R$^{21}$ is hydrogen, or

R$^{21}$ is selected from alkyl of 1–8 carbon atoms, alkenyl of 2–8 carbon atoms, alkynyl of 2–8 carbon atoms, cycloalkyl of 3–8 carbon atoms, cycloalkenyl of 4–8 carbon atoms, 5–7 membered heterocycloalkyl of 3–6 carbon atoms and 1–2 heteroatoms selected from N, S(=O)$_{0-2}$ and O, and 5–7 membered heterocycloalkenyl of 3–6 carbon atoms and 1–2 heteroatoms selected from N, S(=O)$_{0-2}$ and O, all of which may be substituted with 1–3 of R$^5$ and R$^6$ are independently selected from cycloalkyl of 3–8 carbon atoms, cycloalkenyl of 4–8 carbon atoms, aryl of 6–10 carbon atoms, and heteroaryl of 2–9 carbon atoms and 1–4heteroatoms, all of which may be substituted with 1–3 of R$^{10}$, or R$^5$ and R$^6$ are independently selected from 5–7 membered heterocycloalkyl of 3–6 carbon atoms and 1–2 heteroatoms selected from N, S(=O)$_{0-2}$ and O and 5–7 membered heterocycloalkyl of 3–6 carbon atoms and 1–2 heteroatoms selected from N, S(=O)$_{0-2}$ and O, wherein said heterocycloalkyl and said heterocycloalkenyl may further be fused with phenyl or a 5–6 membered heteroaryl of 2–5 carbon atoms and 1–3 heteroatoms selected from N, S(=O)$_{0-2}$ and O, and/or wherein one or more of the carbon atoms in said heterocycloalkyl or heterocycloalkenyl may be oxidized to C(=O), wherein said heterocycloalkyl or said heterocycloalkenyl may be substituted with 1–3 of R$^{10}$, A—R$^{23}$, A—NR$^{24}$R$^{25}$, C(=O)R$^{24}$, C(=O)OR$^{24}$, C(=O)NR$^{24}$R$^{25}$ S(=O)$_2$R$^{26}$, A—C(=O) R$^{24}$, A—C(=O)OR$^{24}$, or A—C(=O)NR$^{24}$R$^{25}$ or R$^5$ and R$^6$ are independently selected from hydrogen, halogen, nitrile, nitro, hydroxy, alkyl of 1–8 carbon atoms, alkenyl of 2–8 carbon atoms, alkynyl of 2–8 carbon atoms, haloalkyl of 1–8 carbon atoms, alkoxy of 1–8 carbon atoms, haloalkoxy of 1–8 carbon atoms, cycloalkoxy of 3–8 carbon atoms, A—R$^{23}$, A(OR$^{22}$)R$^{23}$, NR$^{27}$R$^{28}$, A—NR$^{27}$R$^{28}$, A—Q—R$^{29}$, Q—R$^{29}$, Q—A—NR$^{24}$R$^{25}$, C(=O)R$^{24}$, C(=O)OR$^{24}$, C(=O)NR$^{24}$R$^{25}$, A—C(=O)R$^{24}$, A—C(=O)R$^{24}$, and A—C(=O) NR$^{24}$R$^{25}$;

Q is selected from O and S(=O)$_{0-2}$;

R$^{22}$ is selected from hydrogen, alkyl of 1–8 carbon atoms, haloalkyl of 1–8 carbon atoms, and cycloalkyl of 3–8 carbon atoms;

R$^{23}$ is selected from hydroxy, alkoxy of 1–8 carbon atoms, haloalkoxy of 1–8 carbon atoms, and cycloalkoxy of 3–8 carbon atoms, or R$^{23}$ is selected from cycloalkyl of 3–8 carbon atoms, cycloalkenyl of 4–8 carbon atoms, aryl of 6–10 carbon atoms, and heteroaryl of 2–9 carbon atoms and 1–4 heteroatoms selected from N, S(=O)$_{0-2}$, and O, all of which may be substituted with 1–3 of R$^{10}$, or R$^{23}$ is selected from 5–7 membered heterocycloalkyl of 3–6 carbon atoms and 1–2 heteroatoms selected from N, O, S(=O)$_{0-2}$, and 5–7 membered heterocycloalkenyl of 3–6 carbon atoms and 1–2 heteroatoms selected from N, O, S(=O)$_{0-2}$, wherein said heterocycloalkyl and said heterocycloakenyl may further be fused with phenyl or a 5–6 membered heteroaryl of 2–5 carbon atoms and 1–3 heteroatoms selected from N, S(=O)$_{0-2}$ and O, and/or wherein one or more of the carbon atoms in said heterocycloalkyl or heterocycloalkenyl may be oxidized to C(=O), wherein said heterocycloalkyl or said heterocycloalkenyl maybe substituted with 1–3 of R$^{10}$;

with the proviso for A(OR$^{22}$)—R$^{23}$ that when R$^{23}$ is selected from hydroxy, alkoxy of 1–8 carbon atoms, haloalkoxy of 1–8 carbon atoms, and cycloalkoxy of 3–8 carbon atoms, A is not CH;

R$^{24}$ and R$^{25}$ are independently selected from hydrogen, alkyl of 1–6 carbon atoms, alkenyl of 2–6 carbon atoms, alkynyl of 2–6 carbon atoms, haloalkyl of 1–6 carbon atoms, and A—R$^{23}$, or R$^{24}$ and R$^{25}$ are independently selected from cycloalkyl of 3–6 carbon atoms, cycloalkenyl of 3–6 carbon atoms, aryl of 6–10 carbon atoms, and heteroaryl of 2–9 carbon atoms and 1–4 heteroatoms selected from N, S(=O)$_{0-2}$, and O, all of which may be substituted with 1–3of R$^{10}$, or R$^{24}$ and R$^{25}$ are independently selected from 5–7 membered heterocycloalkyl of 3–6 carbon atoms and 1–2 heteroatoms selected from N, O, S(=O)$_{0-2}$, and 5–7 membered heterocycloalkyl of 3–6 carbon atoms and 1–2 heteroatoms selected from N, O, S(=O)$_{0-2}$, wherein said heterocycloalkyl and said heterocycloakenyl may further be fused with phenyl or a 5–6 membered heteroaryl of 2–5 carbon atoms and 1–3 heteroatoms selected from N, S(=O)$_{0-2}$ and O, and/or wherein one or more of the carbon atoms in said heterocycloalkyl or heterocycloalkenyl may be oxidized to C(=O), wherein said heterocycloalkyl or said heterocycloalkenyl may be substituted with 1–3 of R$^{10}$, or R$^{24}$ and R$^{25}$ combine, together with the nitrogen atom to which they are attached, to form a 5–7 membered heterocycloalkyl of 3–6 carbon atoms and 1–2 heteroatoms selected from N, S(=O)$_{0-2}$, and O, a 5–7 membered heterocycloalkyl of 3–6 carbon atoms and 1–2 heteroatoms selected from N, S(=O)$_{0-2}$, and O, or a heteroaryl of 2–9 carbon atoms and 1–4 heteroatoms, wherein said heterocycloalkyl and said heterocycloakenyl may further be fused with phenyl or a 5–6 membered heteroaryl of 2–5 carbon atoms and 1–3 heteroatoms selected from N, S(=O)$_{0-2}$ and O, and/or wherein one or more of the carbon atoms in said heterocycloalkyl or heterocycloalkenyl may be oxidized to C(=O), all of which may be substituted with 1–3 of R$^{10}$;

R$^{26}$ is selected from alkyl of 1–6 carbon atoms, alkenyl of 2–6 carbon atoms, alkynyl of 2–6 carbon atoms, haloalkyl of 1–6 carbon atoms, A(OR$^{22}$)—R$^{23}$, and A—R$^{23}$, or R$^{26}$ is selected from cycloalkyl of 3–6 carbon atoms, cycloalkenyl of 3–6 carbon atoms, aryl of 6–10 carbon atoms, and heteroaryl of 2–9 carbon atoms and 1–4 heteroatoms selected from N, $S(=O)_{0-2}$, and O, all of which may be substituted with 1–3 of $R^{10}$, or $R^{26}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{27}$ is selected from hydrogen, alkyl of 1–6 carbon atoms, alkenyl of 2–6 carbon atoms, alkynyl of 2–6 carbon atoms, haloalkyl of 1–6 carbon atoms, and A—$R^{23}$, or $R^{27}$ is selected from cycloalkyl of 3–6 carbon atoms, cycloalkenyl of 3–6 carbon atoms, aryl of 6–10 carbon atoms, and heteroaryl of 2–9 carbon atoms and 1–4 heteroatoms selected from N, $S(=O)_{0-2}$, and O, all of which may be substituted with 1–3 of $R^{10}$, or $R^{27}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{28}$ is selected from hydrogen, alkyl of 1–6 carbon atoms, alkenyl of 2–6 carbon atoms, alkynyl of 2–6 carbon atoms, haloalkyl of 1–6 carbon atoms, A—$R^{23}$, $C(=O)R^{24}$, $C(=O)OR^{26}$, $C(=O)NR^{25}R^{30}$, $S(=O)_2R^{26}$, A—$C(=O)R^{24}$, A—$C(=O)OR^{24}$, and A—$C(=O)NR^{24}R^{25}$, or $R^{28}$ is selected from cycloalkyl of 3–6 carbon atoms, cycloalkenyl of 3–6 carbon atoms, aryl of 6–10 carbon atoms, heteroaryl of 2–9 carbon atoms and 1–4 heteroatoms selected from N, $S(=O)_{0-2}$, and O, all of which may be substituted with 1–3 of $R^{10}$, or $R^{28}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{30}$ is selected from alkyl of 1–6 carbon atoms, alkenyl of 2–6 carbon atoms, alkynyl of 2–6 carbon atoms, haloalkyl of 1–6 carbon atoms, $A(OR^{22})$—$R^{23}$, and A—$R^{23}$, or $R^{30}$ is selected from cycloalkyl of 3–6 carbon atoms, cycloalkenyl of 3–6 carbon atoms, aryl of 6–10 carbon atoms, and heteroaryl of 2–9 carbon atoms and 1–4 heteroatoms selected from N, $S(=O)_{0-2}$, and O, all of which may be substituted with 1–3 of $R^{10}$, or $R^{30}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, or $R^{25}$ and $R^{30}$ combine, together with the nitrogen atom to which they are attached, to form a 5–7 membered heterocycloalkyl of 3–6 carbon atoms and 1–2 heteroatoms selected from N, $S(=O)_{0-2}$, and O, a 5–7 membered heterocycloalkenyl of 3–6 carbon atoms and 1–2 heteroatoms selected from N, $S(=O)_{0-2}$, and O, or a heteroaryl of 2–9 carbon atoms and 1–4 heteroatoms, all of which may be substituted with 1–3 of $R^{10}$;

$R^{29}$ is selected from alkyl of 1–6 carbon atoms, alkenyl of 2–6 carbon atoms, alkynyl of 2–6 carbon atoms, haloalkyl of 1–6 carbon atoms, A—$R^{23}$, A—$C(=O)R^{24}$, A—$C(=O)OR^{24}$, A—$C(=O)NR^{24}R^{25}$, A—$NR^{27}R^{28}$, or $R^{29}$ is selected from cycloalkyl of 3–6 carbon atoms, cycloalkenyl of 3–6 carbon atoms, aryl of 6–10 carbon atoms, heteroaryl of 2–9 carbon atoms and 1–4 heteroatoms selected from N, $S(=O)_{0-2}$, and O, all of which may be substituted with 1–3 of $R^{10}$, or $R^{29}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^7$ is selected from cycloalkyl of 3–8 carbon atoms, cycloalkenyl of 4–8 carbon atoms, aryl of 6–10 carbon atoms, and heteroaryl of 2–9 carbon atoms and 1–4 heteroatoms, all of which may be substituted with 1–3 of $R^{10}$, or $R^7$ is selected from 5–7 membered heterocycloalkyl of 3–6 carbon atoms and 1–2 heteroatoms selected from N, $S(=O)_{0-2}$ and O and 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, $A(OR^{22})$—$R^{23}$, A—$R^{23}$, A—$NR^{24}R^{25}$, $C(=O)R^{24}$, $C(=O)OR^{24}$, $C(=O)NR^{24}R^{25}$, $S(=O)_2R^{26}$, A—$C(=O)R^{24}$, or A—$C(=O)NR^{24}R^{25}$, or $R^7$ is selected from hydrogen, nitrile, nitro, hydroxy, alkyl of 1–8 carbon atoms, alkenyl of 2–8 carbon atoms, alkynyl of 2–8 carbon atoms, haloalkyl of 1–8 carbon atoms, alkoxy of 1–8 carbon atoms, haloalkoxy of 1–8 carbon atoms, cycloalkoxy of 3–8 carbon atoms, A—$R^{23}$, $A(OR^{22})$—$R^{23}$, $NR^{27}R^{28}$, A—$NR^{27}R^{28}$, A—Q—$R^{29}$, Q—$R^{29}$, Q—A—$NR^{24}R^{25}$, $C(=O)R^{24}$, $C(=O)OR^{24}$, $C(=O)NR^{24}R^{25}$, A—$C(=O)R^{24}$, A—$C(=O)OR^{24}$, and A—$C(=O)NR^{24}R^{25}$;

and pharmaceutically acceptable salts thereof, with the proviso that the compound is not: 1,5-dimethyl-2-(methylamino)-7-(4-morpholinyl)-1,8-naphthyridin-4(1H)-one, 1,5-dimethyl-2-(methylamino)-7-(4-methyl-1-piperazinyl)-1,8-naphthyridin-4(1H)-one, 1,5-dimethyl-2methylamino)-7-(1-pyrrolidinyl)-1,8-naphthyridin-4(1H)-one, 1,5-dimethyl-2-(methylamino)-7-(1-piperidinyl)-1,8-naphthyridin-4(1H)-one, 1,5-dimethyl-2-(methylamino)-7-(4-methyl-1-piperazinyl)-3-nitro-1,8-naphthyridin-4(1H)-one, 1,5-dimethyl-2-(methylamino)-3-nitro-7-(1-pyrrolidinyl)-1,8-naphthyridin-4(1H)-one, or 1-(3-chlorophenyl)-2-(4-morpholinyl)-1,8-naphthyridin-4(1H)-one.

Another aspect of the invention includes compounds of formula (I) wherein $R^1$ is selected from alkyl of 1–8 carbon atoms, alkenyl of 2–8 carbon atoms, alkynyl of 2–8 carbon atoms, and A—$R^9$, or $R^1$ is selected from aryl of 6–10 carbon atoms, heteroaryl of 2–9 carbon atoms and 1–4 heteroatoms selected from N, $S(=O)_{0-2}$ and O, cycloalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, wherein said heterocycloalkyl and said heterocycloalkenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to C(=O), all of which may be substituted with 1–3 of $R^{10}$;

$R^{10}$ is selected from nitro, nitrile, hydroxy, halogen, acyl of 1–6 carbon atoms, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms, cycloalkoxy of 3–6 carbon atoms, aryl of 6–10 carbon atoms, heteroaryl of 2–9 carbon atoms and 1–4 heteroatoms selected from N, $S(=O)_{0-2}$ and O, $NR^{11}R^{12}$, $C(=O)OR^{11}$, $C(=O)NHR^{11}$, $NHC(=O)R^{13}$, $NHS(=O)_2R^{13}$, $S(=O)_{0-2}R^{13}$, $S(=O)_2NHR^{11}$, cycloalkyl of 3–6 carbon atoms, cycloalkenyl of 3–6 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to C(=O);

$R^{13}$ is selected from alkyl of 1–6 carbon atoms, alkenyl of 2–6 carbon atoms, alkynyl of 2–6 carbon atoms, haloalkyl of 1–6 carbon atoms, cycloalkyl of 3–6 carbon atoms, and cycloalkenyl of 4–6 carbon atoms;

$R^{11}$ and $R^{12}$ are independently selected from hydrogen, alkyl of 1–6 carbon atoms, alkenyl of 2–6 carbon atoms, alkynyl of 2–6 carbon atoms, haloalkyl of 1–6 carbon atoms, cycloalkyl of 3–6 carbon atoms, and cycloalkenyl of 4–6 carbon atoms;

A is selected from alkyl of 1–8 carbon atoms, alkenyl of 2–8 carbon atoms, alkynyl of 2–8 carbon atoms, and haloalkyl of 1–8 carbon atoms;

$R^9$ is selected from hydroxy, alkoxy of 1–6 carbon atoms, cycloalkoxy of 3–6 carbon atoms, O—A—$R^{14}$, $NR^{11}R^{12}$; or $R^9$ is selected from aryl of 6–10 carbon atoms, heteroaryl of 2–9 carbon atoms and 1–4 heteroatoms selected from N, $S(=O)_{0-2}$ and O, cylcoalkyl of 3–8 carbon atoms, cycloalkenyl of 5–8 carbon atoms, all of which may be substituted with 1–3 of $R^{10}$, or $R^9$ is selected from 5–7 membered heterocycloalkyl of 3–6 carbon atoms and 1–2 heteroatoms selected from N, $S(=O)_{0-2}$ and O and 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to C(=O), wherein said heterocycloalkyl or said heterocycloalkenyl may be substituted with 1–3 of $R^{10}$;

$R^{14}$ is selected from cylcoalkyl of 3–8 carbon atoms, cycloalkenyl of 5–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$;

$R^2$ is $NR^{15}R^{16}$;

$R^{15}$ is selected from hydrogen, alkyl of 1–6 carbon atoms, alkenyl of 2–6 carbon atoms, alkynyl of 2–6 carbon atoms, cylcoalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, 5–7 membered heterocycloalkenyl of 3–6 carbon atoms and 1–2 heteroatoms selected from N, $S(=O)_{0-2}$ and O, A—$R^9$, $C(=O)R^{18}$, $C(=O)NHR^{18}$, $S(=O)_2NHR^{18}$;

$R^{18}$ is selected from aryl of 6–10 carbon atoms, heteroaryl of 2–9 carbon atoms and 1–4 heteroatoms selected from N, $S(=O)_{0-2}$ and O, cylcoalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(O)_{0-2}$ and O, all of which may be substituted with 1–3 of $R^{10}$, or $R^{18}$ is selected from alkyl of 1–6 carbon atoms, alkenyl of 2–6 carbon atoms, and alkynyl of 2–6 carbon atoms, all of which maybe substituted with 1–3 of halogen or alkoxy of 1–6 carbon atoms, or $R^{18}$ is A—$R^9$;

$R^{16}$ is selected from alkyl of 1–8 carbon atoms, alkenyl of 2–8 carbon atoms, alkynyl of 2–8 carbon atoms, and A—$R^9$, or $R^{16}$ is selected from aryl of 6–10 carbon atoms, heteroaryl of 2–9 carbon atoms and 1–4 heteroatoms selected from N, $S(=O)_{0-2}$ and O, cycloalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$, or $R^{15}$ and $R^{16}$ combine, together with the nitrogen atom to which they are attached, to form a heteroaryl of 2–9 carbon atoms and 1–4 heteroatoms selected from N, $S(=O)_{0-2}$ and O, or a 5–7 membered heterocycloalkyl of 3–6 carbon atoms and 1–2 heteroatoms selected from N, $S(=O)_{0-2}$ and O, 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, all of which may be substituted with 1–3 of $R^{10}$;

$R^3$ is selected from cycloalkyl of 3–6 carbon atoms, heterocycloalkyl of 3–6 carbon atoms and 1–2 heteroatoms selected from N, $S(O)_{0-2}$ and O, both of which may be substituted with 1–3 of $R^{10}$, or $R^3$ is selected from alkyl of 1–6 carbon atoms, haloalkyl of 1–6 carbon atoms, hydrogen, nitro, halogen, $NR^{19}R^{20}$, A—$OR^{19}$, A—$NR^{19}R^{20}$ and A—$R^{20}$;

$R^{19}$ and $R^{20}$ are independently selected from hydrogen, alkyl of 1–6 carbon atoms, alkenyl of 2–6 carbon atoms, alkynyl of 2–6 carbon atoms, haloalkyl of 1–6 carbon atoms, and A—$R^9$, or $R^{19}$ and $R^{20}$ are independently selected from aryl of 6–10 carbon atoms, heteroaryl of 2–9 carbon atoms and 1–4 heteroatoms selected from N, $S(O)_{0-2}$ and O, cylcoalkyl of 3–8 carbon atoms, cycloalkenyl of 5–8 carbon atoms, 5–7 membered heterocycloalkyl of 3–6 carbon atoms and 1–2 heteroatoms selected from N, $S(O)_{0-2}$ and O, 5–7 membered heterocycloalkenyl of 3–6 carbon atoms and 1–2 heteroatoms selected from N, $S(O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, all of which may be substituted with 1–3 of $R^{10}$;

$R^4$ is selected from $=O$, $=S$, and $OR^{21}$;

$R^{21}$ is hydrogen, or $R^{21}$ is selected from alkyl of 1–8 carbon atoms, alkenyl of 2–8 carbon atoms, alkynyl of 2–8 carbon atoms, cycloalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$;

$R^5$ and $R^6$ are independently selected from cycloalkyl of 3–6 carbon atoms, cycloalkenyl of 4–6 carbon atoms, phenyl, and monocyclic heteroaryl of 2–5 carbon atoms and 1–3 heteroatoms, all of which may be substituted with 1–3 of $R^{10}$, or $R^5$ and $R^6$ are independently selected from is selected from 5–7 membered heterocycloalkyl of 3–6 carbon atoms and 1–2 heteroatoms selected from N, $S(=O)_{0-2}$ and O and 5–7 membered heterocycloalkenyl of 3–6 carbon atoms and 1–2 heteroatoms selected from N, $S(=O)_{0-2}$ and O, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, A—$R^{23}$, A—$NR^{24}R^{25}$, $C(=O)R^{24}$, $C(=O)OR^{24}$, $C(=O)NR^{24}R^{25}$, $S(=O)_2R^{26}$, A—$C(=O)R^{24}$, A—$C(=O)OR^{24}$, or A—$C(=O)NR^{24}R^{25}$, or $R^5$ and $R^6$ are independently selected from hydrogen, halogen, nitrile, nitro, hydroxy, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms, cycloalkoxy of 3–6 carbon atoms, A—$R^{23}$, $A(OR^{22})$—$R^{23}$, $NR^{27}R^{28}$, A—$NR^{27}R^{28}$, A—Q—$R^{29}$, Q—$R^{29}$, Q—A—$NR^{24}R^{25}$, $C(=O)R^{24}$, $C(=O)OR^{24}$, $C(=O)NR^{24}R^{25}$, A—$C(=O)R^{24}$, A—$C(=O)OR^{24}$, and A—$C(=O)NR^{24}R^{25}$;

Q is selected from O and $S(=O)_{0-2}$;

$R^{22}$ is selected from hydrogen, alkyl of 1–6 carbon atoms, haloalkyl of 1–6 carbon atoms, and cycloalkyl of 3–6 carbon atoms;

$R^{23}$ is selected from hydroxy, alkoxy of 1–6 carbon atoms, haloalkoxy of 1–6 carbon atoms, and cycloalkoxy of 3–6 carbon atoms, or $R^{23}$ is selected from cycloalkyl of 3–6 carbon atoms, cycloalkenyl of 4–6 carbon atoms, phenyl, and monocyclic heteroaryl of 2–5 carbon atoms and 1–3 heteroatoms selected from N, $S(=O)_{0-2}$, and O, all of which may be substituted with 1–3 of $R^{10}$, or $R^{23}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$; with the proviso for $A(OR^{22})$—$R^{23}$ that when $R^{23}$ is selected from hydroxy, alkoxy of 1–6 carbon atoms, haloalkoxy of 1–6 carbon atoms, and cycloalkoxy of 3–6 carbon atoms, A is not CH;

$R^{24}$ and $R^{25}$ are independently selected from hydrogen, alkyl of 1–6 carbon atoms, alkenyl of 2–6 carbon atoms, alkynyl of 2–6 carbon atoms, haloalkyl of 1–6 carbon atoms, and A—$R^{23}$, or $R^{24}$ and $R^{25}$ are independently selected from cycloalkyl of 3–6 carbon atoms, cycloalkenyl of 3–6 carbon atoms, phenyl, and monocyclic heteroaryl of 2–5 carbon atoms and 1–3 heteroatoms selected from N, $S(=O)_{0-2}$, and O, all of which may be substituted with 1–3 of $R^{10}$, or $R^{24}$ and $R^{25}$ are independently selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, or $R^{24}$ and $R^{25}$ combine, together with the nitrogen atom to which they are attached, to form a 5–7 membered heterocycloalkyl of 3–6 carbon atoms and 1–2 heteroatoms selected from N, $S(=O)_{0-2}$, and O, a 5–7 membered heterocycloalkyl of 3–6 carbon atoms and 1–2 heteroatoms selected from N, $S(=O)_{0-2}$, and O, or a monocyclic heteroaryl of 2–5 carbon atoms and 1–3 heteroatoms, wherein one or more of the carbon atoms in said heterocycloalkyl or heterocycloalkenyl may be oxidized to $C(=O)$, all of which may be substituted with 1–3 of $R^{10}$;

$R^{26}$ is selected from alkyl of 1–6 carbon atoms, alkenyl of 2–6 carbon atoms, alkynyl of 2–6 carbon atoms, haloalkyl of 1–6 carbon atoms, $A(OR^{22})$—$R^{23}$, and A—$R^{23}$, or $R^{26}$ is selected from cycloalkyl of 3–6 carbon atoms, cycloalkenyl of 3–6 carbon atoms, phenyl, and monocyclic heteroaryl of 2–5 carbon atoms and 1–3 heteroatoms selected from N, $S(=O)_{0-2}$, and O, all of which may be substituted with 1–3 of $R^{10}$, or $R^{26}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{27}$ is selected from hydrogen, alkyl of 1–6 carbon atoms, alkenyl of 2–6 carbon atoms, alkynyl of 2–6 carbon atoms, haloalkyl of 1–6 carbon atoms, and A—$R^{23}$, or $R^{27}$ is selected from cycloalkyl of 3–6 carbon atoms, cycloalkenyl of 3–6 carbon atoms, phenyl, and monocyclic heteroaryl of 2–5 carbon atoms and 1–3 heteroatoms selected from N, $S(=O)_{0-2}$, and O, all of which maybe substituted with 1–3 of $R^{10}$, or $R^{27}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{28}$ is selected from hydrogen, alkyl of 1–6 carbon atoms, alkenyl of 26 carbon atoms, alkynyl of 2–6 carbon atoms, haloalkyl of 1–6 carbon atoms, A—$R^{23}$, $C(=O)R^{24}$, $C(=O)OR^{26}$, $C(=O)NR^{25}R^{30}$, $S(=O)_2R^{26}$, A—$C(=O)R^{24}$, A—$C(=O)OR^{24}$, and A—$C(=O)NR^{24}R^{25}$, or $R^{28}$ is selected from cycloalkyl of 3–6 carbon atoms, cycloalkenyl of 3–6 carbon atoms, phenyl, monocyclic heteroaryl of 2–5 carbon atoms and 1–3 heteroatoms selected from N, $S(=O)_{0-2}$, and O, all of which may be substituted with 1–3 of $R^{10}$, or $R^{28}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^{30}$ is selected from alkyl of 1–6 carbon atoms, alkenyl of 2–6 carbon atoms, alkynyl of 2–6 carbon atoms, haloalkyl of 1–6 carbon atoms, $A(OR^{22})R^{23}$, and A—$R^{23}$, or $R^{30}$ is selected from cycloalkyl of 3–6 carbon atoms, cycloalkenyl of 3–6 carbon atoms, phenyl, and monocyclic heteroaryl of 2–5 carbon atoms and 1–3 heteroatoms selected from N, $S(=O)_{0-2}$, and O, all of which may be substituted with 1–3 of $R^{10}$, or $R^{30}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, or, $R^{25}$ and $R^{30}$ combine, together with the nitrogen atom to which they are attached, to form a 5–7 membered heterocycloalkyl of 3–6 carbon atoms and 1–2 heteroatoms selected from N, $S(=O)_{0-2}$, and O, a 5–7 membered heterocycloalkenyl of 3–6 carbon atoms and 1–2 heteroatoms selected from N, $S(=O)_{0-2}$, and O, or a monocyclic heteroaryl of 2–5 carbon atoms and 1–3 heteroatoms, all of which may be substituted with 1–3 of $R^{10}$; and $R^{29}$ is selected from alkyl of 1–6 carbon atoms, alkenyl of 2–6 carbon atoms, alkynyl of 2–6 carbon atoms, haloalkyl of 1–6 carbon atoms, A—$R^{23}$, A—$C(=O)R^{24}$, A—$C(=O)OR^{24}$, A—$C(=O)NR^{24}R^{25}$, A—$NR^{27}R^{28}$, or $R^{29}$ is selected from cycloalkyl of 3–6 carbon atoms, cycloalkenyl of 3–6 carbon atoms, phenyl, monocyclic heteroaryl of 2–5 carbon atoms and 1–3 heteroatoms selected from N, $S(O)_{0-2}$, and O, all of which may be substituted with 1–3 of $R^{10}$, or $R^{29}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^7$ is selected from cycloalkyl of 3–6 carbon atoms, cycloalkenyl of 4–6 carbon atoms, phenyl, and monocyclic heteroaryl of 2–5 carbon atoms and 1–3 heteroatoms, all of which may be substituted with 1–3 of $R^{10}$, or $R^7$ is selected from 5–7 membered heterocycloalkyl of 3–6 carbon atoms and 1–2 heteroatoms selected from N, $S(=O)_{0-2}$ and O and 5–7 membered heterocycloalkenyl of 3–6 carbon atoms and 1–2 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, A—$R^{23}$, A—$NR^{24}R^{25}$, $C(=O)R^{24}$, $C(=O)OR^{24}$, $C(=O)NR \geq R^{25}$, $S(=O)_2R^{26}$, A—$C(=O)R^{24}$, A—$C(=O)OR^{24}$, or A—$C(=O)NR^{24}R^{25}$, or $R^7$ is selected from hydrogen, nitrile, nitro, hydroxy, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms, cycloalkoxy of 3–6 carbon atoms, A—$R^{23}$, $A(OR^{22})$—$R^{23}$, $NR^{27}R^{28}$, A—$NR^{27}R^{28}$, A—Q—$R^{29}$, Q—$R^{29}$, Q—A—$NR^{24}R^{25}$, $C(=O)R^{24}$, $C(=O)OR^{24}$, $C(=O)NR^{24}R^{25}$, A—$C(=O)R^{24}$, A—$C(=O)OR^{24}$, and A—$C(=O)NR^{24}R^{25}$;

and pharmaceutically acceptable salts thereof with the proviso that the compound is not: 1,5-dimethyl-2-(methylamino)-7-(4-morpholinyl)-1,8-naphthyridin-4(1H)-one, 1,5-dimethyl-2-(methylamino)-7-(4-methyl-1-piperazinyl)-1,8-naphthyridin-4(1H)-one, 1,5-dimethyl-2methylamino)-7-(1-pyrrolidinyl)-1,8-naphthyridin-4(1H)-one, 1,5-dimethyl-2-(methylamino)-7-(1-piperidinyl)-1,8-naphthyridin-4(1H)-one, 1,5-dimethyl-2-(methylamino)-7-(4-methyl-1-piperazinyl)-3-nitro-1,8-naphthyridin-4(1H)-one, 1,5-dimethyl-2-(methylamino)-3-nitro-7-(1-pyrrolidinyl)-1,8-naphthyridin-4(1H)-one, or 1-(3-chlorophenyl)-2-(4-morpholinyl)-1,8-naphthyridin-4(1H)-one.

Methods of the invention provide for the treatment or prevention of diabetes, including Type 1 and Type 2 diabetes, and related disorders by administration of a compound of the invention. Related disorders include maturity-onset diabetes of the young (MODY), latent autoimmune diabetes adult (LADA), impaired glucose tolerance (IGT), impaired fasting glucose (IFG), gestational diabetes, and metabolic syndrome X.

In other embodiments, methods of the invention provide for the administration of a compound of the invention in combination with a PPAR agonist, an insulin sensitizer, a sulfonylurea, an insulin secretagogue, a hepatic glucose output lowering compound, an cc-glucosidase inhibitor or insulin. PPAR agonist includes rosiglitazone and pioglitazone. Sulfonylureas include glibenclamide, glimepiride, chlorpropamride, and glipizide. Insulin secretagogues include GLP-1, GIP, PACNVPAC receptor agonists, secretin, nateglinide, meglitinide, repaglinide, glibenclamide, glimepiride, chlorpropamide, and glipizide. α-glucosidase inhibitors include acarbose, miglitol and voglibose. A hepatic glucose output lowering compound is metformin.

In another embodiment, methods of the invention provide for the administration of a compound of the invention in combination with an HMG-CoA reductase inhibitor, nicotinic acid, a bile acid sequestrant, a fibric acid derivative, antihypertensive drug, or an anti-obesity drug. Anti-obesity drugs include a β-3 agonist, a CB-1 antagonist, and a lipase inhibitor.

In another embodiment of the invention, methods are provided for the treatment or prevention of secondary causes of diabetes, such as glucocorticoid excess, growth hormone excess, pheochromocytoma, and drug-induced diabetes.

Finally, methods of the invention provide for increasing the sensitivity of pancreatic beta cells to an insulin secretagogue, by administering a compound of the invention. Insulin secretagogues include GLP-1, GIP, PAC/VPAC receptor agonists, secretin, nateglinide, meglitinide, repaglinide, glibenclamide, glimepiride, chlorpropamide, and glipizide.

The present invention therefore provides compounds and methods for the treatment of diabetes and related disorders. These and other aspects of the invention will be more apparent from the following description and claims.

DETAILED DESCRIPTION OF THE INVENTION

The invention relates generally to naphthyridine derivatives of the formula

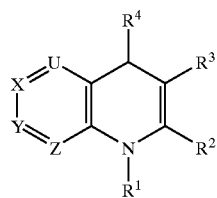

wherein one of U, X, Y and Z is nitrogen and the others are C—R, where R is hydrogen or a substituent such as $R^5$, $R^6$ or $R^7$, as described above for formula (I). $R^1$, $R^2$, $R^3$ and $R^4$ are as defined above for formula (I). The invention also relates to compounds of formula (I), described above, and to compounds of formula (II)

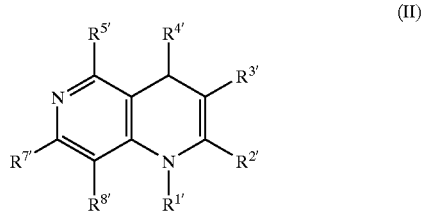

(II)

wherein $R^{1'}$, $R^{2'}$, $R^{3'}$, $R^{4'}$, $R^{5'}$, $R^{7'}$ and $R^{8'}$ correspond to $R^1$, $R^2$, $R^3$, $R^4$, $R^5$, $R^6$ and $R^7$, respectively, of formula (I). Such compounds may be used in the treatment of diabetes and related disorders.

In one embodiment, the invention relates to compounds of formula (I), as described above. In another embodiment, the invention relates to compounds of formula (I), wherein $R^1$ is phenyl, which may be substituted with 1–3 of $R^{10}$, $R^2$ is $NR^{15}R^{16}$, $R^3$ is selected from cycloalkyl of 3–6 carbon atoms, heterocycloalkyl of 3–6 carbon atoms and 1–2 heteroatoms selected from N, $S(O)_{0-2}$ and O, both of which may be substituted with 1–3 of $R^{10}$, or $R^3$ is selected from alkyl of 1–6 carbon atoms, haloalkyl of 1–6 carbon atoms, hydrogen, nitro, halogen, $NR^{19}R^{20}$, A—$OR^{19}$, A—$NR^{19}R^{20}$ and A—$R^{20}$, and $R^4$ is =O.

In another embodiment, the invention relates to methods of treating diabetes and related disorders by administration of compounds of formula (I). Preferred methods relate to the treatment of Type 2 diabetes. In methods of the invention, compounds of formula (I) may be administered in combination with PPAR agonist, insulin sensitizers, sulfonylureas, insulin secretagogues, metformin, α-glucosidase inhibitors and insulin. In another embodiment, compounds of formula (I) are administered in combination with an HMG-CoA reductase inhibitor, nicotinic acid, a bile acid sequestrant, a fibric acid derivative, an anti-hypertensive drug or an anti-obesity drug.

In other methods of the invention, compounds of formula (I) are administered to treat or prevent secondary causes of diabetes or to increase the sensitivity of pancreatic beta cells to an insulin secretagogue.

General Preparative Methods

The compounds of the invention may be prepared by use of known chemical reactions and procedures. Nevertheless, the following general synthetic schemes are presented to aid the reader in synthesizing compounds of this invention, with more detailed particular examples being presented below in the experimental section describing the working examples.

In general, compounds of Formula (I) ($R^4$ is =O) may be prepared from the appropriately substituted nicotinic acid through several routes summarized in Flow Diagram I to IV. Compounds of Formula (II) ($R^4$ is =O) may be prepared from the appropriately substituted nicotinic acid through the route summarized in Flow diagram V. The close analogy between Flow Diagram I and V demonstrates that the routes used to synthesize Formula (I) may be applied to synthesize Formula (II). The routes shown in Flow Diagram II to IV maybe used to synthesize Formula (II) from appropriately substituted nicotinic acid.

Flow Diagram I
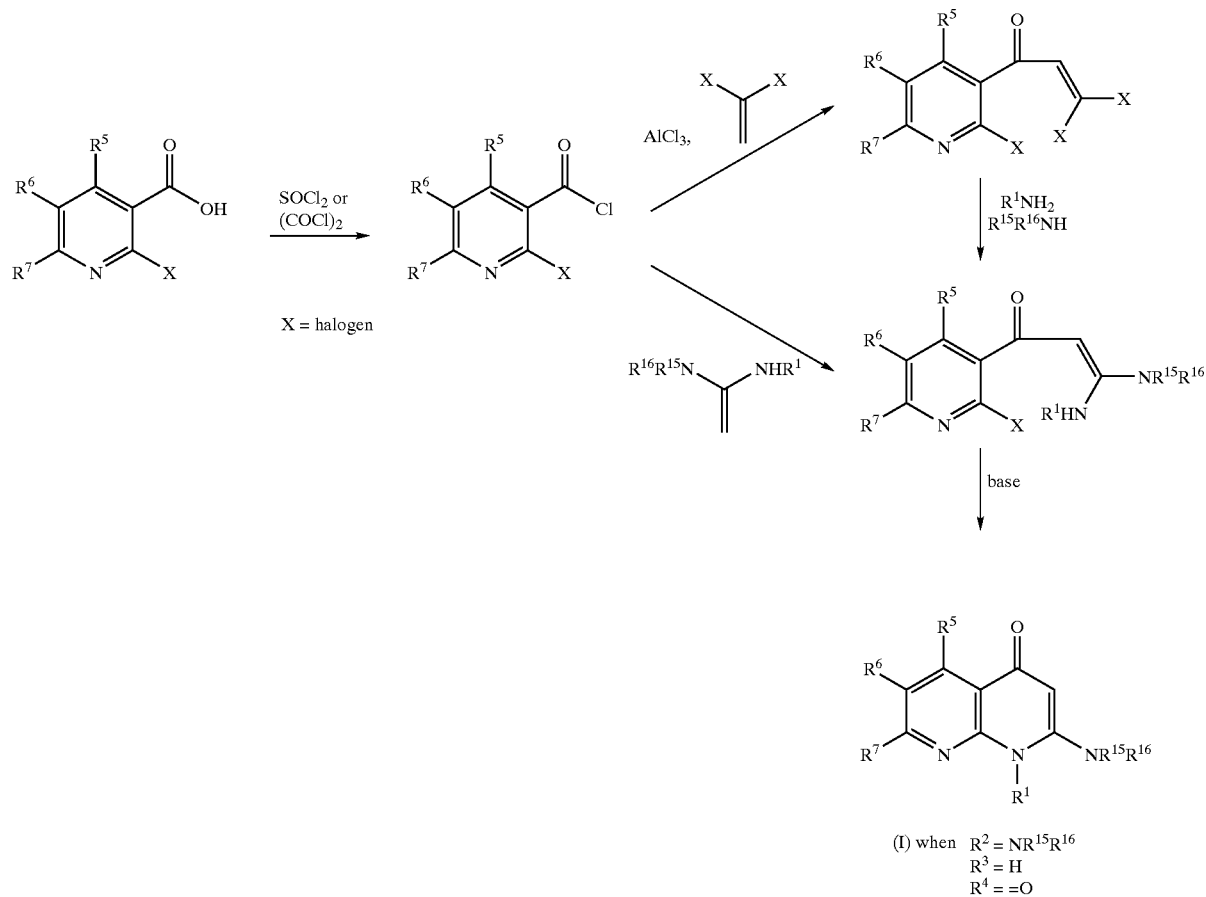
Flow Diagram II
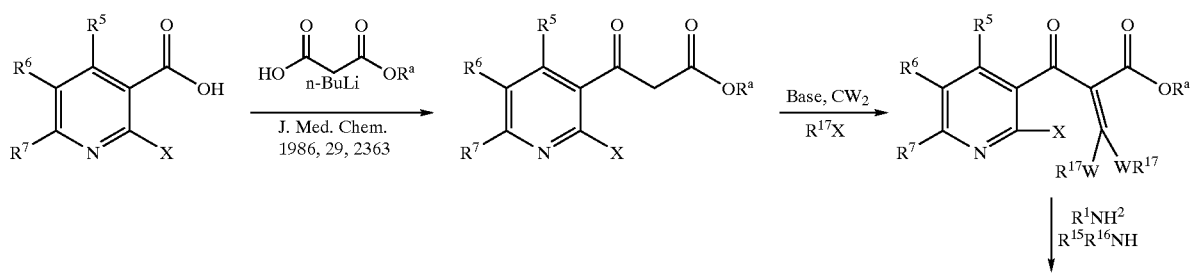

-continued
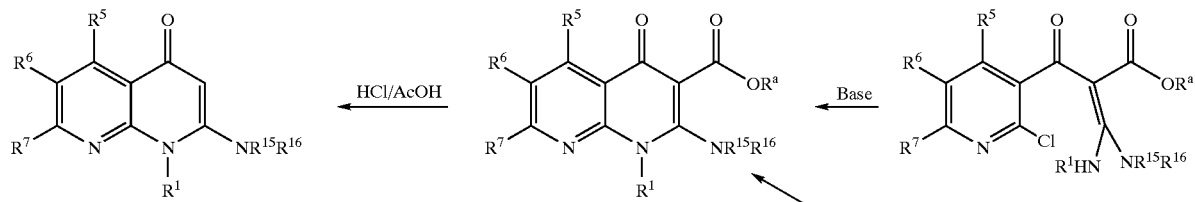
(I) when R² = NR¹⁵R¹⁶
R³ = H
R⁴ = =O
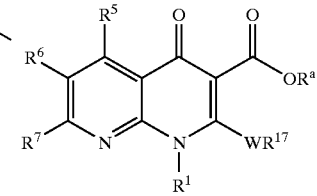
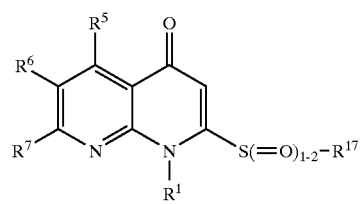
(I) when R² = S(=O)₁₋₂R¹⁷
R³ = H
R⁴ = =O
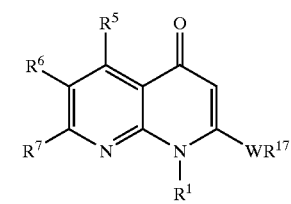
(I) when R² = SR¹⁷ or OR¹⁷
R³ = H
R⁴ = =O
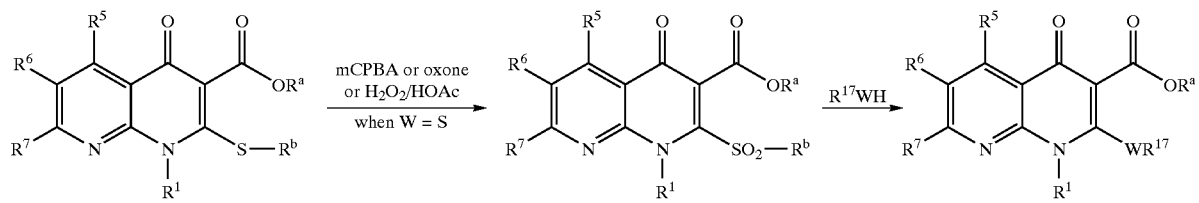
X = halogen
W = S or O
Rᵃ = alkyl, aryl
Rᵇ = alkyl
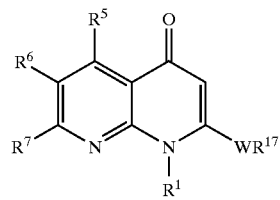
(I) when R² = SR¹⁷ or OR¹⁷
R³ = H
R⁴ = =O Flow Diagram III
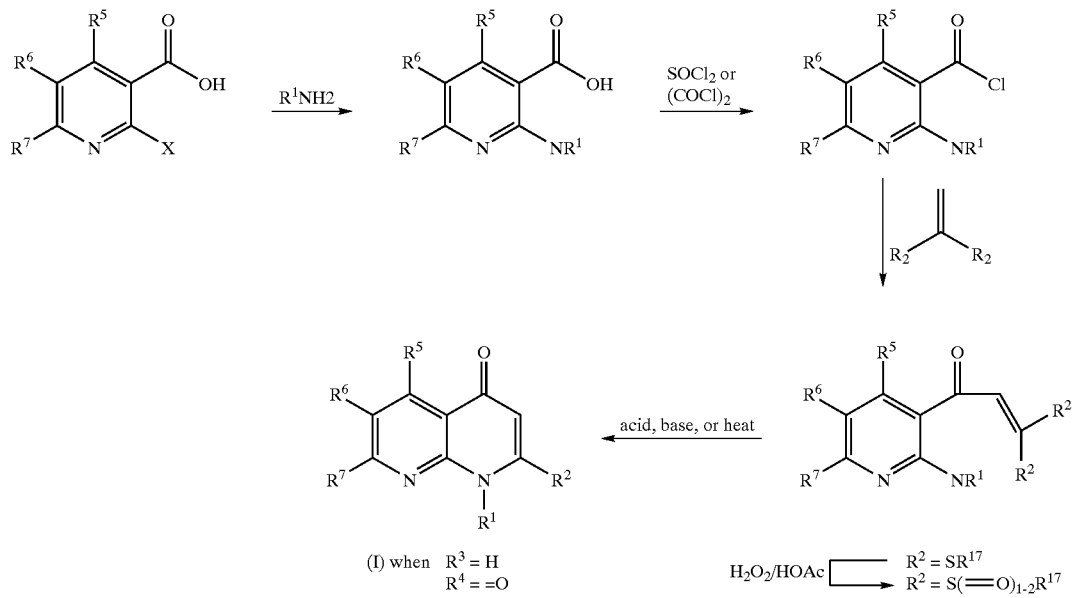
Flow Diagram IV
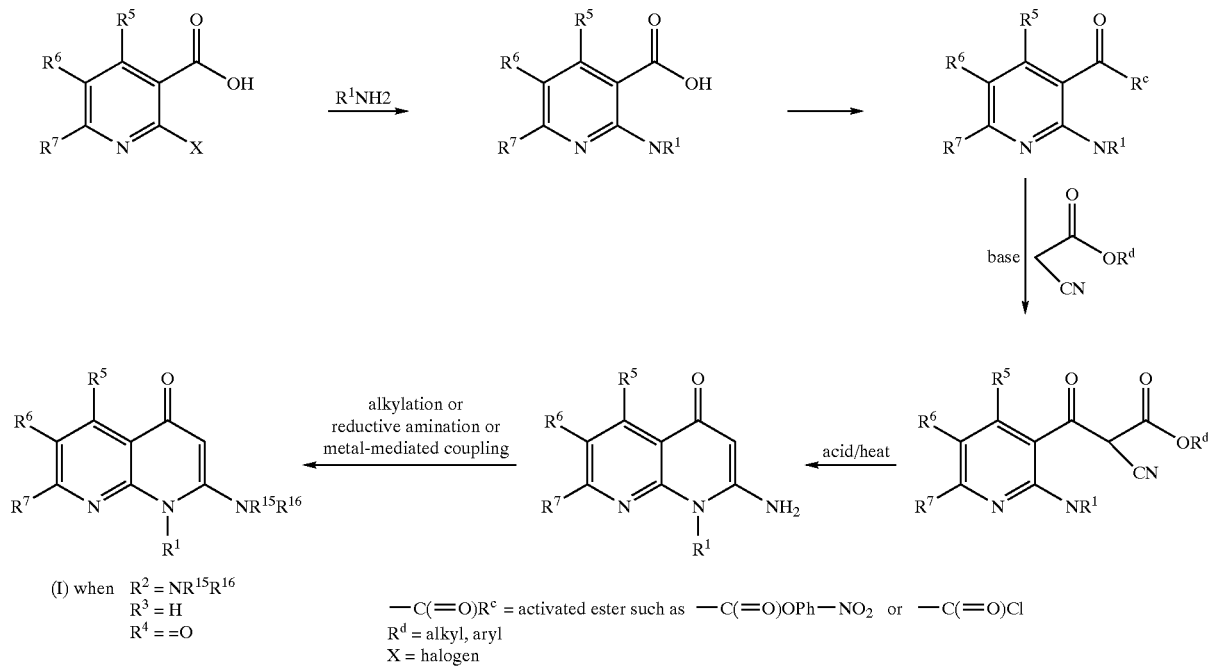

Flow Diagram V
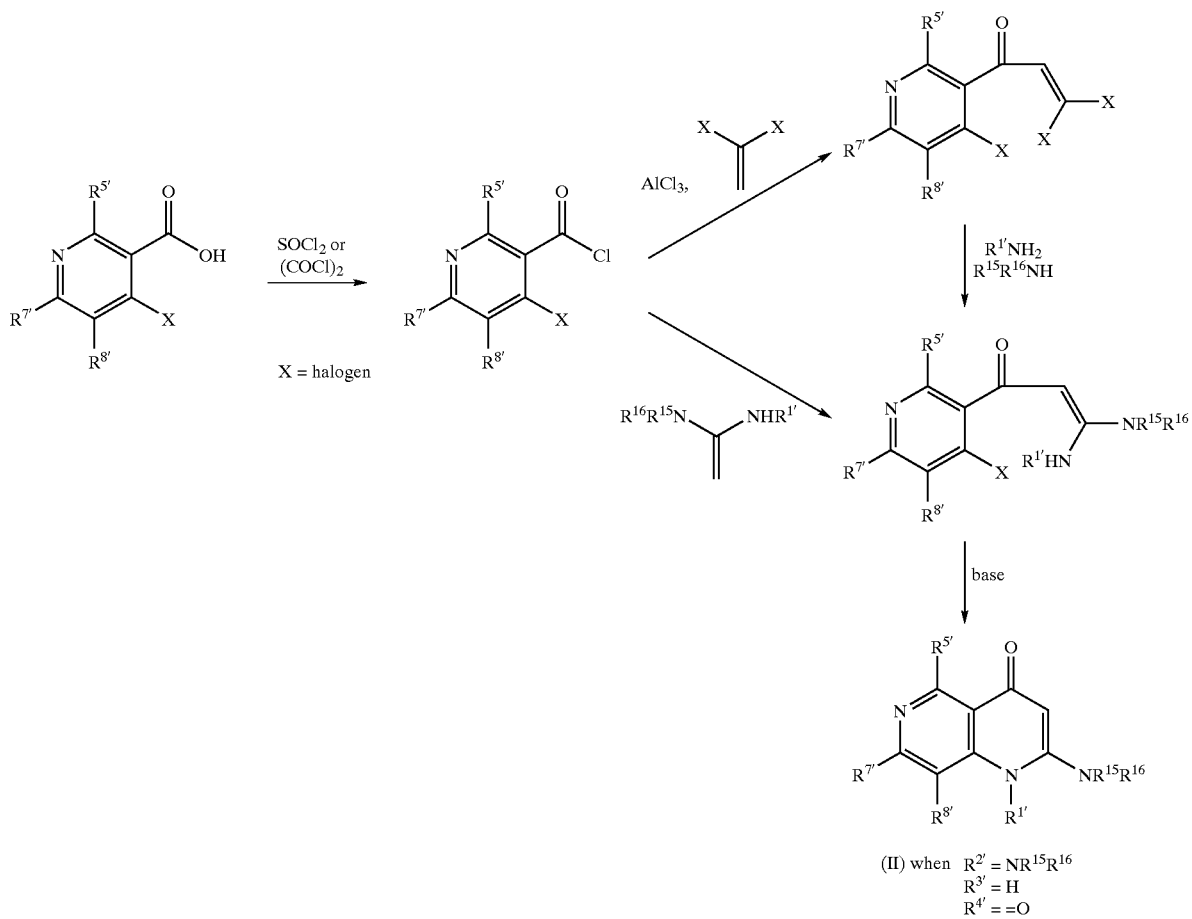
The nicotinic acids used in the above flow diagrams could be purchased from commercial sources, prepared according to Flow Diagram VI, or prepared according to literature in this field (*Biorg. Med. Chem. Lett.* 2001, 475–477; *J. Prakt. Chem.* 2002, 33; *Eur. J. Org. Chem.* 2001, 1371; *J. Org. Chem.* 2000, 65, 4618; *J. Med. Chem.* 1997, 40, 2674; *Bioorg. Med. Chem. Lett.* 2000, 10, 1151; U.S. Pat. No. 3,838,156, etc.).
Flow Diagram VI
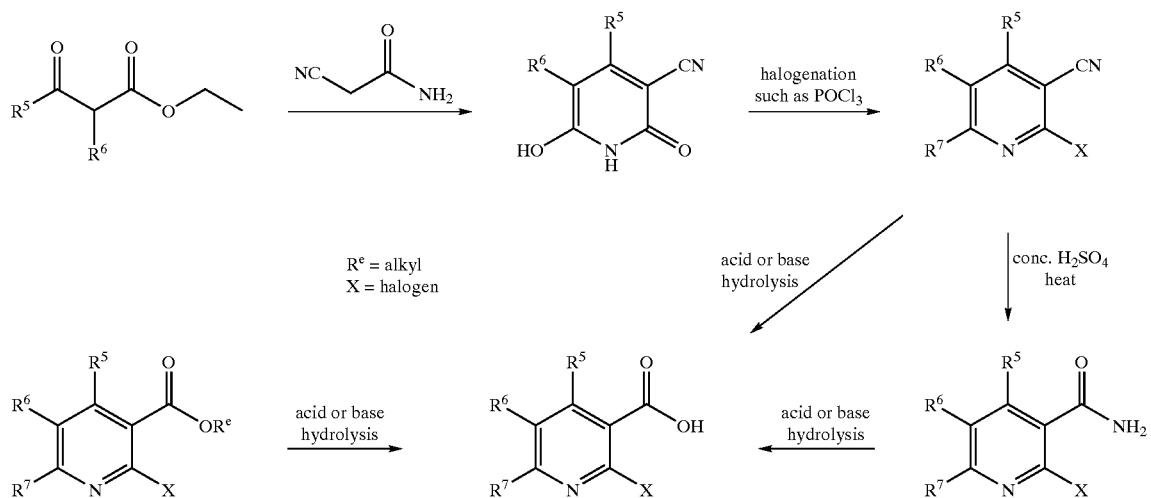

Further manipulations of Formula (I) (when $R^4$ is =O) and (II) (when $R^{4'}$ is =O) could lead to more diversely substituted compounds. These manipulations include aromatic nucleophilic substitutions, metal-mediated couplings, reductions, oxidations, amide formations, etc.

Flow Diagram VII illustrates alkylation, and amide, urea, and sulfonamide formations in Formula (I) when $R^2$=NHR$^{16}$. Similar transformations could be carried out in Formula (II) when $R^{2'}$=NHR$^{16}$.

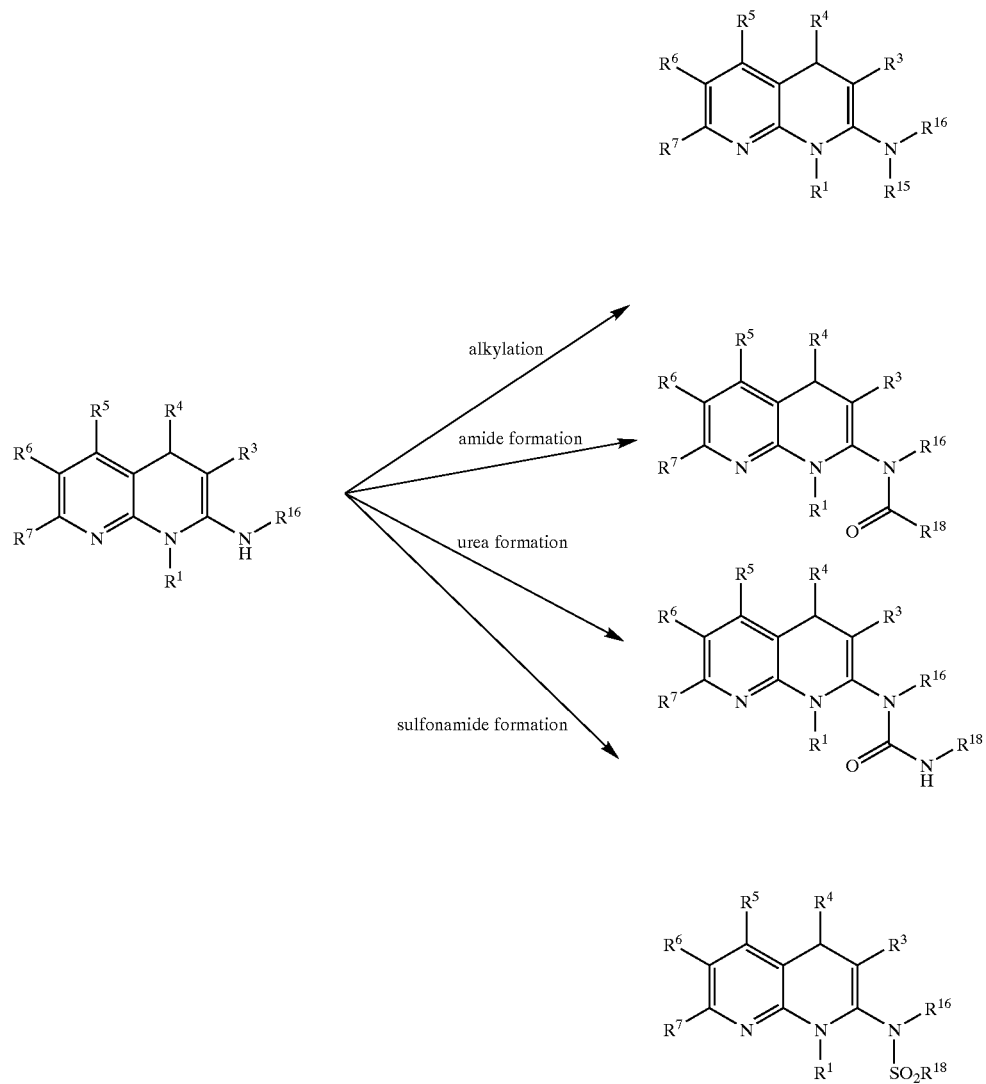

Flow Diagram VII

Flow Diagram VIII and IX illustrate transformations at $R^3$ in Formula (I). These transformations could also be applied to $R^{3'}$ in Formula (II).
Flow Diagram VIII
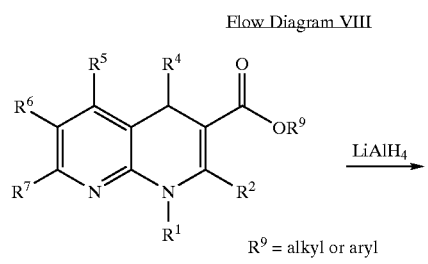
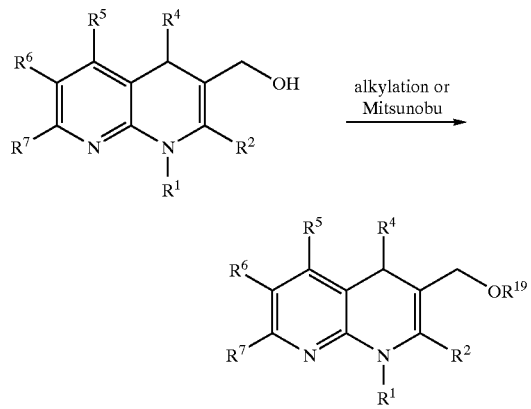
Flow Diagram IX
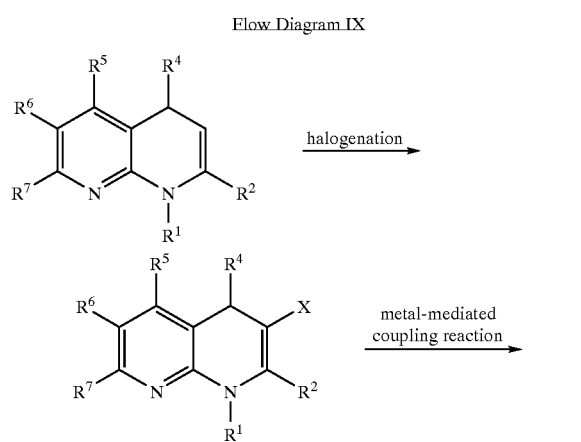
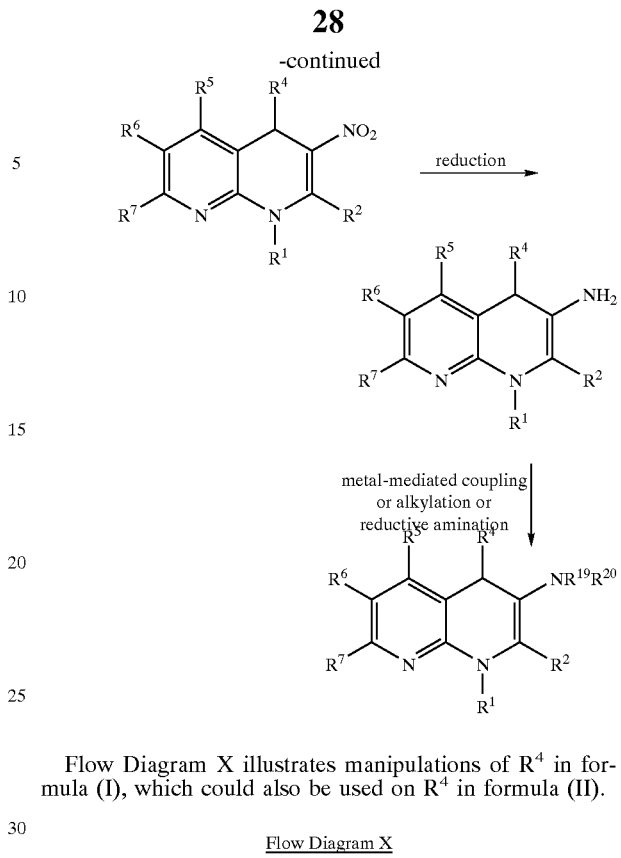
Flow Diagram X illustrates manipulations of $R^4$ in formula (I), which could also be used on $R^4$ in formula (II).
Flow Diagram X
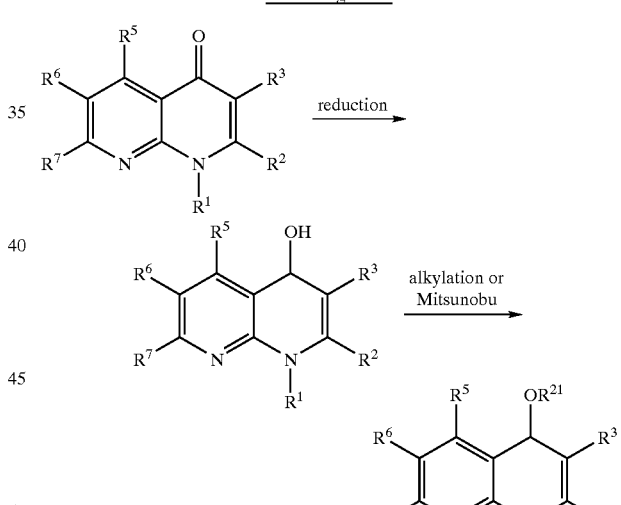
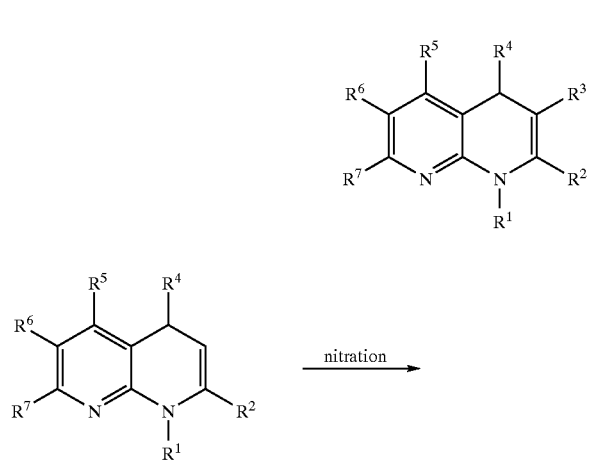
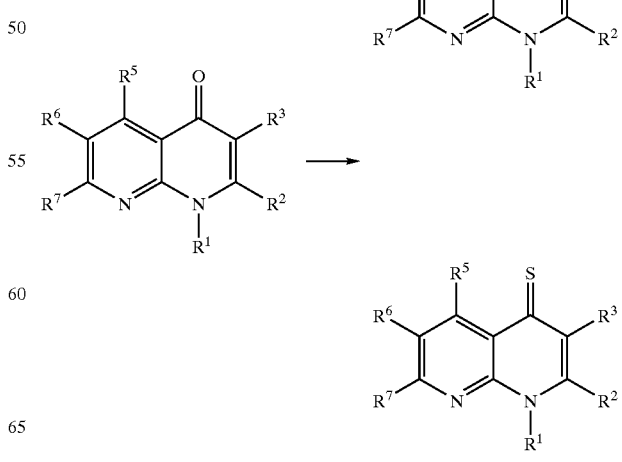

Flow Diagram XI illustrates manipulations of $R^6$ in formula (I). These manipulations could also be applied to $R^5$ and $R^7$ in formula (I), $R^{5'}$, $R^{7'}$, and $R^{8'}$ in formula (II).
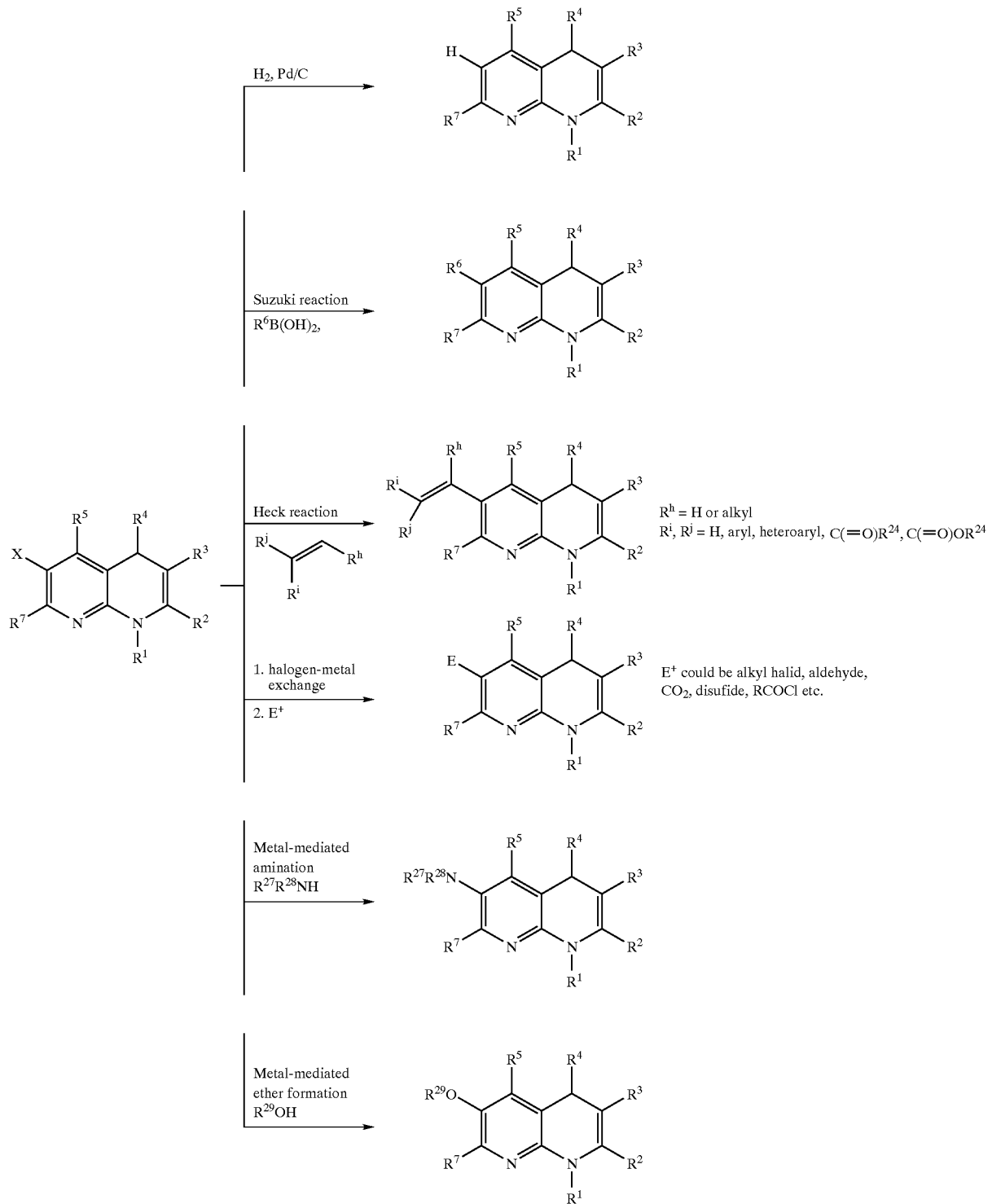

Flow Diagram XII illustrates manipulations on $R^7$ of formula (I). These manipulations could also be applied to $R^5$ in formula (I), $R^{5'}$ and $R^{7'}$ in formula (II).
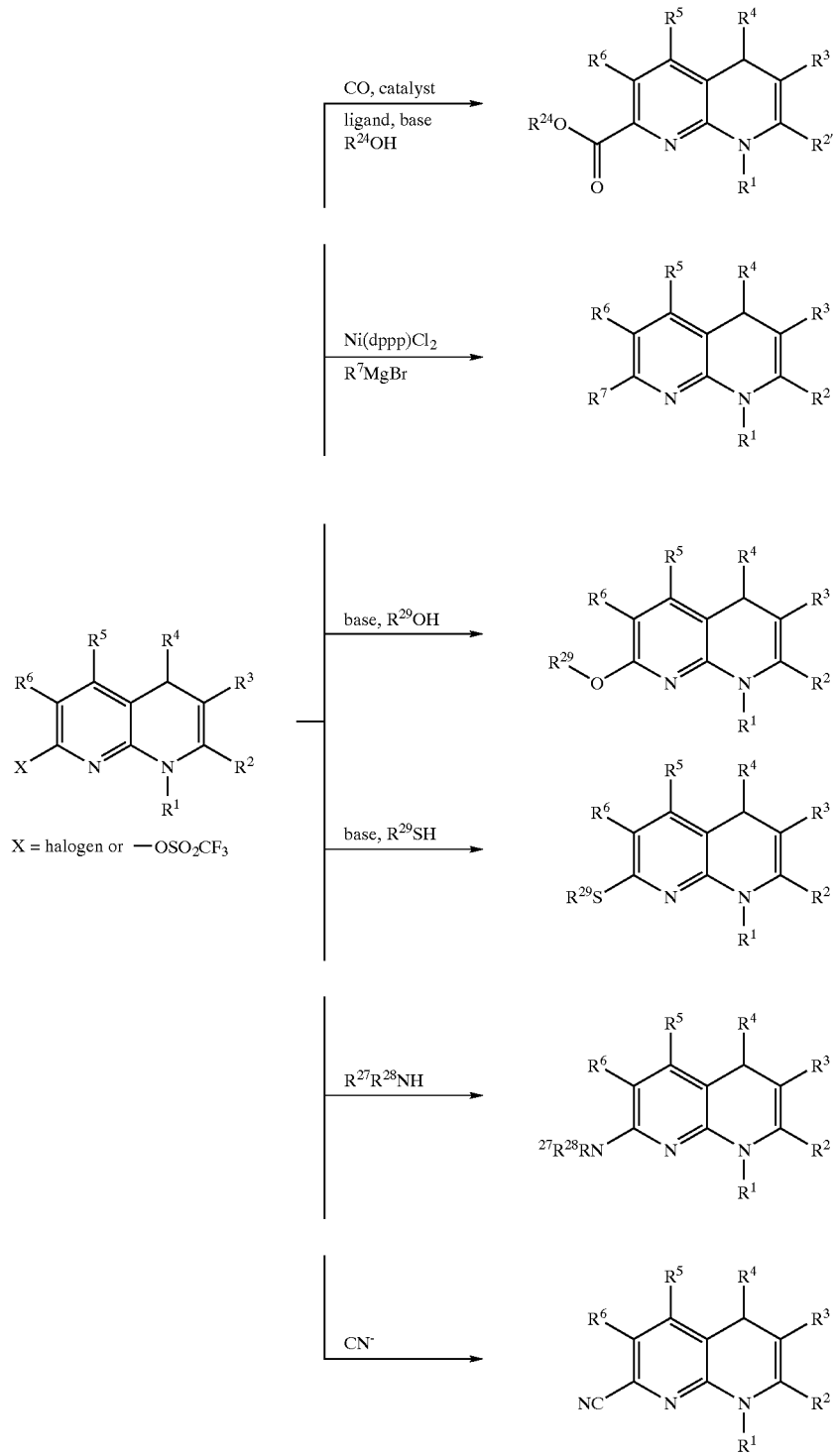

Flow Diagram XIII illustrates manipulations on $R^5$ of formula (I). These manipulations could also be applied to $R^7$ in formula (I), $R^{5'}$ and $R^{7'}$ in formula (II).

Flow Diagram XIII

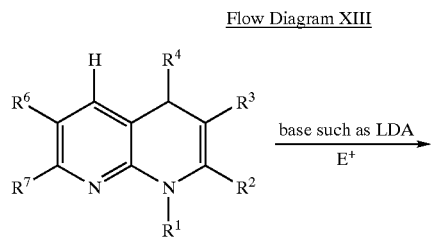

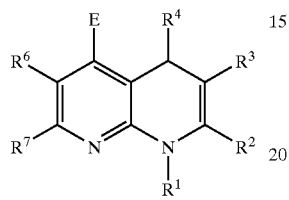

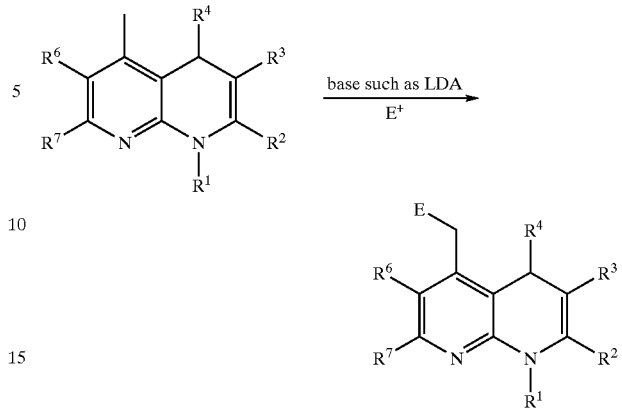

$E^+$ is alkyl halide, aldehydes, halogen, $CO_2$, $O_2$, activated ester, ect.

Flow Diagram XIV illustrates the transformations of some functional groups which are present in Formula (I) or (II).

Flow Diagram XIV

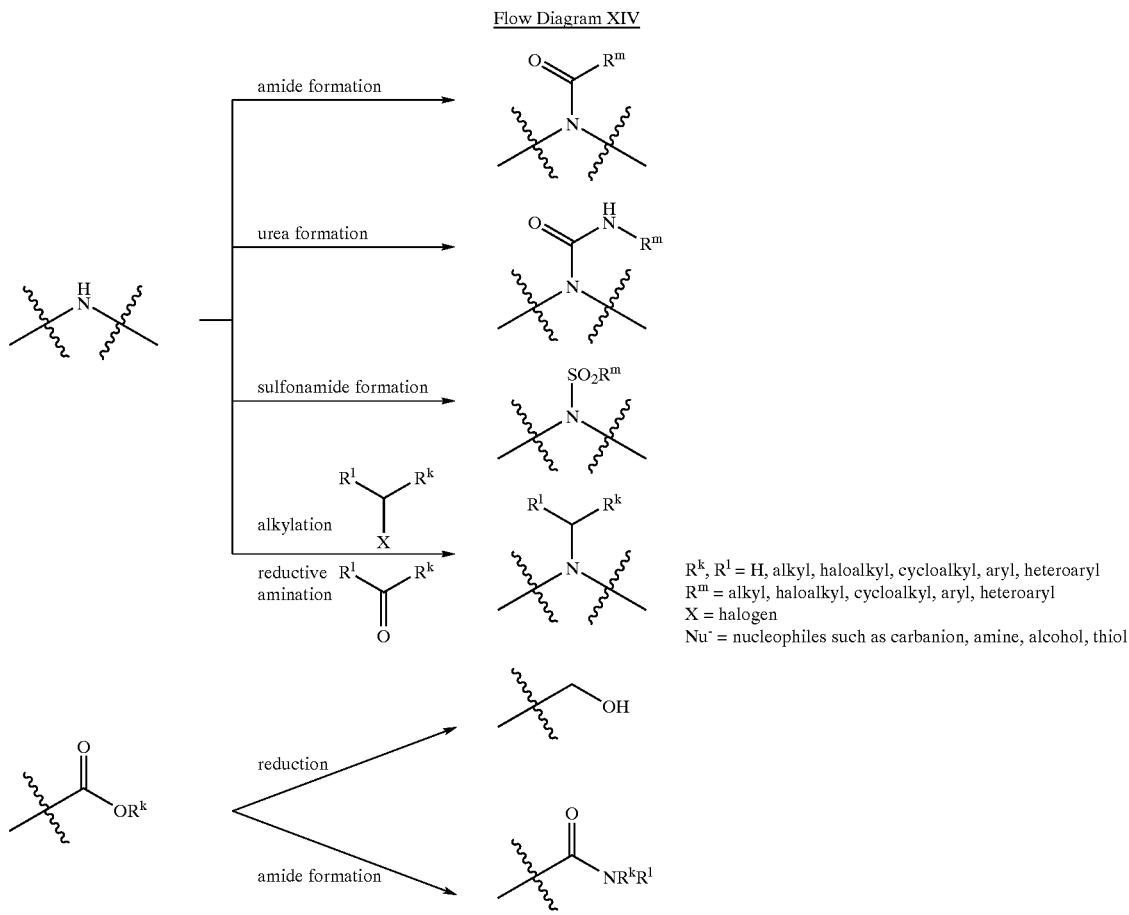

$R^k$, $R^l$ = H, alkyl, haloalkyl, cycloalkyl, aryl, heteroaryl
$R^m$ = alkyl, haloalkyl, cycloalkyl, aryl, heteroaryl
X = halogen
Nu⁻ = nucleophiles such as carbanion, amine, alcohol, thiol

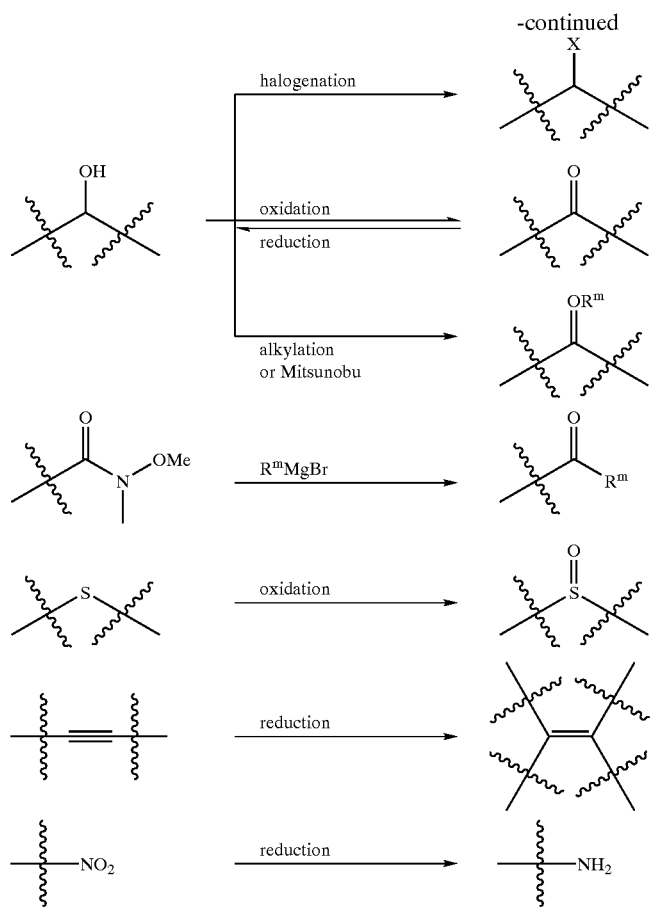
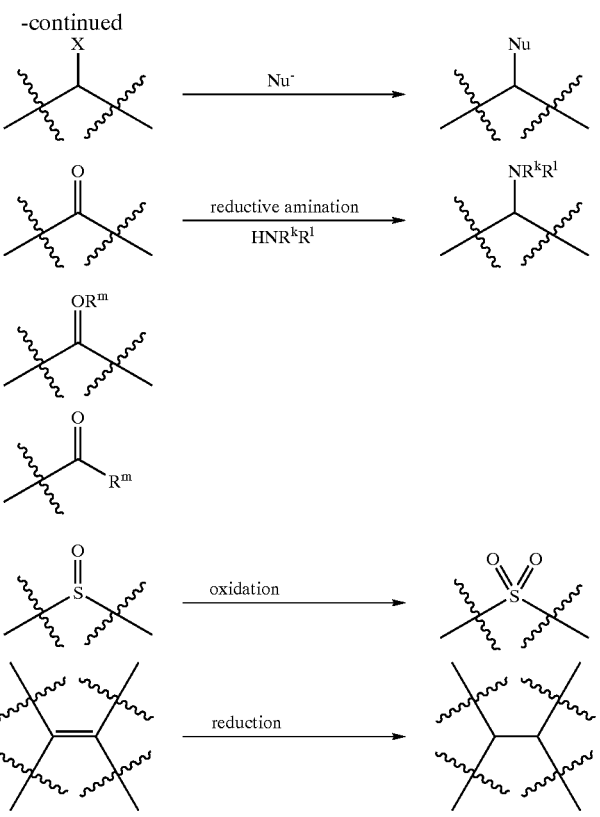

Alternative Forms of Novel Compounds

Also included in the compounds of the present invention are (a) the stereoisomers thereof, (b) the pharmaceutically-acceptable salts thereof, (c) the tautomers thereof, (d) the protected acids and the conjugate acids thereof, and (e) the prodrugs thereof.

(a) The Stereoisomers

The stereoisomers of these compounds may include, but are not limited to, enantiomers, diastereomers, racemic mixtures and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the inhibitors described above.

(b) The Pharmaceutically-acceptable Salts

Pharmaceutically-acceptable salts of the compounds of the present invention include salts commonly used to form alkali metal salts or form addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, heterocyclic, carboxylic and sulfonic classes of organic acids. Examples of organic and sulfonic classes of organic acids includes, but are not limited to, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, N-hydroxybutyric, salicyclic, galactaric and galacturonic acid and combinations thereof.

(c) The Tautomers

Tautomers of the compounds of the invention are encompassed by the present invention. Thus, for example, a carbonyl includes its hydroxy tautomer.

(d) The Protected Acids and the Conjugate Acids

The protected acids include, but are not limited to, esters, hydroxyamino derivatives, amides and sulfonamides.

(e) The Prodrugs

The present invention includes the prodrugs and salts of the prodrugs. Formation of prodrugs is well known in the art in order to enhance the properties of the parent compound; such properties include solubility, absorption, biostability and release time (see "Pharmaceutical Dosage Form and Drug Delivery Systems" (Sixth Edition), edited by Ansel et al., publ. by Williams & Wilkins, pgs. 27–29, (1995) which is hereby incorporated by reference). Commonly used prodrugs are designed to take advantage of the major drug biotransformation reactions and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see *Goodman and Gilman's The Pharmacological Basis of Therapeutics* (Ninth Edition), editor Molinoff et al., publ. by McGraw-Hill, pages 11–13, (1996), which is hereby incorporated by reference).

Dosages And Treatment Regimen

Dosage levels of the compounds of this invention typically are from about 0.001 mg to about 10,000 mg daily, preferably from about 0.005 mg to about 1,000 mg daily. On the basis of mg/kg daily dose, either given in a single dose or in divided doses, dosages typically range from about 0.001/75 mg/kg to about 10,000/75 mg/kg, preferably from about 0.005/75 mg/kg to about 1,000/75 mg/kg.

The total daily dose of each drug can be administered to the patient in a single dose, or in multiple subdoses. Typically, subdoses can be administered two to six times per day, preferably two to four times per day, and even more preferably two to three to times per day. Doses can be in immediate release form or sustained release form sufficiently effective to obtain the desired control over the diabetic condition.

The dosage regimen to prevent, treat, give relief from, or ameliorate a diabetic condition or disorder, or to otherwise protect against or treat a diabetic condition with the combinations and compositions of the present invention is selected in accordance with a variety of factors. These factors include, but are not limited to, the type, age, weight, sex, diet, and medical condition of the subject, the severity of the disease, the route of administration, pharmacological considerations such as the activity, efficacy, pharmacokinetics and toxicology profiles of the particular inhibitors employed, whether a drug delivery system is utilized, and whether the inhibitors are administered with other active ingredients. Thus, the dosage regimen actually employed may vary widely and therefore deviate from the preferred dosage regimen set forth above.

Pharmaceutical Compositions

For the prophylaxis or treatment of the conditions and disorders referred to above, the compounds of this invention can be administered as the compound per se. Alternatively, pharmaceutically-acceptable salts are particularly suitable for medical applications because of their greater aqueous solubility relative to that of the parent compound.

The compounds of the present invention also can be administered with an acceptable carrier in the form of a pharmaceutical composition. The carrier must be acceptable in the sense of being compatible with the other ingredients of the composition and must not be intolerably deleterious to the recipient. The carrier can be a solid or a liquid, or both, and preferably is formulated with the compound as a unit-dose composition, for example, a tablet, which can contain from about 0.05% to about 95% by weight of the active compound(s) based on a total weight of the dosage form. Other pharmacologically active substances can also be present, including other compounds useful in the treatment of a diabetic condition.

The active compounds of the present invention may be administered by any suitable route, preferably in the form of a pharmaceutical composition adapted to such a route, and in a therapeutically effective dose for the treatment intended. The active compounds and compositions, for example, may be administered orally, sublingually, nasally, pulmonarily, mucosally, parenterally, intravascularly, intraperitoneally, subcutaneously, intramuscularly or topically. Unit dose formulations, particularly orally administrable unit dose formulations such as tablets or capsules, generally contain, for example, from about 0.001 to about 500 mg, preferably from about 0.005 mg to about 100 mg, and more preferably from about 0.01 to about 50 mg, of the active ingredient. In the case of pharmaceutically acceptable salts, the weights indicated above for the active ingredient refer to the weight of the pharmaceutically active ion derived from the salt.

For oral administration, the pharmaceutical composition may be in the form of, for example, a tablet, a capsule, a suspension, an emulsion, a paste, a solution, a syrup or other liquid form. The pharmaceutical composition is preferably made in the form of a dosage unit containing a particular amount of the active ingredient. If administered by mouth, the compounds may be admixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration.

Oral delivery of the compounds of the present invention can include formulations, as are well known in the art, to provide immediate delivery or prolonged or sustained delivery of the drug to the gastrointestinal tract by any number of mechanisms. Immediate delivery formulations include, but are not limited to, oral solutions, oral suspensions, fast-dissolving tablets or capsules, sublingual tablets, disintegrating tablets and the like. Prolonged or sustained delivery formulations include, but are not limited to, pH sensitive release of the active ingredient from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethyl-cellulose phthalate and anionic polymers of methacrylic acid and methacrylic acid methyl ester.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the inhibitor(s) and the carrier (which can constitute one or more accessory ingredients). In general, the compositions are prepared by uniformly and intimately admixing the inhibitor(s) with a liquid or finely divided solid carrier, or both, and then, if necessary, shaping the product. For example, a tablet can be prepared by compressing or molding a powder or granules of the inhibitors, optionally with one or more accessory ingredients. Compressed tablets can be prepared by compressing, in a suitable machine, the compound in a free-flowing form, such as a powder or granules optionally mixed with a binder, lubricant, inert diluent and/or surface active\dispersing agent(s). Molded tablets can be made, for example, by molding the powdered compound in a suitable machine.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Pharmaceutical compositions suitable for buccal (sublingual) administration include lozenges comprising a compound of the present invention in a flavored base, usually sucrose, and acacia or tragacanth, and pastilles comprising the inhibitors in an inert base such as gelatin and glycerin or sucrose and acacia.

Formulations for parenteral administration, for example, may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Pharmaceutically acceptable carriers encompass all the foregoing and the like. The pharmaceutical compositions of the invention can be prepared by any of the well-known techniques of pharmacy, such as admixing the components. The above considerations in regard to effective formulations and administration procedures are well known in the art and are described in standard textbooks.

Methods of Use

The present invention also includes methods for the treatment of diabetes and related diseases and conditions. One such method comprises the step of administering to a subject in need thereof, a therapeutically effective amount of one or more compounds of formula (I).

Compounds of formula (I) may be used in methods of the invention to treat diseases, such as diabetes, including both Type 1 and Type 2 diabetes. Such methods may also delay the onset of diabetes and diabetic complications. Other diseases and conditions that may be treated or prevented using compounds of formula (I) in methods of the invention include: Maturity-Onset Diabetes of the Young (MODY) (Herman, et al., *Diabetes* 43:40 (1994)), Latent Autoimmune Diabetes Adult (LADA) (Zimmet, et al., *Diabetes Med.* 11:299 (1994)), impaired glucose tolerance (IGT) (Expert Committee on Classification of Diabetes Mellitus, *Diabetes Care* 22 (Supp. 1) S5 (1999)), impaired fasting glucose (IFG) (Charles, et al., *Diabetes* 40:796 (1991)), gestational diabetes (Metzger, *Diabetes*, 40:197 (1991), and metabolic syndrome X.

Compounds of formula (I) may also be used in methods of the invention to treat secondary causes of diabetes (Expert Committee on Classification of Diabetes Mellitus, *Diabetes Care* 22 (Supp. 1), S5 (1999)). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenytoin, thyroid hormone, β-adrenergic agents, α-interferon and drugs used to treat HIV infection.

The methods and compounds of the present invention may be used alone or in combination with additional therapies and/or compounds known to those skilled in the art in the treatment of diabetes and related disorders. Alternatively, the methods and compounds described herein may be used, partially or completely, in combination therapy.

Compounds of formula (I) may also be administered in combination with other known therapies for the treatment of diabetes, including PPAR agonists, sulfonylurea drugs, non-sulfonylurea secretagogues, α-glucosidase inhibitors, insulin sensitizers, insulin secretagogues, hepatic glucose output lowering compounds, insulin and anti-obesity drugs. Such therapies may be administered prior to, concurrently with or following administration of the compound of formula (I). Insulin includes both long and short acting forms and formulations of insulin. PPAR agonist may include agonists of any of the PPAR subunits or combinations thereof. For example, PPAR agonist may inlcude agonists of PPAR-α, PPAR-γ, PPAR-β or any combination of two or three of the subunits of PPAR. PPAR agonists include, for example, rosiglitazone and pioglitazone. Sulfonylurea drugs include, for example, glyburide, glimepiride, chlorpropamide, and glipizide. α-glucosidase inhibitors that may be useful in treating diabetes when administered with a compound of formula (I) include acarbose, miglitol and voglibose. Insulin sensitizers that may be useful in treating diabetes when administered with a compound of formula (I) include thiazolidinediones and non-thiazolidinediones. Hepatic glucose output lowering compounds that may be useful in treating diabetes when administered with a compound of formula (I) include metformin, such as Glucophage and Glucophage XR. Insulin secretagogues that may be useful in treating diabetes when administered with a compound of formula (I) include sulfonylurea and non-sulfonylurea drugs: GLP-1, GIP, PAC/VPAC receptor agonists, secretin, nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin. In one embodiment of the invention, compounds of formula (I) are used in combination with insulin secretagogues to increase the sensitivity of pancreatic beta cells to the insulin secretagogue.

Compounds of formula (I) may also be used in methods of the invention in combination with anti-obesity drugs. Anti-obesity drugs include β-3 agonists, CB-1 antagonists, appetite suppressants, such as, for example, sibutramine (Meridia), and lipase inhibitors, such as, for example, orlistat (Xenical).

Compounds of formula (I) may also be used in methods of the invention in combination with drugs commonly used to treat lipid disorders in diabetic patients. Such drugs include, but are not limited to, HMG-CoA reductase inhibitors, nicotinic acid, bile acid sequestrants, and fibric acid derivatives. Compounds of formula (I) may also be used in combination with anti-hypertensive drugs, such as, for example, β-blockers and ACE inhibitors.

Such co-therapies may be administered in any combination of two or more drugs (e.g., a compound of formula (I) in combination with an insulin sensitizer and an anti-obesity drug). Such co-therapies may be administered in the form of pharmaceutical compositions, as described above.

Terms

As used herein, various terms are defined below.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "subject" as used herein includes mammals (e.g. humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The phrase "therapeutically-effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

The term "prodrug" includes a compound that is a drug precursor that, following administration to a subject and subsequent absorption, is converted to an active species in vivo. Conversion to the active, species in vivo is typically via some process, such as metabolic conversion. An example of a prodrug is an acylated form of the active compound.

The following definitions pertain to the structure of the compounds: In the groups, radicals, or moieties defined below, the number of carbon atoms is often specified, for example, alkyl of 1–8 carbon atoms or C1–C8 alkyl. The use of a term designating a monovalent radical where a divalent radical is appropriate shall be construed to designate the divalent radical and vice versa. Unless otherwise specified, conventional definitions of terms controls and conventional stable atom valences are presumed and achieved in all formulas and groups.

When symbols such as "A—Q—R" is used, it refers to a group which is formed by linking group A, group Q and group R in the designated order and the attachment of this group "A—Q—R" is any position on group A to form a stable structure. Group Q may be linked to any position on group A to form a stable structure and group R may be linked to any position on group Q to form a stable structure.

When symbols such as "A(OR')—R" is used, it refers to a group which is formed by susbstituting group A with both group OR' and group R and the attachment of this group "A(OR')—R" is any position on group A to form a stable structure. Group OR' and group R maybe linked to any position on group A to form a stable structure.

The term "halogen" refers to a halogen radical selected from fluoro, chloro, bromo or iodo.

The term "alkyl" refers to a saturated aliphatic hydrocarbon radical. "Alkyl" refers to both branched and unbranched alkyl groups. Examples of "alkyl" include alkyl groups that are straight chain alkyl groups containing from one to ten carbon atoms and branched alkyl groups containing from three to ten carbon atoms. Other examples include alkyl groups that are straight chain alkyl groups containing from one to six carbon atoms and branched alkyl groups containing from three to six carbon atoms. This term is examplified by groups such as methyl, ethyl, n-propyl, 1-methylethyl (isopropyl), 1,1-dimethylethyl (tert-butyl), and the like. It may be abbreviated "Alk". It should be understood that any combination term using an "alk" or "alkyl" prefix refers to analogs according to the above definition of "alkyl". For example, terms such as "alkoxy", "alkylthio", "alkylamino" refer to alkyl groups linked to a second group via an oxygen, sulfur, or nitrogen atom, respectively.

The term "haloalkyl" refers to an alkyl group in which one or more hydrogen atoms are replaced with halogen atoms. This term in exemplified by groups such as trifluomethyl.

The more preferred haloalkyl groups are alkyl groups substituted with one or more fluro or chloro. The term "haloalkoxy" refers to haloalkyl groups linked to a second group via an oxygen atom.

The term "alkenyl" refers to a mono or polyunsatuarted aliphatic hydrocarbon radical. The mono or polyunsaturated aliphatic hydrocarbon radical contains at least one carbon-carbon double bond. "Alkenyl" refers to both branched and unbranched alkenyl groups, each optionally partially or fully halogenated. Examples of "alkenyl" include alkenyl groups that are straight chain alkenyl groups containing from two to ten carbon atoms and branched alkenyl groups containing from three to ten carbon atoms. Other examples include alkenyl groups that are straight chain alkenyl groups containing from two to six carbon atoms and branched alkenyl groups containing from three to six carbon atoms. This term is exemplified by groups such as ethenyl, propenyl, n-butenyl, isobutenyl, 3-methylbut-2-enyl, n-pentenyl, heptenyl, octenyl, decenyl, and the like.

The term "alkynyl" refers to a mono or polyunsatuarted aliphatic hydrocarbon radical. The mono or polyunsaturated aliphatic hydrocarbon radical contains at least one carbon-carbon triple bond. "Alkynyl" refers to both branched and unbranched alkynyl groups, each optionally partially or fully halogenated. Examples of "alkynyl" include alkynyl groups that are straight chain alkynyl groups containing from two to ten carbon atoms and branched alkynyl groups containing from four to ten carbon atoms. Other examples include alkynyl groups that are straight chain alkynyl groups containing from two to six carbon atoms and branched alkynyl groups containing from four to six carbon atoms. This term is exemplified by groups such as ethynyl, propynyl, octynyl, and the like.

The term "cycloalkyl" refers to the mono- or polycyclic analogs of an alkyl group, as defined above. Unless otherwise specified, the cycloalkyl ring may be attached at any carbon atom that results in a stable structure and, if substituted, may be substituted at any suitable carbon atom which results in a stable structure. Examples of cycloalkyl groups are saturated cycloalkyl groups containing from three to ten carbon atoms. Other examples include cycloalkyl groups containing three to six carbon atoms. Exemplary cycloalkyl groups include cyclopropyl, cyclobutyl, cyclopentyl, cyclohexyl, cyclooctyl, cyclononyl, cyclodecyl, norbomane, adamantyl, and the like.

The term "cycloalkenyl" refers to the mono- or polycyclic analogs of an alkenyl group, as defined above. Unless otherwise specified, the cycloalkenyl ring may be attached at any carbon atom that results in a stable structure and, if substituted, may be substituted at any suitable carbon atom that results in a stable structure. Examples of cycloalkenyl groups are cycloalkenyl groups containing from four to ten carbon atoms. Other examples include cycloalkenyl groups containing four to six carbon atoms. Exemplary cycloalkenyl groups include cyclobutenyl, cyclopentenyl, cyclohexenyl, norbornene, and the like.

The term "heterocycloalkyl" refers to the mono- or polycyclic structures of "cycloalkyl" where one or more of the carbon atoms are replaced by one or more atoms independently chosen from nitrogen, oxygen, or sulfur atoms. Any nitrogen atom maybe optionally oxidized or quantermized, and any sulfur atom maybe optionally oxidized. Unless otherwise specified, the heterocycloalkyl ring may be attached at any carbon atom or heteroatom that results in a stable structure and, if substituted, may be substituted at any suitable carbon atom or heteroatom which results in a stable structure. Examples of heterocycloalkyl groups are saturated heterocycloalkyl groups containing from two to nine carbon atoms and one to four heteroatoms chosen independently from nitrogen, oxygen, or sulfur atoms. Examples of heterocycloalkyl groups include morpholino, pyrazino, tetrahydrofurano, and the like.

The term "heterocycloalkenyl" refers to the mono- or polycyclic structures of "cycloalkenyl" where one or more of the carbon atoms are replaced by one or more atoms independently chosen from nitrogen, oxygen, or sulfur atoms. Any nitrogen atom maybe optionally oxidized or quanternized, and any sulfur atom maybe optionally oxidized. Unless otherwise specified, the heterocycloalkenyl ring may be attached at any carbon atom or heteroatom that results in a stable structure and, if substituted, may be substituted at any suitable carbon atom or heteroatom which results in a stable structure. Examples of heterocycloalkenyl groups are saturated heterocycloalkenyl groups containing from two to nine carbon atoms and one to four heteroatoms chosen independently from nitrogen, oxygen, or sulfur atoms. Examples of heterocycloalkenyl groups include dihydropyran, dihydrofuran, and the like.

The term "cycloalkyloxy" refers to a monovalent radical of the formula —O-cycloalkyl, i.e., a cycloalkyl group linked to a second group via an oxygen atom.

The term "acyl" refers to a monovalent radical of the formula —C(=O)-alkyl and —C(=O)-cycloalkyl, i.e., an alkyl or cycloakyl group linked to a second group via caronyl group C(=O), wherein said alkyl maybe further substituted with cycloalkyl, aryl, or heteroaryl. Examples of acyl groups include —C(=O)Me(acetyl), —C(=O)CH$_2$-cyclopropyl (cyclopropylacetyl), —C(=O)CH$_2$Ph (phenylacetyl), and the like.

The term "aryl" refers to 6–10 membered mono- or polycyclic aromatic carbocycles, for example, phenyl and naphthyl. Unless otherwise specified, the aryl ring may be attached at any carbon atom that results in a stable structure and, if substituted, may be substituted at any suitable carbon atom which results in a stable structure. The term "aryl" refers to non-substituted aryls and aryls optionally substituted with one or more of the following groups: halogen, C1–C6 alkyl, C3–C6 cycloalkyl, C2–C6 alkenyl, C4–C6 cycloalkenyl, C2–C6 alkynyl, nitro, cyano, hydroxyl, C1–C6 alkoxy, C3–C6 cycloalkoxy, amino, C1–C6 alkylamino (for example, —NHMe and —N(Me)$_2$), C1–C6 acyl, thiol, alkylthio, carboxylic acid. All the above subtsitutions can further be substituted with optionally selected groups to form a stable structure. It may be abbreviated "Ar". It should be understood that any combination term using an "ar" or "aryl" prefix refers to analogs according to the above definition of "aryl". For example, terms such as "aryloxy", "arylthio", "arylamino" refer to aryl groups linked to a second group via an oxygen, sulfur, or nitrogen atom, respectively.

The term "heteroaryl" refers to a stable 5–8 membered (but preferably, 5 or 6 membered) monocyclic or 8–11 membered bicyclic aromatic heterocycle radical. Each heteroaryl contains 1–10 carbon atoms and from 1 to 5 heteroatoms independently chosen from nitrogen, oxygen and sulfur, wherein any sulfur heteroatom may optionally be oxidized and any nitrogen heteroatom may optionally be oxidized or quaternized. Unless otherwise specified, the heteroaryl ring may be attached at any suitable heteroatom or carbon atom that results in a stable structure and, if substituted, may be substituted at any suitable heteroatom or carbon atom that results in a stable structure. The term "heteroaryl" includes heteroaryl groups that are non-substituted or those optionally substituted with one or more of the following groups: halogen, C1–C6 alkyl, C3–C6 cycloalkyl, C2–C6 alkenyl, C4–C6 cycloalkenyl, C2–C6 alkynyl, nitro, cyano, hydroxyl, C1–C6 alkoxy, C3–C6 cycloalkoxy, amino, C1–C6 alkylamino (for example, —NHMe and —N(Me)$_2$), C1–C6 acyl, thiol, alkylthio, carboxylic acid. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyriridinyl, pyrazinyl, indolizinyl, indolyl, isoindolyl, benzofuranyl, benzothienyl, indazolyl, benzimidazolyl, benzothiazolyl, benzoxazolyl, benzisoxazolyl, benzisothiazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl. Terms such as "heteroaryloxy", "heteroarylthio", "heteroarylamino" refer to heteroaryl groups linked to a second group via an oxygen, sulfur, or nitrogen atom, respectively.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

A comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

For purposes of this invention, the chemical elements are identified in accordance with the Periodic Table of the Elements, CAS version, Handbook of Chemistry and Physics, 67th Ed., 1986–87, inside cover.

Abbreviations and Acronyms

When the following abbreviations are used throughout the disclosure, they have the following meaning:

$CH_2Cl_2$ methylene chloride

THF tetrahydrofuran $CH_3CN$ acetonitrile $Na_2SO_4$ anhydrous sodium sulfate $MgSO_4$ anhydrous magnesium sulfate DMSO dimethylsulfoxide EtOAc ethyl acetate $Et_2O$ diethyl ether $Et_3N$ triethylamine $H_2$ hydrogen CO carbon monoxide HCl hydrochloric acid Hex hexanes $^1H$ NMR proton nuclear magnetic resonance HPLC high performance liquid chromatography $K_2CO_3$ potassium carbonate $Cs_2CO_3$ cesium carbonate $NH_4Cl$ ammonium chloride LC/MS liquid chromatography/mass spectroscopy MeOH methanol MS ES mass spectroscopy with electrospray NaHCO$_3$ sodium bicarbonate
NaOH sodium hydroxide
RT retention time
h hour
min minutes
Pd(OAc)$_2$ palladium acetate
Ni(dppp)Cl$_2$ [1,3-bis(diphenylphosphino)propane] dichloronickel(II)
DMF N,-dimethylformamide
EDCI 1-(3-dimethylaminopropyl)-3-ethylcarbodiimide hydrochloride
LTMP Lithium tetramethylpiperidine
BuLi butyllithium
TLC thin layer chromatography
TFA trifluoacetic acid
TMEDA tetramethylethylenediamine
BINAP 2,2'-bis(diphenylphosphino)-1,1'binaphthyl
HOBt 1-hydroxybenzotiazole hydrate
NaH sodium hydride
MeMgBr methylmagnesium bromide
DPPP (diphenylphosphino)propane
DME dimethoxyethane
AlCl$_3$ aluminum chloride
TEA triethyl amine
CS$_2$ carbon disulfide
MeI methyl iodide
t-BuOK potassium tert-butoxide
KHMDS potassium hexamethyldisilazide
LiHMDS lithium hexamethyldisilazide
NaOBr sodium hypobromite
Br$_2$ bromine
Conc. Concentrated
Pd/C palladium on carbon
EtOH ethanol
NH$_3$ ammonia
NaOMe sodium methoxide
PPh$_3$ triphenylphosine
NaH sodium hydride
LDA lithium diisopropylamide
SOCl$_2$ thionyl chloride
MsCl methanesulfonyl chloride
DMAP 4-dimethylaminopyridine
NMM 4-methylmorpholine
AcOH acetic acid
Na$_2$S$_2$O$_3$ sodium thiosulfate
H$_2$SO$_4$ sulfric acid
CHCl$_3$ chloroform
MnO$_2$ manganese(IV) oxide
LAH lithium aluminum hydride
ADDP 1,1'-(azodicarbonyl)-dipiperidine
EDTA ethylenediaminetetraacetic acid
CCl$_2$FCClF$_2$ 1,1,2-trichlorotrifluoroethane
NaNO$_2$ sodium nitrite

PREPARATIVE EXAMPLES

Examples of preparations of compounds of the invention are provided in the following detailed synthetic procedures.

In tables 1A and 2A, the synthesis of each compound is referenced back to these exemplary preparative steps. In tables 1B and 2B, the proposed synthesis of each compound is referenced back to these exemplary preparative steps.

All reactions were carried out under a positive pressure of dry argon or dry nitrogen, and were stirred magnetically unless otherwise indicated. Sensitive liquids and solutions were transferred via syringe or cannula, and introduced into reaction vessels through rubber septa. Commercial grade reagents and solvents were used without further purification.

Unless otherwise stated, the term 'concentration under reduced pressure' refers to use of a Buchi rotary evaporator at approximately 15 mm of Hg. All temperatures are reported uncorrected in degrees Celsius (° C.). Unless otherwise indicated, all parts and percentages are by volume.

Proton ($^1$H) nuclear magnetic resonance (NMR) spectra were measured with a Varian Mercury (300 MHz) or a Bruker Avance (500 MHz) spectrometer with either Me$_4$Si (δ 0.00) or residual protonated solvent (CHCl$_3$ δ 7.26; MEOH δ 3.30; DMSO δ 2.49) as standard. The NMR data of the synthesized examples, which are not disclosed in the following detailed charaterizations, are in agreements with their corresponding structural assignments.

The HPLC-MS spectra were obtained using a Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120–1200 amu using a variable ion time according to the number of ions in the source. The eluents were A: 2% CH$_3$CN in water with 0.02% TFA and B: 2% water in CH$_3$CN with 0.018% TFA. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes.

Elemental analyses were conducted by Robertson Microlit Labs, Madison N.J. The results of elemental analyses, if conducted but not disclosed in the following detailed charaterizations, are in agreements with their corresponding structural assignments.

The following specific examples are presented to illustrate the invention related to Formula (I) as described herein, but they should not be construed as limiting the scope of the invention in any way.

Intermediate A:

2,6-dichloro-4-methyl-nicotinic acid

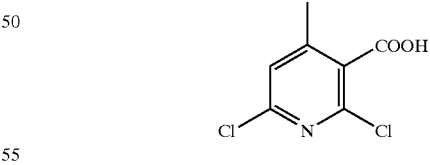

Method 1

A solution of sodium nitrite (2.73 g, 39.6 mmol) in water (15 mL) was added slowly to a solution of commercially available (Maybridge) 2,6-dichloro-4-methyl-nicotinamide (4.5 g, 22 mmol) in concentrated sulfuric acid resulting in evolution of heat and brown gas. The mixture was stirred at room temperature for 15 min, and then heated to 60° C. for 7 h. The solution was cooled to 0° C. and then water (15 mL) was added. The resulting white precipitate was collected by filtration and washed with hexane. The aqueous filtrate was extracted with EtOAc (3×) and the combined organic extracts were dried over MgSO$_4$ and concentrated in vacuo. The residue was combined with the white precipitate to afford 2,6-dichloro-4-methyl-nicotinic acid (4.39 g, 97%) as a white solid: LCMS RT: 1.20 min, MH$^+$: 206.3.

Method 2

Concentrated nitric acid (1–4 mL) was added to cooled (0° C.) concentrated sulfuric acid (43 mL) maintaining the internal temperature below 10° C. After addition, the acid mixture was heated to 70° C. and commercially available (Avocado) 2,6-dichloro-4-methylnicotinonitrile (20.0 g, 107 mmol) was added. The temperature was raised until the internal temperature of the reaction reached 105° C. At this point the heating was stopped and after 2 h, TLC analysis revealed that the reaction was complete. The reaction mixture was cooled to room temperature, and slowly added to ice (100 g) with strong agitation. The solid was filtered and washed with cold water (10 mL). The solid was dissolved in EtOAc (100 mL) and the solution was dried over Na$_2$SO$_4$ and concentrated to give 2,6-dichloro-4-methyl-nicotinic acid (21.0 g, 96%) as a white solid: R$_f$=0.20 (1:1 EtOAc:Hex).

Intermediate B:

2,6-dichloro-4-methyl-nicotinoyl chloride

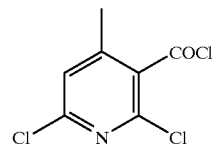

A solution of 2,6-dichloro-4-methyl-nicotinic acid (3.94 g, 19.1 mmol) in thionyl chloride (18 mL) was heated to 80° C. for 2 h. After cooling, the solution was concentrated in vacuo to give 2,6-dichloro-4-methyl-nicotinoyl chloride as yellow oil. It was carried on to the next step without further purification. This transformation can also be accomplished using oxalyl chloride with catalytic DMF in place of thionyl chloride.

Intermediate C:

3,3-dichloro-1-(2,6-dichloro-4-methyl-pyridin-3-yl)-propenone

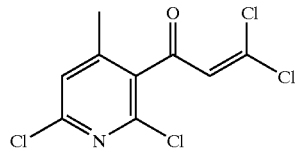

A solution of the 2,6-dichloro-4-methyl-nicotinoyl chloride from the previous reaction in CH$_2$Cl$_2$ (10 mL) was added slowly to a cooled (0° C.) and stirred slurry solution of AlCl$_3$ (2.54 g, 19.1 mmol) in CH$_2$Cl$_2$ (54 mL). After 15 min, vinylidene chloride (1.5 mL, 1.85 g, 19.1 mmol) was added to the mixture dropwise. The reaction was allowed to warm to room temperature and was stirred overnight. The mixture was poured over ice and the ice slurry was acidified using 1 N HCl (50 mL). Stirring was continued for 20 min and then the product was extracted with CH$_2$Cl$_2$ (3×). The combined organic extracts were dried over Na$_2$SO$_4$ and concentrated in vacuo to give 3,3-dichloro-1-(2,6-dichloro-4-methyl-pyridin-3-yl)-propenone (4.22 g, 77%) as a yellow oil: LCMS RT: 3.25, MH$^+$: 284.3, R$_f$=0.47 (4:1 Hex:EtOAc).

Intermediate D:

1-(2,6-Dichloro-4-methyl-pyridin-3-yl)-3,3-bis-phenylamino-propenone

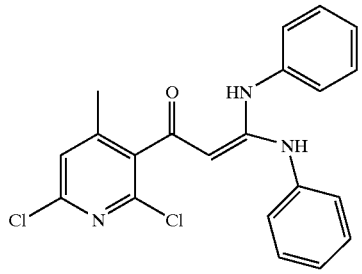

A solution of aniline (4.04 mL, 44.4 mmol) in TEA (6.2 mL, 44.4 mmol) was added slowly to a cooled (0° C.) and stirred solution of 3,3-dichloro-1-(2,6-dichloro-4-methyl-pyridin-3-yl)-propenone (4.22 g, 14.8 mmol) in dioxane (50 mL). The reaction was allowed to warm to room temperature and was stirred overnight. The mixture was concentrated in vacuo until most of the solvent was removed and then the residue was diluted with water and extracted with EtOAc (3×). The combined organic extracts were washed with water, dried over Na$_2$SO$_4$ and concentrated in vacuo. Silica gel flash chromatography of the residue using 7:1 EtOAc:Hex gave 1-(2,6-dichloro-4-methyl-pyridin-3-yl)-3,3-bis-phenylarino-propenone as yellow solid (2.22 g, 40%): LCMS RT: 3.21 min; MH$^+$: 398.2, R$_f$=0.27 (2:1 Hex:EtOAc).

Intermediate E:

7-Chloro-5-methyl-1-phenyl-2-phenylaniino-1H-[1,8]-naphthyridin-4-one

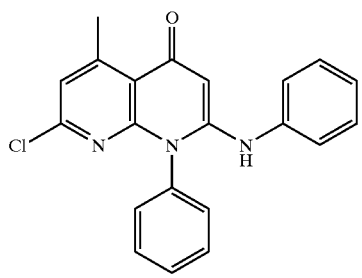

A mixture of 1-(2,6-dichloro-4-methyl-pyridin-3-yl)-3,3-bis-phenylamino-propenone (2.17 g, 5.45 mmol) and t-BuOK (1.10 g, 9.81 mmol) in dioxane (55 mL) was heated to 80° C. overnight. The reaction was cooled, concentrated in vacuo, diluted with water and extracted with EtOAc. The combined organic extracts were washed with brine, dried over Na$_2$SO$_4$, and concentrated in vacuo. Silica gel flash chromatography of the residue using 1:1 EtOAc:Hex provided 7-chloro-5-methyl-1-phenyl-2-phenylamino-1H-[1,8] naphthyridin-4-one (1.297 g, 66%) as an orange solid: LCMS RT: 2.52 min, MH$^+$: 362.3, R$_f$=0.18 (1:1 EtOAc:Hex) This transformation can also be accomplished by using the combination of other aprotic solvents such as DMF, and THF with other bases such as NaH.

Intermediate F:

2,6-dichloro-4-(trifluoromethyl)nicotinic acid

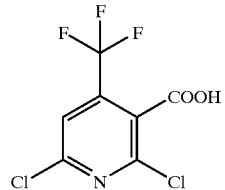

Method 1

A solution of NaNO$_2$ (9.59 g, 139 mmol) in water (95 mL) was added slowly to a solution of commercially available (Oakwood) 2,6-dichloro-4-(trifluoromethyl)nicotinamide (20.0 g, 77 mmol) in conc. H$_2$SO$_4$ resulting in evolution of heat and brown gas. The mixture was stirred at room temperature for 15 min, and then heated to 60° C. for 18 h. The solution was cooled to 0° C. and then water (15 mL) was added. The resulting mixture was extracted with Et$_2$O (3×) and the combined organic extracts were dried over MgSO$_4$ and concentrated in vacuo. The residue was triturated with hexanes and vacuum-filtered to afford 2,6-dichloro-4-(trifluoromethyl)nicotinic acid (19 g, 95%) as an off-white solid: R$_f$=0.30 (9:1 CH$_2$Cl$_2$:MeOH), $^1$H-NMR (d6-DMSO, 300 MHz) δ 8.18 (s, 1H).

Method 2

Conc. HNO$_3$ (13.3 mL) was added to cooled (0° C.) conc. H$_2$SO$_4$ (60 mL) maintaining the internal temperature below 10° C. After addition, the acid mixture was heated to 70° C. and commercially available (Maybridge) 2,6-dichloro-4-(trifluoromethyl)nicotinonitrile (20.0 g, 83 mmol) was added. The temperature was raised until the internal temperature of the reaction reached 100° C. After heating for 1 h TLC analysis revealed that the reaction was complete. The reaction mixture was cooled to room temperature, and slowly added to ice (100 g) with strong agitation and extracted with Et$_2$O (3×). The organic layers were combined and washed with brine. The solution was dried over Na$_2$SO$_4$ and concentrated in vacuo to give 2,6-dichloro-4-(trifluoromethyl)nicotinic acid (19.1 g, 89%) as an off-white solid: R$_f$=0.30 (9:1 CH$_2$Cl$_2$:MeOH), $^1$H-NMR (d$_6$-DMSO, 300 MHz) δ 8.18 (s, 1H).

Intermediate G:

2,6-dichloro-4-(trifluoromethyl)nicotinoyl chloride

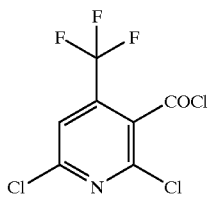

A solution of 2,6-dichloro-4-(trifluoromethyl)nicotinic acid (3.22 g, 13.2 mmol) in thionyl chloride (9 mL) was heated at reflux for 3 h. After cooling, the solution was concentrated in vacuo to give 2,6-dichloro-4-(trifluoromethyl)nicotinoyl chloride as a yellow oil which was carried on to the next step without further purification. This transformation can also be accomplished using oxalyl chloride with catalytic DMF in place of thionyl chloride.

Intermediate H:

3,3-dichloro-1-[2,6-dichloro-4-(trifluoromethyl)-3-pyridinyl]-2-propen-1-one

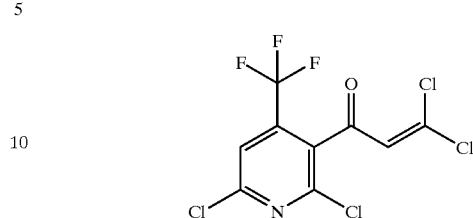

A solution of the 2,6-dichloro-4-(trifluoromethyl) nicotinoyl chloride from the previous reaction in CH$_2$Cl$_2$ (14 mL) was added slowly to a cooled (0° C.) and stirred slurry solution of AlCl$_3$ (4.4 g, 33.0 mmol) in CH$_2$Cl$_2$ (14 mL). After 15 min, vinylidene chloride (2.6 mL, 33.0 mmol) was added to the mixture dropwise. The reaction was allowed to warm to room temperature and was stirred overnight. The mixture was poured over ice and partitioned with CH$_2$Cl$_2$. The organic layer was collected and cooled to 0° C. before TEA (4.6 mL, 33 mmol) was added. After 15 min, the ice bath was removed and the reaction was allowed to warm to room temperature and stirred for an additional 30 min. The solution was washed with 1N HCl, NaHCO$_3$, and water. The organic layer was passed through a pad of silica gel and concentrated in vacuo to afford 3,3-dichloro-1-[2,6-dichloro-4-(trifluoromethyl)-3-pyridinyl]-2-propen-1-one: (4.3 g, 95%) as a brown oil: LCMS RT: 3.59, MH$^+$: 488.1, R$_f$=0.44 (EtOAc).

Intermediate I:

3,3-dianilino-1-[2,6-dichloro-4-(trifluoromethyl)-3-pyridinyl]-2-propen-1-one

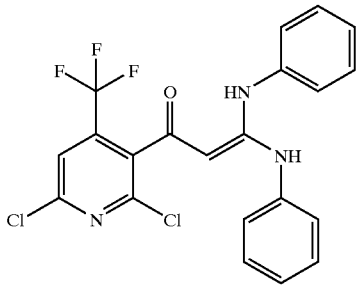

A solution of aniline (18.4 mL, 202 mmol) in TEA (28.2 mL, 202 mmol) was added slowly to a cooled (0° C.) and stirred solution of 3,3-dichloro-1-[2,6-dichloro-4-(trifluoromethyl)-3-pyridinyl]-2-propen-1-one (22.9 g, 67.4 mmol) in dioxane (220 mL). The reaction was allowed to warm to room temperature and was stirred overnight. The mixture was treated with 10% HCl and extracted with Et$_2$O (3×). The combined organic extracts were washed with brine, dried over Na$_2$SO$_4$ and concentrated in vacuo. Silica gel flash chromatography of the residue using 6:1 Hex:EtOAc gave 3,3-dianilino-1-[2,6-dichloro-4-(trifluoromethyl)-3-pyridinyl]-2-propen-1-one as an off-white solid (13.10 g, 43%): $^1$H-NMR (d$_6$-DMSO, 300 MHz) δ 12.24 (brs, 1H), 9.20 (brs, 1H), 7.95 (s, 1H), 7.12–7.42 (m, 10H), 4.82 (s, 1H); R$_f$=0.60 (6:1 Hex:EtOAc).

51

Intermediate J:

2-anilino-7-chloro-1-phenyl-5-trifluoromethyl)-1,8-naphthyridin-4(1H)-one

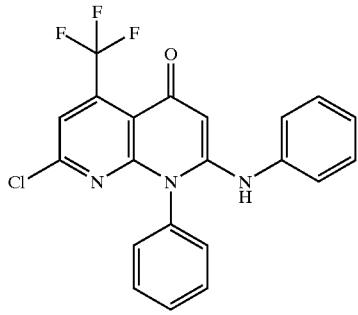

A mixture of 3,3-dianilino-1-[2,6-dichloro-4-(trifluoromethyl)-3-pyridinyl]-2-propen-1-one (12.9 g, 28.5 mmol) and t-BuOK (28.5 mL, 28.5 mmol, 1M in THF) in dioxane (200 mL) was heated at reflux overnight. The reaction was cooled, concentrated in vacuo, treated with saturated NH$_4$Cl and extracted with EtOAc (3×). The combined organic extracts were washed with brine, dried over MgSO$_4$, and concentrated in vacuo. Silica gel flash chromatography of the residue using 6:1 Hex:EtOAc provided 2-anilino-7-chloro-1-phenyl-5-(trifluoromethyl)-1,8-naphthyridin-4(1H)-one (11.2 g, 95%) as an off-white solid: LCMS RT: 3.00 min, MH$^+$: 416.7, R$_f$=0.25 (3:1 Hex:EtOAc). This transformation can be accomplished by using the combination of other aprotic solvents such as DMF, and THF with other bases such as NaH.

Intermediate K:

2,6-dichloro-5-fluoronicotinoyl chloride

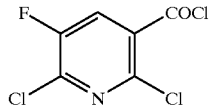

A solution of commercially available (Aldrich) 2,6-dichloro-5-fluoronicotinic acid (5.00 g, 23.8 mmol) in thionyl chloride (15 mL) was heated at reflux for 3 h. After cooling, the solution was concentrated in vacuo to give 2,6-dichloro-5-fluoronicotinoyl chloride as a brown oil which was carried on to the next step without further purification. This transformation can also be accomplished using oxalyl chloride with catalytic DMF in place of thionyl chloride.

Intermediate L:

3,3-dichloro-1-(2,6-dichloro-5-fluoro-3-pyridinyl)-2-propen-1-one

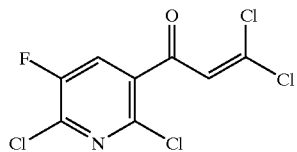

A solution of the 2,6-dichloro-5-fluoronicotinoyl chloride from the previous reaction in CH$_2$Cl$_2$ (25 mL) was added

52 slowly to a cooled (0° C.) and stirred slurry solution of AlCl$_3$ (7.9 g, 59.5 mmol) in CH$_2$Cl$_2$ (25 mL). After 15 min, vinylidene chloride (4.75 mL, 59.5 mmol) was added to the mixture dropwise. The reaction was allowed to warm to room temperature and was stirred overnight. The mixture was poured over ice and partitioned with CH$_2$Cl$_2$. The organic layer was collected and cooled to 0° C. before TEA (8.3 mL, 59.5 mmol) was added. After 15 min, the ice bath was removed and the reaction was allowed to warm to room temperature and stirred for an additional 30 min. The solution was washed with 1N HCl, NaHCO$_3$, and water. The organic layer was passed through a pad of silica gel and concentrated in vacuo to afford 3,3-dichloro-1-(2,6-dichloro-5-fluoro-3-pyridinyl)-2-propen-1-one: (6.1 g, 90%) as a brown oil: $^1$H-NMR (d$_6$-DMSO, 300 MHz) δ 8.43 (d, 1H, J=8.4 Hz), 7.56 (s, 1H), R$_f$=0.76(3:1 Hex:EtOAc).

Intermediate M:

3,3-dianilino-1-(2,6-dichloro-5-fluoro-3-pyridinyl)-2-propen-1-one

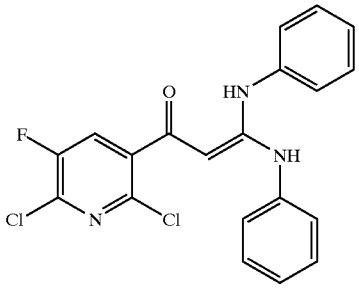

To a 0° C. solution of 3,3-dichloro-1-(2,6-dichloro-5-fluoro-3-pyridinyl)-2-propen-1-one (6.70 g, 23.2 mmol) in dioxane (50 mL) was added TEA (9.7 mL, 69.6) followed by aniline (6.3 mL, 69.6 mmol). After 1 h the reaction was allowed to warm to room temperature and was stirred overnight. The mixture was concentrated in vacuo until most of the solvent was removed and then the residue was diluted with water and extracted with CH$_2$Cl$_2$ (2×). The combined organic extracts were washed with water, dried over Na$_2$SO$_4$ and concentrated in vacuo. Purification of the residue by silica gel Biotage chromatography provided 3,3-dianilino-1-(2,6-dichloro-5-fluoro-3-pyridinyl)-2-propen-1-one as yellow solid (4.2 g, 49%): LCMS RT: 3.47 min; MH$^+$: 402.6.

Intermediate N:

2-anilino-7-chloro-6-fluoro-1-phenyl-1,8-naphthyridin-4(1H)-one

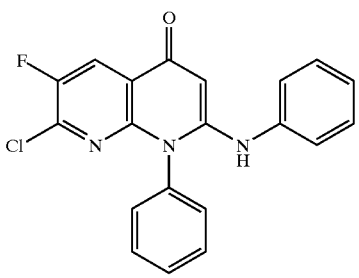

A mixture of 3,3-dianilino-1-(2,6-dichloro-5-fluoro-3-pyridinyl)-2-propen-1-one (2.3 g, 5.7 mmol) and t-BuOK (1.28 g, 11.4 mmol) in dioxane (80 mL) was stirred at 80° C. overnight. The reaction was cooled, concentrated in vacuo, diluted with water and extracted with EtOAc. The combined organic extracts were washed with brine, dried over Na$_2$SO$_4$, and concentrated in vacuo. Silica gel flash chromatography of the residue provided 2-anilino-7-chloro-6-fluoro-1-phenyl-1,8-naphthyridin-4(1H)-one (1.0 g, 50%10) as a light yellow solid: LCMS RT: 2.60 min, MH$^+$: 366.8. Tis transformation can be accomplished by using the combination of other aprotic solvents such as DMF, and THF with other bases such as NaH.

Intermediates N$_1$–N$_{12}$ were synthesized from 3,3-dichloro-1-(2,6-dichloro-5-fluoro-3-pyridinyl)-2-propen-1-one as above for Intermediate N using the appropriate amine:

Intermediate N$_1$:

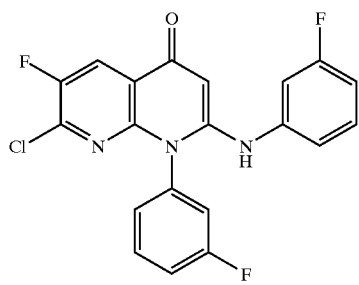

LCMS RT: 2.81 min, MH$^+$: 402.3

Intermediate N$_2$:

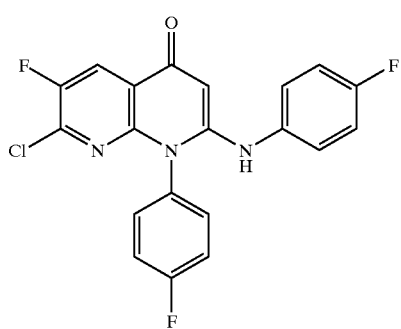

LCMS RT: 2.73 min, MH$^+$: 402.4

Intermediate N$_3$:

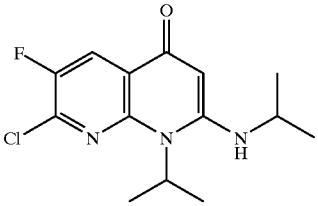

LCMS RT: 2.30 min, MH$^+$: 298.1

Intermediate N$_4$:

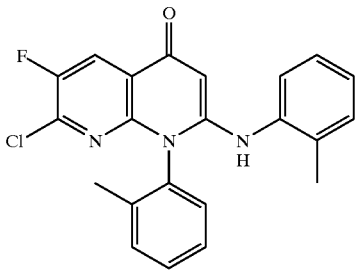

LCMS RT: 2.88 min, MH$^+$: 394.3

Intermediate N$_5$:

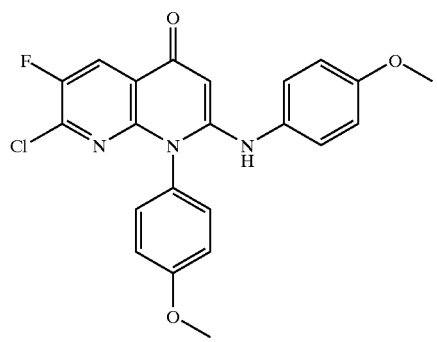

LCMS RT: 2.78 min, MH$^+$: 426.3

Intermediate N$_6$:

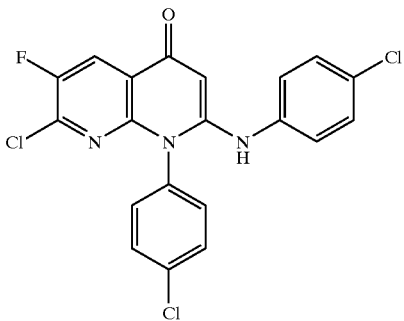

LCMS RT: 3.09 min, MH$^+$: 434.5

Intermediate N$_7$:

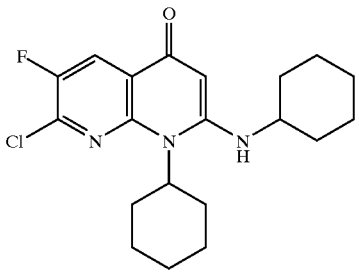

LCMS RT: 3.07 min, MH$^+$: 378.2

Intermediate N8:

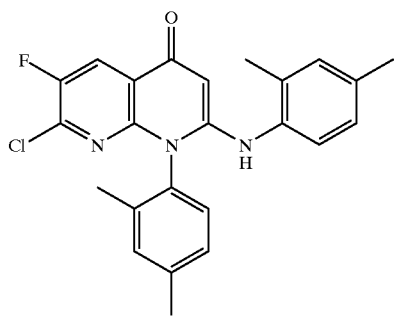

LCMS RT: 3.15 min, MH+: 422.4

Intermediate N9:

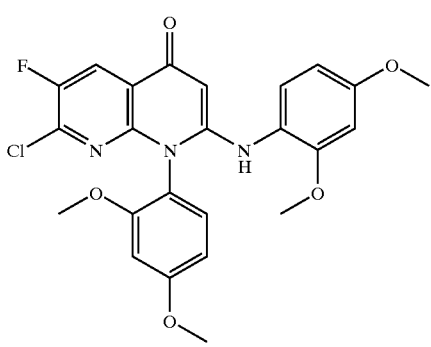

LCMS RT: 2.90 min, MH+: 486.3

Intermediate N10:

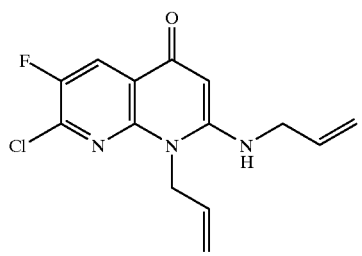

LCMS RT: 2.22 min, MH+: 294.2

Intermediate N11:

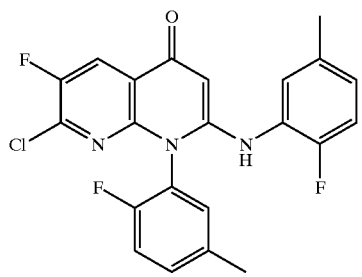

LCMS RT: 3.05 min, MH+: 430.4

Intermediate N12:

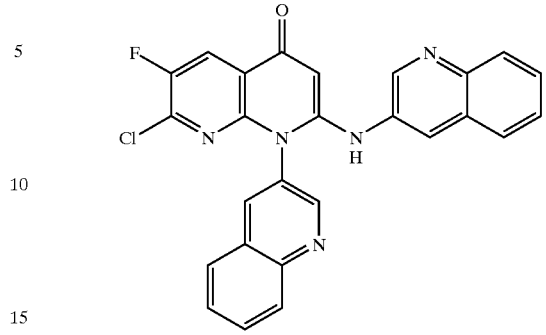

LCMS RT: 2.51 min, MH+: 468.3

Intermediate N13

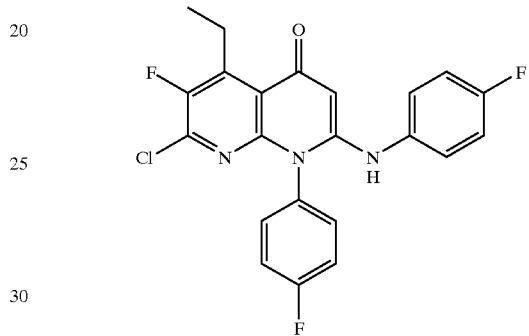

LCMS RT: 3.10 min, MH+: 430.4

Intermediate O:

2,6-dichloronicotinoyl chloride

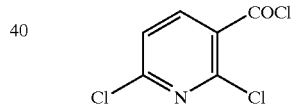

A solution of commercially available (Aldrich) 2,6-dichloro-nicotinic acid (2.0 g, 10.4 mmol) in thionyl chloride (10 mL) was heated to 80° C. for 2 h. After cooling, the solution was concentrated in vacuo to give 2,6-dichloro-nicotinoyl chloride as yellow oil which was carried on to the next step without further purification. This transformation can also be accomplished using oxalyl chloride with catalytic DMF in place of thionyl chloride.

Intermediate P:

3,3-dichloro-1-(2,6-dichloro-3-pyridinyl)-2-propen-1-one

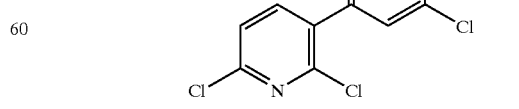

A solution of the 2,6-dichloro-nicotinoyl chloride (1.0 g, 4.76 mmol) from the previous reaction in CH$_2$Cl$_2$ (5 mL) was added slowly to a cooled (0° C.) and stirred slurry solution of AlCl₃ (0.64 g, 4.76 mmol) in CH₂Cl₂ (20 mL). After 15 min, vinylidene chloride (0.38 mL, 0.46 g, 4.76 mmol) was added to the mixture dropwise. The reaction was allowed to warm to room temperature and was stirred overnight. The mixture was then poured over ice and was acidified using 1 N HCl (15 mL). Stirring was continued for 20 min and the product was extracted with CH₂Cl₂ (3×). The combined organic extracts were dried over Na₂SO₄ and concentrated in vacuo to give 3,3-dichloro-1-(2,6-dichloro-3-pyridinyl)-2-propen-1-one (0.88 g, 68%) as a light yellow oil: ¹H-NMR (CDCl₃, 300 MHz) δ 8.38, d, J=8.4, 1H). 7.40 (d, J=8.4, 1H), 7.10 (s, 1H); R$_f$=0.51 (4:1 Hex:EtOAc).

Intermediate Q:

3,3-dianilino-1-(2,6-dichloro-3-pyridinyl)-2-propen-1-one

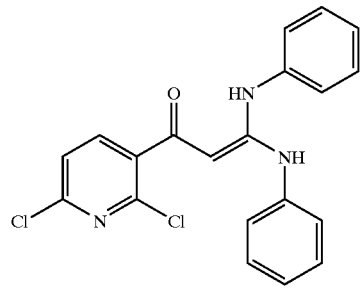

A solution of aniline (1.01 mL, 11.1 mmol) in TEA (1.55 mL, 11.1 mmol) was added slowly to a cooled (0° C.) and stirred solution of 3,3-dichloro-1-(2,6-dichloro-3-pyridinyl)-2-propen-1-one (1.0 g, 3.69 mmol) in dioxane (20 mL). The reaction was allowed to warm to room temperature and was stirred overnight. The mixture was concentrated in vacuo until most of the solvent was removed. The residue was diluted with water and extracted with EtOAc (3×). The combined organic extracts were washed with water, dried over Na₂SO₄ and concentrated in vacuo. Silica gel flash chromatography of the residue using 6:1 EtOAc:Hex gave 3,3-dianilino-1-(2,6-dichloro-3-pyridinyl)-2-propen-1-one as pale yellow solid (0.69 g, 49%): LCMS RT: 3.81 min; MH⁺: 384.2.

Intermediate R:

2-anilino-7-chloro-1-phenyl-2,3-dihydro-1,8-naphthyridin-4(1H)-one

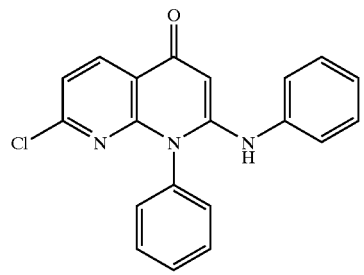

A mixture of 3,3-dianilino-1-(2,6-dichloro-3-pyridinyl)-2-propen-1-one (0.08 g, 0.21 mmol) and NaH (0.009 g, 0.23 mmol) in THF (6 mL) was heated to 80° C. overnight. The reaction was cooled, concentrated in vacuo, diluted with water and extracted with EtOAc. The combined organic extracts were washed with brine, dried over Na₂SO₄, and concentrated in vacuo. Silica gel flash chromatography of the residue using 3:1 Hex:EtOAc provided 2-anilino-7-chloro-1-phenyl-2,3-dihydro-1,8-naphthyridin-4(1H)-one (49 mg, 68%) as an off-white solid: LC-MS RT: 2.56 min, MH⁺: 348.2. This transformation can be accomplished by using the combination of other aprotic solvents such as dioxane and DMF with other bases such as t-BuOK.

Intermediate S:

Ethyl 3-(2-chloro-6-methyl(3-pyridyl))-3-oxopropanoate

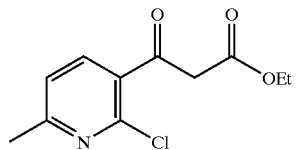

Ethyl 3-(2-chloro-6-methyl(3-pyridyl))-3-oxopropanoate was prepared by the general procedure described in the *Journal of Medicinal Chemistry*, 1986, 29, 2363. The product had: MH⁺: 242.1, LCMS RT: 2.33 and 3.06 min (keto-enol).

Intermediate T:

Ethyl (2Z)-2-[(2-chloro-6-methyl(3-pyridyl))carbonyl]-3,3-dimethylthio-prop-2-enoate

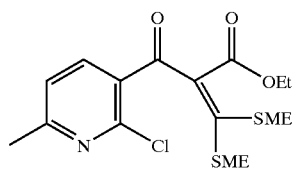

Cs₂CO₃ (24.0 g, 72.5 mmol) was added to a solution of ethyl 3-(2-chloro-6-methyl(3-pyridyl))-3-oxopropanoate (7.0 g, 29 mmol) in THF (290 mL). The reaction mixture was cooled to −10° C. and after 15 min, CS₂ (8.7 mL, 145 mmol) was added. Stirring was continued for 2 h and MeI (4.5 mL, 72.5 mmol) was added. The reaction was slowly warmed to room temperature over 18 h and filtered. The filtrate was concentrated in vacuo to provide ethyl (2Z)-2-[(2-chloro-6-methyl(3-pyridyl))carbonyl]-3,3-dimethylthioprop-2-enoate as a yellow oil that was used without purification. LCMS RT: 2.79 min, MH⁺: 345.8. A variety of alkyl halides can be used to quench the generated sulfur anion.

Intermediate U:

Ethyl (2E)-3,3-bis(phenylamino)-2-[(2-chloro-6methyl(3-pyridyl))-carbonyl]prop-2-enoate

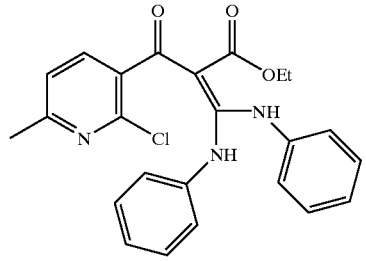

A solution of ethyl (2Z)-2-[(2-chloro-6-methyl(3-pyridyl))carbonyl]-3,3-dimethylthioprop-2-enoate (100. mg, 0.28 mmol) and aniline (0.076 mL, 0.83 mmol) in THF (1.4 mL) was heated at reflux for 18 h. The reaction was cooled to room temperature and concentrated in vacuo. Silaca gel flash chromatography of the residue using 1:1 EtOAc:Hex provided ethyl (2E)-3,3-bis(phenylamino)-2-[(2-chloro-6-methyl(3-pyridyl))carbonyl]prop-2-enoate (55.6 mg, 44%): LCMS RT: 3.56 min, MH+: 436.3.

Intermediate V:

Ethyl 7-methyl-2-methylio-4-oxo-1-phenylhydropyridino[2,3-b]-pyridine-3-carboxylate

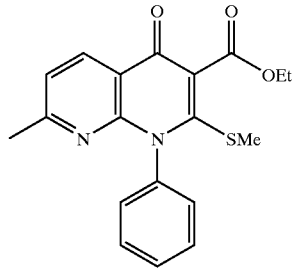

Aniline (3.96 mL, 43.5 mmol) was added to a solution of ethyl (2Z)-2-[(2-chloro-6-methyl(3-pyridyl))carboyl]-3,3-dimethylthioprop-2-enoate (5.13 g, 14.5 mmol) in DMSO (72.5 mL). The reaction solution was heated to 70° C. for 18 h and then cooled to room temperature. The reaction solution was diluted with EtOAc, washed with water and brine, dried over $Na_2SO_4$, and concentrated in Trituration of the resulting orange oil with $Et_2O$ afforded some desired product as yellow solid. Additional product was obtained by silica gel flash chromatography of the mother liquor using 1:1 EtOAc:Hex. The two purifications provided ethyl 7-methylthio-4-oxo-1-phenylhydropyridino[2,3-b]pyridine-3-carboxylate (2.87 g, 56%) as a yellow solid: LCMS RT: 2.85 min, MH$^{30}$ : 355.0.

Intermediate W:

Ethyl 7-methyl-4-oxo-1-phenyl-2-(phenylamino) hydro-pyridino[2,3b]-pyridine-3-carboxylate

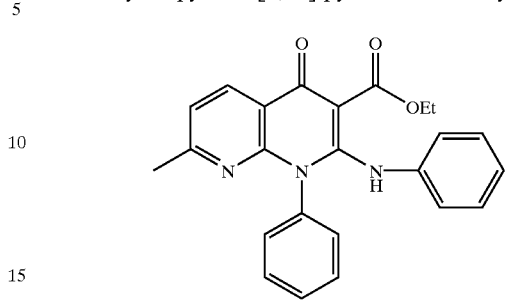

A solution of ethyl (2E)-3,3-bis(phenylamino)-2-((2-chloro-6-methyl(3-pyridyl))carbonyl)prop-2-enoate (85.0 mg, 0.195 mmol) and t-BuOK (67 mg, 0.60 mmol) in dioxane (2 mL) was heated at reflux for 48 h. The reaction was cooled to room temperature and concentrated in vacuo. Silica gel flash chromatography of the residue using 3:1 Hex:EtOAc to 100% EtOAc gave ethyl 7-methyl-4-oxo-1-phenyl-2-(phenylamino)hydropyridino[2,3-b]pyridine-3-carboxylate (39 mg, 49%) as a white solid: LCMS RT: 2.80 min, MH+400.0. This transformation can be accomplished by using the combination of other aprotic solvents such as DMF and THF with other bases such as NaH.

Intermediate X:

Ethyl 2-[(4-chlorophenyl)amino]-7-methyl-4-oxo-1-phenyl-hydropyridino-[2,3-b]pyridine-3-carboxylate

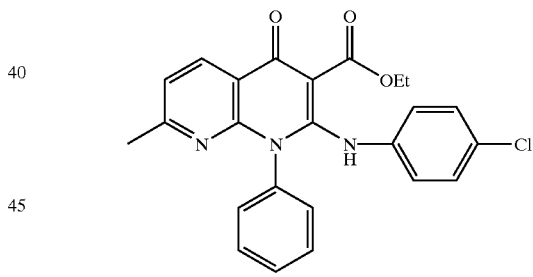

KHMDS (0.5 M in toluene, 0.84 mL, 0.42 mmol) was added to a cooled (−78° C.) solution of 4-chloroaniline (71.4 mg, 0.560 mmol) in THF (0.70 mL). After 2 h, a solution of ethyl 7-methyl-2-methylthio4-oxo-1-phenylhydropyridino [2,3-b]pyridine-3-carboxylate (100 mg, 0.28 mmol) in THF (0.70 mL) was added resulting in immediate formation of an orange solution. The reaction was slowly warmed to room temperature, stirred for 21 h, and quenched with saturated aqueous $NH_4Cl$. The aqueous solution was extracted with $Et_2O$ (3×) and the combined organic extracts were washed with water and brine, dried over $Na_2SO_4$, and concentrated in vacuo. Silica gel flash chromatography of the residue using 1:1 EtOAc:Hex gave ethyl 2-[(4-chlorophenyl) amino]-7-methyl-4-oxo-1-phenylhydropyridino[2,3-b] pyridine-3-carboxylate (30.0 mg, 25%) as a white solid: LCMS RT: 2.98 min, MH+434.0.

Intermediate Y:

5-Bromo-2-hydroxy-6-methylnicotinc acid

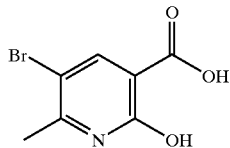

A solution of NaOBr was prepared by adding Br$_2$(11.4 g, 3.66 mL, 71.3 mmol) to a cooled (0° C.) and stirred solution of NaOH (7.8 g, 196 mmol) in water (90 mL). This solution was warmed to room temperature and was then added to a solution of commercially available (Aldrich) 2-hydroxy-6-methylpyridine-3-carboxylic acid (10.0 g, 65.1 mmol) and NaOH (7.8 g, 196 mmol) in water (30 mL). After stirring for 5 min, the mixture was cooled to 0° C. and carefully acidified with conc. HCl. The precipitate was filtered and dried over MgSO$_4$ to afford 5-bromo-2-hydroxy-6-methylnicotinc acid (15.0 g, 99%): $^1$H NMR (DMSO-d$_6$) 8.25 (s, 1H), 2.41 (s, 3H); MH$^+$: 232.0. Elemental analysis calculated for C$_7$H$_6$BrNO$_3$: C, 36.23; H, 2.61; N, 6.04; Br, 34.44; Found: C, 3607; H, 2.44; N, 5.91; Br, 34.43.

Intermediate Z (Same as Intermediate BA):

2,4-dichloro-6-methylnicotinic acid

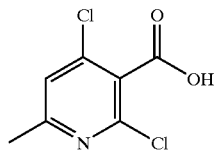

A solution of commercially available (Maybridge) ethyl 2,4-dichloro-6-methylpyridine-3-carboxylate (1.0 g, 4.3 mmol) and NaOH (342 mg, 8.6 mmol) in water (1.7 mL) and MeOH (1.5 mL) was heated to 80° C. for 4 h. The mixture was acidified using 50% H$_2$SO$_4$ and filtered. The solid was washed with cold water and dried to give of 2,4-dichloro-6-methylpyridine-3-carboxylic acid (582 mg, 66%): LCMS RT: 0.70 min, MH$^+$: 206.2.

Intermediate AA (Same as Intermediate BB):

3,3-dichloro-1-(2,4-dichloro-6-methyl-3-pyridinyl)-2-propen-1-one

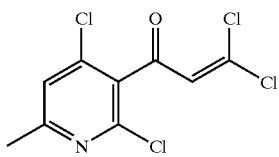

The compound was prepared according to the procedure described for Intermediate BB below. LCMS RT: 3.13 min, MH$^+$: 284.6.

Intermediate AB (Same as Intermediate BC):

3, dianilino-1-(2,4-dichloro-6methyl-3-pyridinyl)-2-propen-1-one

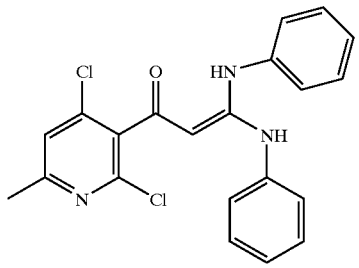

The compound was prepared according to the procedure described for Intermediate BC below: LCMS RT: 3.06 min, MH$^+$: 398.7.

Intermediate AC:

(2Z)-3-anilino-1-(2,6-dichloro-5-fluoro-3-pyridinyl)-3-(isopropylamino)-2-propen-1-one

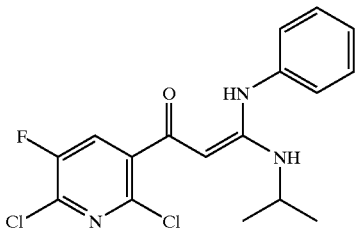

3,3-dichloro-1-(2,6-dichloro-5-fluoro-3-pyridinyl)-2-propen-1-one (374.0 mg, 1.29 mmol) was dissolved in CH2Cl$_2$ (5 mL) and cooled to 10° C. Aniline (120.0 mg, 1.29 mmol) and isopropylamine (76.5 mg, 1.29 mmol) were added dropwise as a mixture in 3 mL of 1,4-dioxane. TEA (0.897 mL, 6.45 mmol) was added and the reaction mixture was warmed to room temperature and left to stir for 2 h. The dioxane was removed in vacuo and the brown residue was partitioned between EtOAc and saturated aqueous NaHCO$_3$. The aqueous layer was extracted with EtOAc. The combined organic extracts were washed with brine, dried over MgSO$_4$ and concentrated in vacuo. Purification of the residue using Biotage silica gel chromatography eluting with 6:1 to 7:3 Hex:EtOAc provided (2Z)-3-anilino-1-(2,6-dichloro-5-fluoro-3-pyridinyl)-3-(isopropylamino)-2-propen-1-one (45 mg, 10%) as an off-white solid: LCMS RT: 3.63 min, MH$^+$: 3–68.2.

Intermediate AD:

4-Nitrophenyl 2-{[3-(trifluoromethyl)phenyl]amino}nicotinate

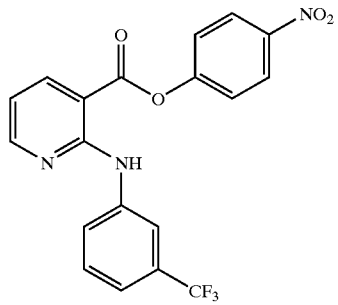

To a warmed (40° C.) suspension of niflumic acid (10.0 g, 35.4 mmol) and 4-nitrophenol (4.9 g, 35.4 mmol) in CH$_2$Cl$_2$ (80 mL) was added a suspension of EDCI (6.8 g, 35.4 mmol) in CH$_2$Cl$_2$ (20 mL). The reaction was stirred for 16 h, and then cooled to room temperature. The solution was quenched with water (50 mL), and the aqueous layer was extracted with CH$_2$Cl$_2$. The combined organic extracts were washed with water and dried over Na$_2$SO$_4$. The solvent was removed in vacuo, and the residue was purified by trituration with Hex:CH$_2$Cl$_2$ to afford 4-Nitrophenyl 2-{[3-(trifluoromethyl)phenyl]amino}nicotinate (4.5 g, 31%): LCMS RT: 4.03 min, MH$^+$: 404.1.

Intermediate AE:

Ethyl 2-cyano-3-oxo-3-(2-{[3-(trifluoromethyl)phenyl]amino}-3-pyridinyl)propanoate

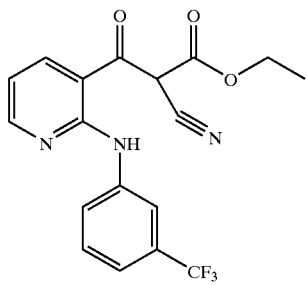

To a stirred mixture of NaH (524 mg, 21.8 mmol) in toluene (20 mL) was added dropwise ethyl cyanoacetate (3.7 g, 32.7 mmol, 3.5 mL). The slurry was stirred for 1 h and then 4-nitrophenyl 2-{[3-(trifluoromethyl)phenyl]amino}nicotinate (4.4 g, 10.9 mmol) was added. The reaction mixture was stirred for 1 h and then quenched with water (20 mL). CH$_2$Cl$_2$ (30 mL) was added and the layers were partitioned. The organic layer was washed with brine (2×) and dried over Na$_2$SO$_4$. The solvent was removed in vacuo and the residue was purified by silica gel flash chromatography (5:1 to 2:1 Hex:EtOAc) to afford 3 Ethyl 2-cyano-3-oxo-3-(2-{[3-(trifluoromethyl)phenyl]amino}-3-pyridinyl)propanoate. (6 g, 87%): LCMS RT: 2.83 min, MH$^+$: 378.0.

Intermediate AF:

2-Amino-1-[3-(trifluoromethyl)phenyl]-1,8-naphthyrldin-4(1H)-one

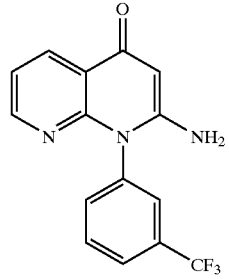

Ethyl 2-cyano-3-oxo-3-(2-{[3-(trifluoromethyl)phenyl]amino}-3-pyridinyl) propanoate (2.0 g, 5.3 mmol) was heated to 120° C. in a mixture of conc. HCl (4 mL) and glacial acetic acid (2 mL) for 3 h. The reaction mixture was cooled to room temperature, and neutralized by slow addition of NaOH pellets. The mixture was extracted with CH$_2$Cl$_2$ (3×). The combined organic extracts were washed with saturated aqueous NaHCO$_3$ (10 mL) and brine (10 mL), dried over MgSO$_4$, and concentrated in vacuo. The residue was purified by prep-HPLC (YMC-Pack Pro C18 Column, 150×20 mm I.D.; 30–70% CH$_3$CN in water, 20 min.) to afford 2-Amino-1-[3-(trifluoromethyl)phenyl]-1,8-naphthyridin-4(1H)-one (880 mg, 55%): LCMS RT: 2.03 min, MH$^+$: 306.3.

Intermediate AG:

7chloro-6-fluoro-2-(isopropylamino)-1-phenyl-1,8-naphthyridin-4(1H)-one

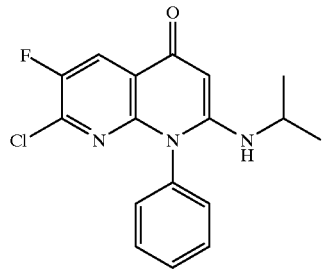

(2Z)-3-Anilino-1-(2,6-dichloro-5-fluoro-3-pyridinyl)-3-(isopropylamino)-2-propen-1-one (40.0 mg, 0.109 mmol) was dissolved in 4 mL of DMF. NaH (8.70 mg, 0.217 mmol, 60% dispersion in oil) was added and the reaction was heated to 85° C. under argon for 2 h. The reaction mixture was cooled to room temperature and diluted with water and the aqueous layer was extracted with EtOAc. The combined organic extracts were washed with brine, dried over MgSO$_4$ and concentrated in vacuo. Purification of the residue using Biotage silica gel chromatography eluting with 100% EtOAc to 95:5 EtOAc:MeOH provided 7-chloro-6-fluoro-2-(isopropylamino)-1-phenyl-1,8-naphthyridin-4(1H)-one (21 mg, 64%) as a white solid: LCMS RT: 2.57 min, MH$^+$: 332.2.

Intermediate AH:

2-anilino-7-chloro-6-fluoro-5-methyl-1-phenyl-1,8-naphthyridin-4(1H)-one

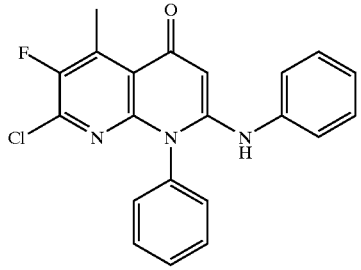

A solution of LTMP [freshly prepared at 0° C. from tetramethylpiperidine (227.2 mg, 1.62 mmol), TMEDA (188.3 mg, 1.62 mmol) and n-BuLi (1 mL, 1.62 mmol)) in THF (5 mL) was added to a cooled (40° C.) and stirred solution of 2-anilino-7-chloro-6-fluoro-1-phenyl-1,8-naphthyridin-4(1H)-one (200 mg, 0.54 mmol) in THF (10 mL). The reaction mixture was warmed to 0° C., for 1 h and then re-cooled to 40° C. MeI (766 mg, 5.35 mmol) was added and the reaction mixture was allowed to warm to room temperature and was stirred overnight. The reaction was quenched carefully with water (50 mL) and then extracted with EtOAc. The combined organic extracts were washed with brine, dried over $Na_2SO_4$, and concentrated in vacuo. Silica gel flash chromatography of the residue using 1:1 EtOAc:Hex afforded 2-anilino-7-chloro-6-fluoro-5-methyl-1-phenyl-1,8-naphthyridin-4(1H)-one (184 mg, 88%) as a white solid: LCMS RT: 2.74 min, $MH^+$: 380.3. This transformation can also be accomplished by using other amide bases such as LDA.

Intermediate AI:

2-anilino-7chloro-6-fluoro1-phenyl-5-(trifluoroacetyl)-1,8-naphthyridin-4(1H)-one

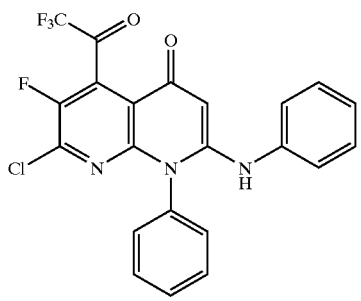

A solution of LTMP [freshly prepared at 0° C. from tetramethylpiperidine (154 mg, 1.10 mmol), TMEDA (127.8 mg, 1.10 mmol) and n-BuLi (0.688 mL, 1.10 mmol)] in THF (5 mL) was added to a cooled (−40° C.) stirred solution of 2-anilino-7-chloro-6-fluoro-1-phenyl-1,8-naphthyridin-4(1H)-one (100 mg, 0.273 mmol) in THF (10 mL). The reaction was stirred for 1 h and then cooled to −78° C. Methyl trifluoroacetate (350 mg, 2.74 mmol) was added and stirring was continued for 2 h. The reaction was quenched carefully with water (50 mL), warmed to room temperature and extracted with EtOAc. The combined organic extracts were washed with brine, dried over $Na_2SO_4$, and concentrated in vacuo. Silica gel flash chromatography of the residue using 3:1 Hex:EtOAc gave 2-anilino-7-chloro-6-fluoro-1-phenyl-5-(trifluoroacetyl)-1,8-naphthyridin-4(1H)-one (71 mg, 56%) as a light yellow solid: LCMS RT: 3.43 min, $MH^+$: 462.3. The anion generated from LTMP deprotonation can be quenched with other electrophiles including carbon dioxide and 4-nitrophenyl acetate.

Intermediate AJ:

7-chloro-5-methyl-2-[methyl(phenyl)amino]-1-phenyl-1,8-naphthyridin-4(1H)-one

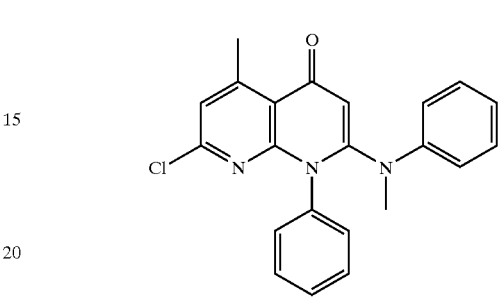

MeI (0.10 mL, 228 mg, 1.6 mmol) was added to a stirred suspension of $K_2CO_3$ (23.5 mg, 0.17 mmol) and 2-anilino-7-chloro-5-methyl-1-phenyl-1,8-naphthyridin-4(1H)-one (50 mg, 0.14 mmol) in THF (3 mL). The suspension was heated to 40° C. and stirred was overnight. The reaction was quenched with water (5.0 mL) and extracted with EtOAc. The combined organic extracts were dried over $Na_2SO_4$ and concentrated in vacuo. Recrystallization of the residue using EtOAc afforded 7-chloro-5-methyl-2-[methyl(phenyl)amino]-1-phenyl-1,8-naphthyridin-4(1H)-one (18 mg, 35%): LCMS RT: 2.24 min, $MH^+$: 376.6, $R_f$=0.76 (4:1 Hex:EtOAc).

Intermediate AK:

N-(7-chloro-5-methyl-4-oxo-1-phenyl-1,4-dihydro-1,8-naphthyridin-2-yl)-N'-(4-fluorophenyl)-N-phenylurea

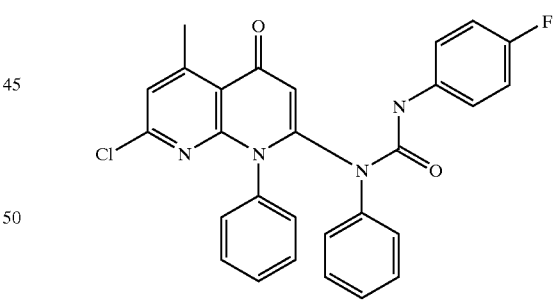

4-Fluorophenyl isocyanate (45.0 mg, 0.33 mmol) was added to a stirred solution of 2-anilino-7-chloro-5-methyl-1-phenyl-1,8-naphthyridin-4(1H)-one (100 mg, 0.276 mmol) in $CH_2Cl_2$ (3 mL). After 16 h, an additional equivalent of 4-fluorophenyl isocyanate (45.0 mg) was added, and the reaction stirred for an additional 16 h. The reaction was concentrated in vacuo and the residue was dissolved in EtOAc. The solution was washed with 1 N HCl, dried over $MgSO_4$, and concentrated in vacuo. Purification of the residue using reverse phase prep-HPLC afforded N-(7-chloro-5-methyl-4-oxo-1-phenyl-1,4-dihydro-1,8-naphthyridin-2-yl)-N'-(4-fluorophenyl)-N-phenylurea (2.2 mg, 1.6%): LCMS RT: 3.47 min, MH⁺: 499.1, $R_f$=0.52 (1:1 EtOAc:Hex).

Intermediate AL:

2-anilino-7-chloro-3-iodo-5-methyl-1-phenyl-1,8-naphthyridin-4(1H)-one

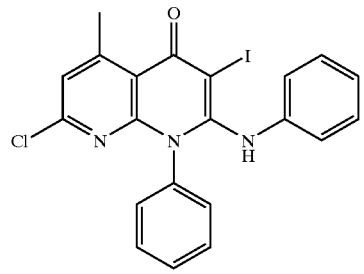

$K_2CO_3$ (210 mg, 1.52 mmol) and $I_2$ (390 mg, 1.52 mmol,) were added to a solution 2-anilino-7-chloro-5-methyl-1-phenyl-1,8-naphthyridin-4(1H)-one (500 mg, 1.38 mmol) in DMF (10 mL). The mixture was stirred for 30 min and then poured into an aqueous solution of saturated $Na_2S_2O_3$ (10 mL). The aqueous solution was extracted with EtOAc. The combined organic extracts were dried over $MgSO_4$, and concentrated in vacuo. Silica gel flash chromatography of the residue using 4:1 to 1:1 Hex:EtOAc afforded 2-anilino-7-chloro-3-iodo-5-methyl-1-phenyl-1,8-naphthyridin-4 (1H)-one (380 mg, 56%): LCMS RT: 3.45 min, MH⁺: 488.2, $R_f$=0.5 (2:1 Hex:EtOAc).

Intermediate AM:

2-anilino-7-chlorofluoro-5-(1-hydroxypropyl)-1-phenyl-1,8-naphthyridin-4(1H)-one

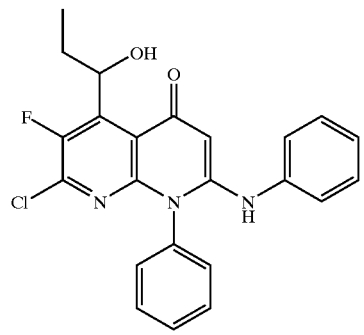

A −40° C. solution of 2-anilino-7-chloro-6-fluoro-1-phenyl-1,8-naphthyridin-4(1H)-one (100 mg, 0.274 mmol) in THF (10 mL) was treated with LTMP (1.10 mmol, freshly prepared by mixing 2,2,6,6-Tetramethyl piperidine and n-BuLi at 0° C. for 30 min.). The mixture was then allowed to warm to 0° C. for 2 h. The reaction mixture was cooled to −30° C. and propionaldehyde (159 mg, 2.74 mmol) was added. The reaction was stirred at −30° C. for 2 h before it was slowly quenched with saturated aqueous $NH_4Cl$. The mixture was extracted with EtOAc and the organic layer was dried over $MgSO_4$ and concentrated in vacuo. The residue was purified by silica gel flash chromatography to afford 2-anilino-7-chloro-6-fluoro-5-(1-hydroxypropyl)-1-phenyl-1,8-naphthyridin-4(1H)-one (120 mg, 97%) as a white solid: LCMS RT: 3.14 min, MH⁺: 424.2. Other electrophiles such as disulfide may be used to quench the anion.

Example 1

2-anilino-5-methyl-1-phenyl-1,8-naphthyridin-4 (1H)-one

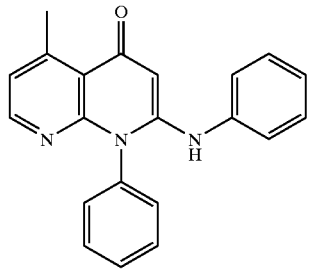

A solution of 2-anilino-7-chloro-5-methyl-1-phenyl-1,8-naphthyridin-4(1H)-one (95.0 mg, 0.263 mmol), TEA (0.65 mmol), and 10% Pd/C in EtOAc (2.5 mL) and EtOH (2.5 mL) was stirred under $H_2$ (1 atm) for 3.5 h. The reaction mixture was filtered through a pad of Celite using EtOH and EtOAc to rinse. The combined filtrates were concentrated in vacuo, and purified with Biotage silica gel chromatography using 1:1 EtOAc:Hex to afford 2-anilino-5-methyl-1-phenyl-1,8-naphthyridin-4(1H)-one (84 mg, 98%) as a pale yellow solid. LCMS RT: 2.26 min, MH⁺: 328.4, $R_f$=0.1 (1:1 EtOAc:Hex).

Example 2

5-Methyl-7-morpholin-4-yl-1-phenyl-2-phenylamino-1H-[1,8]-naphthyridin-4one

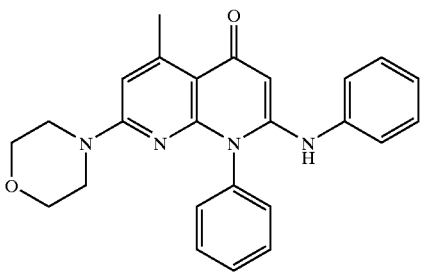

A mixture of 7-chloro-5-methyl-1-phenyl-2-phenylamino-1H-1,8]naphthyridin-4-one (68.3 mg, 0.189 mmol) and morpholine (0.05 mL, 0.48 mmol) in dioxane (3 mL) was heated to 80° C. for 2 d. The reaction was cooled, concentrated in vacuo, diluted with water and extracted with EtOAc (3×). The combined organic extracts were washed with brine, dried over $Na_2SO_4$, and concentrated in vacuo to give 5-methyl-7-morpholin-4-yl-1-phenyl-2-phenylamino-1H-[1,8]naphthyridin-4-one (67 mg, 92%) as yellow solid: LCMS RT: 2.33 min, MH⁺: 413.4, $R_f$=0.49 (EtOAc).

Example 3

5-Methyl-1-phenyl-2,7-bis-phenylamino-1H-[1,8]naphthyridin-4-one

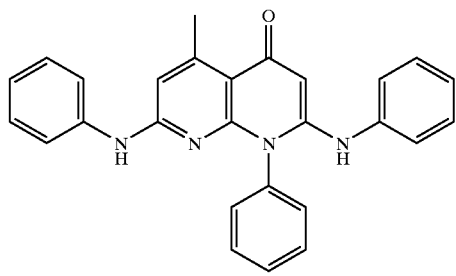

A mixture of 7-chloro-5-methyl-1-phenyl-2-phenylamino-1H-[1,8]naphthyridin-4-one (15.1 mg, 0.042 mmol), aniline (2 drops), Pd(OAc)$_2$ (0.27 mg, 0.001 mmol), Cs$_2$CO$_3$ (19.5 mg, 0.06 mmol), and BINAP (1.68 mg, 0.003 mmol) in THF (0.5 mL) was heated at reflux for 16 h. The reaction was quenched with water and extracted with EtOAc (3×). The combined organic extracts were washed brine, dried over Na$_2$SO$_4$, and concentrated in vacuo to give 5-methyl-1-phenyl-2,7-bis-phenylamino-1H-[1,8]naphthyridin-4-one (6.0 mg, 38%): LCMS RT: 2.57 min, MH$^+$: 419.5, R$_f$=0.18 (EtOAc).

Example 4

2-anilino-1,7-diphenyl-5-(trifluoromethyl)-1,8-naphthyridin-4(1H)-one

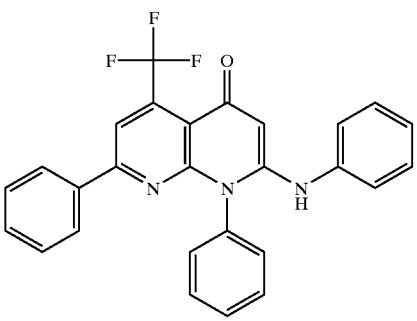

A solution of 2-anilino-7-chloro-1-phenyl-5-(trifluoromethyl)-1,8-naphthyridin-4(1H)-one (10.0 mg, 0.241 mmol), Ph$_3$P (6.00 mg, 0.024 mmol) and phenylboronic acid (36.0 mg, 0.290 mmol) in DME was treated with 2M K$_2$CO$_3$ (0.482 mL, 0.964 mmol) and Pd(OAc)$_2$ (1.35 mg, 0.006 mmol). The mixture was heated at reflux for 24 h. After cooling to room temperature, the mixture was diluted with water and extracted with EtOAc. The organic layer was washed with brine, dried over MgSO$_4$, and concentrated in vacuo. Purification by preparative HPLC (10% CH$_3$CN in water with 0.1% TFA to 95% CH$_3$CN in water, 10 mL/min, 10 min) provided 2-anilino-1,7-diphenyl-5-(trifluoromethyl)-1,8-naphthyridin-4(1H)-one (45.0 mg, 41%): LCMS RT: 3.76 min, MH$^+$: 458.4.

Example 5

2-anilino-7-benzyl-5-methyl-1-phenyl-1,8-naphthyridin-4(1H)-one

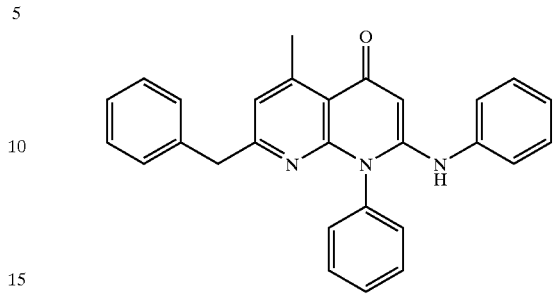

To a solution of 2-anilino-7-chloro-5-methyl-1-phenyl-1,8-naphthyridin-4(1H)-one (100 mg, 0.277 mmol) in THF was added Ni(dppp)Cl$_2$ (37.0 mg, 0.069 mmol). After stirring for 5 min, benzylmagnesium chloride (2M, 1.45 mL, 2.90 mmol) was added dropwise via syringe and the mixture was allowed to stir for 24 h. The mixture was quenched with 1 N HCl and extracted with EtOAc. The organic layer was washed brine, dried over MgSO$_4$, and concentrated in vacuo. Purification by preparative HPLC (10% MeNC in water with 0.1% TFA to 95% CH$_3$CN in water, 10 mL/min, 10 min) provided 2-anilino-7-benzyl-5-methyl-1-phenyl-1,8-naphthyridin-4(1H)-one (47.3 mg, 41%): LCMS RT: 2.85 min, MH$^+$: 418.3.

Example 6

Ethyl{[7-anilino-5-oxo-8-phenyl-4-(trifluoromethyl)-5,8-dihydro-1,8-naphthyridin-2-yl]sulfanyl}acetate

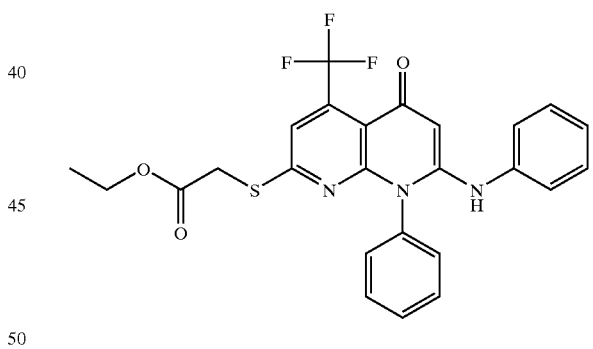

NaH (60% dispersion in oil, 18.0 mg, 0.434 mmol) was added to a cooled (0° C.) and stirred solution of ethyl mercaptoacetate (0.05 mL, 0.434 mmol) in DMF. After 0.5 h, 2-anilino-7-chloro-1-phenyl-5-(trifluoromethyl)-1,8-naphthyridin-4(1H)-one (150.0 mg, 0.361 mmol) was added as a solid in a single portion. The mixture was allowed to warm to room temperature and was stirred for 24 h. The reaction was quenched with water and extracted with EtOAc. The organic layer was washed with brine, dried over MgSO$_4$, and concentrated in vacuo. Purification by preparative HPLC (10% CH$_3$CN in water with 0.1% TFA to 95% CH$_3$CN in water, 10 mL/min, 10 min) provided ethyl {[7-anilino-5-oxo-8-phenyl-4-(trifluoromethyl)-5,8-dihydro-1,8-naphthyridin-2-yl]sulfanyl}acetate (50 mg, 53%): LCMS RT: 3.91 min, MH$^+$: 500.2, R$_f$=0.24 (1:1 EtOAc:Hex).

Example 7

{[7-anilino-5-oxo-8-phenyl-4-(trifluoromethyl)-5,8-dihydro-1,8-naphthyridin-2-yl]sulfanyl}acetic acid

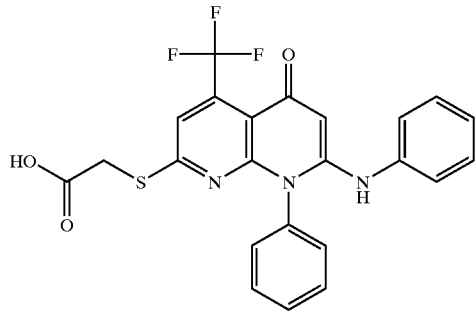

NaOH (160 mg, 4.0 mmol) was added to a stirred solution of ethyl {[7-anilino-5-oxo-8-phenyl-4-(trifluoromethyl)-5,8-dihydro-1,8-naphthyridin-2-yl]sulfanyl}acetate (30.0 mg, 0.060 mmol) in aqueous EtOH (10 mL EtOH in 4mL $H_2O$). The mixture was allowed to stir for 4 h and was then concentrated in vacuo. The reaction was acidified with 1N HCl and extracted with $CH_2Cl_2$. The organic layer was dried over $MgSO_4$, and concentrated in vacuo. Purification by preparative HPLC (10% $CH_3CN$ in water with 0.1% TFA to 95% $CH_3CN$ in water, 10 mL/min, 10 min) provided {[7-anilino-5-oxo-8-phenyl-4-(trifluoromethyl)-5,8-dihydro-1,8-naphthyridin-2-yl]sulfanyl}acetic acid (19.0 mg, 66%): LCMS RT: 2.50 min, $MH^+$: 472.1.

Example 8

2-anilino-1-phenyl-7-(1-piperidinyl)-5-(trifluoromethyl)-1,8-naphthyridin-4(1H)-one

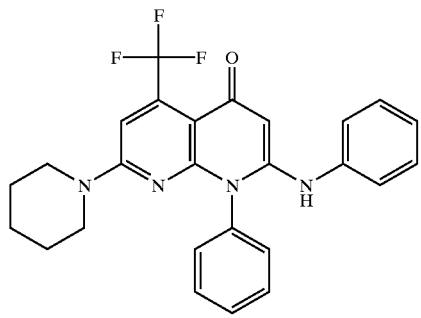

To a solution of 2-anilino-7-chloro-1-phenyl-5-(trifluoromethyl)-1,8-naphthyridin-4(1H)-one (100.0 mg, 0.241 mmol) in dioxane (2.5 mL) was added piperdine (40.9 mg, 0.481 mmol). The mixture was left to stir at 80° C. overnight. The mixture was cooled to room temperature, poured into 1N HCl (1 mL) and extracted with $CH_2Cl_2$. The organic extracts were combined, washed with saturated aqueous $NaHCO_3$, dried over $Na_2SO_4$, and concentrated in vacuo. The residue was purified by Biotage silica gel chromatography (1:1 EtOAc:Hex) to provide 2-anilino-1-phenyl-7-(1-piperidinyl)-5-(trifluoromethyl)-1,8-naphthyridin-4(1H)-one (89.5 mg, 80%) as a pale yellow solid: LCMS RT: 2.76 min, $MH^+$: 465.5.

Example 9

2-anilino-7-[2-(2-oxo-0-pyrrolidinyl)ethoxy]-1-phenyl-5-(trifuoromethyl)-1,8-naphthyridin-4(1H)-one

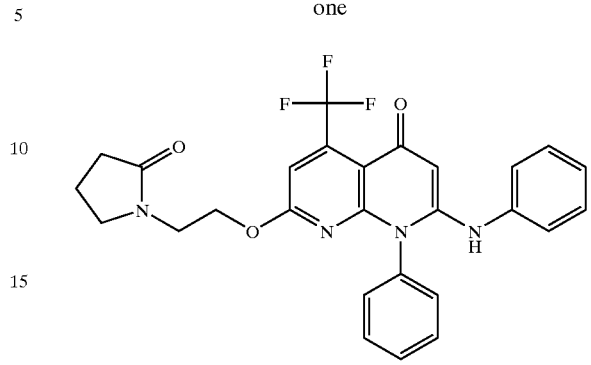

NaH (60% dispersion, 20.0 mg, 0.514 mmol) was added to a cooled (0° C.) and stirred solution of 1-(2-hydroxyethyl)-2-pyrrolidinone (0.06 mL, 0.514 mmol) in DMF. After 0.5 h, 2-anilino-7-chloro-1-phenyl-5-(trifluoromethyl)-1,8-naphthyridin-4(1H)-one (178 mg, 0.428 mmol) was added as a solid in a single portion and the mixture was heated to 130° C. for 48 h. After cooling to room temperature the mixture was quenched with saturated aqueous $NH_4Cl$ and extracted with EtOAc. The organic layer was washed with brine, dried over $MgSO_4$, and concentrated in vacuo. Purification by preparative HPLC (10% $CH_3CN$ in water with 0.1% TFA to 95% $CH_3CN$ in water, 10 mL/min, 10 mm) provided 2-anilino-7-[2-(2-oxo-1-pyrrolidinyl)ethoxy]-1-phenyl-5-(trifluoromethyl)-1,8-naphthyridin-4(1H)-one (0.047 g, 64%): LCMS RT: 2.40 min, $MH^+$: 509.2. This transformation can be accomplished by using other aprotic solvents such as DMSO, THF and dioxane with temperatures appropriate for these solvents. Commercially available alkoxides can also be used in the absence of base.

Example 10

2-anilino-5-(hydroxymethyl)-1-phenyl-1,8-naphthyridin-4(1H)-one

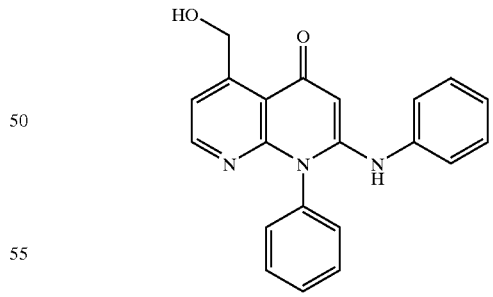

A solution of LDA (38.2 mmol, freshly prepared from n-BuLi and diisopropylamine) in THF (53 mL) was added to a cooled (-78° C.) and stirred suspension of 2-anilino-5-methyl-1-phenyl-1,8-naphthyridin-4(1H)-one (2.50 g, 7.64 mmol) in THF (100 mL). The resulting mixture was stirred for 1 h, and then oxygen gas was bubbled, through a fritted glass tube, into the bottom of the reaction vessel. The mixture was stirred overnight, with continued bubbling of oxygen with slow warming to room temperature. The reaction was quenched with water and 1M HCl (5 mL), and then extracted with CH$_2$Cl$_2$. The organic phase was dried over Na$_2$SO$_4$ and concentrated in vacuo to afford an orange solid which was recrystalized from EtOAc to obtain 2-anilino-5-(hydroxymethyl)-1-phenyl-1,8-naphthyridin-4(1H)-one (1.38 g, 53%): LCMS RT: 2.01 min, MH$^+$: 344.3, R$_f$=0.22 (95:5 CH$_2$Cl$_2$:MeOH).

Example 11

2-anilino-1-phenyl-5-(1-piperazinylmethyl)-1,8-naphthyridin-4(1H)-one

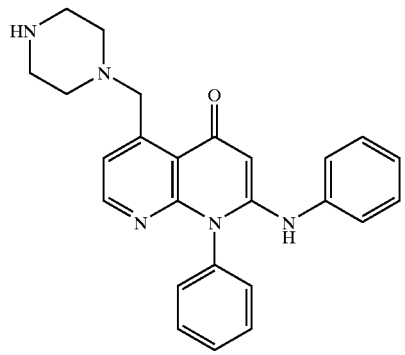

A solution of 2-anilino-5-(hydroxymethyl)-1-phenyl-1,8-naphthyridin-4(1)-one (180 mg, 0.52 mmol), N,N-diisopropylethylamine (0.10 mL, 0.52 mmol) and SOCl$_2$ (0.12 mL, 1.57 mmol) in CH$_2$Cl$_2$ (7 mL) was stirred at room temperature for 2 h. Excess SOCl$_2$ and solvent were removed in vacuo to afford a brownish solid. Crude 2-anilino-5-(chloromethyl)-1-phenyl-1,8-naphthyridin-4(1H)-one was used without further purification: LCMS RT: 2.50 min, MH$^+$: 362.3.

DMF (1 mL) was added to a stirred suspension of crude 2-anilino-5-(chloromethyl)-1-phenyl-1,8-naphthyridin-4-(1H)-one (15.0 mg, 0.041 mmol), N,N-diisopropylethylamine (0.036 mL, 0.21 mmol), and piperazine (36 mg, 0.21 mmol) in 1,4-dioxane (2 mL). The solution was heated to 50° C. overnight, cooled to room temperature and concentrated in vacuo. Reverse phase preparative HPLC (0.1% TFA in CH$_3$CN and water) of the residue gave 2-anilino-1-phenyl-5-(1-piperazinylmethyl)-1,8-naphthyridin-4(1H)-one (8.0 mg, 37%) as the TFA salt: LCMS RT: 0.71 min, MH$^+$: 412.2.

Example 12

5-Methyl-1-phenyl-2-phenylamino-7-piperazin-1-yl-1H-[1,8]-naphthyridin-4-one

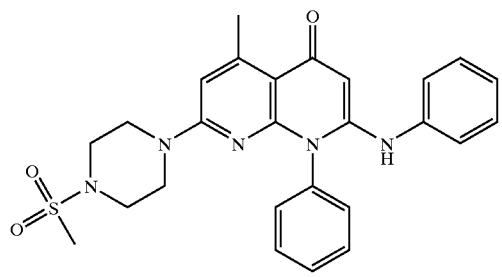

A mixture of 5-methyl-1-phenyl-2-phenylamino-7-piperazin-1-yl-1H-[1,8]naphthyridin-4-one (22.6 mg, 0.055 mmol) and MsCl (0.083 mmol, 0.006 mL) in CH$_2$Cl$_2$ (0.8 mL) was stirred at room temperature overnight at which time the solvent was removed in vacuo. The resulting residue was purified by prep-TLC to give 7-(4-methanesulfonyl-piperazin-1-yl)-5-methyl-1-phenyl-2-phenylamino-1H-[1,8]naphthyridin-4-one (3.4 mg, 6%): LCMS RT: 2.36 min, MH$^+$: 490.3.

Example 13

5-methyl-1-phenyl-2-phenylamino-7-(4-propionyl-piperazin-1-yl)-1H-[1,8]naphthyridin-4-one

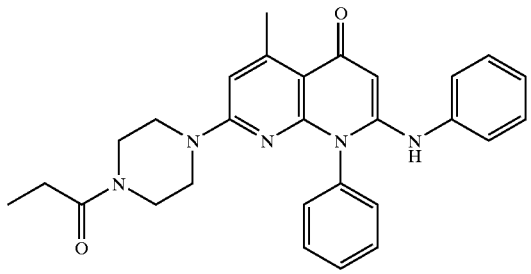

A mixture of 5-methyl-1-phenyl-2-phenylamino-7-piperazin-1-yl-1H-[1,8]naphthyridin-4-one (21.0 mg, 0.052 mmol), propionic acid (0.004 mL, 0.055 mmol), EDCI (11.9 mg, 0.062 mmol), DMAP (7.6 mg, 0.062 mmol), and NMM (0.006 mL, 0.062) in CH$_2$Cl$_2$ (0.8 mL) was stirred at room temperature overnight. The reaction was diluted with water and extracted with CH$_2$Cl$_2$. The combined organic extracts were washed with 0.5 N HCl and brine and concentrated in vacuo. The residue was purified by prep-TLC eluting with 100% EtOAc to give 5-methyl-1-phenyl-2-phenylamino-7-(4-propionyl-piperazin-1-yl)-1H-[1,8]naphthyridin-4-one (9.0 mg, 37%): LCMS RT: 2.29 min, MH$^+$: 468.3.

Example 14

2-anilino-5-bromo-6-fluoro-7-methoxy-1-phenyl-1,8-naphthyridin-4(1H)-one

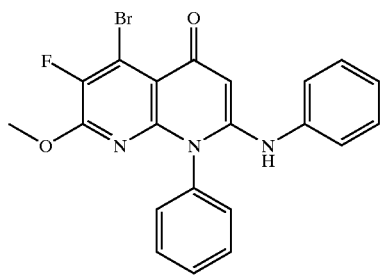

A solution of LTMP [freshly prepared at 0° C. from tetramethylpiperidine (785.4 mg, 5.6 mmol), TMEDA (651 mg, 5.6 mmol) and n-BuLi (3.5 mL, 5.6 mmol)] in THF (10 mL) was added to a cooled (40° C.) stirred solution of 2-anilino-6-fluoro-7-methoxy-1-phenyl-1,8-naphthyridin-4(1H)-one (507 mg, 104 mmol) in THF (20 mL). The reaction mixture was warmed to room temperature. After 1 h, the mixture was cooled to −30° C. and 1,2-dibromotetrachloroethane (457 mg, 1.4 mmol) was added. After 30 min, water (50 mL) was added slowly, and then the reaction was warmed to room temperature and extracted with EtOAc. The combined organic extracts were washed with brine, dried over Na$_2$SO$_4$, and concentrated in vacuo. Silica gel flash chromatography of the residue using EtOAc afforded 2-anilino-5-bromo-6-fluoro-7-methoxy-1-phenyl-1,8-naphthyridin-4(1H)-one (101 mg, 16%) as a light yellow solid: LCMS RT: 2.75 min, MH$^+$: 440.3.

Example 15

7-Methyl-1-phenyl-2-(phenylamino)hydropyridino[2,3-b]pyridin-4-one

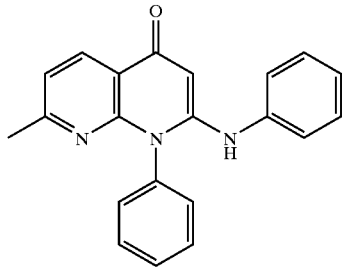

Ethyl 7-methyl-4-oxo-1-phenyl-2-(phenylamino)hydropyridino[2,3-b]pyridine-3-carboxylate (67 mg, 0.17 mmol) was dissolved in a 2:1 HCl:AcOH solution (8.5 mL). The reaction was heated to 120° C. for 5 h then cooled to room temperature. The aqueous solution was washed with Et$_2$O and then neutralized with 2 N NaOH and extracted with EtOAc. The combined organic extracts were washed with saturated aqueous NaHCO$_3$ and brine, dried over anhydrous Na$_2$SO$_4$, and concentrated in vacuo to provide 7-methyl-1-phenyl-2-(phenylamino)hydropyridino[2,3-b]pyridin-4-one (40 mg, 72%): LCMS RT: 2.28 min, MH$^+$:328.4.

Example 16

2-anilino-5-chloro-7-methyl-1-phenyl-1,8-naphthyridin-4(1H)-one

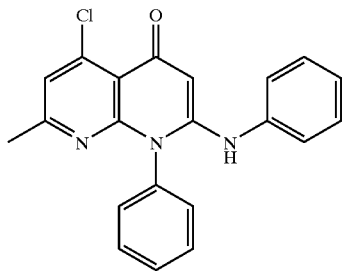

A mixture of 3,3-dianilino-1-(2,4-dichloro-6-methyl-3-pyridinyl)-2-propen-1-one(100 mg, 0.25 mmol) and t-BuOK (42 mg, 0.38 mmol) in anhydrous dioxane (4 mL) was heated to 80° C. for 4 h. The solvent was removed in vacuo and the residue was dissolved in EtOAc. The solution was washed with water and brine, dried over MgSO$_4$, and concentrated in vacuo. Silica gel flash chromatography of the residue using 1:1 EtOAc:Hex gave 2-anilino-5-chloro-7-methyl-1-phenyl-1,8-naphthyridin-4(1H)-one (13 mg, 14%): LCMS RT: 2.47 min, MH$^+$: 362.6. 2-anilino-5-chloro-7-methyl-1-phenyl-1,6-naphthyridin-4(1H)-one was also isolated (68 mg, 75%): LCMS RT: 2.24 min, MH$^+$: 362.6. This transformation can be accomplished by using the combination of other aprotic solvents such as DMF and THF with other bases such as NaH.

Example 17

Ethyl 7-anilino-3-fluoro-5-oxo-8-phenyl-5,8-dihydro-1,8-naphthyridine carboxylate

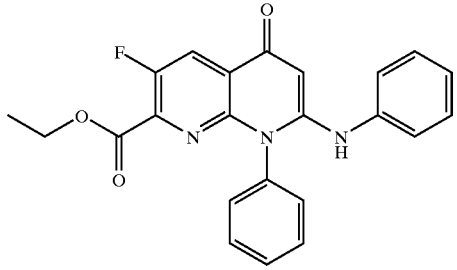

2-anilino-7-chloro-6-fluoro-1-phenyl-1,8-naphthyridin-4(1H)-one (200 mg, 0.55 mmol), DPPP (12 mg, 0.030 mmol), Pd(OAc)$_2$ (6.0 mg, 0.028 mmol), and Cs$_2$CO$_3$ (114 mg, 0.42 mmol) was dissolved in a 1:1 mixture of EtOH (3 mL)/DMF (3 mL). A balloon filled with CO was attached to the flask and the solution was stirred vigorously. The solution was saturated with CO by evacuating the flask followed by back filling the flask with CO. This was repeated 3 times before heating the solution to 70° C. After 4 h of stirring all of the starting material had been consumed and the reaction was cooled to room temperature. The solution was diluted with EtOAc and was washed with water. The organic layer was collected, dried over Na$_2$SO$_4$, and concentrated in vacuo. The crude solid was triturated with Et$_2$O, filtered and dried to give ethyl 7-anilino-3-fluoro-5-oxo-8-phenyl-5,8-dihydro-1,8-naphthyridine-2-carboxylate as a light brown solid (900 mg, 81%): LCMS RT: 2.63 min, MH$^+$: 404.4.

Example 18

7-anilino-3-fluoro-5-oxo-8-phenyl-5,8-dihydro-1,8-naphthyridine-2-carboxamide

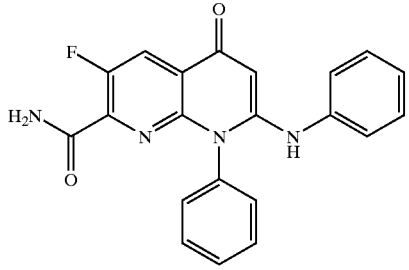

A suspension of ethyl 7-anilino-3-fluoro-5-oxo-8-phenyl-5,8-dihydro-1,8-naphthyridine-2-carboxylate (50 mg, 0.12 mmol), and NH$_4$Cl (10 mg, 0.1 9 mmol) in concentrated NH$_3$ (3 mL) and MeOH (8 drops) was stirred for 16 h at room temperature. The solid was collected by filtration washing with water. Trituration with Et$_2$O, provided 7-anilino-3-fluoro-5-oxo-8-phenyl-5,8-dihydro-1,8-naphthyridine-2-carboxamide as a yellow solid (32 mg, 71%): LCMS RT: 1.93 min, MH$^+$: 375.3. This trasformation can to also be accomplished using EDCI/HOBT coupling with NH$_3$.

Example 19

7-anilino-N-methoxy-N,4-dimethyl-5-oxo-8-phenyl-5,8-dihydro-1,8-naphthyridine-2-carboxamide

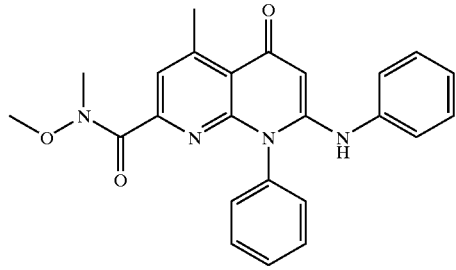

7-anilino-4-methyl-5-oxo-8-phenyl-5,8-dihydro-1,8-naphthyridine-2-carboxylic acid (50 mg, 0.14 mmol), N,O-dimethylhydroxylamine hydrochloride (39 mg, 0.40 mmol), HOBT (28 mg, 0.21 mmol), EDCI (40 mg, 0.21 mmol) were dissolved in $CH_2Cl_2$ (3 mL). To this solution was added TEA (78 uL, 0.56 mmol). The reaction was stirred for 1 h and was diluted with $CH_2Cl_2$, washed with 0.5N HCl, saturated $NaHCO_3$, and brine. The organic layer was collected, dried over $Na_2SO_4$, and concentrated in vacuo. The solid obtained was triturated with $Et_2O$ and dried to give 7-anilino-N-methoxy-N,4-dimethyl-5-oxo-8-phenyl-5,8-dihydro-1,8-naphthyridine-2-carboxamide as a light yellow solid (34 mg, 59%): LCMS RT: 2.28 min, $MH^+$: 415.2. This transformation can also be accomplished by coupling the appropriate amine with the corresponding acid chloride.

Example 20

7-acetyl-2-anilino-5-methyl-1-phenyl-1,8-naphthyridin-4(1H)-one

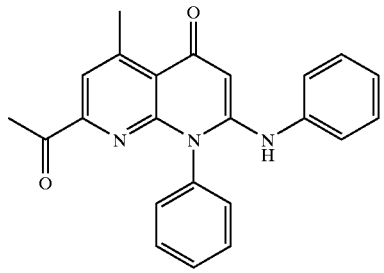

To a suspension of 7-anilino-N-methoxy-N,4-dimethyl-5-oxo-8-phenyl-5,8-dihydro-1,8-naphthyridine-2-carboxamide (100 mg, 0.24 mmol) in THF (5 mL) at 0° C. was added MeMgBr (3M in $Et_2O$, 322 uL, 0.97 mmol). The suspension became a red solution. As the reaction proceeded the solution lost its red color. After 1 h the reaction was quenched with saturated $NH_4Cl$, diluted with EtOAc, and washed with brine. The organic layer was dried over $Na_2SO_4$ and concentrated in vacuo. The crude residue was purified by a Biotage silica gel chromatography using EtOAc to afford 7-acetyl-2-anilino-5-methyl-1-phenyl-1,8-naphthyridin-4(1H)-one as a light yellow solid (65 mg, 74%): LCMS RT: 2.63 min, $MH^+$: 370.4.

Example 21

2-anilino-7-(butylsulfonyl)-1-phenyl-5-(trifluoromethyl)-1,8-naphthyrldin-4(1H)-one

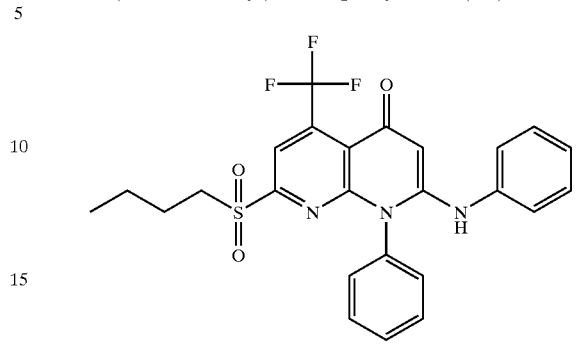

To a solution of montmorillonite K10 (107.5 mg) in $CHCl_3$ was added 13 uL of water. 2-anilino-7-(butylsulfanyl)-1-phenyl-5-(trifluoromethyl)-1,8-naphthyridin-4(1H)-one (25 mg, 0.06 mmol) was then added followed by oxone (85.2 mg, 0.14 mmol). The reaction was allowed to stir for 24 h at room temperature. After 24 h the solution was bright bluish-green in color and was filtered and washed with copious amounts of $CHCl_3$. The filtrate was then concentrated in vacuo. Silica gel flash chromatography using 3:1 Hex:EtOAc provided 2-anilino-7-(butylsulfonyl)-1-phenyl-5-(trifluoromethyl)-1,8-naphthyridin-4(1H)-one as a yellow oil (13.8 mg, 46%): LCMS RT: 3.14, $MH^+$502.2.

Example 22

N-[7-anilino-5-oxo-8-phenyl-4-(trifluoromethyl)-5,8-dihydro-1,8-naphthyridin-2-yl]methanesulfonamide

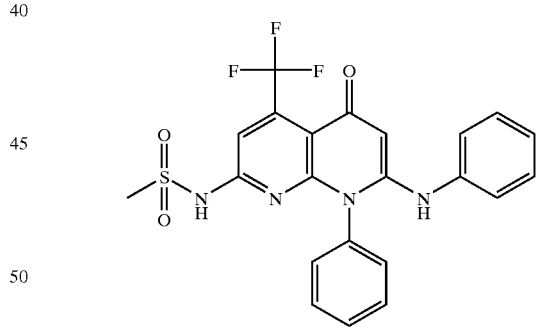

To a solution of 2-anilino-7-chloro-1-phenyl-5-(trifluoromethyl)-1,8-naphthyridin-4(1H)-one (100 mg, 0.241 mmol) in DMSO (5 mL) was added methyl sulfonamide and $K_2CO_3$ (76.5 mg, 0.554 mmol). The reaction was stirred at 120° C. for 24 h. The reaction was then cooled to room temperature, quenched with water and extracted with $Et_2O$. The organic layers were dried over $MgSO_4$, and concentrated in vacuo. The crude residue was then passed through a plug of silica gel eluting with 1:1 Hex:EtOAc to 9:1 $CH_2Cl_2$:MeOH to afford N-[7-anilino-5-oxo-8-phenyl-4-(trifluoromethyl)-5,8-dihydro-1,8-naphthyridin-2-yl]methanesulfonamide as a white solid (4.4 mg, 4%): LCMS RT: 2.45, $MH^+$: 475.2.

Example 23

7-anilino-3-fluoro-5-oxo-8-phenyl-5,8-dihydro-1,8-naphthyridine-2-carbaldehyde

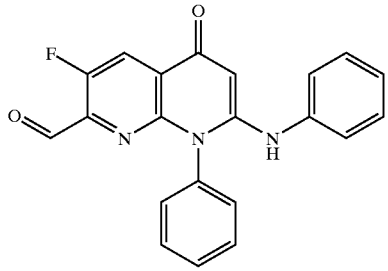

2-anilino-6-fluoro-7-(hydroxymethyl)-1-phenyl-1,8-naphthyridin-4(1H)-one (100 mg, 0.277 mmol) was dissolved in 4.5 mL CHCl$_3$. MnO$_2$ (311 mg, 3.05 mmol) was added and the reaction was heated to 70° C. under argon for 3 d. The reaction mixture was filtered through celite and concentrated in vacuo. Purification by silica gel flash chromatography eluting with 3:1 to 100:0 EtOAc:Hex provided 7-anilino-3-fluoro-5-oxo-8-phenyl-5,8-dihydro-1,8-naphthyridine-2-carbaldehyde (15 mg, 15%) as a white solid: LCMS RT: 2.18 mn, MH$^{30}$ : 360.2.

Example 24

7-amino-2-anilino-5-methyl-1-phenyl-1,8-naphthyridin-4(1H)-one

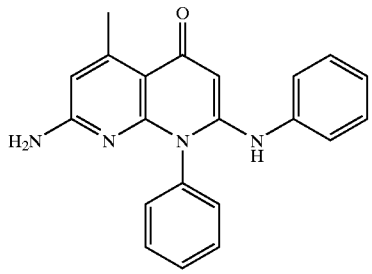

Pd/C (30 mg, 1.75 mmol, 10%) was added to a 25 mL round bottom flask and was blanketed with argon. 7-(allylamino)-2-anilino-5-methyl-1-phenyl-1,8-naphthyridin-4(1H)-one (150 mg, 0.392 mmol) was dissolved in EtOH (2 mL) and was added to the Pd/C followed by methane sulfonic acid (0.041 mL, 0.63 mmol). The reaction was heated to 80° C. for 3 d at which time it was cooled to room temperature, diluted with EtOAc and filtered through celite. The filtrate was concentrated in vacuo and the residue was purified by Biotage silica gel chromatography eluting with 100% EtOAc to provide 7-amino-2-anilino-5-methyl-1-phenyl-1,8-naphthyridin-4(1H)-one (182 mg, 41%) as a yellow solid: LCMS RT: 2.01 min, MH$^+$: 343.3.

Example 25

2-anilino-7-(hydroxymethyl)-5-methyl-1-phenyl-1,8-naphthyrldin-4(1H)-one

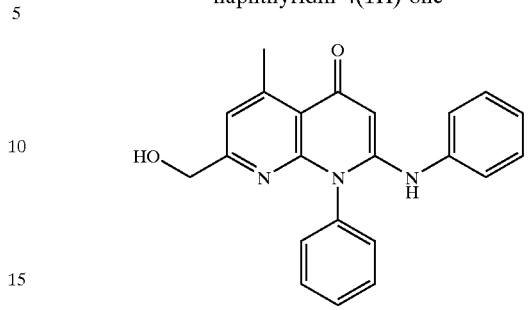

To a 0° C. suspension of ethyl 7-anilino-3-fluoro-5-oxo-8-phenyl-5,8-dihydro-1,8-naphthyridine-2-carboxylate (100.0 mg, 0.25 mmol) in THF (2.5 mL) was added LAH (0.750 mmol, 1M in THF) dropwise over 10 min. After 5 min. the reaction was slowly quenched with EtOAc (10 mL), was left to stir for 15 min and was concentrated in vacuo. The resiude was taken up in CH$_2$Cl$_2$ (10 mL) and 1N HCl (5 mL) and was left to stir for 30 min. The layers were separated and the aqueous layer was extracted with CH$_2$Cl$_2$. The combined organic extracts were washed with brine, dried over MgSO$_4$, and concentrated in vacuo. Trituration with Et$_2$O provided 2-anilino-6-fluoro-7-(hydroxymethyl)-1-phenyl-1,8-naphthyridin-4(1H)-one (55.2 mg, 61%) as a tan solid: LCMS RT: 2.01 min, MH$^+$: 362.3.

Example 26

2-anilino-7-[(4-methoxyphenoxy)methyl]-5-methyl-1-phenyl-1,8-naphthyridin-4(1H)-one

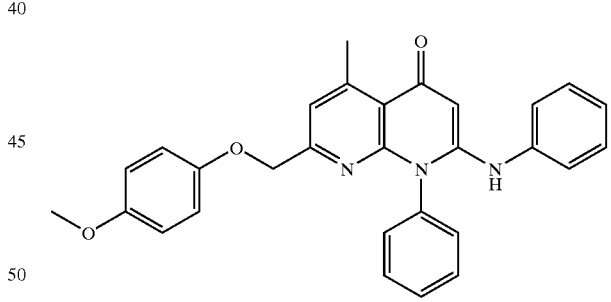

2-anilino-6-fluoro-7-(hydroxymethyl)-1-phenyl-1,8-naphthyridin-4(1H)-one (62 mg, 0.175 mmol) was dissolved in CH$_2$Cl$_2$ (1.2 mL). 4-methoxyphenol (22 mg, 0.175 mmol) was added followed by Ph$_3$P (91.8 mg, 0.35 mmol), and ADDP (88.31 mg, 0.35 mmol). The reaction was left to stir overnight at room temperature under argon. Hexanes (5 mL) were added and the reaction was filtered. The filtrate was concentrated in vacuo. Purification of the residue using Biotage silica gel chromatography eluting with 7:3 to 9:1 EtOAc:Hex provided 2-anilino-6-fluoro-7-[(4-methoxyphenoxy)methyl]-1-phenyl-1,8-naphthyridin-4(1H)-one (30.0 mg, 37%) as a white solid: LCMS RT 2.87 min, MH$^+$: 464.2.

Example 27

7-ethoxy-5-ethyl-2-[methyl (phenyl)ammo]-1-phenyl-1,8-naphthyridin-4(1H)-one

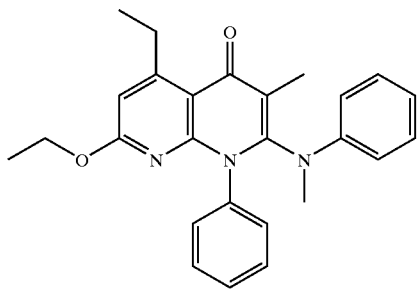

Example 28

2-anilino-7-ethoxy-5-ethyl-3-methyl-1-phenyl-1,8-naphthyridin-4(1H)-one

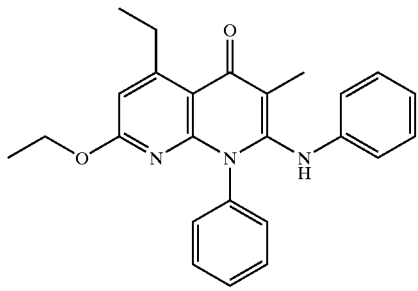

Example 29

7-ethoxy-5-ethyl-3-methyl-2-[methyl(phenyl)amino]-1-phenyl-1,8-naphthyridin-4(1H)-one

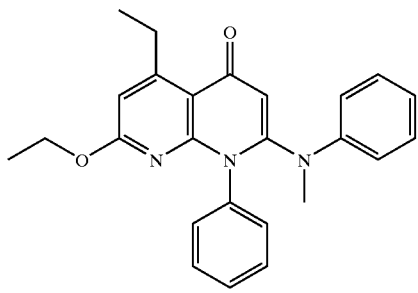

To a suspension of 2,2,6,6-tetramethylpiperidine (153 mg, 0.18 mL, 1.08 mmol) in THF (10 mL) at 0° C., was added n-BuLi via syringe (1.6 M, 0.68 mL, 1.08 mmol) and TMEDA. The reaction mixture was stirred for 1 h under argon. The reaction mixture was cooled to −60° C. using an acetone/dry ice bath and 2-anilino-7-ethoxy-5-methyl-1-phenyl-1,8-naphthyridin-4(1H)-one (100 mg, 0.269 mmol) was added via syringe as a solution in THF (5 mL). The mixture was stirred for 1 h. MeI was added via syringe and the reaction was allowed to warm to room temperature and stirred for 18 h. A saturated aqueous solution of NH₄Cl (20 mL) and EtOAc (20 mL) was added, and the organic layer was separated, dried over MgSO₄ and concentrated in vacuo. The residue was purified by silica gel flash chromatography using 7:3 to 100:0 EtOAc:Hex to give 3 products as follows:

Example 27: (35 mg, 32%), Example 28: (11 mg, 10%), Example 29: (16 mg, 14%).

Example 30

2-anilino-6-fluoro-7-methyl-1-phenyl-1,8-naphthyridin-4(1H)-one

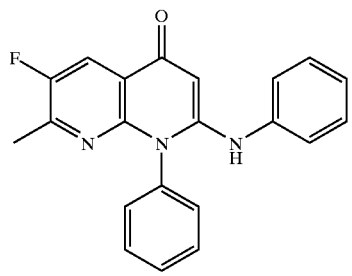

To 2-anilino-7-chloro-6-fluoro-1-phenyl-1,8-naphthyridin-4(1H)-one (100 mg, 0.273 mmol) in THF (5 mL) was added Pd(PPh₃)₄ (13 mg, 0.001 mmol) and methyl zinc chloride (2M, 0.819 mL, 1.64 mmol) and the reaction was heated to 75° C. for 18 h. The reaction was then cooled to room temperature and poured into a solution of EDTA in water (2.5 g/20 mL) and extracted with Et₂O. The organic layer was washed with brine and concentrated in vacuo. The residue was then taken up in MEOH and filtered. The filtrate was concentrated in vacuo to give 2-anilino-6-fluoro-7-methyl-1-phenyl-1,8-naphthyridin-4(1H)-one (83.0 mg, 89%): LCMS RT: 2.43 min, MH⁺: 346.4.

Example 31

Methyl (2E)-3-(7-anilino-2-methyl-5-oxo-8-phenyl-5,8-dihydro-1,8-naphthyridin-3-yl)-2-propenoate

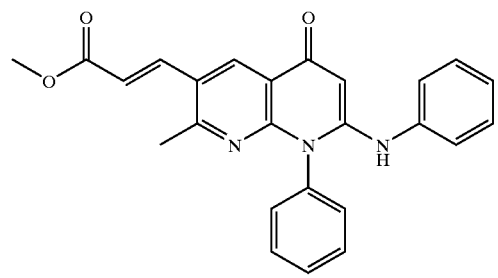

To a suspension of 2-anilino-6-bromo-7-methyl-1-phenyl-1,8-naphthyridin-4(1H)-one (41 mg, 0.1 mmol) in DMF (2.0 mL) were successively added Pd(OAc)₂ (0.70 mg, 0.003 mmol), Ph₃P (5.2 mg, 0.02 mmol), TEA (0.03 mL) and methyl acrylate (17.2 mg, 0.2 mmol). The suspension was heated at 120° C. in a sealed tube for 64 h. The residue obtained after concentration in vacuo was washed with water and extracted with EtOAc. The organic layer was dried over MgSO₄ and concentrated in vacuo. Purification by prep-HPLC provided methyl (2E)-3-(7-anilino-2-methyl-5-oxo-8-phenyl-5,8-dihydro-1,8-naphthyridin-3-yl)-2-propenoate (10.0 mg, 24%): LCMS RT: 2.61 min, MH⁺: 412.3, $R_f$=0.26 (1:1 EtOAc:Hex).

Example 32

(2E)-3-(7-anilino-2-methyl-5-oxo-8-phenyl-5,8-dihydro-1,8-naphthyridin-3-yl)-2-propenoic acid

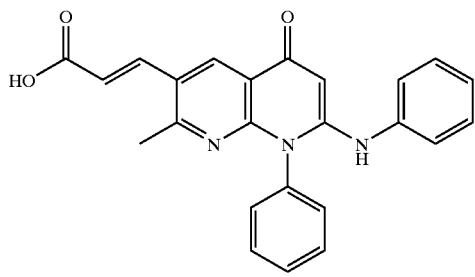

To a suspension of 2-anilino-6-[(E)-3-methoxy-3-oxo-1-propenyl]-7-methyl-1-phenyl-1,8-naphthyridin-4(1H)-one (10 mg, 0.025 mmol) in CH$_3$CN (2.0 mL) was added 1N NaOH (2.0 mL). The suspension was stirred at room temperature for 18 h. The mixture was diluted with water (10 mL) and extracted with EtOAc. The organic layer was dried over MgSO$_4$ and concentrated in vacuo to afford (2E)-3-(7-anilino-2-methyl-5-oxo-8-phenyl-5,8-dihydro-1,8-naphthyridin-3-yl)-2-propenoic acid (6.2 mg, 63%): LCMS RT: 2.37 min, MH$^+$: 398.3, R$_f$=0.51 (EtOAc).

Example 33

3-(7-anilino-2-methyl-5-oxo-8-phenyl-5,8-dihydro-1,8-naphthyridin-3-yl)propanoic acid

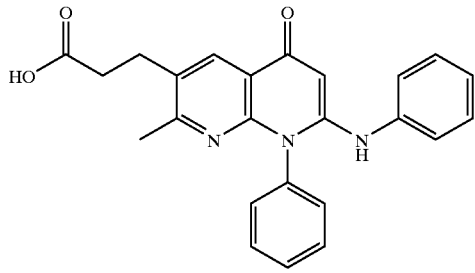

To a stirred suspension of 2-anilino-6-[(E)-3-hydroxy-3-oxo-1-propenyl]-7-methyl-1-phenyl-1,8-naphthyridin-4(1H)-one (40.0 mg, 0.100 mmol) in MeOH (2.0 mL), was added Pd/C (5.3 mg, 10% weight on carbon) under an argon atmosphere, followed by the addition of ammonia formate (19.0 mg, 0.30 mmol) in a single portion. The reaction mixture was heated at reflux for 2 h, cooled and filtered. The filtrate was diluted with water (10 mL) and extracted with EtOAc. The organic layer was dried over MgSO$_4$ and concentrated in vacuo. The residue was washed with water and dried in vacuo to afford 3-(7-anilino-2-methyl-5-oxo-8-phenyl-5,8-dihydro-1,8-naphthyridin-3-yl)propanoicacid (34.5 mg, 86%): LCMS RT: 2.31 min, MH$^+$: 400.4, R$_f$=0.61 (4:1 EtOAc:MeOH).

Example 34

2-anilino-6,7-dimethyl-1-phenyl-1,8-naphthyridin-4(1H)-one

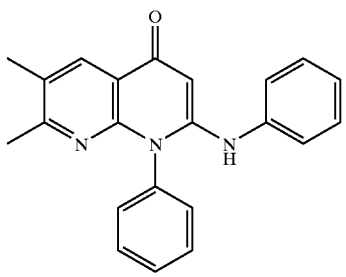

Example 35

2-anilino-7-ethyl-1-(3-methylphenyl)-1,8-naphthyridin-4(1H)-one

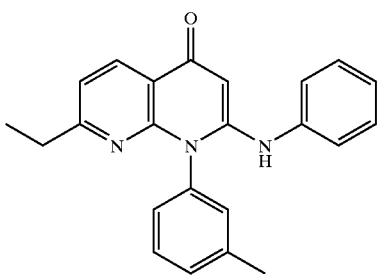

A suspension of 2-anilino-6-bromo-7-methyl-1-phenyl-1,8-naphthyridin-4(1H)-one (203 mg, 0.5 mmol) in THF (10 mL) in an atmosphere of argon was cooled to −78° C. A solution of n-BuLi in hexanes (1.0 mL, 1.6 mmol, 1.6 M) was added and the suspension was stirred for 10 min at 0° C. until it became a clear solution. Excessive MeI (0.2 mL, 3.2 mmol) was added, and the reaction was stirred for another 10 min. The reaction was quenched with saturated aqueous NH$_4$Cl (2.0 mL) and water (10 mL) and the mixture was extracted with EtOAc. The organic layer was dried over MgSO$_4$ and concentrated in vacuo. The residue was purified by prep-HPLC to afford 2-anilino-6,7-dimethyl-1-phenyl-1,8-naphthyridin-4(1H)-one (55 mg, 32%): LCMS RT: 2.33 min, MH$^+$: 342.4, R$_f$=0.39 (EtOAc). 2-anilino-7-ethyl-1-(3-methylphenyl)-1,8-naphthyridin-4(1H)-one (13.3 mg, 7.5%) was also obtained as a side product: LCMS RT: 2.54 min, MH$^+$: 356.3, R$_f$=0.40 (EtOAc). Other electrophiles such as aldehydes, carbon dioxide, disulfides, trifluoroacetates acid chlorides and other alkyl halides can also be used to quench the generated aryl lithium.

Example 36

Ethyl 7-anilino-4-chloro-3-fluoro-5-oxo-8-phenyl-5,8-dihydro-1,8-naphthyridine-2-carboxylate

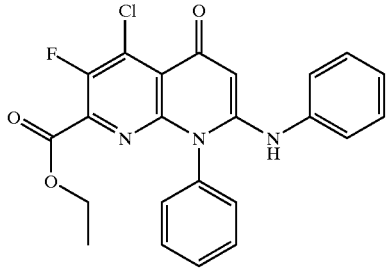

A suspension of ethyl 7-anilino-3-fluoro-5-oxo-8-phenyl-5,8-dihydro-1,8-naphthyridine-2-carboxylate (40.0 mg, 0.099 mmol) in anhydrous THF (10 mL) in an atmosphere of argon was cooled to −78° C. LiHMDS (5 mL, 5 mmol) was then added to the suspension, and the suspension was stirred for 2 h at 0° C. and then cooled to −78° C. and treated with $CCl_2FCClF_2$ (94 mg, 0.5 mmol). The reaction was stirred for another hour at 0° C. before being quenched with saturated aqueous $NH_4Cl$ (2.0 mL) and water (10 mL) and extracted with EtOAc. The organic layer was dried over $MgSO_4$ and concentrated in vacuo. Purification of the residue by prep-HPLC provided Ethyl 7-anilino-4-chloro-3-fluoro-5-oxo-8-phenyl-5,8-dihydro-1,8-naphthyridine-2-carboxylate (13.2 mg, 31%): LCMS RT: 2.80min, $MH^+$: 437.1, $R_f$=0.78 (EtOAc).

Example 37

7-anilino-4-chloro-3-fluoro-N,N-diisopropyl-5-oxo-8-phenyl-5,8-dihydro-1,8-naphthyridine-2-carboxamide

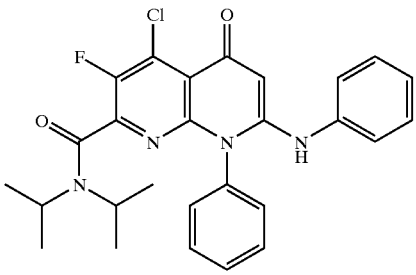

LDA was made by adding n-BuLi (0.31 mL, 0.5 mmol, 1.6 M) to diisopropylamine (50 mg, 0.5 mmol) in THF (15 mL) at −15° C. A suspension of ethyl 7-anilino-3-fluoro-5-oxo-8-phenyl-5,8-dihydro-1,8-naphthyridine-2-carboxylate (40.0 mg, 0.915 mmol) in anhydrous THF (10 mL) in an atmosphere of argon was cooled to −78° C. LDA was added and the suspension was stirred for 2 h at 0° C. and then cooled to −78° C. and treated with $CCl_2FCClF_2$ (94 mg, 0.5 mmol). The reaction was stirred for another hour at 0° C. before being quenched with saturated aqueous $NH_4Cl$ (2.0 mL) and water (10 mL). The aqueous solution was extracted with EtOAc and the organic layer was dried over $MgSO_4$ and concentrated in vacuo. Purification of the residue by prep-HPLC provided 7-anilino-3-bromo4chloro-N,N-diisopropyl-5-oxo-8-phenyl-5,8-dihydro-1,8-naphthyridine-2-carboxamide (20 mg, 41%): LCMS RT: 3.02 min, $MH^+$: 493.3, $R_f$=0.78 (EtOAc).

Example 38

2-[(4-Methylbenzyl)amino]-1-[3-(trifluoromethyl)phenyl]-1,8-naphthyridin-4(1H)-one

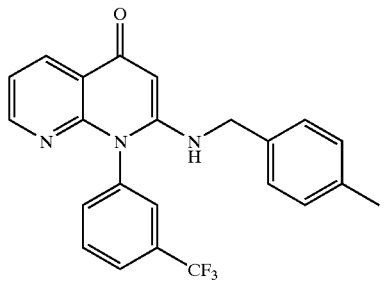

A mixture of 2-amino-1-[3-(trifluoromethyl)phenyl]-1,8-naphthyridin-4(1H)-one (50 mg, 0.16 mmol), $CsCO_3$ (160 mg, 0.49 mmol) and 4-methylbenzyl bromide (35 mg, 0.25 mmol) in THF (3 mL) was heated to 80° C. in a sealed tube for 16 h. The reaction was cooled to room temperature and quenched with water (3 mL). The mixture was extracted with $CH_2Cl_2$ (3×), and the combined organic extracts were dried with $Na_2SO_4$ and concentrated in vacuo. The residue was purified by prep-HPLC (YMC-Pack Pro C18 Column, 150×20 mm I.D.; first run: 20–80% $CH_3CN$ in water, 11 min.; second run: 50–90% MEOH in water, 20 min.) to afford 2-[(4-Methylbenzyl)amino]-1-[3-(trifluoromethyl)phenyl]-1,8-naphthyridin-4(1H)-one (2.2 mg, 3%): LCMS RT: 2.75 min, $MH^+$: 410.2.

The following specific examples are presented to illustrate the invention related to Formula (II) as described herein, but they should not be construed as limiting the scope of the invention in any way.

Intermediate BA:

2,4-dichloro-6-methylnicotinic acid

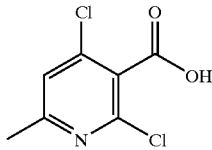

A solution of commercially available (Maybridge) ethyl 2,4-dichloro-6-methylpyridine-3-carboxylate (1.0 g, 4.3 mmol) and NaOH (342 mg, 8.6 mmol) in water (1.7 mL) and MeOH (1.5 mL) was heated to 80° C. for 4 h. The mixture was acidified using 50% $H_2SO_4$ and then filtered. The solid collected was washed with cold water and dried to give of 2,4-dichloro-6-methylpyridine-3-carboxylic acid (582 mg, 66%): LCMS RT: 0.70 min, $MH^+$: 206.2.

Intermediate BB:

3,3-dichloro-1-(2,4-dichloro-6-methyl-3-pyridinyl)-2-propen-1-one

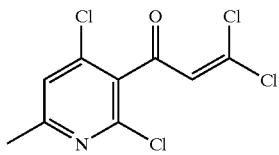

2,4-Dichloro-6-methylnicotinic acid (8.7 g, 43.0 mmol) was mixed with SOCl$_2$ (31 mL). The resulting mixture was heated to 80° C. for 2 h and concentrated in vacuo to give the acid chloride as yellow oil. The oil was then dissolved in CH$_2$Cl$_2$ (10 mL) and the solution was added to a cooled suspension of AlCl$_3$ (21.3 g, 160.0 mmol) in CH$_2$Cl$_2$ (50 mL) at 0° C. After 2 h at 0° C., vinylidene chloride (2.16 mL, 80.0 mmol) was added to the above suspension. The resulting mixture was then left to warm to room temperature and stirred overnight. The reaction mixture was poured into crushed ice and the resulting mixture was extracted with CH$_2$Cl$_2$ The combined organic layers were cooled to 0° C. and TEA (14.9 mL) was added. After 1 h of stirring, the organic layer was washed with 10% aqueous HCl (100 mL), water (200 mL), brine (100 mL), and dried over Na$_2$SO$_4$. Solvents were removed in vacuo and the residue was purified by passing it through a pad of silica gel with 15% EtOAc in Hex as the eluent to provide 3,3-dichloro-1-(2,4-dichloro-6-methyl-3-pyridinyl)-2-propen-1-one (5.2 g, 46%): LCMS RT: 3.13 min, MH$^+$: 284.6. Alternatively, the acid chloride could be prepared by using oxalyl chloride with a catalytic amount of DMF.

Intermediate BC:

3,3-dianilino-1-(2,4-dichloro-6-methyl-3-pyridinyl)-2-propen-1-one

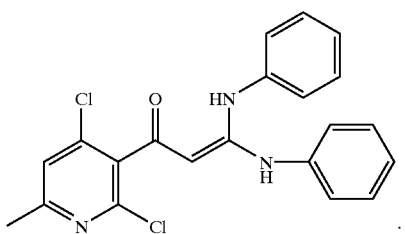

A solution of 3,3-dichloro-1-(2,4)-dichloro-6-methyl-3-pyridinyl)-2-propen-1-one (5.2 g, 18.0 mmol) in 1,4-dioxane (25 mL) was cooled to 0° C. and aniline (5.1 mL, 55.0 mmol) and TEA (7.7 mL, 55.0 mmol) were added dropwise. The reaction mixture was stirred at 0° C. for 1 h and at room temperature for 2 h. The solvents were removed in vacuo. The residue was purified by passing it through a pad of silica gel with EtOAc:Hex (1:5) as the eluent to provide 3,3-dianilino-1-(2,4-dichloro-6-methyl-3-pyridinyl)-2-propen-1-one (7.1 g, 99%): LCMS RT: 3.06 min, MH$^{30}$: 398.7.

Intermediates BA1, BB1, BC1, BA2, BB2, BC2 can be prepared in the same manner shown above for BA, BB and BC starting with the appropriate known starting nicotinic acid (*Eur. J. Org. Chem.* 2001, 1371).

Intermediate BA1:

4,6-dichloronicotinic acid

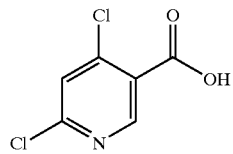

Intermediate BB1:

3,3-dichloro-1-(4,6-dichloro-3-pyridinyl)-2-propen-1-one

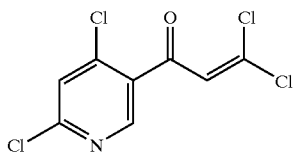

Intermediate BC1:

3,3-dianilino-1-(4,6-dichloro-3-pyridinyl)-2-propen-1-one

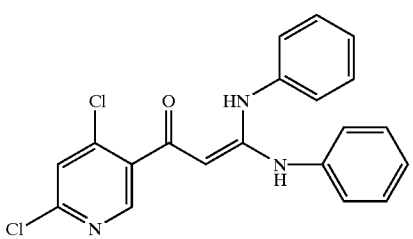

Intermediate BA2:

4,5-dichloronicotinic acid

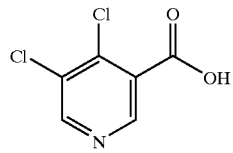

Intermediate BB2:

3,3-dichloro-1-(4,5-dichloro-3-pyridinyl)-2-propen-1-one

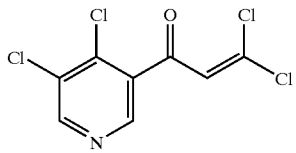

Intermediate BC2:

3,3-dianilino-1-(4,5-dichloro-3-pyridinyl)-2-propen-1-one

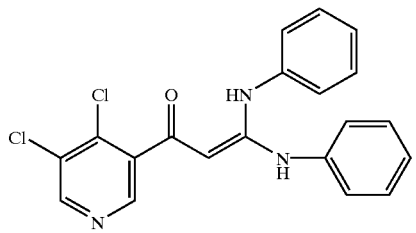

Example 39

2-anilino-5-chloro-7-methyl-1-phenyl-1,6-naphthyridin-4(1H)-one

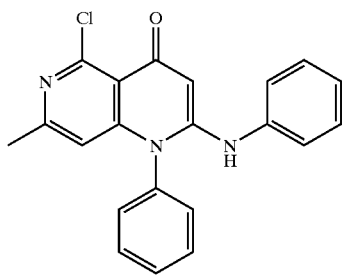

A mixture of 3,3-dianilino-1-(2,4-dichloro-6-methyl-3-pyridinyl)-2-propen-1-one (100 mg, 0.25 mmol) and t-BuOK (42 mg, 0.38 mmol) in anhydrous dioxane (4 mL) was heated to 80° C. for 4 h. The solvent was removed in vacuo and the residue was dissolved in EtOAc. The solution was washed with water and brine, dried over MgSO$_4$, and concentrated in vcaco. Silica gel flash chromatography of the residue using 1:1 EtOAc:Hex gave 2-anilino-5-chloro-7-methyl-1-phenyl-1,8-naphthyridin-4(1H)-one (13 mg, 14%): LCMS RT: 2.47 min, MH$^+$: 362 and 2-anilino-5-chloro-7-methyl-1-phenyl-1,6-naphthyridin-4(1H)-one (68 mg, 75%): LCMS RT: 2.24 min, MH$^+$: 362.3. Alternatively, the cyclization could be achieved by using other bases such as NaH and other aprotic solvents such as THF and DMF.

Examples 40 and 41 can be prepared in the same manner as that for Example 39 above.

Example 40

2-anilino-7-chloro-1-phenyl-1,6-naphthyridin-4(1H)-one

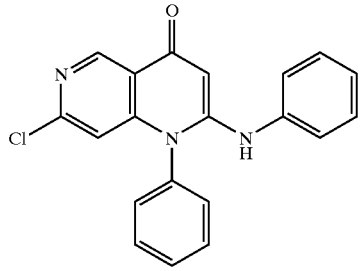

Example 41

2-anilino-8-chloro-1-phenyl-1,6-naphthyridin-4(1H)-one

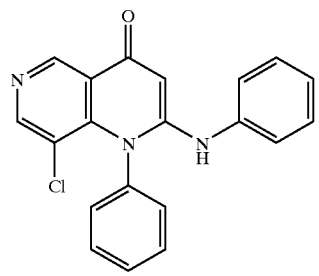

Example 42

2-anilino-5-chloro-7-methyl-1-phenyl-1,6-naphthyridin-4(1H)-one

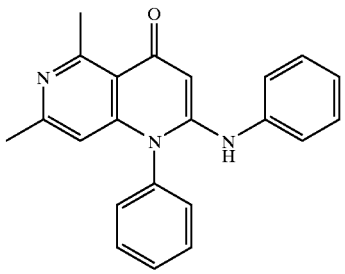

To a solution of 2-anilino-5-chloro-7-methyl-1-phenyl-1,6-naphthyridin-4(1H)-one (80 mg, 0.22 mmol) in THF (3mL) was added Ni(dppp)Cl$_2$ (24 mg, 0.044 mmol) at room temperature. After stirring for a few minutes MeMgBr (3M , 0.59 mL, 1.76 mmol) was added and the mixture was allowed to stir for 24 h. The mixture was quenched with 1N HCl and extracted with EtOAc. The organic layer was washed with brine, dried over MgSO$_4$, and concentrated in vacuo. Purification by reverse-phase preparative HPLC (10% CH$_3$CN in water with 0.1% TFA to 95% CH$_3$CN in water, 10 mL/min, 10 min) provided 2-anilino-5,7-dimethyl-1-phenyl-1,6-naphthyridin-4(1H)-one (31 mg, 40%): LCMS RT: 1.51 min, MH$^+$: 342.4.

Example 43

2-anilino-5-(dimethylamino)-7-methyl-1-phenyl-1,6-naphthyridin-4(1H)-one

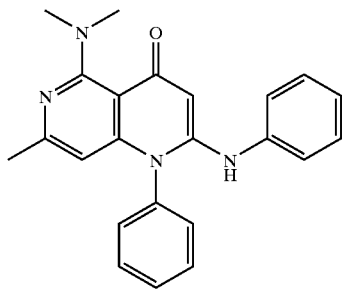

A mixture of 2-anilino-5-chloro-7-methyl-1-phenyl-1,6-naphthyridin-4(1H)-one (80 mg, 0.22 mmol) and dimethyl amine (3M in THF, 0.73 mL, 2.20 mmol) in dioxane (3 mL) was heated to 80° C. for 24 h. The reaction mixture was cooled, concentrated in vacuo, diluted with water and the resulting mixture was extracted with EtOAc. The combined organic extracts were washed with brine, dried over $Na_2SO_4$, and concentrated in vacuo to give 2-anilino-5-(dimethylamino)-7-methyl-1-phenyl-1,6-naphthyridin-4(1H)-one (74 mg, 91%): LCMS RT: 1.86 min, $MH^+$: 371.3

Example 44

Ethyl[(2-anilino-7-methyl-4-oxo-1-phenyl-1,4-dihydro-1,6-naphthyridin-5-yl)sulfanyl]acetate

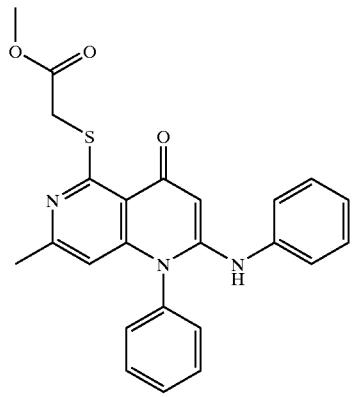

A solution of 2-anilino-5-chloro-7-methyl-1-phenyl-1,6-naphthyridin-4(1H)-one (200 mg, 0.55 mmol) in EtOH (10 mL) was added ethyl 2-mercaptoacetate (0.12 mL, 1.10 mmol) and TEA (0.23 mL, 1.65 mmol). The reaction was heated at reflux for 24 h. The reaction mixture was cooled, concentrated in vacuo, diluted with water and extracted with EtOAc. The combined organic extracts were washed with water, brine, and dried over $Na_2SO_4$. Solvents were removed in vacuo and the residue was purified by reverse-phase preparative HPLC (10% $CH_3CN$ in water with 0.1% TFA to 95% $CH_3CN$ in water, 10 mL/min, 10 min) to provide ethyl[(2-anilino-7-methyl-4-oxo-1-phenyl-1,4-dihydro-1,6-naphthyridin-5-yl)sulfanyl]acetate (120 mg, 49%): LCMS RT: 3.07 min, $MH^{30}$: 446.2.

Example 45

[(2-anilino-7-methyl-4-oxo-1-phenyl-1,4-dihydro-1,6-naphthyridin-5-yl)sulfanyl]acetic acid

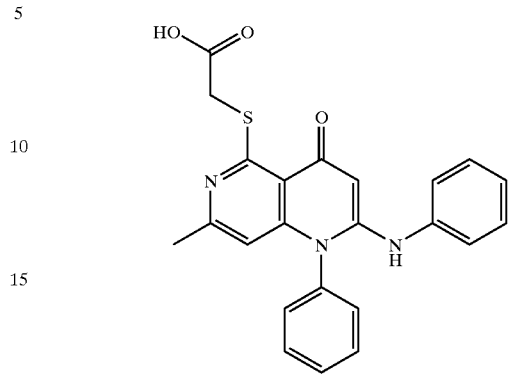

Aqueous NaOH (2N, 1 mL) was added to a stirred solution of ethyl[(2-anilino-7-methyl-4-oxo-1-phenyl-1,4-dihydro-1,6-naphthyridin-5-yl)sulfanyl]acetate (100 mg, 0.23 mmol) in EtOH (8 mL) at room temperature. The mixture was allowed to stir for 4 h and was concentrated in vacuo. The reaction mixture was acidified with 1N HCl and extracted with $CH_2Cl_2$. The organic layer was dried over $MgSO_4$ and concentrated in vacuo. Purification by reverse-phase preparative HPLC (10% $CH_3CN$ in water with 0.1% TFA to 95% $CH_3CN$ in water, 10 mL/min, 10 min) provided [(2-anilino-7-methyl-4-oxo-1-phenyl-1,4-dihydro-1,6-naphthyridin-5-yl)sulfanyl]acetic acid (56 mg, 60%): LCMS RT: 2.61 min, $MH^{30}$: 418.2.

Example 46

Ethyl N-(2-anilino-7-methyl-4-oxo-1-phenyl-1,4-dihydro-1,6-naphthyridin-5-yl)glycinate

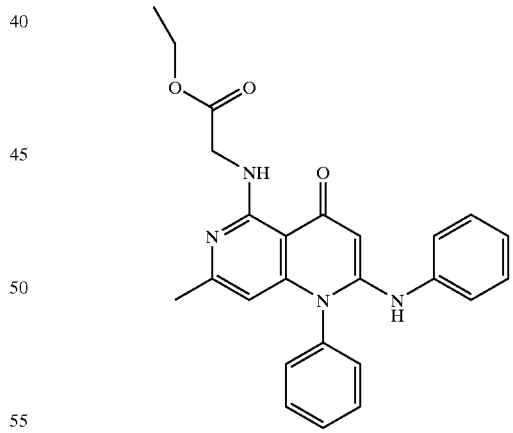

To a solution of 2-anilino-5-chloro-7-methyl-1-phenyl-1,6-naphthyridin-4(1H)-one (80 mg, 0.22 mmol) in EtOH (8 mL) was added glycine ethyl ester hydrochloride (46 mg, 0.44 mmol) and TEA (0.23 mL, 1.65 mmol). The reaction was heated at reflux for 3 d. The reaction mixture was cooled, concentrated in vacuo, diluted with water and extracted with EtOAc. The combined organic extracts were washed with water, brine, dried over $Na_2SO_4$ and concentrated in vacuo. The residue was purified by reverse-phase preparative HPLC (10% $CH_3CN$ in water with 0.1% TFA to 95% CH₃CN in water, 10 mL/min, 10 min) to provide ethyl N-(2-anilino-7-methyl-4-oxo-1-phenyl-1,4-dihydro-1,6-naphthyridin-5-yl)glycinate (43 mg, 46%): LCMS RT: 2.16 min, MH⁺: 429.3.

Example 47

2-[(2-anilino-7-methyl-4-oxo-1-phenyl-1,4-dihydro-1,6-naphthyridin-5-yl)sulfanyl]-N-cyclopropylacetamide

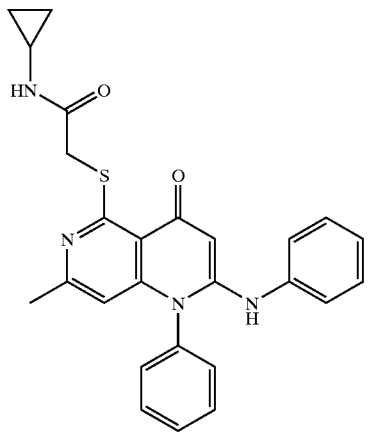

To a mixture of [(2-anilino-7-methyl-4-oxo-1-phenyl-1,4-dihydro-1,6-naphthyridin-5-yl)sulfanyl]acetic acid (20 mg, 0.05 mmol), EDCI (18 mg, 0.10 mmol), HOBT (13 mg, 0.10 mmol) and cyclopropylamine (0.004 mL, 0.06 mmol) in CH₂Cl₂ (5 mL) was added TEA (0.02 mL, 0.14 mmol). The reaction solution was stirred at room temperature for 24 h before the mixture was diluted with CH₂Cl₂, washed with 0.5N HCl, saturated aqueous NaHCO₃, brine and dried over Na₂SO₄. Solvents were removed in vacuo and the residue was purified by reverse-phase preparative HPLC (10% CH₃CN in water with 0.1% TFA to 95% CH₃CN in water, 10 mL/min, 10 min) to provide 2-[(2-anilino-7-methyl-4-oxo-1-phenyl-1,4-dihydro-1,6-naphthyridin-5-yl)sulfanyl]-N-cyclopropylacetaide (13 mg, 59%): LCMS RT: 2.55 min, MH⁺: 457.1.

Example 48

2-anilino-7-methyl-1-phenyl-5-(2,2,2-trifluoroethoxy)-1,6-naphthyridin-4(1H)-one

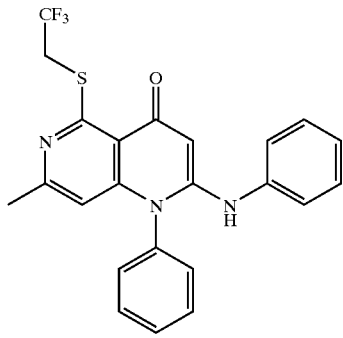

Trifluoroethanol (0.08 mL, 1.1 mmol) was added to a suspension of NaH (60% oil dispersion, 44 mg, 1.1 mmol) in DMSO (4 mL) at 0° C., and the mixture was heated at 60° C. for 1 h. The mixture was cooled to room temperature and a solution of 2-anilino-5-chloro-7-methyl-1-phenyl-1,6-naphthyridin-4(1H)-one (200 mg, 0.55 mmol) in DMSO (2 mL) was added. The resulting mixture was stirred at 50° C. for 16 h. The reaction mixture was cooled, poured into ice water and extracted with CH₂Cl₂. The organic layer was washed with brine, dried over MgSO₄, and concentrated in vacuo. The residue was purified by a Biotage silica gel chromatography (2:1 EtOAc:Hex) to provide 2-anilino-7-methyl-1-phenyl-5-(2,2,2-trifluoroethoxy)-1,6-naphthyridin-4(1H)-one (159 mg, 68%): LCMS RT: 2.65 min, MH⁺: 426.4. This transformation can be accomplished by using other aprotic solvents such as DMF, THF and dioxane with temperatures appropriate for these solvents. Commercially available alkoxides can also be used in the absence of base.

Example 49

2-anilino-7-methyl-4-oxo-1-phenyl-1,4-dihydro-1,6-naphthyridine-5-carboxylic acid

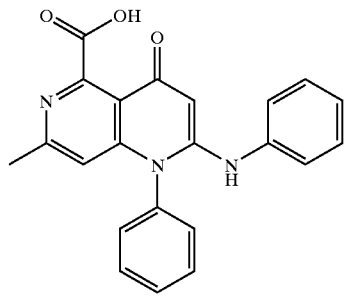

2-Anilino-5-chloro-7-methyl-1-phenyl-1,6-naphthyridin-4(1H)-one (1.0 g, 2.8 mmol), DPPP (64 mg, 0.15 mmol), Pd(OAc)₂ (31 mg, 0.14 mmol), Cs₂CO₃ (580 mg, 4.20 mmol) were dissolved in EtOH (10 mL) and DMF (10 mL). A balloon filled with CO was attached to the flask and the solution was stirred vigorously. The flask was purged with CO for 5 min before it was heated to 70° C. After 4 h the mixture was cooled to room temperature and diluted with EtOAc. The mixture was washed with water, brine, and dried over Na₂SO₄. Solvents were removed in vacuo and the residue was triturated with Et₂O to give ethyl 2-anilino-7-methyl-4-oxo-1-phenyl-1,4-dihydro-1,6-naphthyridine-5-carboxylate (800 mg, 71%). The ethyl ester was then dissolved in MeOH (5 mL), and THF (20 mL). To this stirring solution was added KOH (3N, 10 mL) and the mixture was stirred at room temperature for 6 h before it was extracted with Et₂O. The aqueous layer was acidified with 2N HCl to pH=1 and the product precipitated out of the solution. The solid was filtered and dried to give 2-anilino-7-methyl-4-oxo-1-phenyl-1,4-dihydro-1,6-naphthyridine-5-carboxylic acid as a white solid (683 mg, 92%): LCMS RT: 1.75 min, MH⁺: 372.9.

Example 50

2-anilino-N-methoxy-N,7-dimethyl-4-oxo-1-phenyl-1,4-dihydro-1,6-naphthyridine-5-carboxamide

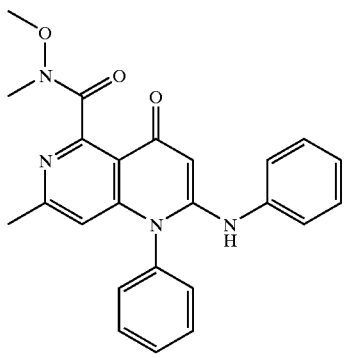

2-anilino-7-methyl-4-oxo-1-phenyl-1,4-dihydro-1,6-naphthyridine-5-carboxylic acid (80 mg, 0.22 mmol), N,O-dimethylhydroxylamine hydrochloride (64 mg, 0.66 mmol), HOBT (89 mg, 0.66 mmol) and EDCI (126 mg, 0.66 mmol) were dissolved in $CH_2Cl_2$ (9 mL). To this solution was added TEA (120 uL, 0.88 mmol). The reaction was stirred for 1 h and was diluted with $CH_2Cl_2$, washed with 0.5N HCl, saturated $NaHCO_3$, and brine. The organic layer was collected, dried over $Na_2SO_4$, and concentrated in vacuo. The solid obtained was triturated with $Et_2O$ and dried to give 2-anilino-N-methoxy-N,7-dimethyl-4-oxo-1-phenyl-1,4-dihydro-1,6-naphthyridine-5-carboxamide as a light yellow solid (50 mg, 55%): LCMS RT: 2.08 min, $MH^+$: 414.9. This transformation can also be accomplished by coupling the appropriate amine with the corresponding acid chloride.

Example 51

5-acetyl-2-anilino-7-methyl-1-phenyl-1,6-naphthyridin-4(1H)-one

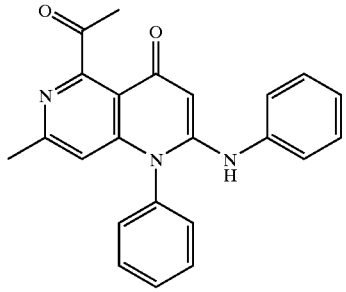

2-Anilino-N-methoxy-N,7-dimethyl-4-oxo-1-phenyl-1,4-dihydro-1,6-naphthyridine-5-carboxamide (60 mg, 0.14 mmol) was suspended in THF (5 mL). To this stirring suspension at 0° C. was added MeMgBr (0.19 mL, 0.56 mmol, 3M in $Et_2O$). The reaction was stirred at room temperature for 6 h and quenched with saturated aqueous $NH_4Cl$, diluted with EtOAc, and washed with brine. The organic layer was collected, dried over $Na_2SO_4$, and concentrated in vacuo. The residue was purified by Biotage silica gel chromatography using EtOAc as the eluent to provide 5-acetyl-2-anilino-7-methyl-1-phenyl-1,6-naphthyridin-4(1H)-one as a light yellow solid (34 mg, 66%): LCMS RT: 2.20 min, $MH^+$: 370.4.

Example 52

2-anilino-7-methyl-1-phenyl-5-(trifluoromethyl)-1,6-naphthyridin-4(1H)-one

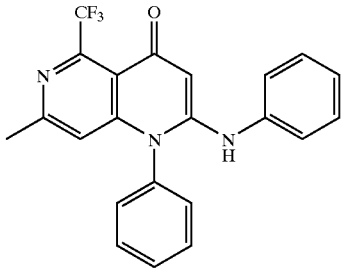

Example 53

7-methyl-2-[methyl(phenyl)amino]-1-phenyl-5-(trifluoromethyl)-1,6-naphthyridin-4(1H)-one

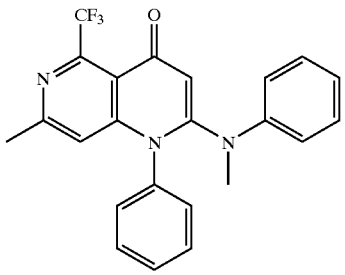

A mixture of methyl fluorosulphonyldifluoroacetate (0.78 mL, 6.10 mmol) and 2-anilino-5-chloro-7-methyl-1-phenyl-1,6-naphthyridin-4(1H)-one (2.0 g, 5.50 mmol) in DMF (15 mL) was mixed with Copper(I) iodide (1.05 g, 5.50 mmol) at 80° C. for 6 h before the mixture was filtered and concentrated in vacuo. The residue was diluted with $CH_2Cl_2$, washed with water and brine, and dried over $MgSO_4$. Solvents were removed in vacuo and the residue was purified by Biotage silica gel chromatography using 1:1 EtOAc:Hex to provide 2-anilino-7-methyl-1-phenyl-5-(trifluoromethyl)-1,6-naphthyridin-4(1H)-one as a light yellow solid (477 mg 22%): LCMS RT: 2.68 min, $MH^+$: 396.2. 7-Methyl-2-[methyl(phenyl)amino]-1-phenyl-5-(trifluoromethyl)-1,6-naphthyridin-4(1H)-one (270 mg, 12%) was also isolated: LCMS RT: 2.32 min, $MH^+$: 410.4.

Example 54

2-anilino-7-methyl-1-phenyl-1,6-naphthyridin-4(1H)-one

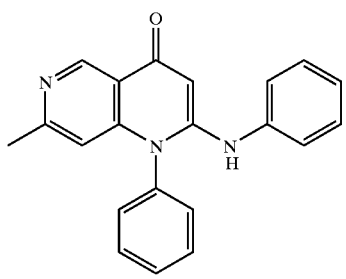

To a flask containing 2-anilino-5-chloro-7-methyl-1-phenyl-1,6-naphthyridin-4(1H)-one (10 mg, 0.03 mmol) in EtOAc (2 mL) and EtOH (2 mL) at room temperature was added a drop of TEA, and Pd/C (10 weight % on activated carbon Degussa type E101, 2 mg). The system was purged with $H_2$ and left stirring at room temperature overnight. The reaction mixture was filtered and concentrated in vacuo to provide 2-anilino-7-methyl-1-phenyl-1,6-naphthyridin-4(1H)-one (8 mg, 91%): LCMS RT: 1.22 min, $MH^+$: 328.3.

Example 55
2-anilino-5-(4-methoxyphenyl)-7-methyl-1-phenyl-1,6-naphthyridin-4(1H)-one

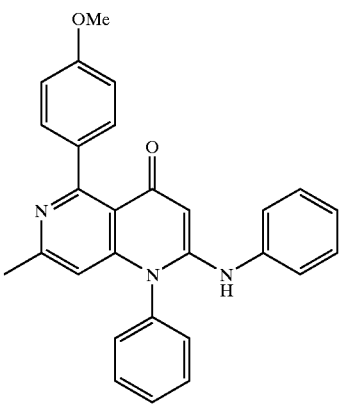

An 8-mL amber vial was charged with 2-anilino-5-chloro-7-methyl-1-phenyl-1,6-naphthyridin-4(1H)-one (72 mg, 0.20 mmol), 4-methoxyphenylboronic acid (3–6 mg, 0.24 mmol), Pd(OAc)$_2$ (1 mg, 0.02 mmol), Ph$_3$P (5 mg, 0.02 mmol), K$_2$CO$_3$ (110 mg, 0.8 mmol, 2 M), and DME (2 mL). The mixture was heated to 90° C. 2 d. Water was added to the reaction mixture and it was extracted with CH$_2$Cl$_2$. The organic layer was dried over Na$_2$SO$_4$. The residue after concentration in vacuo was triturated with Et$_2$O to provide 2-anilino-5-(4-methoxyphenyl)-7-methyl-1-phenyl-1,6-naphthyridin-4(1H)-one (54 mg, 63%): LCMS RT: 1.92 min, $MH^+$: 434.5.

Utilizing the above described procedures for intermediates and examples alone or in combination, a variety of Formula I compounds were prepared using the appropriate starting material and the representative procedure described. These results are summarized in Table 1A.

TABLE 1A

| Example | Structure | LCMS RT (min) | [M + H] | Representative Procedure |
|---|---|---|---|---|
| 56 | 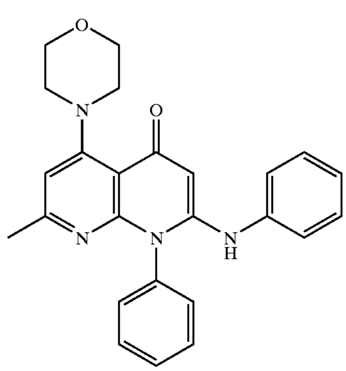 | 2.07 | 413.4 | Intermediate Z, AA, AB and Example 16, 2 |

TABLE 1A-continued

| Example | Structure | LCMS RT (min) | [M + H] | Representative Procedure |
|---|---|---|---|---|
| 57 | 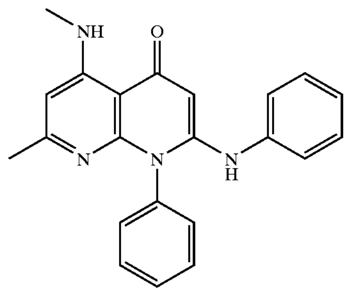 | 1.85 | 357.3 | Intermediate Z, AA, AB and Example 16, 2 |
| 58 | 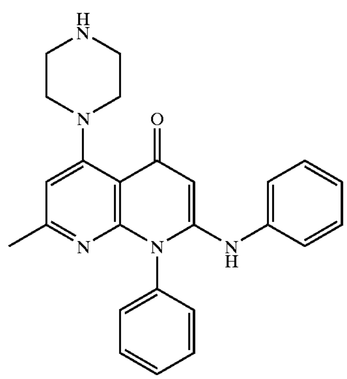 | 1.67 | 412.2 | Intermediate 7, AA, AB and Example 16, 2 |
| 59 | 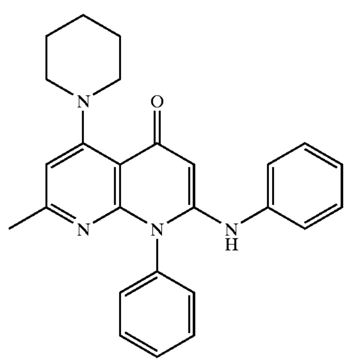 | 2.18 | 411.4 | Intermediate Z, AA, AB and Example 16, 2 |
| 60 | 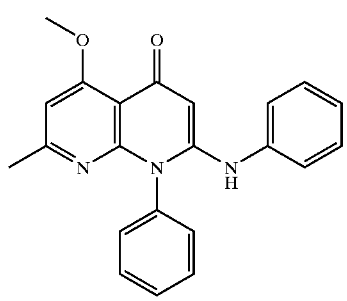 | 2.02 | 358.4 | Intermediate Z, AA, AB and Example 16, 9 |

TABLE 1A-continued

| Example | Structure | LCMS RT (min) | [M + H] | Representative Procedure |
|---|---|---|---|---|
| 61 | 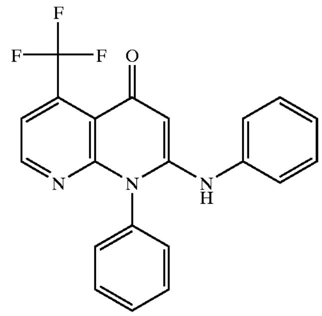 | 2.54 | 382.3 | Intermediate F, G, H, I, J and Example 1 |
| 62 | 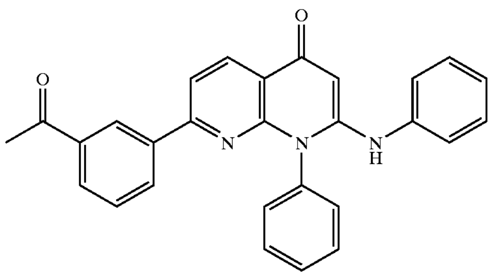 | 2.58 | 432.4 | Intermediate O, P, Q, R and Example 4 |
| 63 | 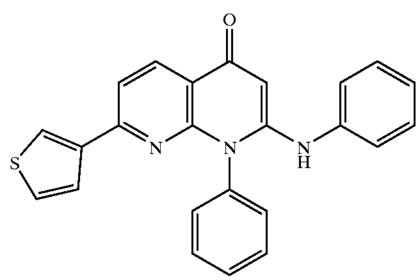 | 2.63 | 296.3 | Intermediate O, P, Q, R and Example 4 |
| 64 | 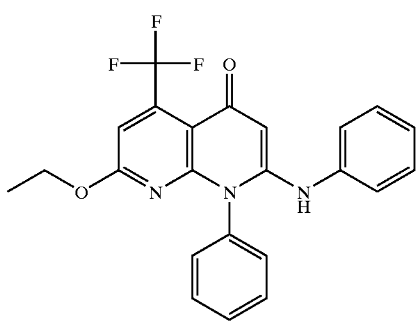 | 2.89 | 426.2 | Intermediate F, G, H, I, J and Example 9 |
| 65 | 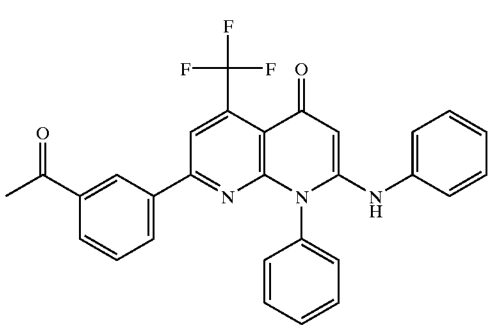 | 3.00 | 426.2 | Intermediate Intermediate F, G, H, I, J and Example 4 |

TABLE 1A-continued

| Example | Structure | LCMS RT (min) | [M + H] | Representative Procedure |
|---------|-----------|---------------|---------|--------------------------|
| 66 | 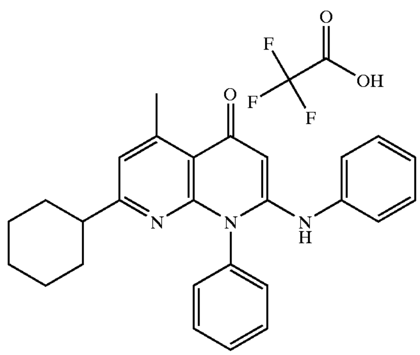 | 3.02 | 410.4 | Intermediate A, B, C, D, E and Example 5 |
| 67 | 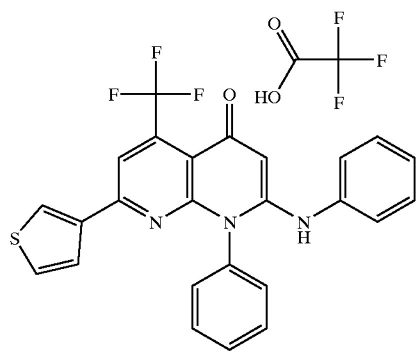 | 3.00 | 464.2 | Intermediate F, G, H, I, J and Example 4 |
| 68 | 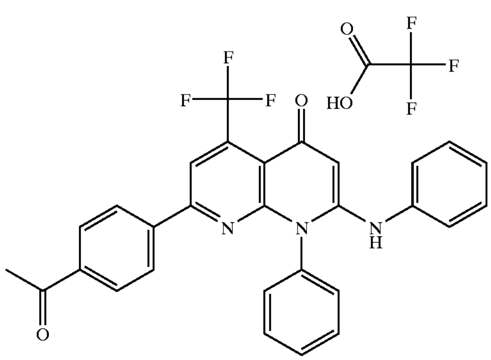 | 2.98 | 500.3 | Intermediate F, G, H, I, J and Example 4 |
| 69 | 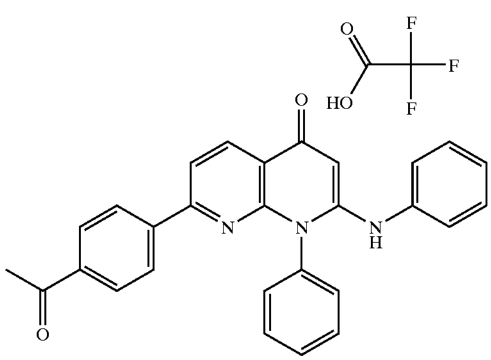 | 2.57 | 432.3 | Intermediate O, P, Q, R and Example 4 |

TABLE 1A-continued

| Example | Structure | LCMS RT (min) | [M + H] | Representative Procedure |
|---|---|---|---|---|
| 70 | 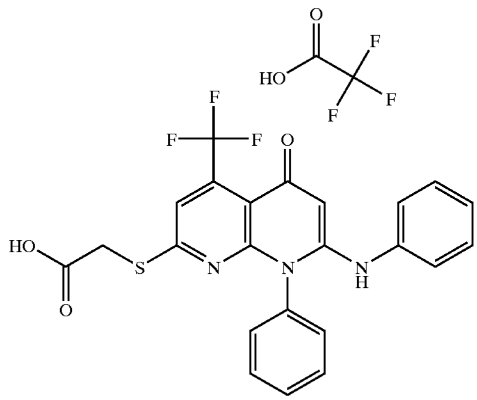 | 2.50 | 471.1 | Intermediate F, G, H, I, J and Example 6, 7 |
| 71 | 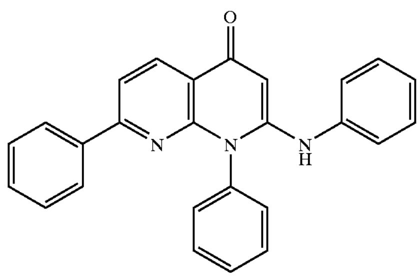 | 2.73 | 390.4 | Intermediate O, P, Q, R and Example 4 |
| 72 | 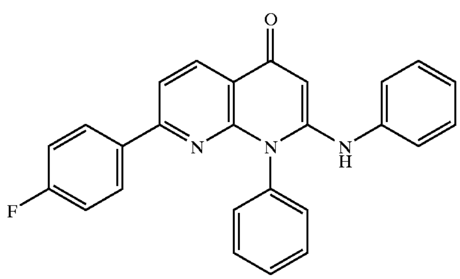 | 2.73 | 408.5 | Intermediate O, P, Q, R and Example 4 |
| 73 | 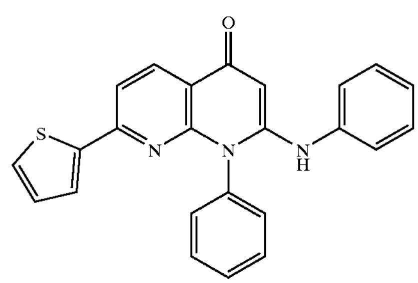 | 3.30 | 396.4 | Intermediate O, P, Q, R and Example 4 |
| 74 | 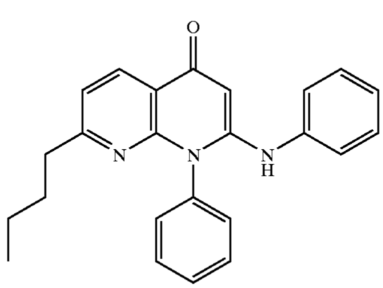 | 3.41 | 370.4 | Intermediate O, P, Q, R and Example 5 |

TABLE 1A-continued

| Example | Structure | LCMS RT (min) | [M + H] | Representative Procedure |
|---------|-----------|---------------|---------|--------------------------|
| 75 | 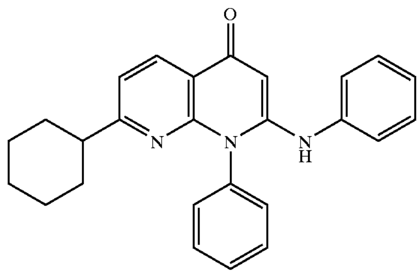 | 3.56 | 396.5 | Intermediate O, P, Q, R and Example 5 |
| 76 | 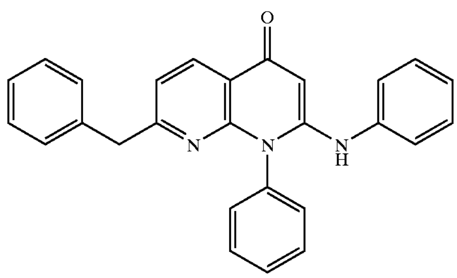 | 3.39 | 404.4 | Intermediate O, P, Q, R and Example 5 |
| 77 | 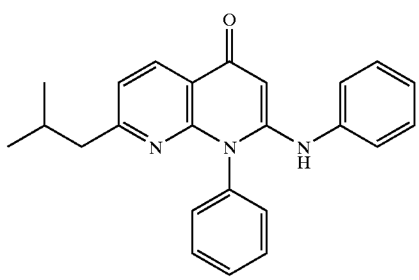 | 2.69 | 370.3 | Intermediate O, P, Q, R and Example 5 |
| 78 | 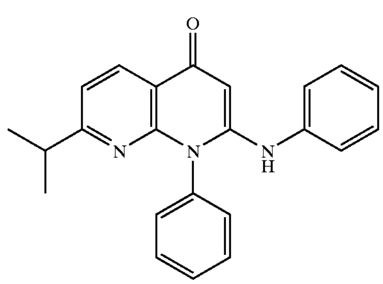 | 2.59 | 356.3 | Intermediate O, P, Q, R and Example 5 |
| 79 | 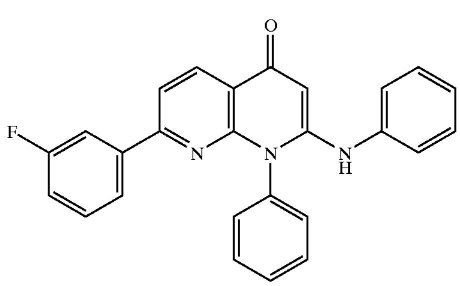 | 2.74 | 408.4 | Intermediate O, P, Q, R and Example 4 |

TABLE 1A-continued

| Example | Structure | LCMS RT (min) | [M + H] | Representative Procedure |
|---------|-----------|---------------|---------|--------------------------|
| 80 | 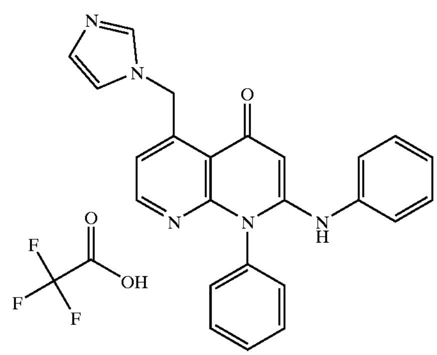 | 1.60 | 394.0 | Intermediate A, B, C, D, E and Example 1, 10, 11 |
| 81 | 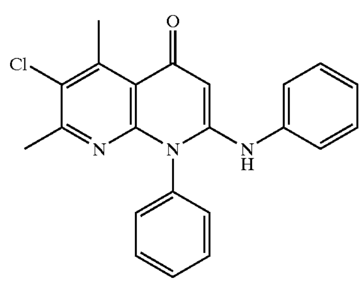 | 2.88 | 376.4 | Intermediate S, T, U, W and Example 15 |
| 82 | 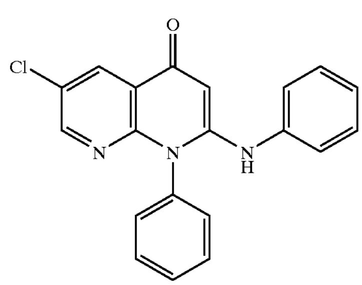 | 2.42 | 348.3 | Intermediate S, T, U, W and Example 15 |
| 83 | 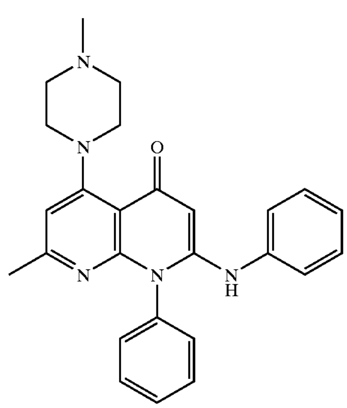 | 1.69 | 426.2 | Intermediate Z, AA, AB and Example 16, 2 |

TABLE 1A-continued

| Example | Structure | LCMS RT (min) | [M + H] | Representative Procedure |
|---------|-----------|---------------|---------|--------------------------|
| 84 | 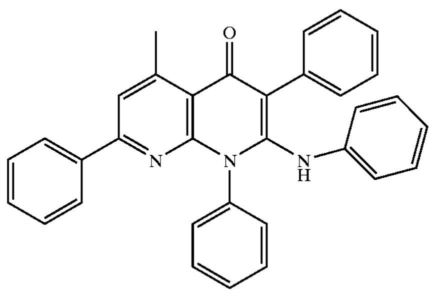 | 3.87 | 480.4 | Intermediate A, B, C, D, E, AL and Example 4 |
| 85 | 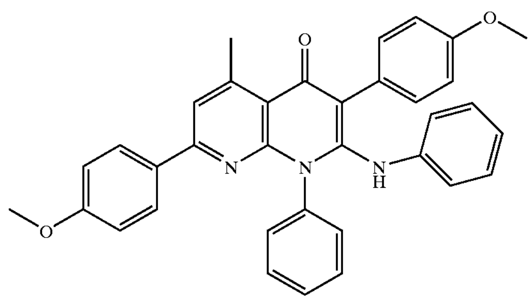 | | | Intermediate A, B, C, D, E, AL and Example 4 |
| 86 | 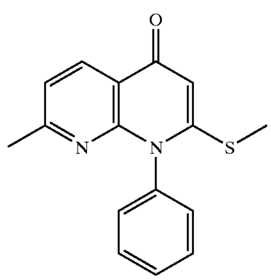 | 2.43 | 283.6 | Intermediate S, T, V and Example 15 |
| 87 | 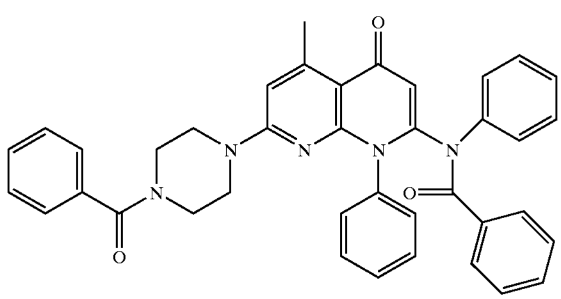 | 2.82 | 620.4 | Intermediate A, B, C, D, E and Example 2, 13 |
| 88 | 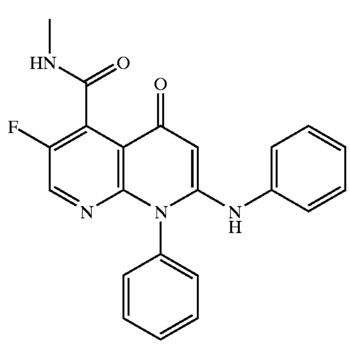 | 1.86 | 389.1 | Intermediate K, L, M, N, AM, and Example 1, 13 |

TABLE 1A-continued

| Example | Structure | LCMS RT (min) | [M + H] | Representative Procedure |
|---|---|---|---|---|
| 89 | 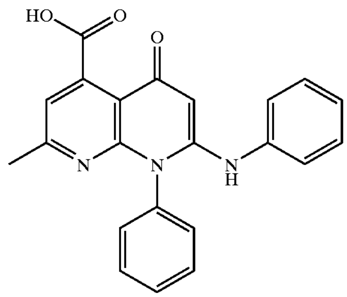 | 2.56 | 372.3 | Intermediate Z, AA, AB and Example 16, 17, 7 |
| 90 | 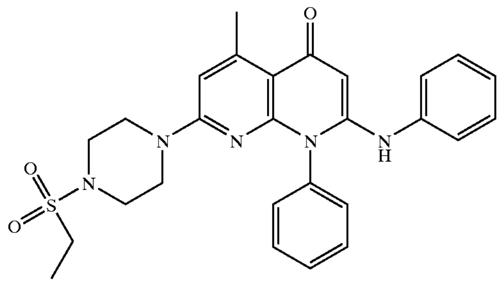 | 2.41 | 504.2 | Intermediate A, B, C, D, E and Example 2, 12 |
| 91 | 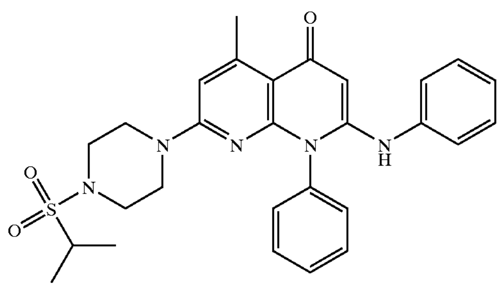 | 2.50 | 518.3 | Intermediate A, B, C, D, E and Example 2, 12 |
| 92 | 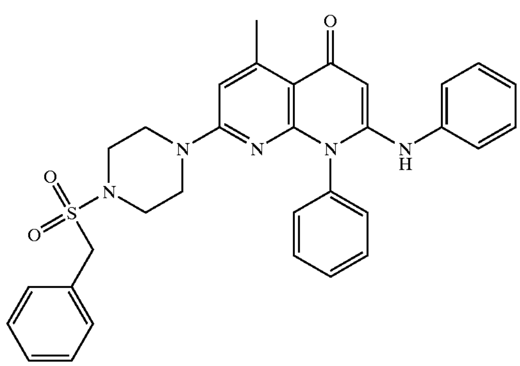 | 2.71 | 566.3 | Intermediate A, B, C, D, E and Example 2, 12 |
| 93 | 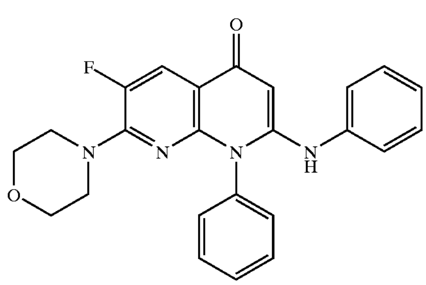 | 2.54 | 417.4 | Intermediate K, L, M, N, and Example 2 |

TABLE 1A-continued

| Example | Structure | LCMS RT (min) | [M + H] | Representative Procedure |
|---|---|---|---|---|
| 94 | 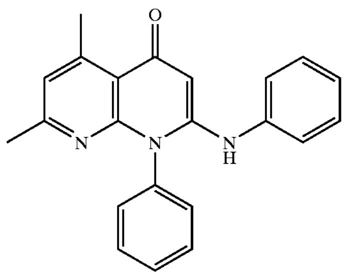 | 2.27 | 342.4 | Intermediate S, T, U, W and Example 15 |
| 95 | 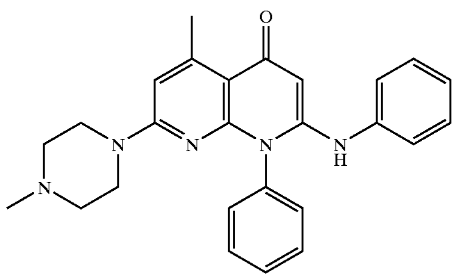 | 1.71 | 426.2 | Intermediate A, B, C, D, E and Example 2 |
| 96 | 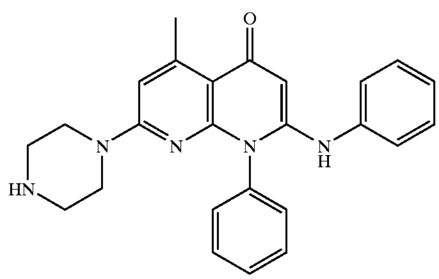 | 1.74 | 412.1 | Intermediate A, B, C, D, E and Example 2 |
| 97 | 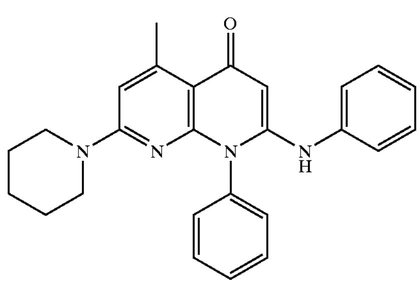 | 2.75 | 411.2 | Intermediate A, B, C, D, E and Example 2 |
| 98 | 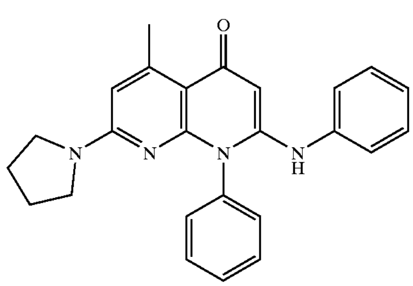 | 2.70 | 397.2 | Intermediate A, B, C, D, E and Example 2 |

TABLE 1A-continued

| Example | Structure | LCMS RT (min) | [M + H] | Representative Procedure |
|---------|-----------|---------------|---------|--------------------------|
| 99 | 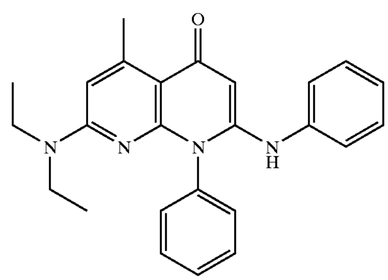 | 2.52 | 399.4 | Intermediate A, B, C, D, E and Example 2 |
| 100 | 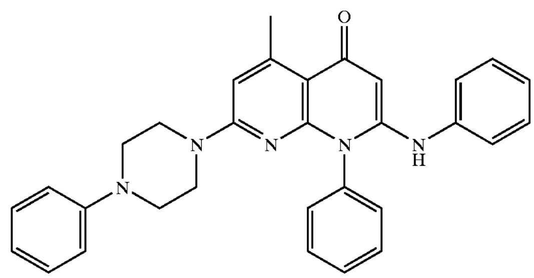 | 2.80 | 488.6 | Intermediate A, B, C, D, E and Example 2 |
| 101 | 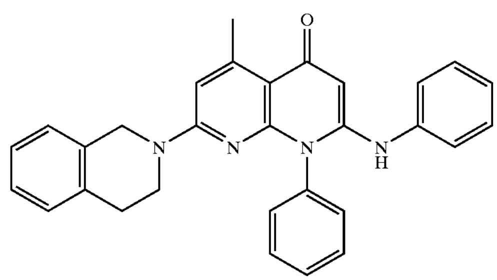 | 2.89 | 459.7 | Intermediate A, B, C, D, E and Example 2 |
| 102 | 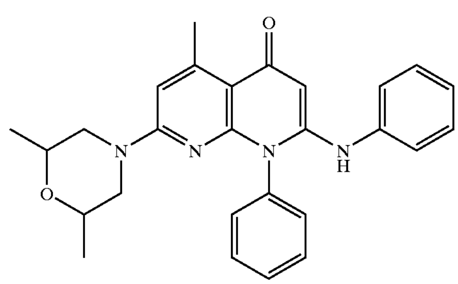 | 2.54 | 441.6 | Intermediate A, B, C, D, E and Example 2 |
| 103 | 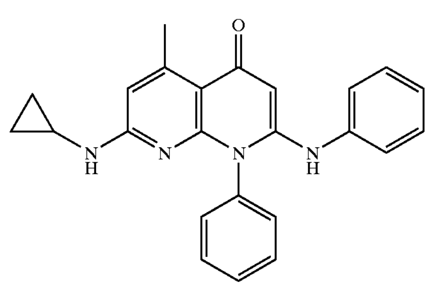 | 2.40 | 383.5 | Intermediate A, B, C, D, E and Example 2 |

TABLE 1A-continued

| Example | Structure | LCMS RT (min) | [M + H] | Representative Procedure |
|---|---|---|---|---|
| 104 | 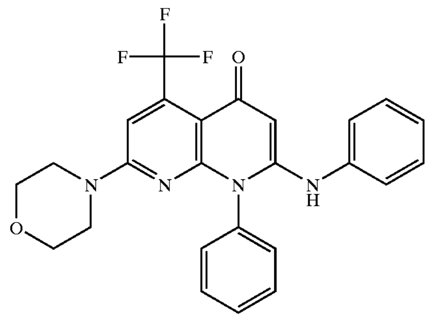 | 2.44 | 467.5 | Intermediate F, G, H, I, J and Example 8 |
| 105 | 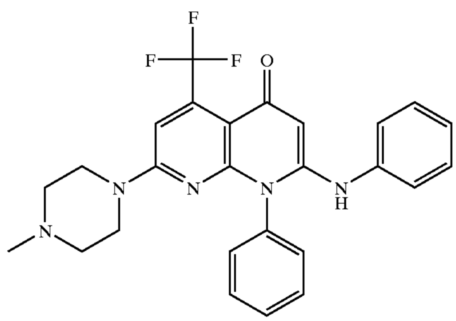 | 2.51 | 480.4 | Intermediate F, G, H, I, J and Example 8 |
| 106 | 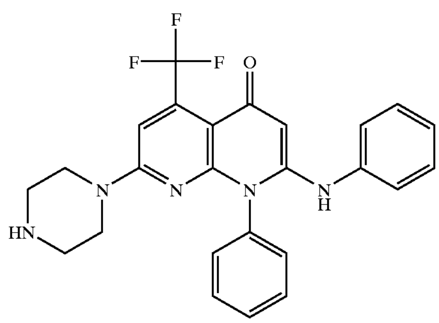 | 1.80 | 466.4 | Intermediate F, G, H, I, J and Example 8 |
| 107 | 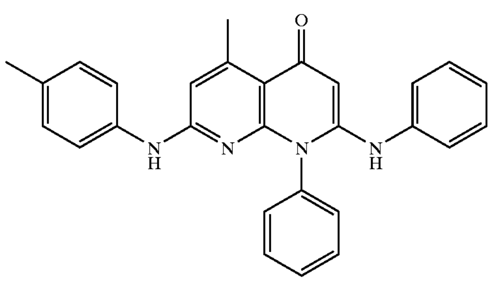 | 2.65 | 433.4 | Intermediate A, B, C, D, E and Example 3 |
| 108 | 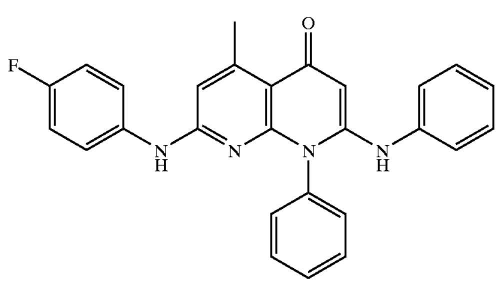 | 2.60 | 437.4 | Intermediate A, B, C, D, E and Example 3 |

TABLE 1A-continued
| Example | Structure | LCMS RT (min) | [M + H] | Representative Procedure |
|---|---|---|---|---|
| 109 | 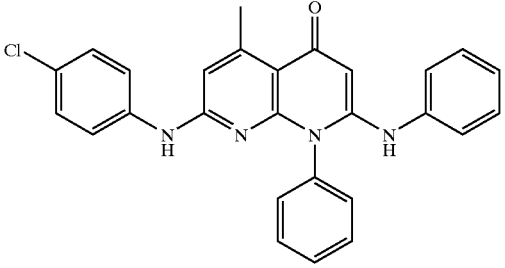 | 2.71 | 453.4 | Intermediate A, B, C, D, E and Example 3 |
| 110 | 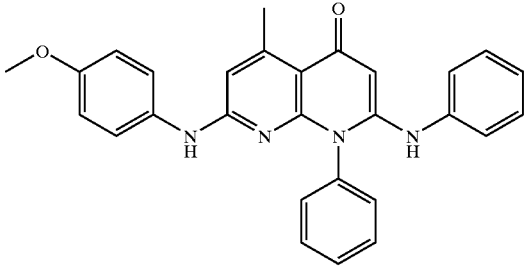 | 2.53 | 449.4 | Intermediate A, B, C, D, E and Example 3 |
| 111 | 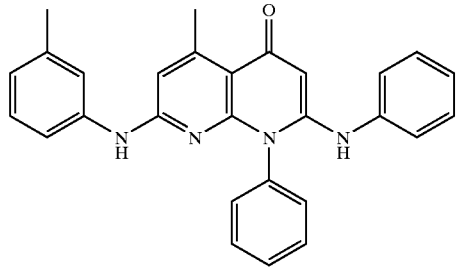 | 2.65 | 433.4 | Intermediate A, B, C, D, E and Example 3 |
| 112 | 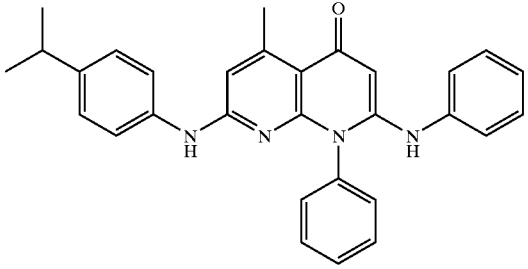 | 2.84 | 461.5 | Intermediate A, B, C, D, E and Example 3 |
| 113 | 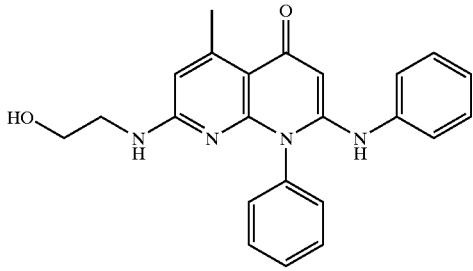 | 2.08 | 387.4 | Intermediate A, B, C, D, E and Example 2 |

TABLE 1A-continued

| Example | Structure | LCMS RT (min) | [M + H] | Representative Procedure |
|---|---|---|---|---|
| 114 | 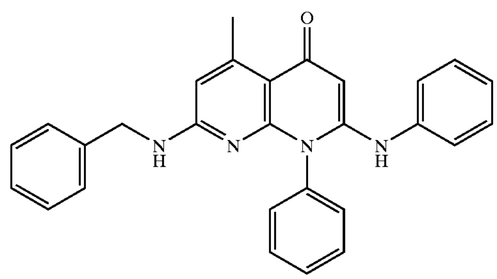 | 2.46 | 433.4 | Intermediate A, B, C, D, E and Example 2 |
| 115 | 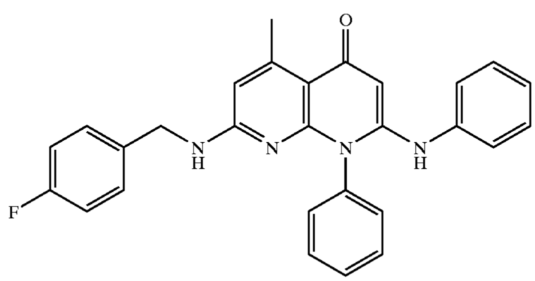 | 2.64 | 451.3 | Intermediate A, B, C, D, E and Example 2 |
| 116 | 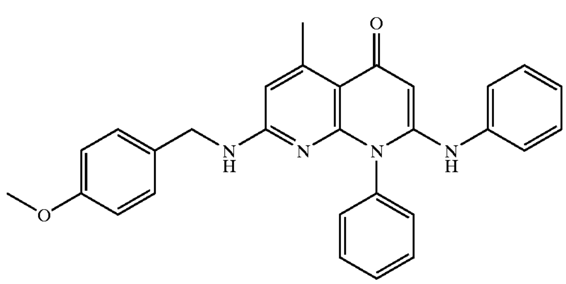 | 2.61 | 463.4 | Intermediate A, B, C, D, E and Example 2 |
| 117 | 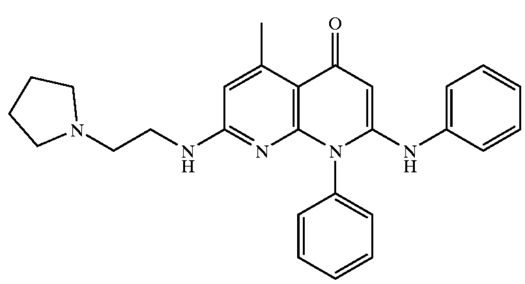 | 2.03 | 440.4 | Intermediate A, B, C, D, E and Example 2 |
| 118 | 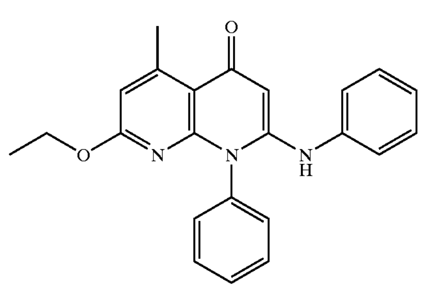 | 2.58 | 372.2 | Intermediate A, B, C, D, E and Example 9 |

TABLE 1A-continued

| Example | Structure | LCMS RT (min) | [M + H] | Representative Procedure |
|---|---|---|---|---|
| 119 | 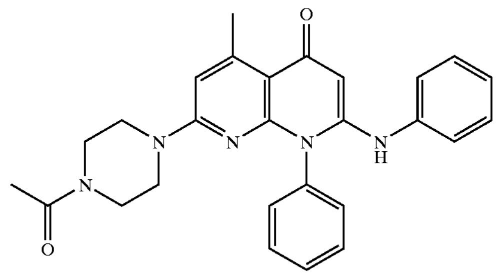 | 2.20 | 454.4 | Intermediate A, B, C, D, E and Example 2, 13 |
| 120 | 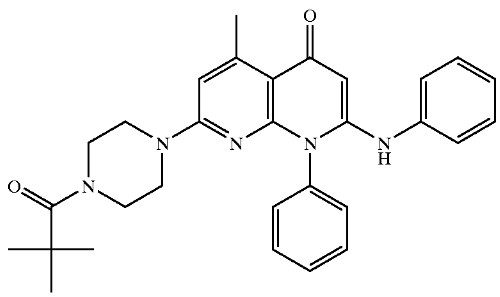 | 2.55 | 496.4 | Intermediate A, B, C, D, E and Example 2, 13 |
| 121 | 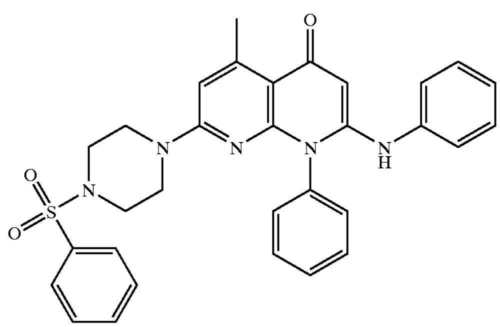 | 2.52 | 552.2 | Intermediate A, B, C, D, E and Example 2, 12 |
| 122 | 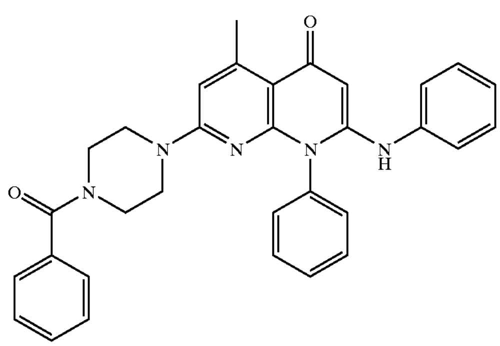 | 2.44 | 516.3 | Intermediate A, B, C, D, E and Example 2, 13 |
| 123 | 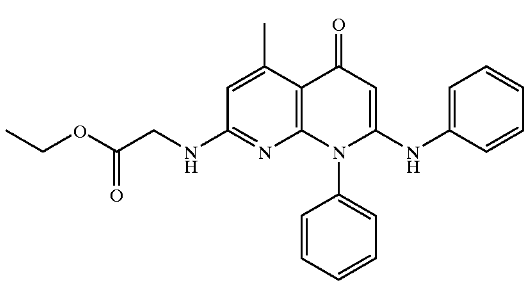 | 2.28 | 429.3 | Intermediate A, B, C, D, E and Example 3 |

TABLE 1A-continued

| Example | Structure | LCMS RT (min) | [M + H] | Representative Procedure |
|---|---|---|---|---|
| 124 | 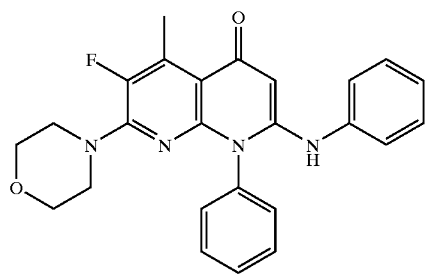 | 2.45 | 431.4 | Intermediate K, L, M, N, AH and Example 2 |
| 125 | 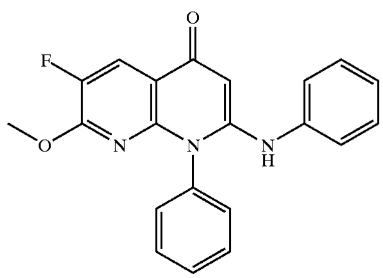 | 2.45 | 362.3 | Intermediate K, L, M, N and Example 9 |
| 126 | 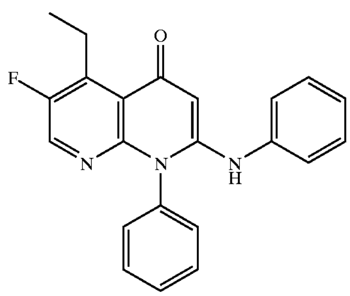 | 2.51 | 360.3 | Intermediate K, L, M, N, AH and Example 1 |
| 127 | 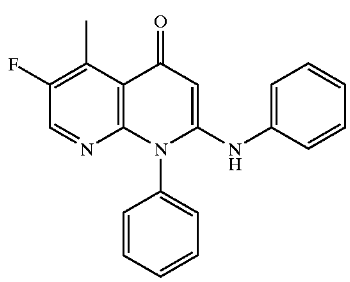 | 2.30 | 346.4 | Intermediate K, L, M, N, AH and Example 1 |
| 128 | 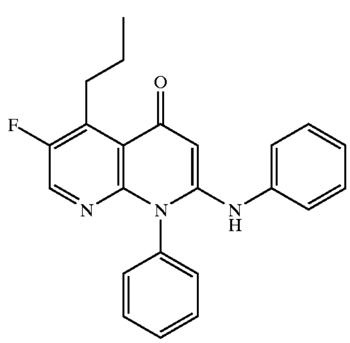 | 2.70 | 374.4 | Intermediate K, L, M, N, AH and Example 1 |

TABLE 1A-continued

| Example | Structure | LCMS RT (min) | [M + H] | Representative Procedure |
|---|---|---|---|---|
| 129 | 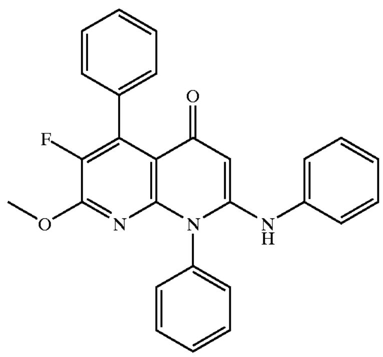 | 2.69 | 438.3 | Intermediate K, L, M, N and Example 9, 14, 4 |
| 130 | 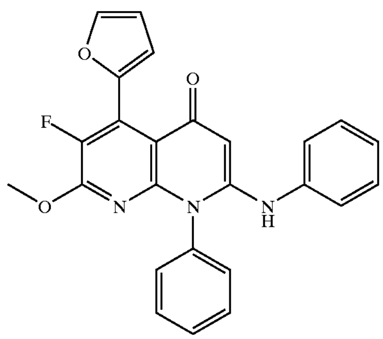 | 2.64 | 428.3 | Intermediate K, L, M, N and Example 9, 14, 4 |
| 131 | 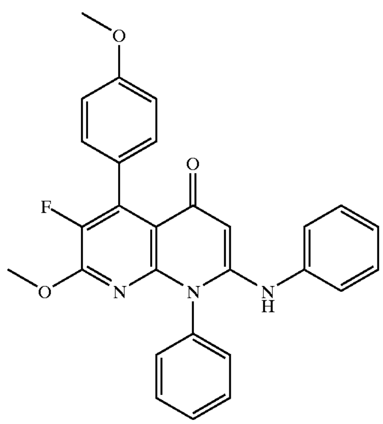 | 2.74 | 468.3 | Intermediate 2 K, L, M, N and Example 9, 14, 4 |
| 132 | 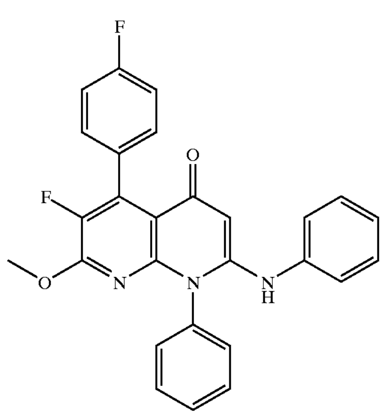 | 2.77 | 456.4 | Intermediate K, L, M, N and Example 9, 14, 4 |

TABLE 1A-continued

| Example | Structure | LCMS RT (min) | [M + H] | Representative Procedure |
|---|---|---|---|---|
| 133 | 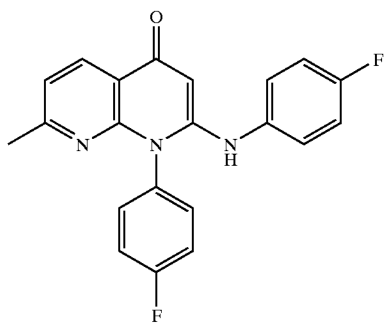 | 2.37 | 364.3 | Intermediate S, T, U, W and Example 15 |
| 134 | 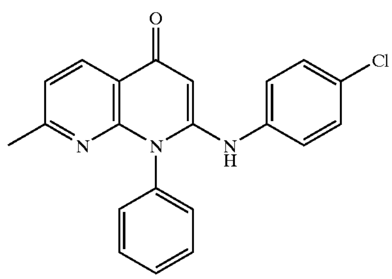 | 2.40 | 362.3 | Intermediate S, T, V, X and Example 15 |
| 135 | 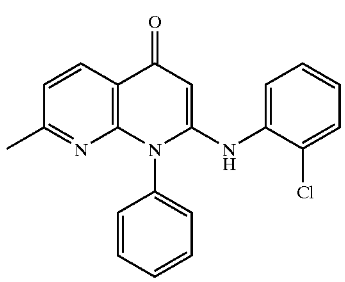 | 2.46 | 362.2 | Intermediate S, T, V, X and Example 15 |
| 136 | 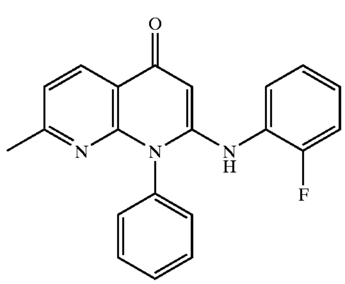 | 2.28 | 346.3 | Intermediate S, T, V, X and Example 15 |
| 137 | 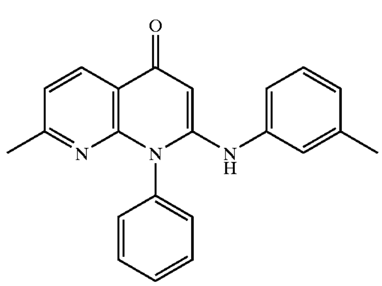 | 2.32 | 342.3 | Intermediate S, T, V, X and Example 15 |

TABLE 1A-continued

| Example | Structure | LCMS RT (min) | [M + H] | Representative Procedure |
|---|---|---|---|---|
| 138 | 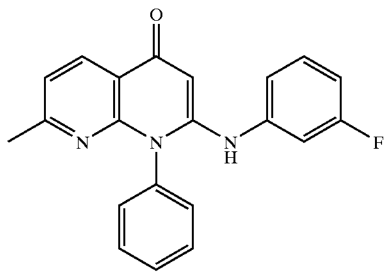 | 2.27 | 346.3 | Intermediate S, T, V, X and Example 15 |
| 139 | 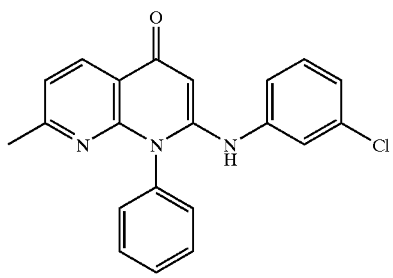 | 2.41 | 362.3 | Intermediate S, T, V, X and Example 15 |
| 140 | 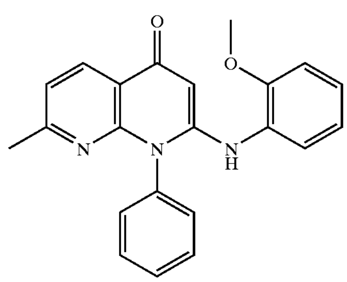 | 2.36 | 358.3 | Intermediate S, T, V, X and Example 15 |
| 141 | 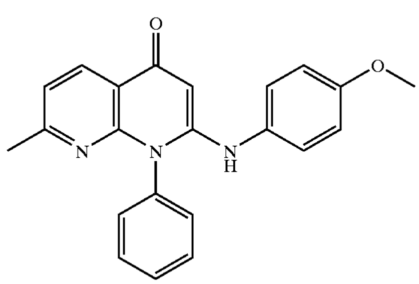 | 2.32 | 358.3 | Intermediate S, T, V, X and Example 15 |
| 142 | 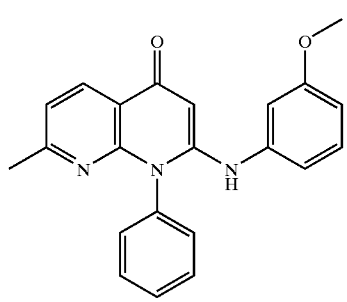 | 2.36 | 358.3 | Intermediate S, T, V, X and Example 15 |

TABLE 1A-continued

| Example | Structure | LCMS RT (min) | [M + H] | Representative Procedure |
|---------|-----------|---------------|---------|--------------------------|
| 143 | 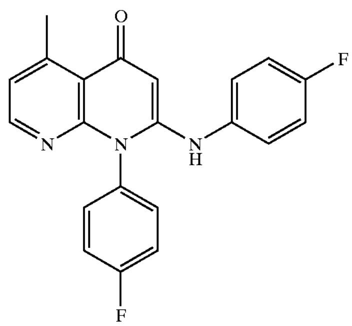 | 2.35 | 364.3 | Intermediate A, B, C, D, E and Example 1 |
| 144 | 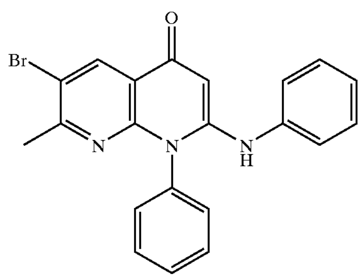 | 2.60 | 406.3 | Intermediate Y, S, T, U, W and Example 15 |
| 145 | 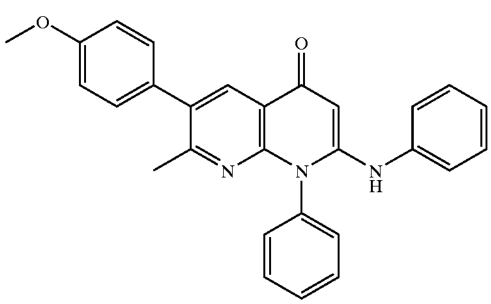 | 5.35 | 434.4 | Intermediate Y, S, T, U, W and Example 15, 4 |
| 146 | 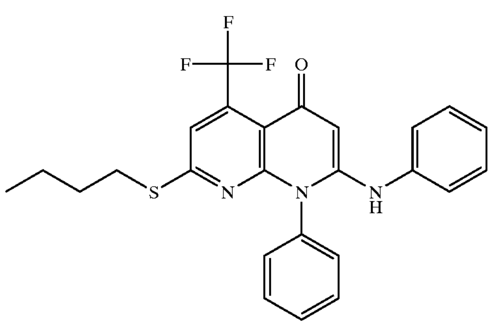 | 3.43 | 470.3 | Intermediate F, G, H, I, J and Example 6 |

TABLE 1A-continued

| Example | Structure | LCMS RT (min) | [M + H] | Representative Procedure |
|---|---|---|---|---|
| 147 | 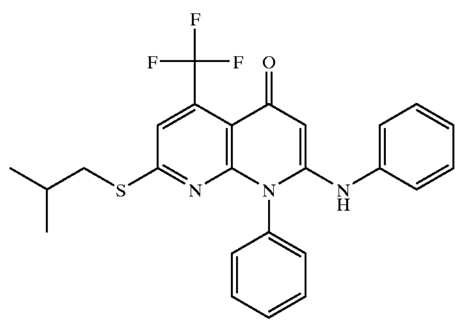 | 3.43 | 470.3 | Intermediate F, G, H, I, J and Example 6 |
| 148 | 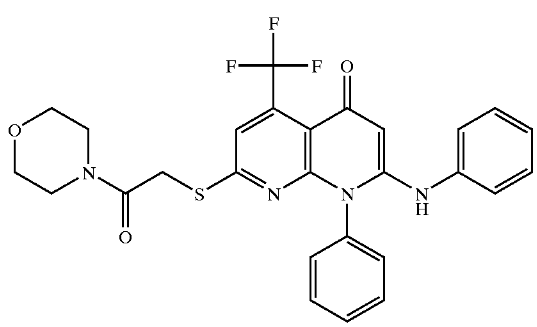 | 2.59 | 541.3 | Intermediate F, G, H, I, J and Example 6, 7, 13 |
| 149 | 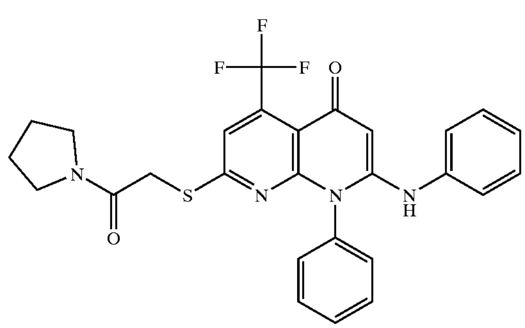 | 2.66 | 525.2 | Intermediate F, G, H, I, J and Example 6, 7, 13 |
| 150 | 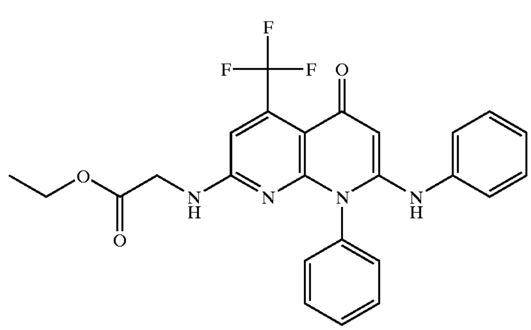 | 2.49 | 483.4 | Intermediate F, G, H, I, J and Example 8 |

TABLE 1A-continued

| Example | Structure | LCMS RT (min) | [M + H] | Representative Procedure |
|---|---|---|---|---|
| 151 | 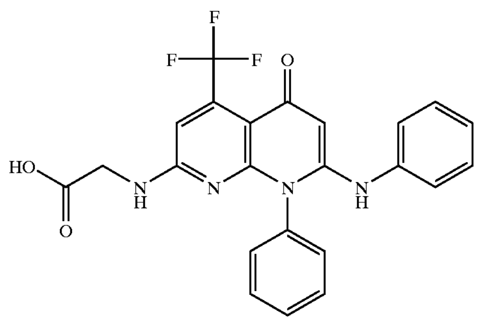 | 2.38 | 455.3 | Intermediate F, G, H, I, J and Example 8, 7 |
| 152 | 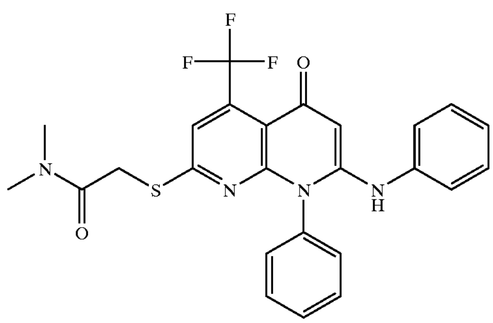 | 2.60 | 499.4 | Intermediate F, G, H, I, J and Example 6, 7, 13 |
| 153 | 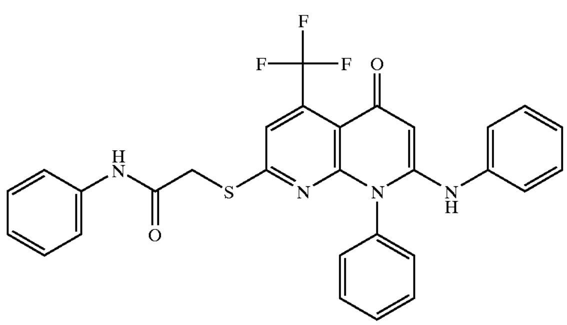 | 2.95 | 547.4 | Intermediate F, G, H, I, J and Example 6, 7, 13 |
| 154 | 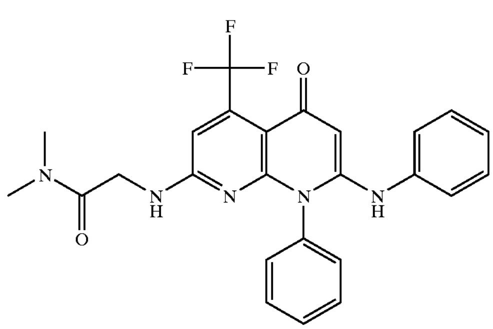 | 2.19 | 482.3 | Intermediate F, G, H, I, J and Example 8, 7, 13 |

TABLE 1A-continued

| Example | Structure | LCMS RT (min) | [M + H] | Representative Procedure |
|---------|-----------|---------------|---------|--------------------------|
| 155 | 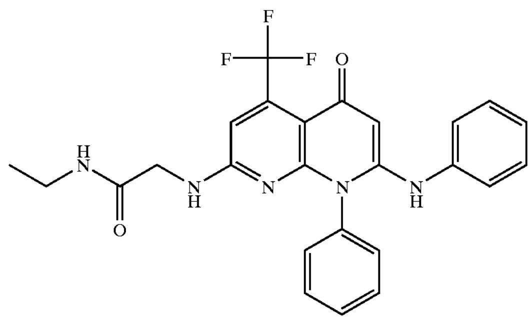 | 2.07 | 482.3 | Intermediate F, G, H, I, J and Example 8, 7, 13 |
| 156 | 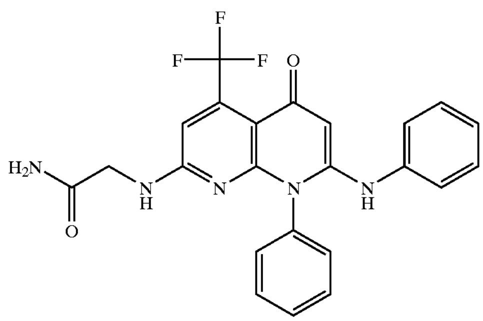 | 1.95 | 454.3 | Intermediate F, G, H, I, J and Example 8, 7, 13 |
| 157 | 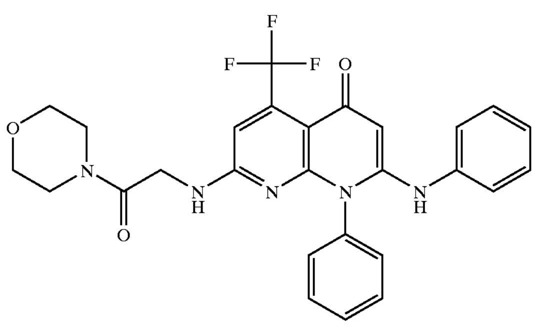 | 2.18 | 524.3 | Intermediate F, G, H, I, J and Example 8, 7, 13 |
| 158 | 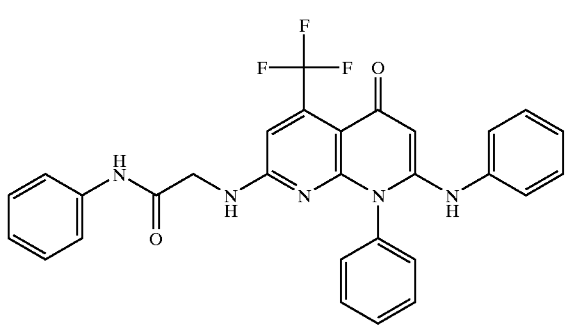 | 2.44 | 530.3 | Intermediate F, G, H, I, J and Example 8, 7, 13 |

TABLE 1A-continued

| Example | Structure | LCMS RT (min) | [M + H] | Representative Procedure |
|---|---|---|---|---|
| 159 | 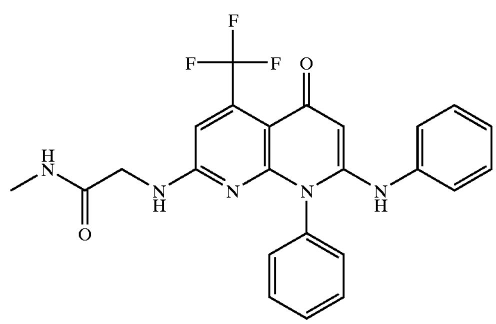 | 1.99 | 468.3 | Intermediate F, G, H, I, J and Example 8, 7, 13 |
| 160 | 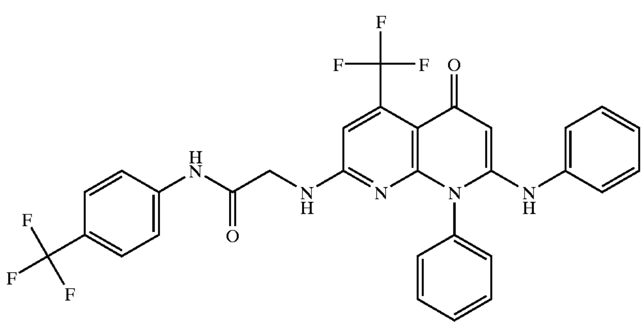 | 2.74 | 598.3 | Intermediate F, G, H, I, J and Example 8, 7, 13 |
| 161 | 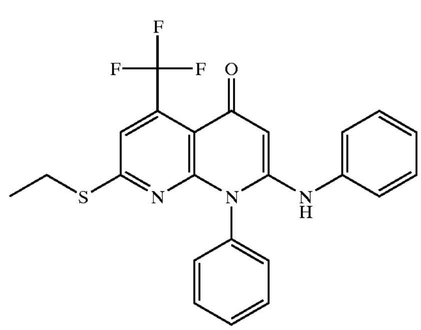 | 3.15 | 442.3 | Intermediate F, G, H, I, J and Example 6 |
| 162 | 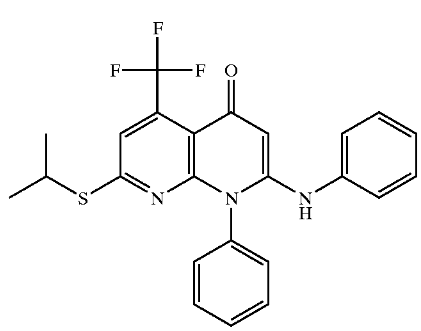 | 328 | 456.2 | Intermediate F, G, H, I, J and Example 6 |

TABLE 1A-continued

| Example | Structure | LCMS RT (min) | [M + H] | Representative Procedure |
|---|---|---|---|---|
| 163 | 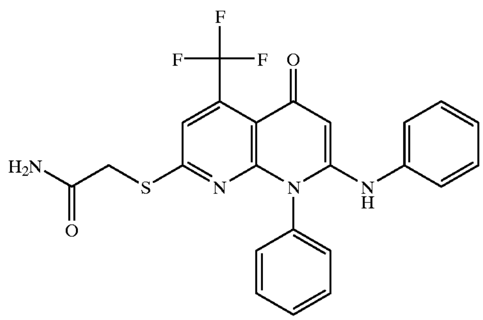 | 2.26 | 471.3 | Intermediate F, G, H, I, J and Example 6, 7, 13 |
| 164 | 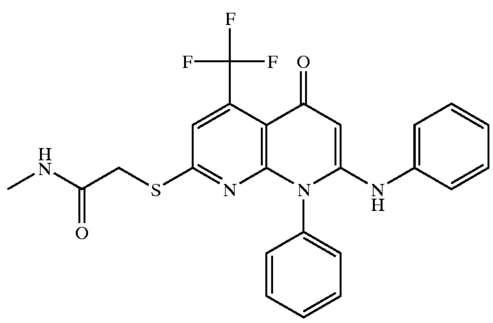 | 2.34 | 485.3 | Intermediate F, G, H, I, J and Example 6, 7, 13 |
| 165 | 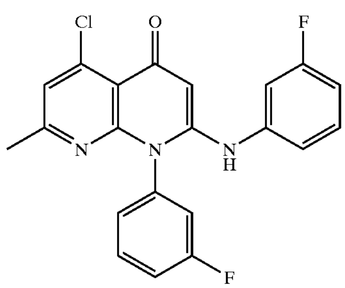 | 2.71 | 398.4 | Intermediate Z, AA, AB and Example 16 |
| 166 | 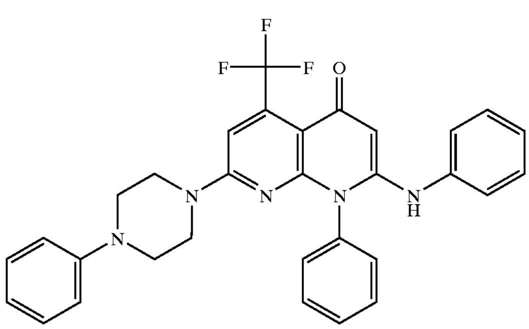 | 2.88 | 542.6 | Intermediate F, G, H, I, J and Example 8 |

TABLE 1A-continued

| Example | Structure | LCMS RT (min) | [M + H] | Representative Procedure |
|---------|-----------|---------------|---------|--------------------------|
| 167 | 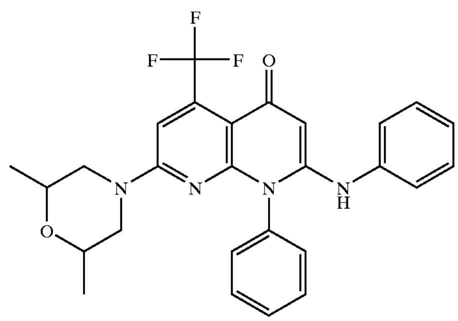 | 2.66 | 495.6 | Intermediate F, G, H, I, J and Example 8 |
| 168 | 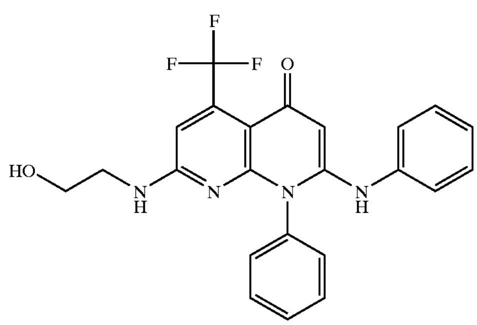 | 2.20 | 441.5 | Intermediate F, G, H, I, J and Example 8 |
| 169 | 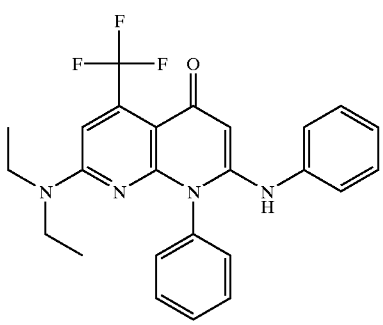 | 2.76 | 453.5 | Intermediate F, G, H, I, J and Example 8 |
| 170 | 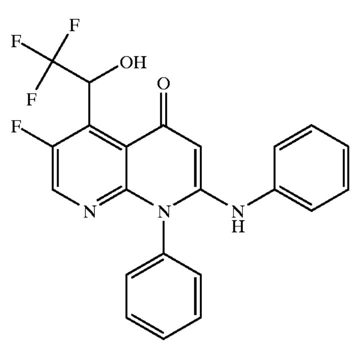 | 3.05 | 430.3 | Intermediate K, L, M, N, AI and Example 1 |

TABLE 1A-continued

| Example | Structure | LCMS RT (min) | [M + H] | Representative Procedure |
|---------|-----------|---------------|---------|--------------------------|
| 171 | 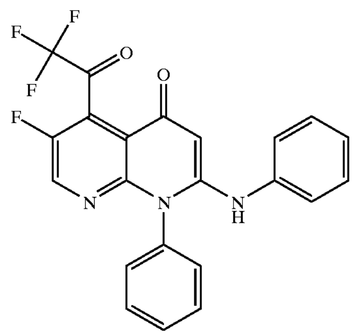 | 3.14 | 428.4 | Intermediate K, L, M, N, AI and Example 1 |
| 172 | 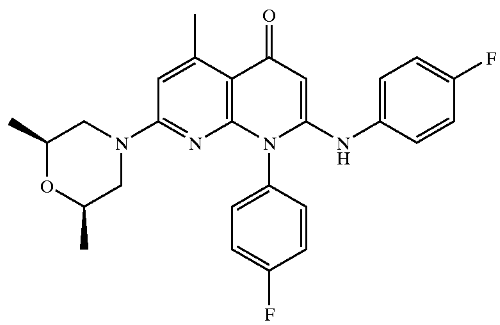 | 2.72 | 477.5 | Intermediate A, B, C, D, E and Example 2 |
| 173 | 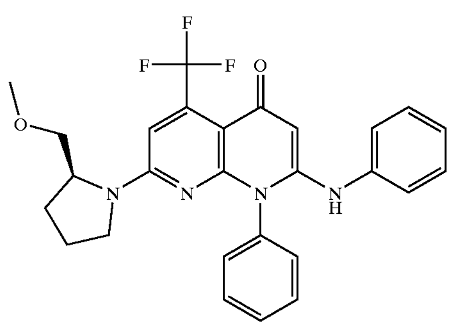 | 2.72 | 495.5 | Intermediate F, G, H, I, J and Example 8 |
| 174 | 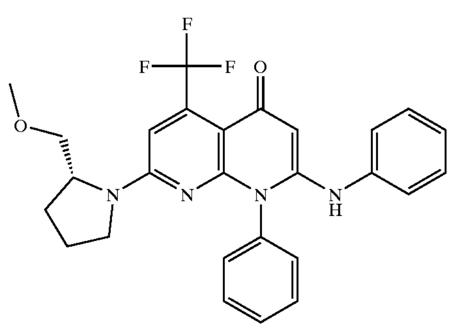 | 2.72 | 495.6 | Intermediate F, G, H, I, J and Example 8 |

TABLE 1A-continued

| Example | Structure | LCMS RT (min) | [M + H] | Representative Procedure |
|---------|-----------|---------------|---------|--------------------------|
| 175 | 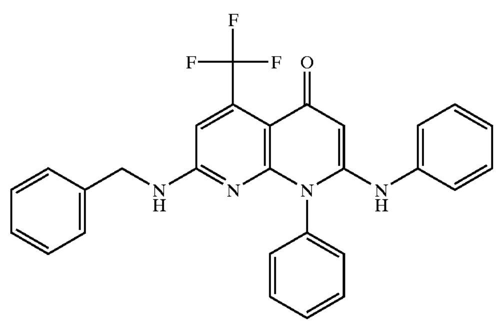 | 2.77 | 487.5 | Intermediate F, G, H, I, J and Example 8 |
| 176 | 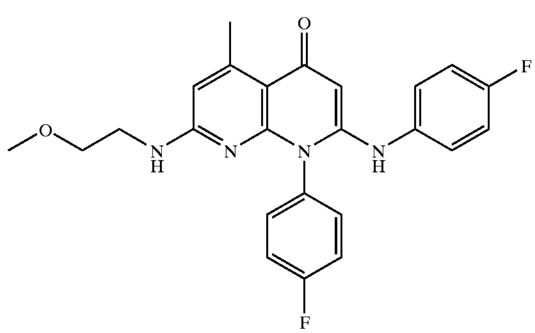 | 2.43 | 437.4 | Intermediate A, B, C, D, E and Example 2 |
| 177 | 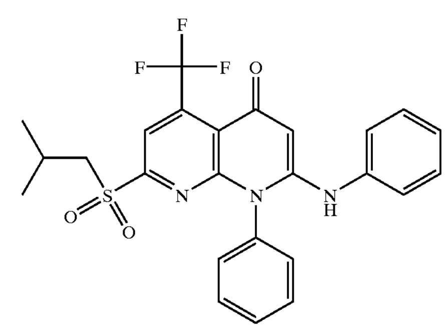 | 3.13 | 502.5 | Intermediate F, G, H, I, J and Example 6, 21 |
| 178 | 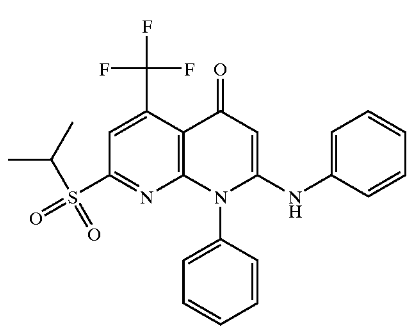 | 2.93 | 488.3 | Intermediate F, G, H, I, J and Example 6, 21 |

TABLE 1A-continued

| Example | Structure | LCMS RT (min) | [M + H] | Representative Procedure |
|---|---|---|---|---|
| 179 | 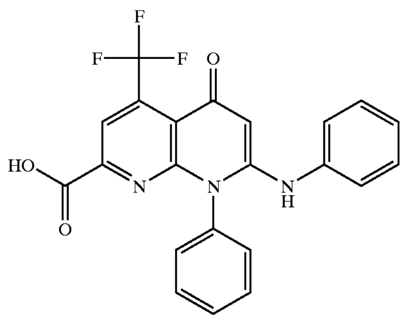 | 2.41 | 426.3 | Intermediate F, G, H, I, J and Example 17, 7 |
| 180 | 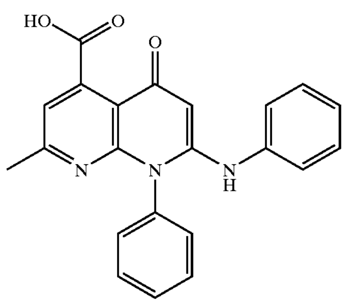 | 2.56 | 372.3 | Intermediate Z, AA, AB and Example 16, 17, 7 |
| 181 | 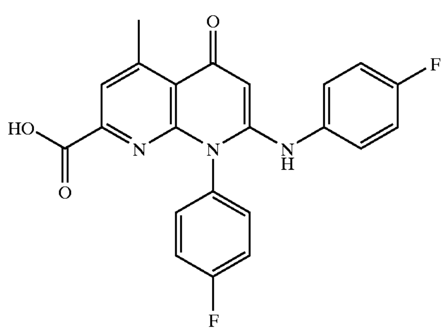 | 2.19 | 408.2 | Intermediate A, B, C, D, E and Example 17, 7 |
| 182 | 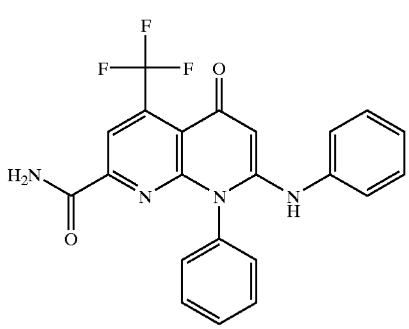 | 2.39 | 425.4 | Intermediate F, G, H, I, J and Example 17, 18 |

TABLE 1A-continued

| Example | Structure | LCMS RT (min) | [M + H] | Representative Procedure |
|---|---|---|---|---|
| 183 | 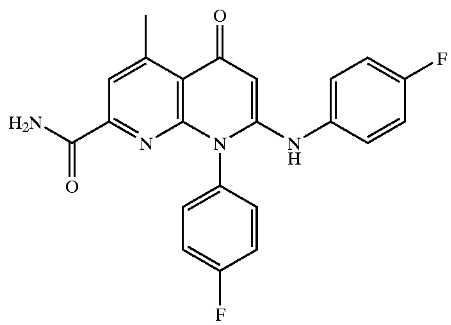 | 2.18 | 407.4 | Intermediate A, B, C, D, E and Example 17, 18 |
| 184 | 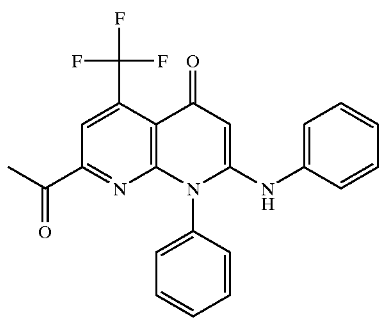 | 2.88 | 424.4 | Intermediate F, G, H, I, J and Example 17, 7, 19, 20 |
| 185 | 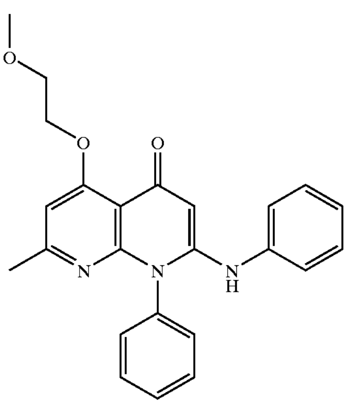 | 2.27 | 402.2 | Intermediate Z, AA, AB and Example 16, 9 |
| 186 | 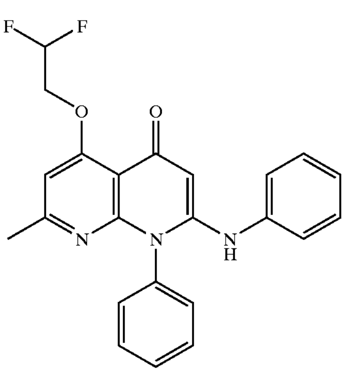 | 2.41 | 408.3 | Intermediate Z, AA, AB and Example 16, 9 |

TABLE 1A-continued
| Example | Structure | LCMS RT (min) | [M + H] | Representative Procedure |
|---|---|---|---|---|
| 187 | 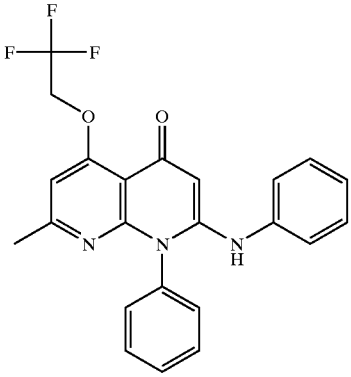 | 2.50 | 426.3 | Intermediate Z, AA, AB and Example 16, 9 |
| 188 | 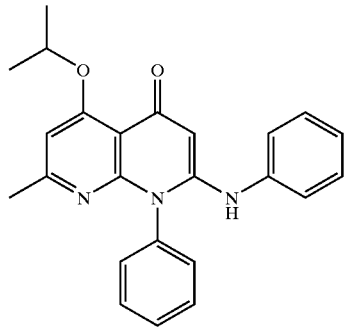 | 2.43 | 386.1 | Intermediate Z, AA, AB and Example 16, 9 |
| 189 | 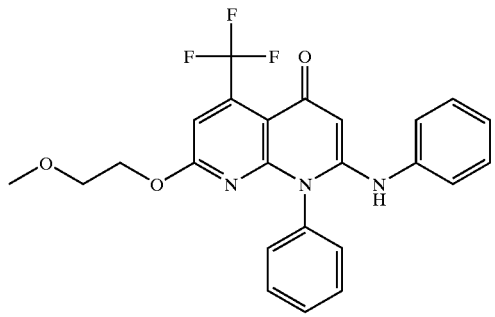 | 2.66 | 456.4 | Intermediate F, G, H, I, J and Example 9 |
| 190 | 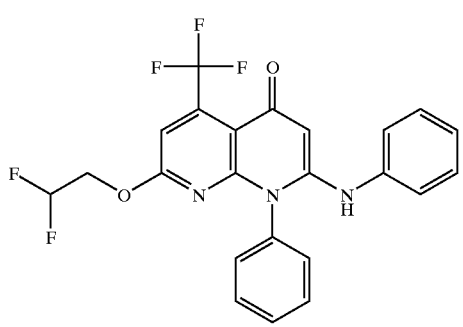 | 2.88 | 462.5 | Intermediate F, G, H, I, J and Example 9 |

TABLE 1A-continued

| Example | Structure | LCMS RT (min) | [M + H] | Representative Procedure |
|---|---|---|---|---|
| 191 | 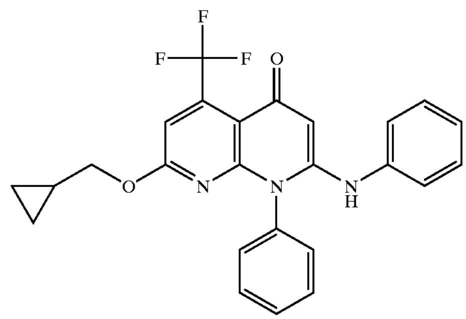 | 2.98 | 452.4 | Intermediate F, G, H, I, J and Example 9 |
| 192 | 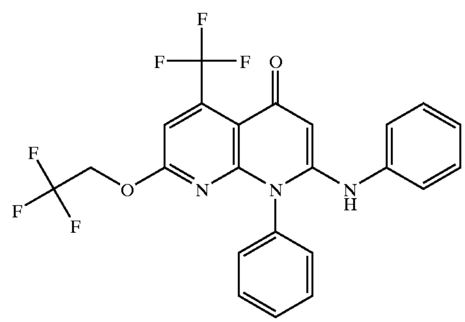 | 3.12 | 480.3 | Intermediate F, G, H, I, J and Example 9 |
| 193 | 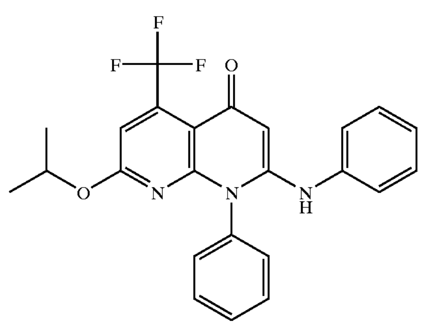 | 3.10 | 440.1 | Intermediate F, G, H, I, J and Example 9 |
| 194 | 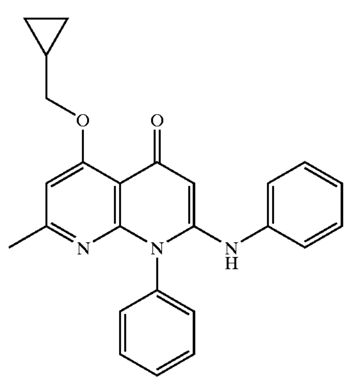 | 2.51 | 398.1 | Intermediate Z, AA, AB and Example 16, 9 |

TABLE 1A-continued

| Example | Structure | LCMS RT (min) | [M + H] | Representative Procedure |
|---------|-----------|---------------|---------|--------------------------|
| 195 | 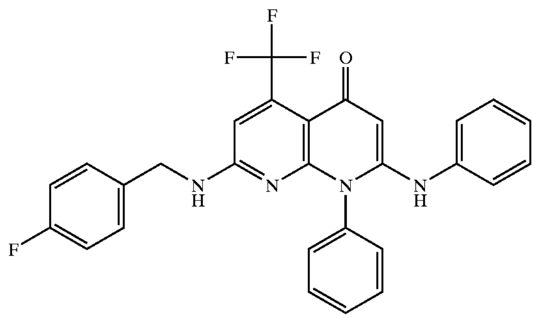 | 2.99 | 505.4 | Intermediate F, G, H, I, J and Example 8 |
| 196 | 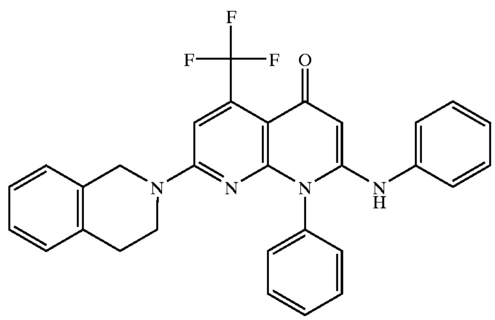 | 3.05 | 513.5 | Intermediate F, G, H, I, J and Example 8 |
| 197 | 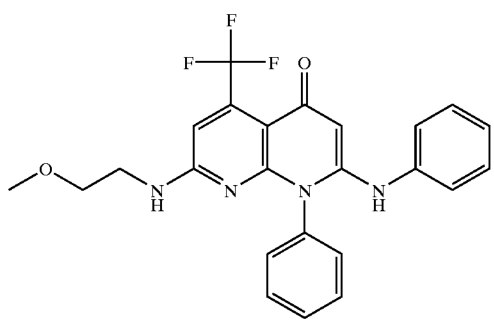 | 2.47 | 455.4 | Intermediate F, G, H, I, J and Example 8 |
| 198 | 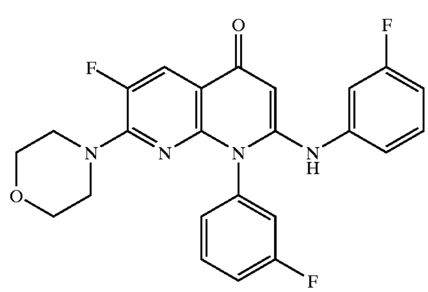 | 2.57 | 453.4 | Intermediate K, L, M, N$_1$ and Example 2 |

TABLE 1A-continued

| Example | Structure | LCMS RT (min) | [M + H] | Representative Procedure |
|---|---|---|---|---|
| 199 | 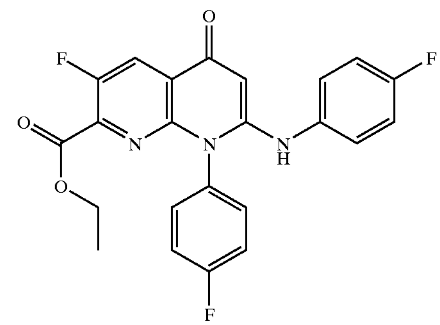 | 2.70 | 440.2 | Intermediate K, L, M, N₂ and Example 17 |
| 200 | 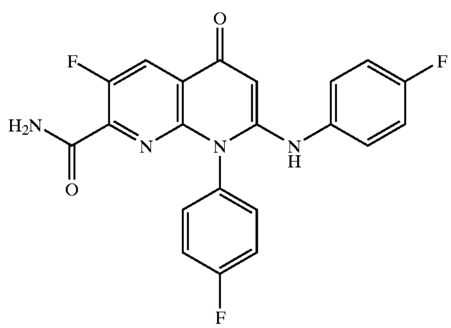 | 2.19 | 411.3 | Intermediate K, L, M, N₂ and Example 17, 18 |
| 201 | 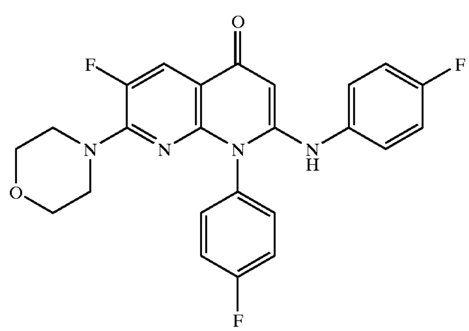 | 2.48 | 453.4 | Intermediate K, L, M, N₂ and Example 2 |
| 202 | 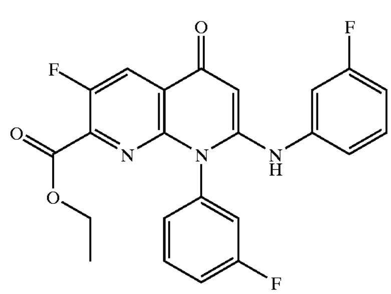 | 2.76 | 440.2 | Intermediate K, L, M, N₁ and Example 17 |

TABLE 1A-continued

| Example | Structure | LCMS RT (min) | [M + H] | Representative Procedure |
|---------|-----------|---------------|---------|--------------------------|
| 203 | 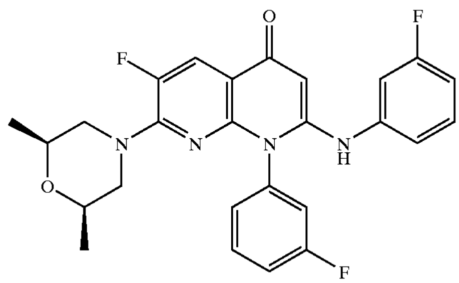 | 2.76 | 481.5 | Intermediate K, L, M, N$_1$ and Example 2 |
| 204 | 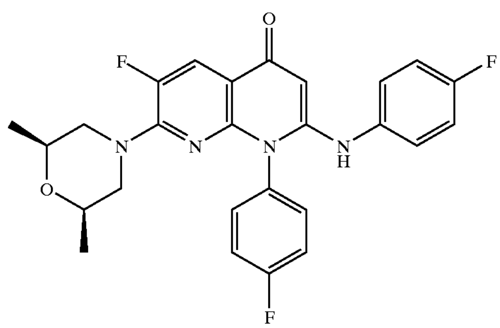 | 2.69 | 481.5 | Intermediate K, L, M, N$_2$ and Example 2 |
| 205 | 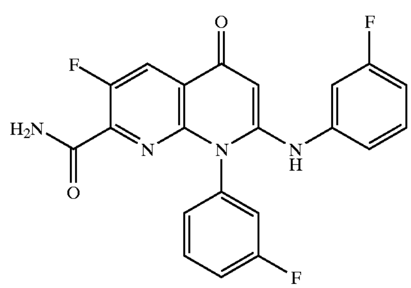 | 2.23 | 411.3 | Intermediate K, L, M, N$_1$ and Example 17, 18 |
| 206 | 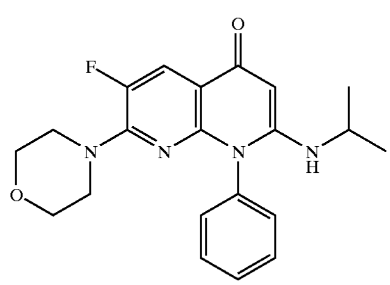 | 2.27 | 383.4 | Intermediate K, L, AC, AG and Example 2 |
| 207 | 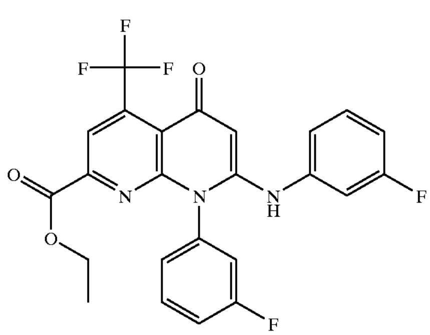 | 3.12 | 490.3 | Intermediate F, G, H, I, J and Example 17 |

TABLE 1A-continued

| Example | Structure | LCMS RT (min) | [M + H] | Representative Procedure |
|---|---|---|---|---|
| 208 | 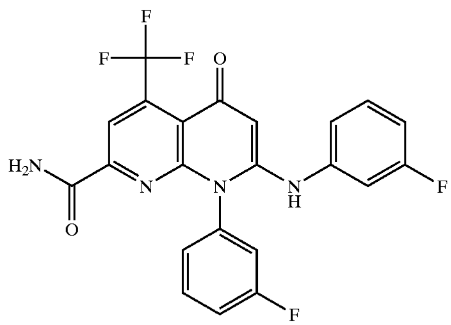 | 2.55 | 461.3 | Intermediate F, G, H, I, J and Example 17, 18 |
| 209 | 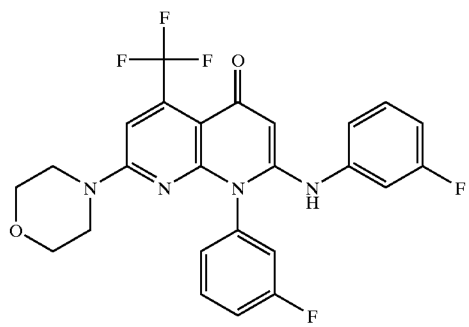 | 2.62 | 503.4 | Intermediate F, G, H, I, J and Example 8 |
| 210 | 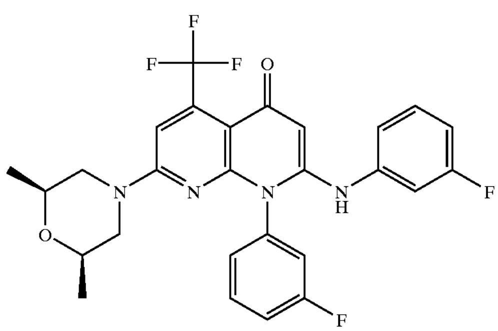 | 2.82 | 531.5 | Intermediate F, G, H, I, J and Example 8 |
| 211 | 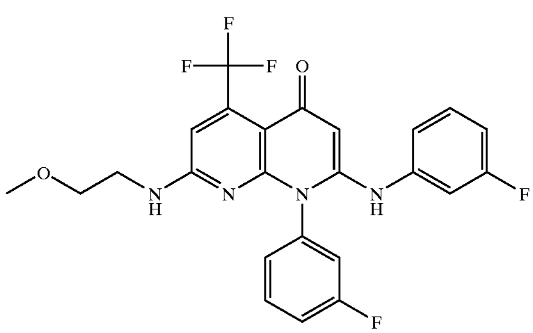 | 2.54 | 491.4 | Intermediate F, G, H, I, J and Example 8 |

TABLE 1A-continued

| Example | Structure | LCMS RT (min) | [M + H] | Representative Procedure |
|---|---|---|---|---|
| 212 | 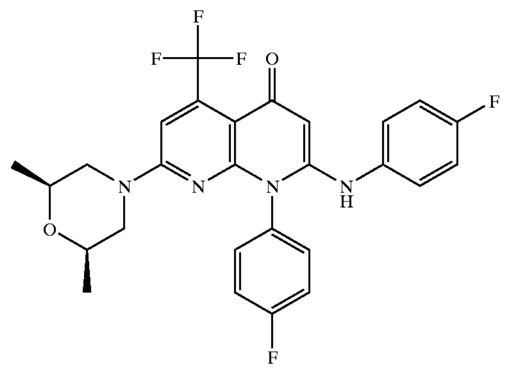 | 2.93 | 531.4 | Intermediate F, G, H, I, J and Example 8 |
| 213 | 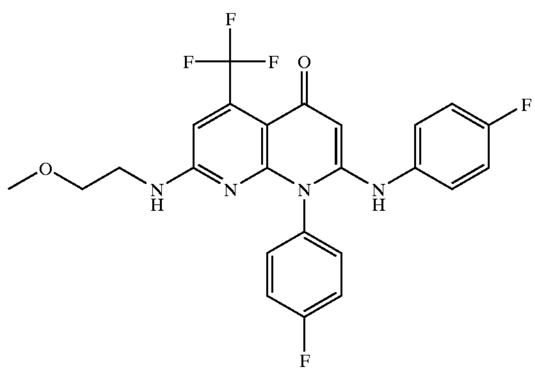 | 2.47 | 491.4 | Intermediate F, G, H, I, J and Example 8 |
| 214 | 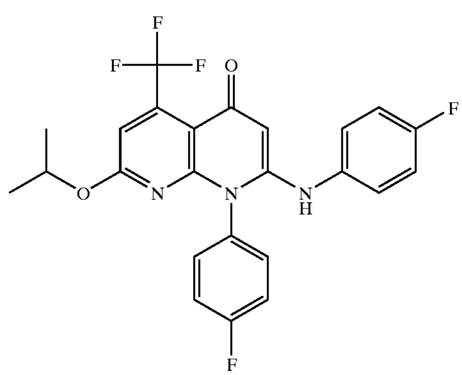 | 3.02 | 476.3 | Intermediate F, G, H, I, J and Example 9 |
| 215 | 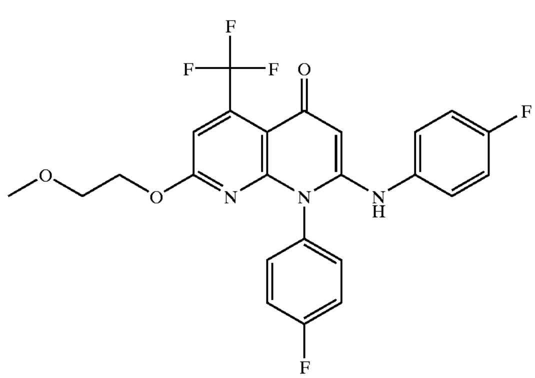 | 2.75 | 492.3 | Intermediate F, G, H, I, J and Example 9 |

TABLE 1A-continued

| Example | Structure | LCMS RT (min) | [M + H] | Representative Procedure |
|---|---|---|---|---|
| 216 | 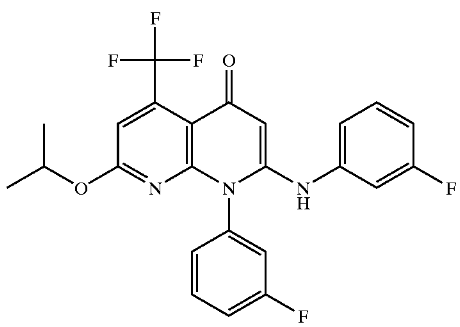 | 3.14 | 476.2 | Intermediate F, G, H, I, J and Example 9 |
| 217 | 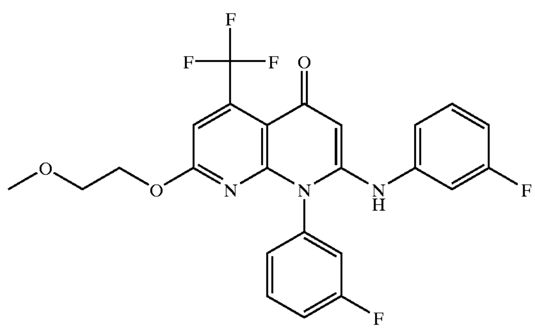 | 2.83 | 492.3 | Intermediate F, G, H, I, J and Example 9 |
| 218 | 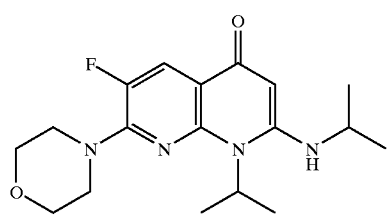 | 2.15 | 349.1 | Intermediate K, L, M, N$_3$ and Example 2 |
| 219 | 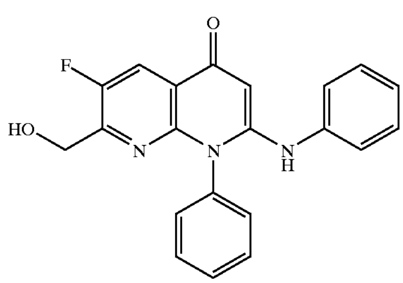 | 2.01 | 362.3 | Intermediate K, L, M, N and Example 17, 25 |
| 220 | 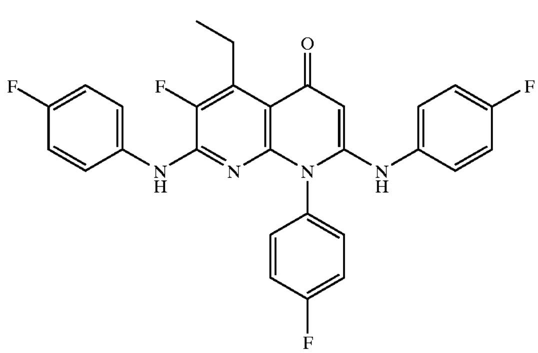 | 2.87 | 505.4 | Intermediate AH, K, L, M, N$_2$ |

TABLE 1A-continued

| Example | Structure | LCMS RT (min) | [M + H] | Representative Procedure |
|---|---|---|---|---|
| 221 | 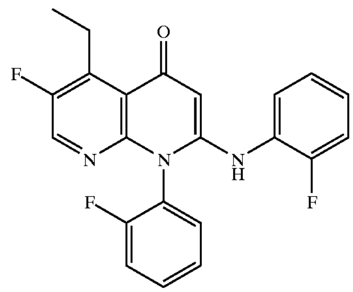 | 2.90 | 396.3 | Intermediate AH, K, L, M, N and Example 1 |
| 222 | 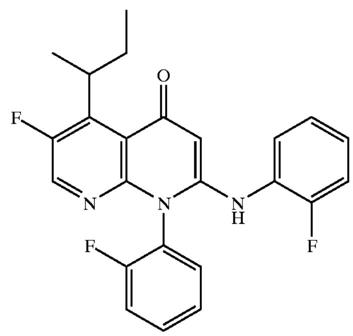 | 3.23 | 424.3 | Intermediate AH, K, L, M, N and Example 1 |
| 223 | 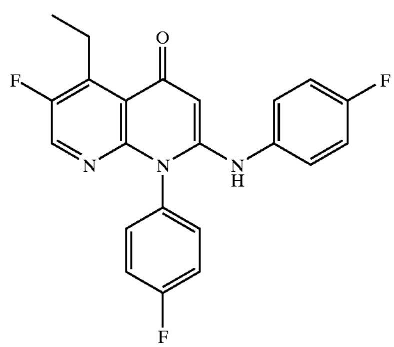 | 2.67 | 396.3 | Intermediate AH, K, L, M, N$_2$ and Example 1 |
| 224 | 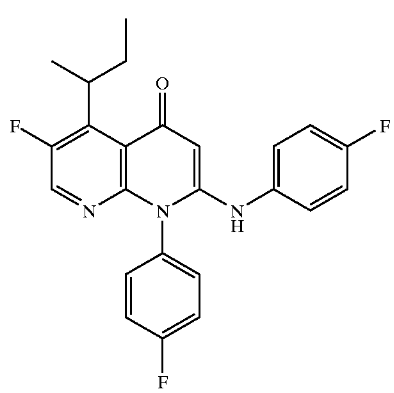 | 3.02 | 424.4 | Intermediate AH, K, L, M, N$_2$ and Example, 1 |

TABLE 1A-continued

| Example | Structure | LCMS RT (min) | [M + H] | Representative Procedure |
|---|---|---|---|---|
| 225 | 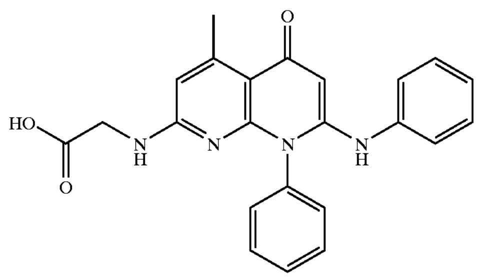 | 2.12 | 401.3 | Intermediate A, B, C, D, E and Example 3, 7 |
| 226 | 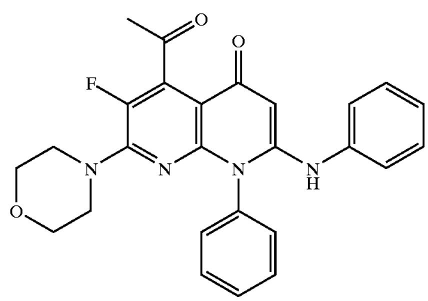 | 2.45 | 459.4 | Intermediate K, L, M, N, AI and Example 2 |
| 227 | 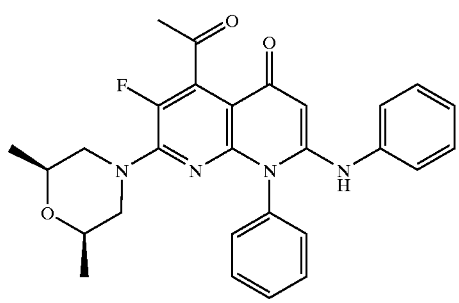 | 2.69 | 487.5 | Intermediate K, L, M, N, AI and Example 2 |
| 228 | 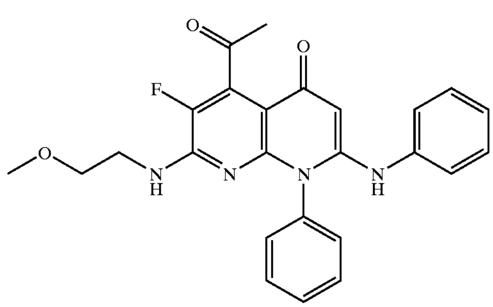 | 2.37 | 447.4 | Intermediate K, L, M, N, AI and Example 2 |
| 229 | 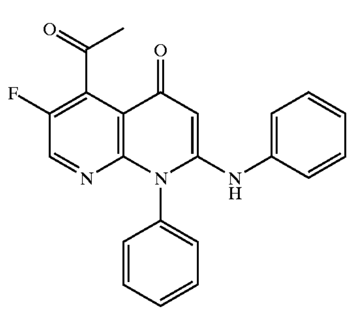 | 2.60 | 374.3 | Intermediate K, L, M, N, AI and Example 1 |

TABLE 1A-continued

| Example | Structure | LCMS RT (min) | [M + H] | Representative Procedure |
|---------|-----------|---------------|---------|--------------------------|
| 230 | 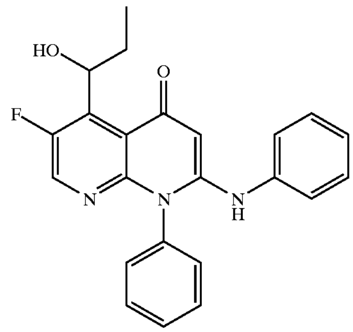 | 2.78 | 390.1 | Intermediate K, L, M, N, AM and Example 1 |
| 231 | 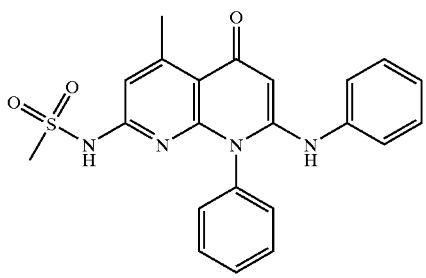 | 2.09 | 421.2 | Intermediate A, B, C, D, E and Example 22 |
| 232 | 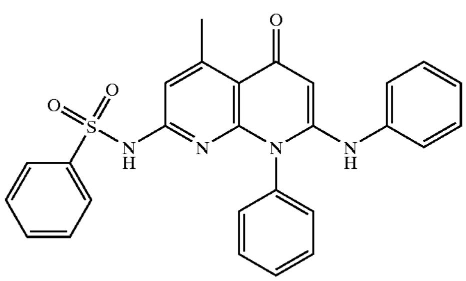 | 2.44 | 483.2 | Intermediate A, B, C, D, E and Example 22 |
| 233 | 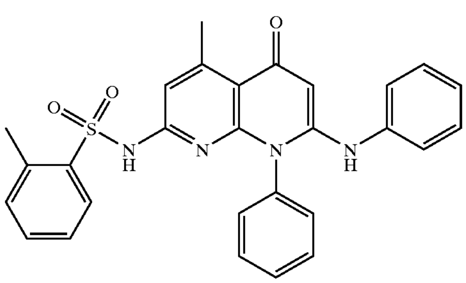 | 2.51 | 497.2 | Intermediate A, B, C, D, E and Example 22 |
| 234 | 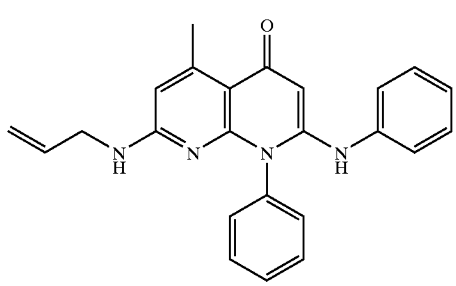 | 2.44 | 383.2 | Intermediate A, B, C, D, E and Example 3 |

TABLE 1A-continued

| Example | Structure | LCMS RT (min) | [M + H] | Representative Procedure |
|---------|-----------|---------------|---------|--------------------------|
| 235 | 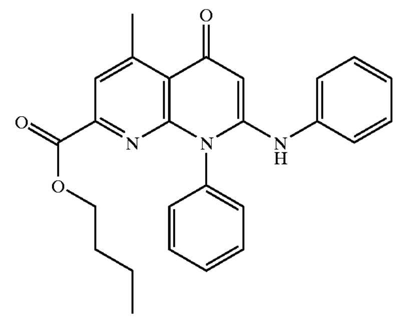 | 2.84 | 428.4 | Intermediate A, B, C, D, E and Example 17 |
| 236 | 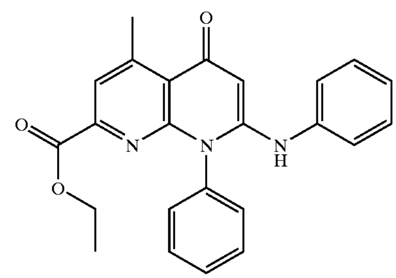 | 2.77 | 400.3 | Intermediate A, B, C, D, E and Example 17 |
| 237 | 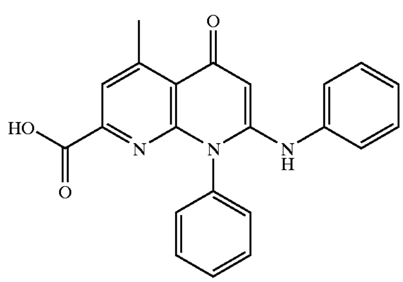 | 2.30 | 372.2 | Intermediate A, B, C, D, E and Example 17, 7 |
| 238 | 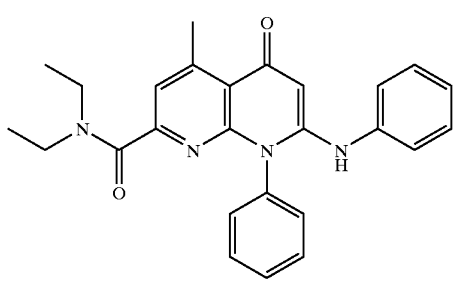 | 2.50 | 427.4 | Intermediate A, B, C, D, E and Example 17, 7, 13 |
| 239 | 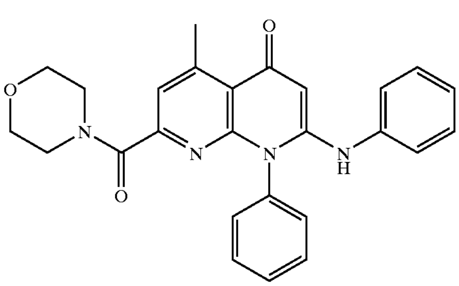 | 2.18 | 441.5 | Intermediate A, B, C, D, E and Example 17, 7, 13 |

TABLE 1A-continued

| Example | Structure | LCMS RT (min) | [M + H] | Representative Procedure |
|---------|-----------|---------------|---------|--------------------------|
| 240 | 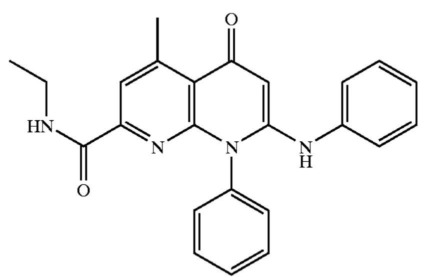 | 2.44 | 399.4 | Intermediate A, B, C, D, E and Example 17, 7, 13 |
| 241 | 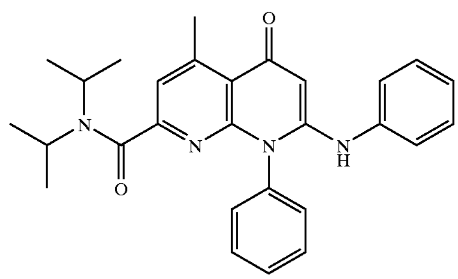 | 2.66 | 455.5 | Intermediate A, B, C, D, E and Example 17, 7, 13 |
| 242 | 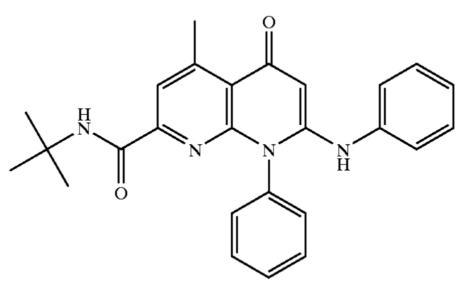 | 2.79 | 427.3 | Intermediate A, B, C, D, E and Example 17, 7, 13 |
| 243 | 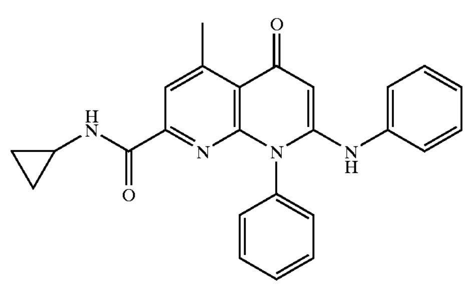 | 2.58 | 411.3 | Intermediate A, B, C, D, E and Example 17, 7, 13 |
| 244 | 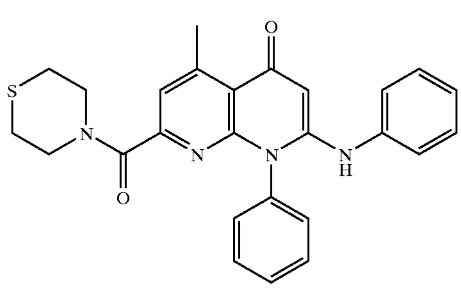 | 2.58 | 457.3 | Intermediate A, B, C, D, E and Example 17, 7, 13 |

TABLE 1A-continued

| Example | Structure | LCMS RT (min) | [M + H] | Representative Procedure |
|---|---|---|---|---|
| 245 | 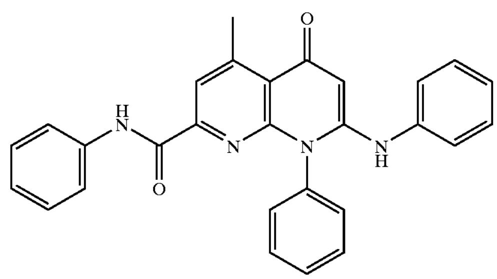 | 2.80 | 447.5 | Intermediate A, B, C, D, E and Example 17, 7, 13 |
| 246 | 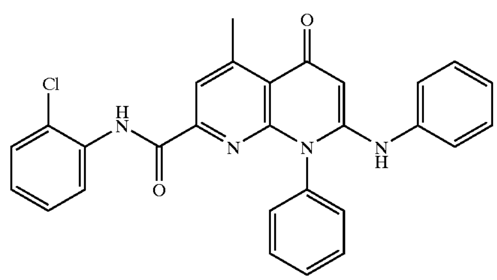 | 2.97 | 481.8 | Intermediate A, B, C, D, E and Example 17, 7, 13 |
| 247 | 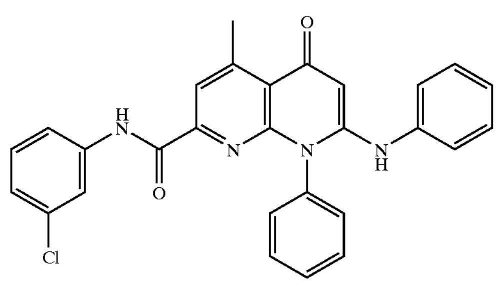 | 3.30 | 481.3 | Intermediate A, B, C, D, E and Example 17, 7, 13 |
| 248 | 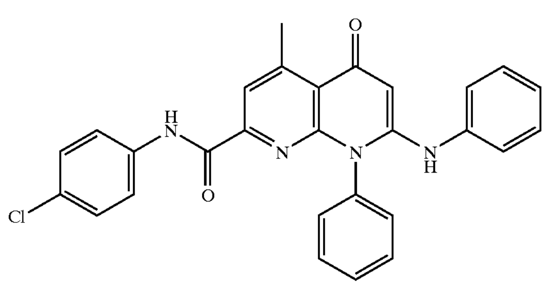 | 3.05 | 481.7 | Intermediate A, B, C, D, E and Example 17, 7, 13 |
| 249 | 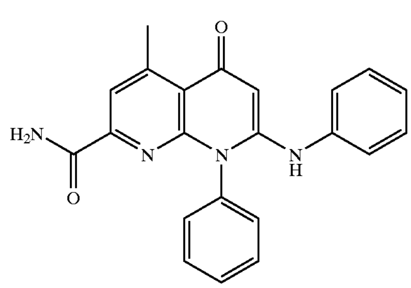 | 1.99 | 371.4 | Intermediate A, B, C, D, E and Example 17, 18 |

TABLE 1A-continued
| Example | Structure | LCMS RT (min) | [M + H] | Representative Procedure |
|---|---|---|---|---|
| 250 | 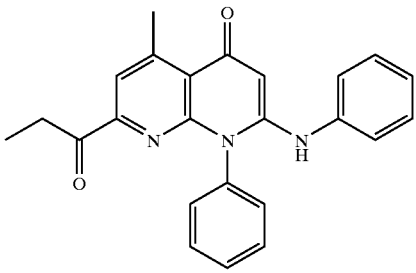 | 2.82 | 384.4 | Intermediate A, B, C, D, E and Example 17, 7, 19, 20 |
| 251 | 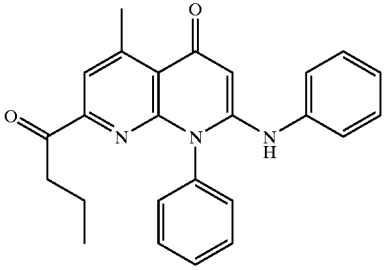 | 2.94 | 398.4 | Intermediate A, B, C, D, E and Example 17, 7, 19, 20 |
| 252 | 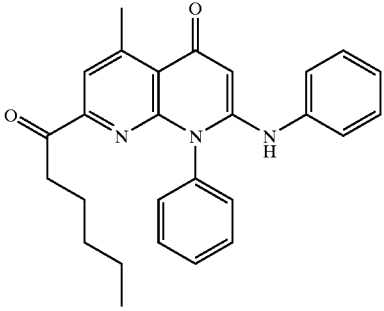 | 3.22 | 426.4 | Intermediate A, B, C, D, E and Example 17, 7, 19, 20 |
| 253 | 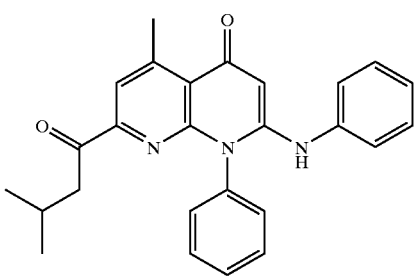 | 3.05 | 412.4 | Intermediate A, B, C, D, E and Example 17, 7, 19, 20 |
| 254 | 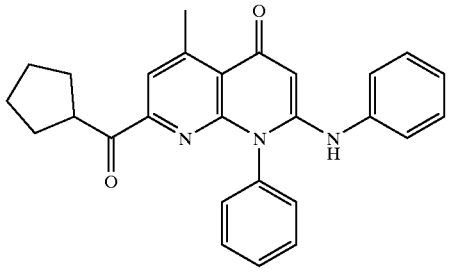 | 3.10 | 424.4 | Intermediate A, B, C, D, E and Example 17, 7, 19, 20 |

TABLE 1A-continued

| Example | Structure | LCMS RT (min) | [M + H] | Representative Procedure |
|---------|-----------|---------------|---------|--------------------------|
| 255 | 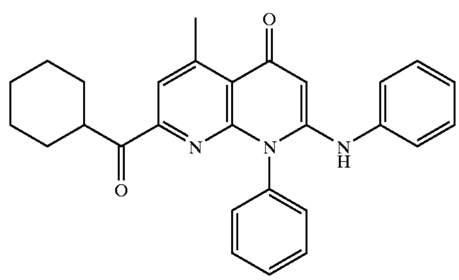 | 3.19 | 438.4 | Intermediate A, B, C, D, E and Example 17, 7, 19, 20 |
| 256 | 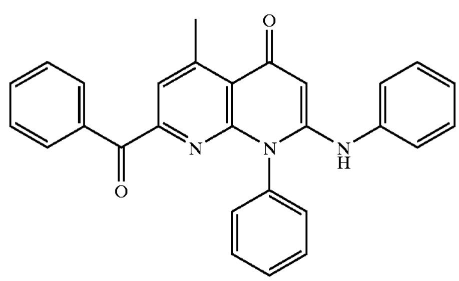 | 2.96 | 432.4 | Intermediate A, B, C, D, E and Example 17, 7, 19, 20 |
| 257 | 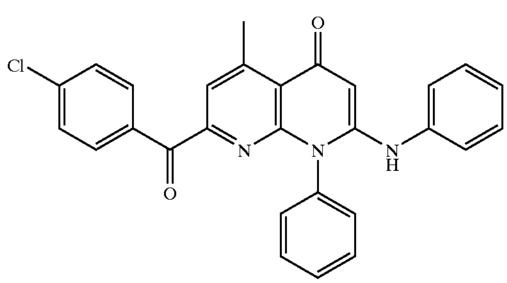 | 3.16 | 466.4 | Intermediate A, B, C, D, E and Example 17, 7, 19, 20 |
| 258 | 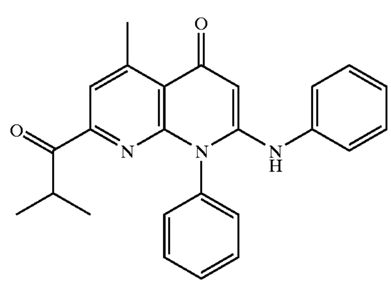 | 2.80 | 398.5 | Intermediate A, B, C, D, E and Example 17, 7, 19, 20 |
| 259 | 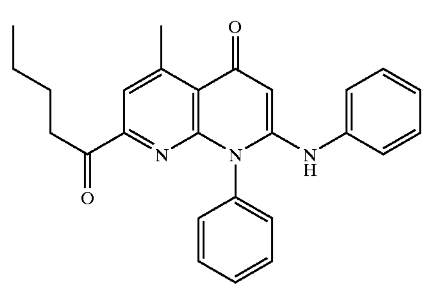 | 2.95 | 412.5 | Intermediate A, B, C, D, E and Example 17, 7, 19, 20 |

TABLE 1A-continued

| Example | Structure | LCMS RT (min) | [M + H] | Representative Procedure |
|---------|-----------|---------------|---------|--------------------------|
| 260 | 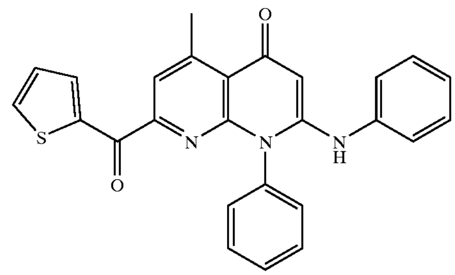 | 2.80 | 438.6 | Intermediate A, B, C, D, E and Example 17, 7, 19, 20 |
| 261 | 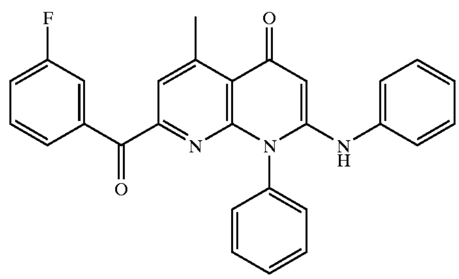 | 3.06 | 450.3 | Intermediate A, B, C, D, E and Example 17, 7, 19, 20 |
| 262 | 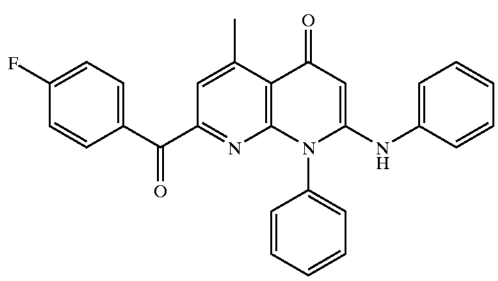 | 3.05 | 450.4 | Intermediate A, B, C, D, E and Example 17, 7, 19, 20 |
| 263 | 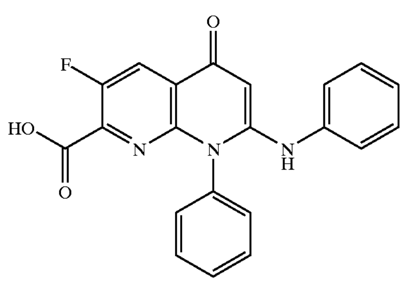 | 1.94 | 376.2 | Intermediate K, L, M, N and Example 17, 7 |
| 264 | 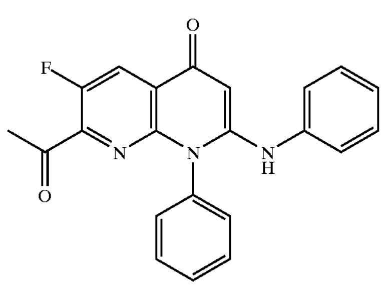 | 2.44 | 374.4 | Intermediate K, L, M, N and Example 17, 7, 19, 20 |

TABLE 1A-continued

| Example | Structure | LCMS RT (min) | [M + H] | Representative Procedure |
|---------|-----------|---------------|---------|--------------------------|
| 265 | 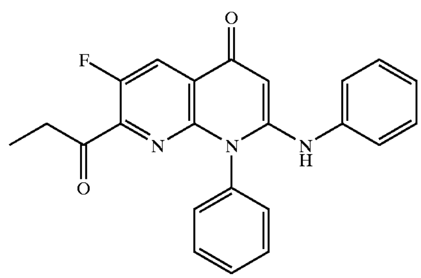 | 2.59 | 388.3 | Intermediate K, L, M, N and Example 17, 7, 19, 20 |
| 266 | 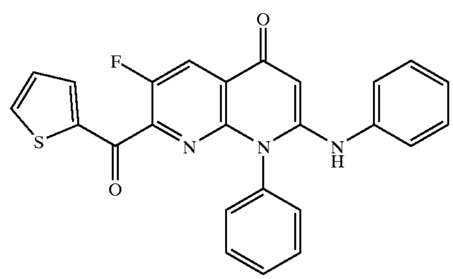 | 2.68 | 442.4 | Intermediate K, L, M, N and Example 17, 7, 19, 20 |
| 267 | 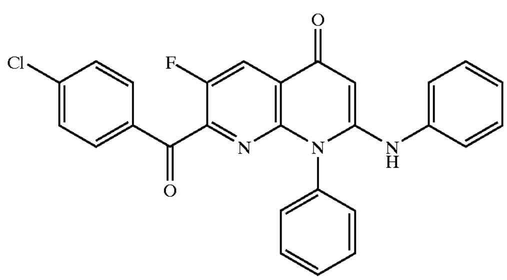 | 2.97 | 470.5 | Intermediate K, L, M, N and Example 17, 7, 19, 20 |
| 268 | 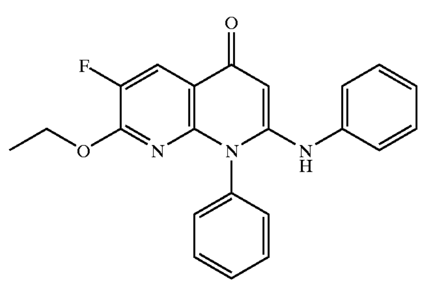 | 2.53 | 376.3 | Intermediate K, L, M, N and Example 9 |
| 269 | 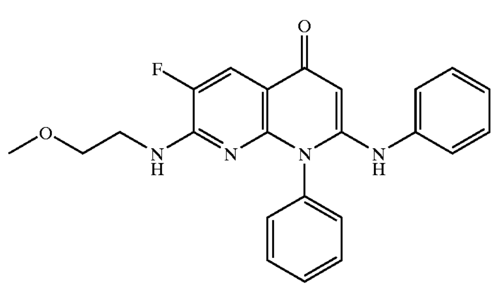 | 2.28 | 405.4 | Intermediate K, L, M, N and Example 2 |

TABLE 1A-continued
| Example | Structure | LCMS RT (min) | [M + H] | Representative Procedure |
|---|---|---|---|---|
| 270 | 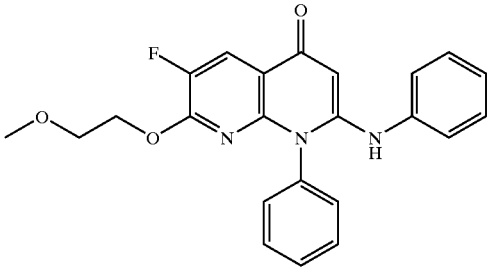 | 2.35 | 406.2 | Intermediate K, L, M, N and Example 9 |
| 271 | 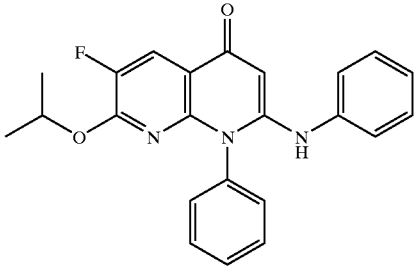 | 2.70 | 390.2 | Intermediate K, L, M, N and Example 9 |
| 272 | 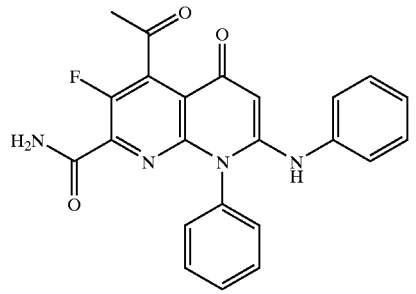 | 2.20 | 417.3 | Intermediate K, L, M, N, AI and Example 17, 18 |
| 273 | 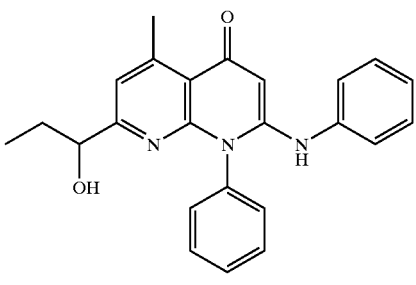 | 2.38 | 386.3 | Intermediate A, B, C, D, E and Example 17, 7, 19, 20, 25 |
| 274 | 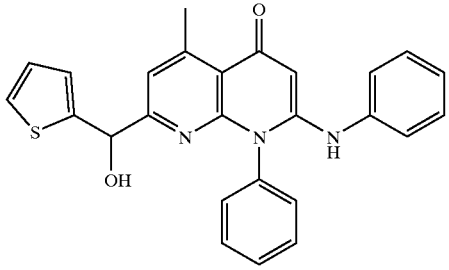 | 2.63 | 440.3 | Intermediate A, B, C, D, E and Example 17, 7, 19, 20, 25 |

TABLE 1A-continued

| Example | Structure | LCMS RT (min) | [M + H] | Representative Procedure |
|---|---|---|---|---|
| 275 | 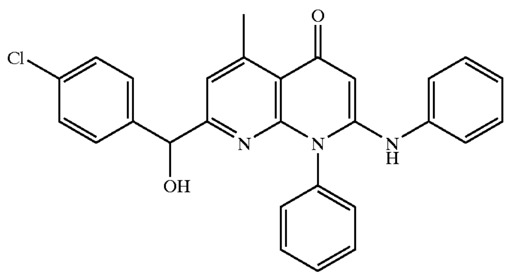 | 2.83 | 468.3 | Intermediate A, B, C, D, E and Example 17, 7, 19, 20, 25 |
| 276 | 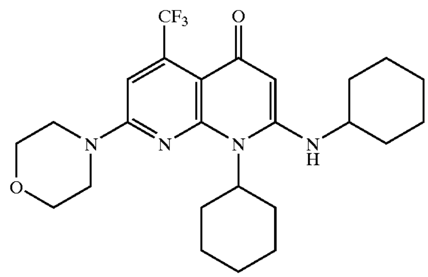 | 2.79 | 479.3 | Intermediate F, G, H, I, J and Example 8 |
| 277 | 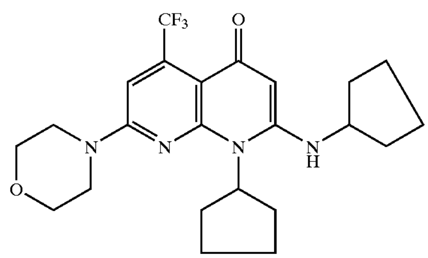 | 2.58 | 451.2 | Intermediate F, G, H, I, J and Example 8 |
| 278 | 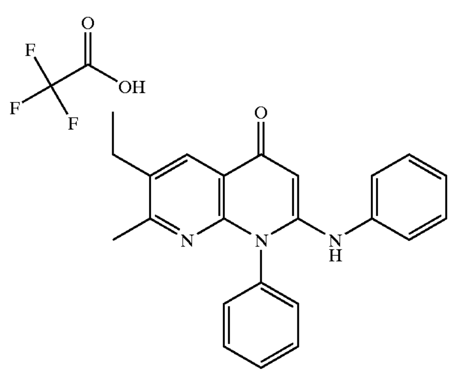 | 2.58 | 356.4 | Intermediate Y, S, T, U, W and Example 15, 34 |
| 279 | 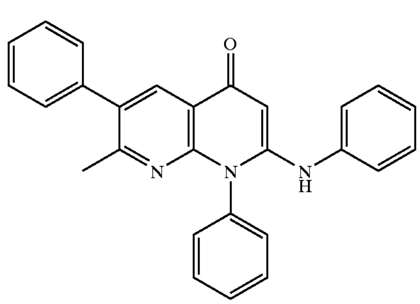 | 2.79 | 404.4 | Intermediate Y, S, T, U, W and Example 15, 4 |

TABLE 1A-continued
| Example | Structure | LCMS RT (min) | [M + H] | Representative Procedure |
|---|---|---|---|---|
| 280 | 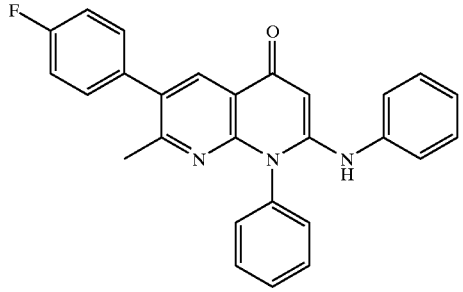 | 2.93 | 422.4 | Intermediate Y, S, T, U, W and Example 15, 4 |
| 281 | 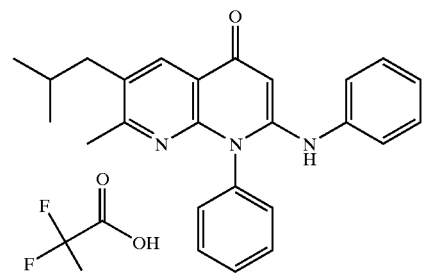 | 2.78 | 384.4 | Intermediate Y, S, T, U, W and Example 15, 34 |
| 282 | 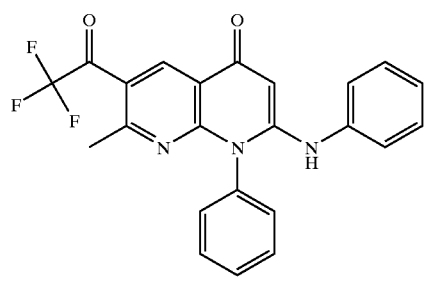 | 2.50 | 442.2 (423 + H2O + 1) | Intermediate Y, S, T, U, W and Example 15, 34 |
| 283 | 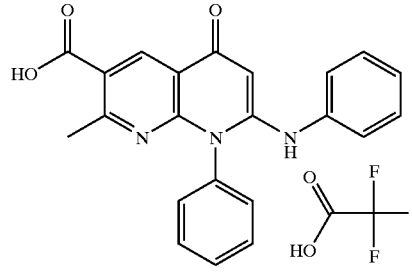 | 2.26 | 372.4 | Intermediate Y, S, T, U, W and Example 15, 34 |
| 284 | 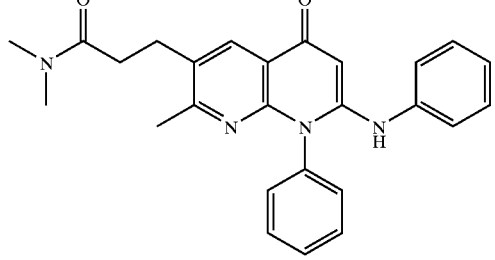 | 2.29 | 427.4 | Intermediate Y, S, T, U, W and Example 15, 31, 32, 33, 13 |

TABLE 1A-continued

| Example | Structure | LCMS RT (min) | [M + H] | Representative Procedure |
|---------|-----------|---------------|---------|--------------------------|
| 285 | 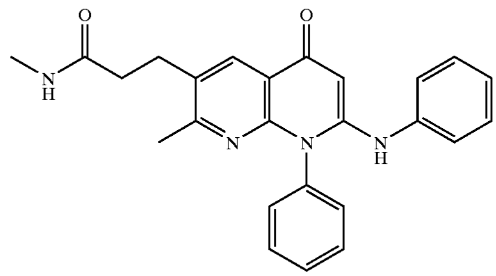 | 2.19 | 413.4 | Intermediate Y, S, T, U, W and Example 15, 31, 32, 33, 13 |
| 286 | 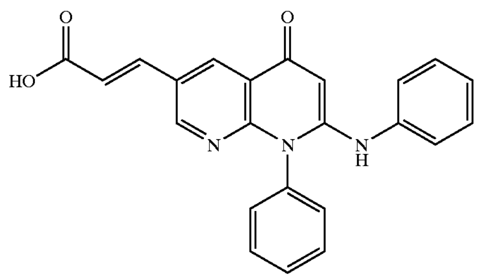 | 2.15 | 384.4 | Intermediate Y, S, T, U, W and Example 15, 31, 32 |
| 287 | 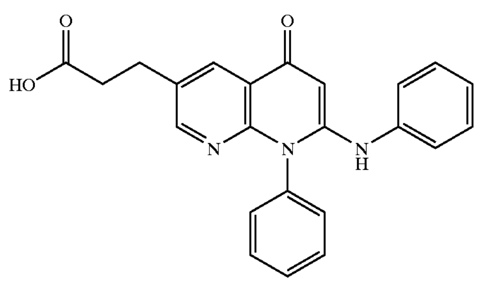 | 2.01 | 386.4 | Intermediate Y, S, T, U, W and Example 15, 31, 32, 33 |
| 288 | 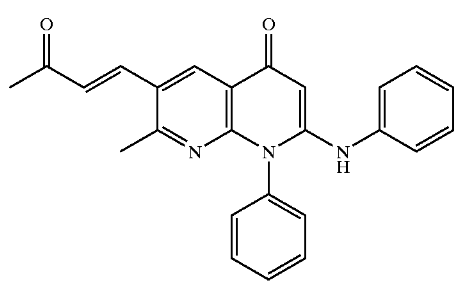 | 2.42 | 396.5 | Intermediate Y, S, T, U, W and Example 15, 31 |
| 289 | 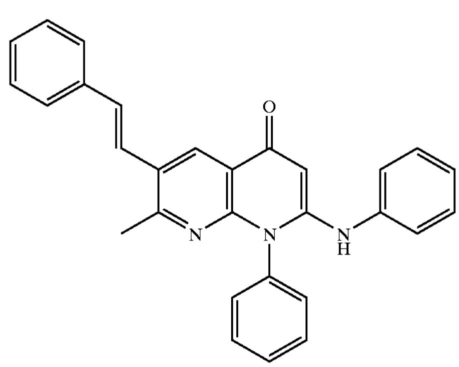 | 2.97 | 430.6 | Intermediate Y, S, T, U, W and Example 15, 31 |

TABLE 1A-continued

| Example | Structure | LCMS RT (min) | [M + H] | Representative Procedure |
|---|---|---|---|---|
| 290 | 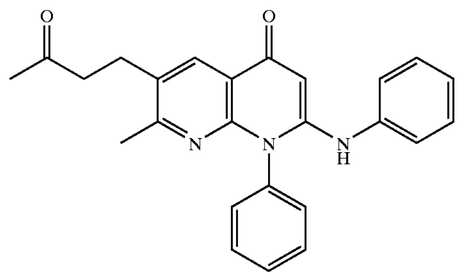 | 2.33 | 398.6 | Intermediate Y, S, T, U, W and Example 15, 31, 33 |
| 291 | 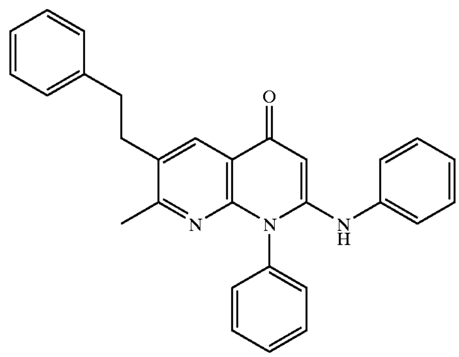 | 2.87 | 432.4 | Intermediate Y, S, T, U, W and Example 15, 31, 33 |
| 292 | 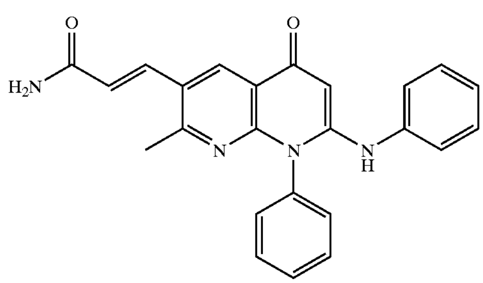 | 2.01 | 397.3 | Intermediate Y, S, T, U, W and Example 15, 31, 32, 13 |
| 293 | 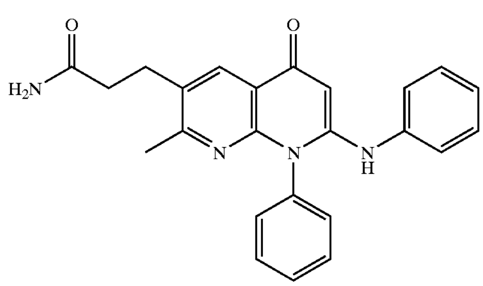 | 2.00 | 399.5 | Intermediate Y, S, T, U, W and Example 15, 31, 32, 33, 13 |

TABLE 1A-continued

| Example | Structure | LCMS RT (min) | [M + H] | Representative Procedure |
|---|---|---|---|---|
| 294 | 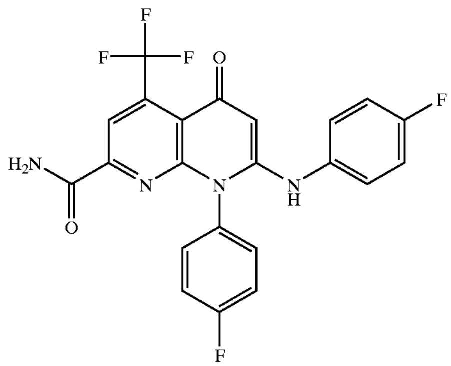 | 2.63 | 461.3 | Intermediate F, G, H, I, J and Example 17, 18 |
| 295 | 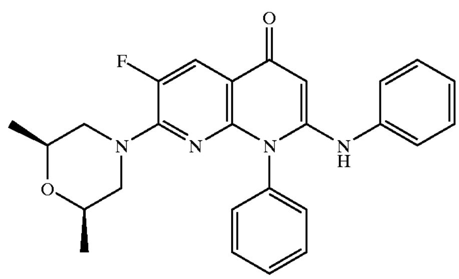 | 2.54 | 445.5 | Intermediate K, L, M, N and Example 2 |
| 296 | 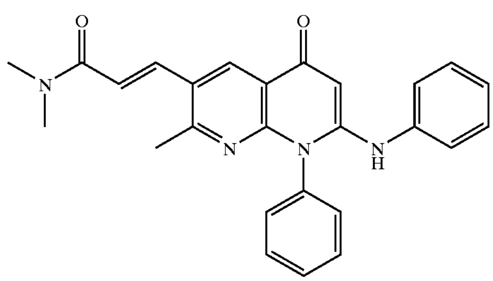 | 2.27 | 425.3 | Intermediate Y, S, T, U, W and Example 15, 31, 32, 13 |
| 297 | 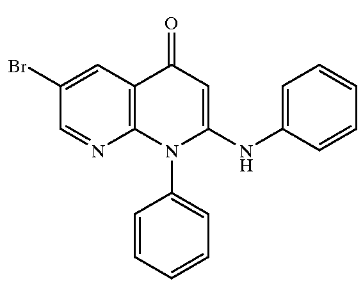 | 2.43 | 392.3 | Intermediate Y, S, T, U, W and Example 15 |
| 298 | 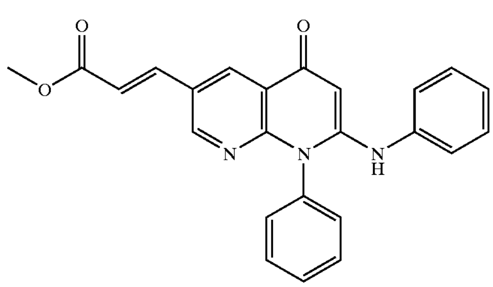 | 2.40 | 398.5 | Intermediate Y, S, T, U, W and Example 15, 31 |

TABLE 1A-continued

| Example | Structure | LCMS RT (min) | [M + H] | Representative Procedure |
|---------|-----------|---------------|---------|--------------------------|
| 299 | 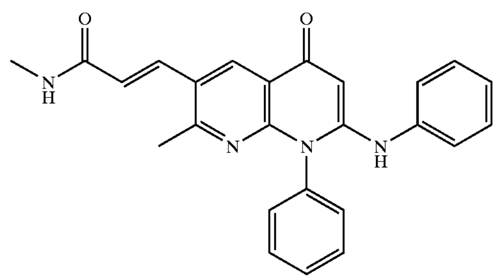 | 2.28 | 411.4 | Intermediate Y, S, T, U, W and Example 15, 31, 32, 13 |
| 300 | 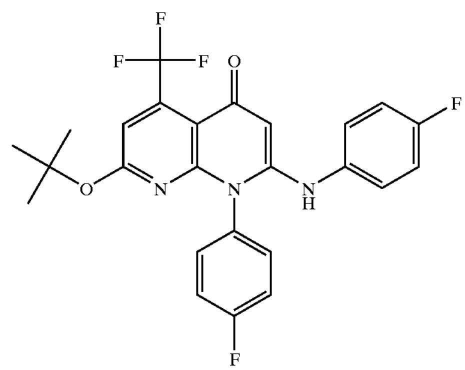 | 3.18 | 490.0 | Intermediate F, G, H, I, J and Example 9 |
| 301 | 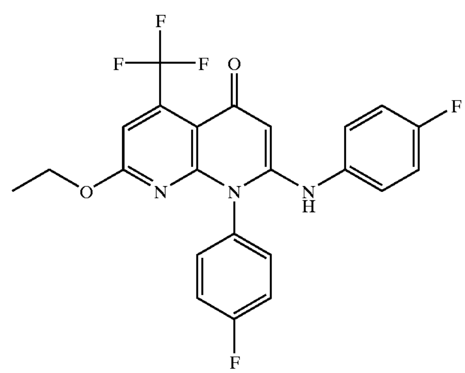 | 2.90 | 462.3 | Intermediate F, G, H, I, J and Example 9 |
| 302 | 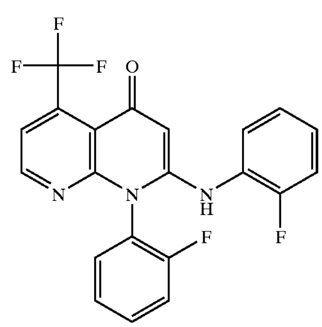 | 2.90 | 418.3 | Intermediate F, G, H, I, J and Example 1 |

TABLE 1A-continued

| Example | Structure | LCMS RT (min) | [M + H] | Representative Procedure |
|---|---|---|---|---|
| 303 | 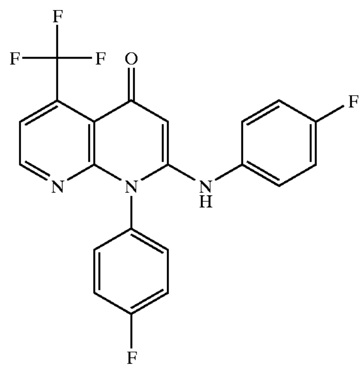 | 2.66 | 418.3 | Intermediate F, G, H, I, J and Example 1 |
| 304 | 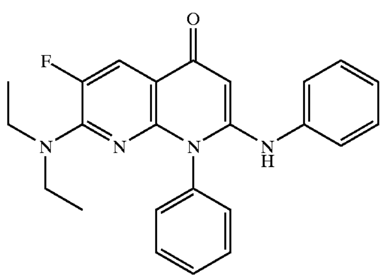 | 2.70 | 403.6 | Intermediate K, L, M, N and Example 2 |
| 305 | 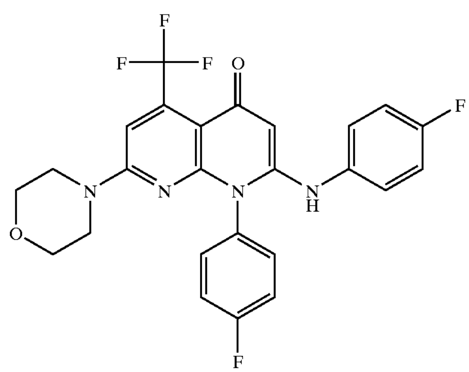 | 2.52 | 503.6 | Intermediate F, G, H, I, J and Example 8 |
| 306 | 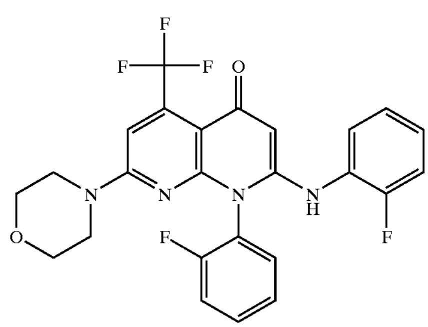 | 3.03 | 502.2 | Intermediate F, G, H, I, J and Example 8 |

TABLE 1A-continued

| Example | Structure | LCMS RT (min) | [M + H] | Representative Procedure |
|---------|-----------|---------------|---------|--------------------------|
| 307 | 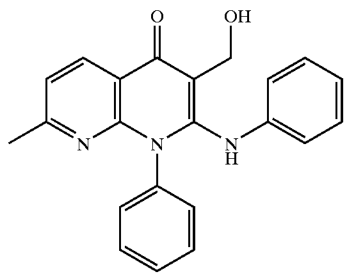 | 2.68 | 358.0 | Intermediate S, T, U, W and Example 25 |
| 308 | 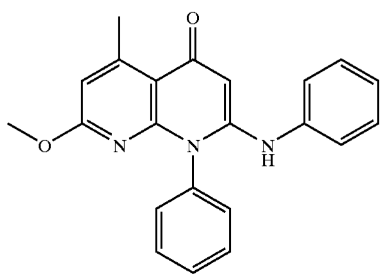 | 2.40 | 358.4 | Intermediate A, B, C, D, E and Example 9 |

Utilizing the above described procedures for intermediates and examples alone or in combination, a variety of Formula I compounds can be prepared using the appropriate starting material and the representative procedure described. These compounds are summarized in Table 1B.

TABLE 1B

| Example | Structure | Representative Procedure |
|---------|-----------|--------------------------|
| 309 | 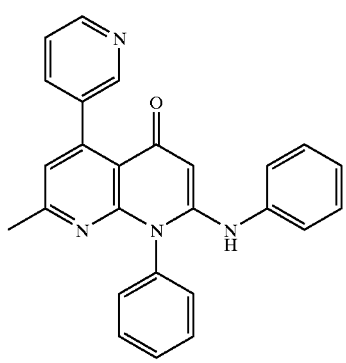 | Intermediate Z, AA, AB and Example 16, 4 |

TABLE 1B-continued
| Example | Structure | Representative Procedure |
|---|---|---|
| 310 | 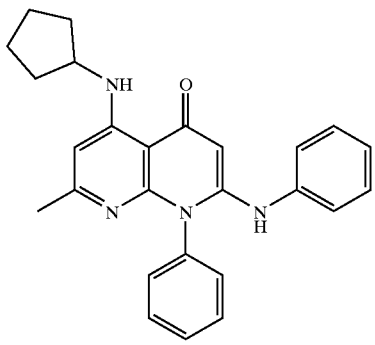 | Intermediate Z, AA, AB and Example 16, 2 |
| 311 | 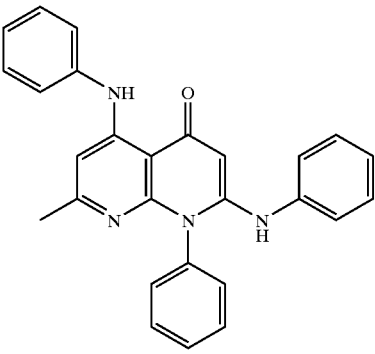 | Intermediate Z, AA, AB and Example 16, 3 |
| 312 | 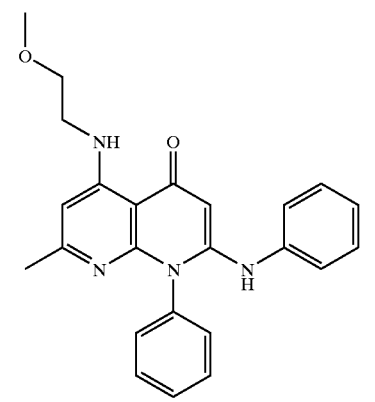 | Intermediate Z, AA, AB and Example 16, 2 |
| 313 | 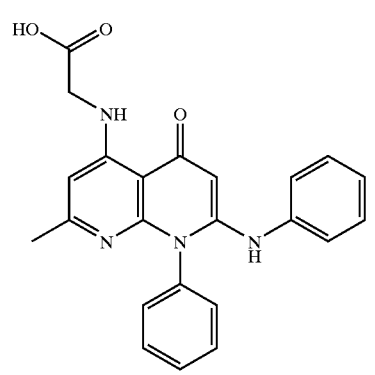 | Intermediate Z, AA, AB and Example 16, 2, 7 |

TABLE 1B-continued
| Example | Structure | Representative Procedure |
|---|---|---|
| 314 | 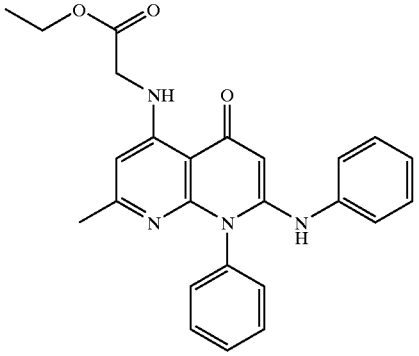 | Intermediate Z, AA, AB and Example 16, 2 |
| 315 | 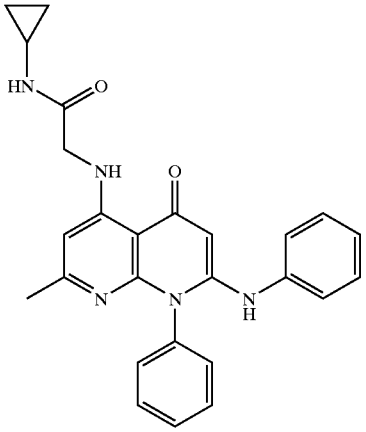 | Intermediate Z, AA, AB and Example 16, 2, 7, 13 |
| 316 | 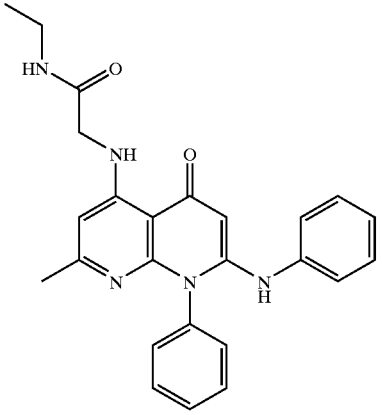 | Intermediate Z, AA, AB and Example 16, 2, 7, 13 |

TABLE 1B-continued
| Example | Structure | Representative Procedure |
|---|---|---|
| 317 | 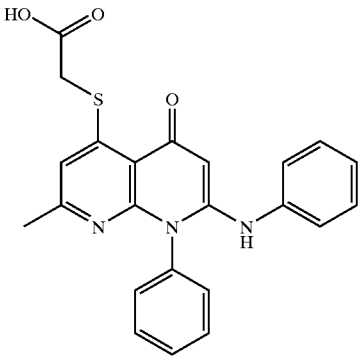 | Intermediate Z, AA, AB and Example 16, 6, 7 |
| 318 | 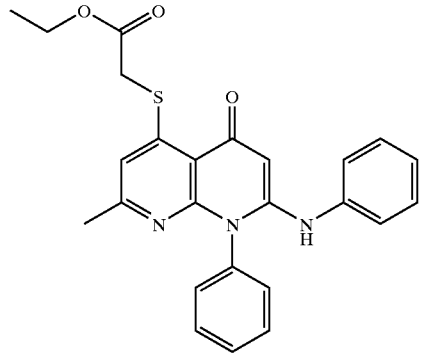 | Intermediate Z, AA, AB and Example 16, 6 |
| 319 | 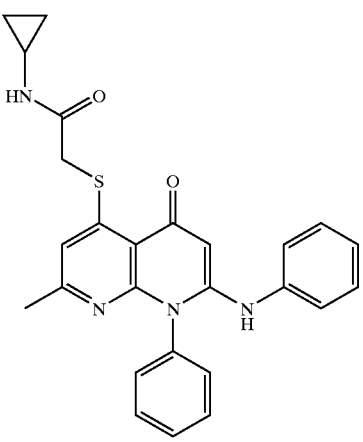 | Intermediate Z, AA, AB and Example 16, 6, 7, 13 |

TABLE 1B-continued
| Example | Structure | Representative Procedure |
| --- | --- | --- |
| 320 | 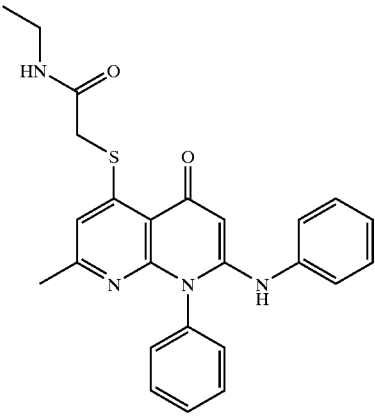 | Intermediate Z, AA, AB and Example 16, 6, 7, 13 |
| 321 | 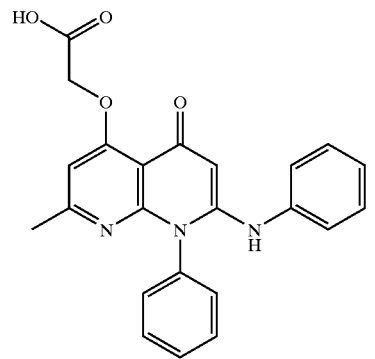 | Intermediate Z, AA, AB, and Example 16, 9, 7 |
| 322 | 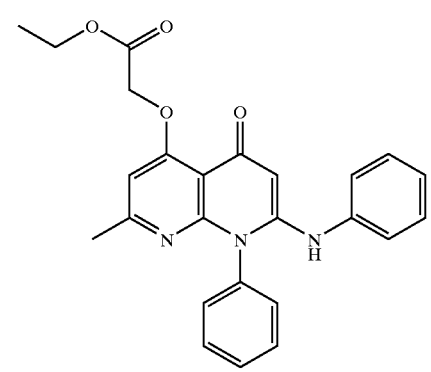 | Intermediate Z, AA, AB, and Example 16, 9 |

TABLE 1B-continued

| Example | Structure | Representative Procedure |
|---|---|---|
| 323 | 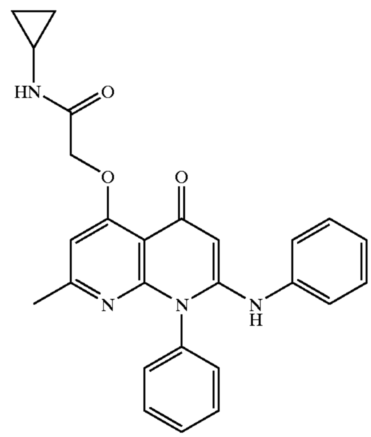 | Intermediate Z, AA, AB, and Example 16, 9, 7, 13 |
| 324 | 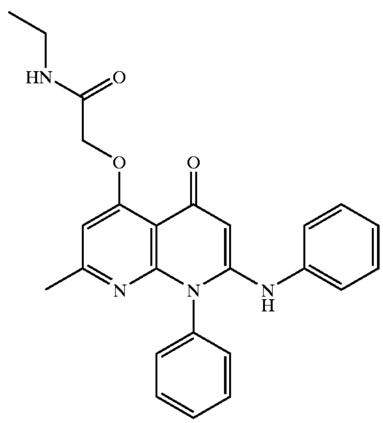 | Intermediate Z, AA, AB, and Example 16, 9, 7, 13 |
| 325 | 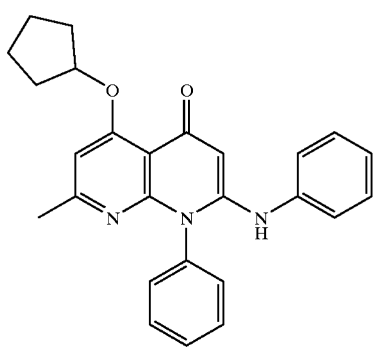 | Intermediate Z, AA, AB, and Example 16, 9 |

TABLE 1B-continued
| Example | Structure | Representative Procedure |
|---------|-----------|--------------------------|
| 326 | 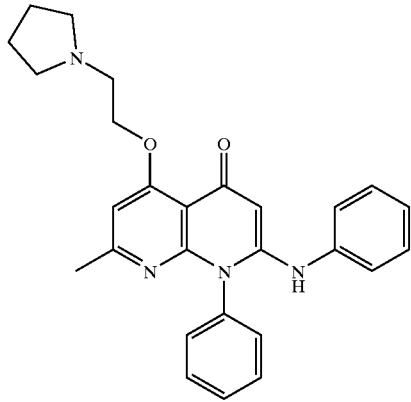 | Intermediate Z, AA, AB, and Example 16, 9 |
| 327 | 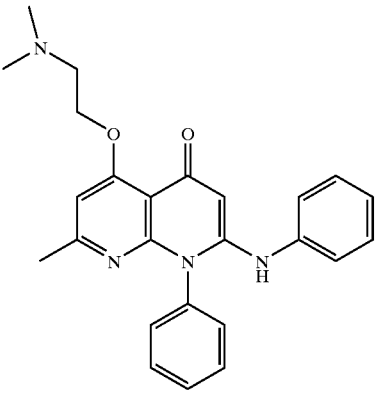 | Intermediate Z, AA, AB, and Example 16, 9 |
| 328 | 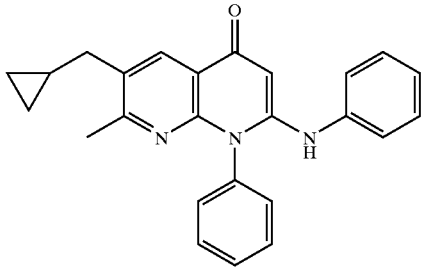 | Intermediate Y, S, T, U, W and Example 15, 34 |
| 329 | 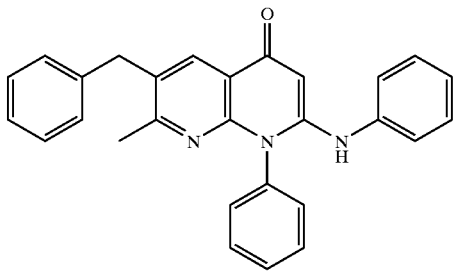 | Intermediate Y, S, T, U, W and Example 15, 34 |

TABLE 1B-continued

| Example | Structure | Representative Procedure |
|---------|-----------|--------------------------|
| 330 | 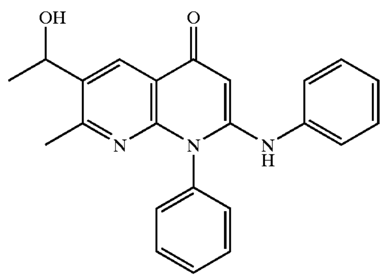 | Intermediate Y, S, T, U, W and Example 15, 34 |
| 331 | 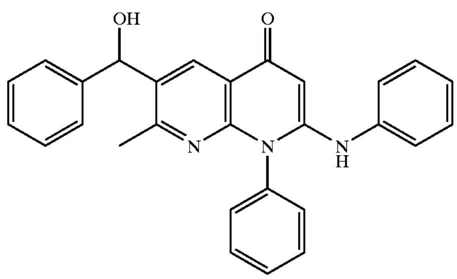 | Intermediate Y, S, T, U, W and Example 15, 34 |
| 332 | 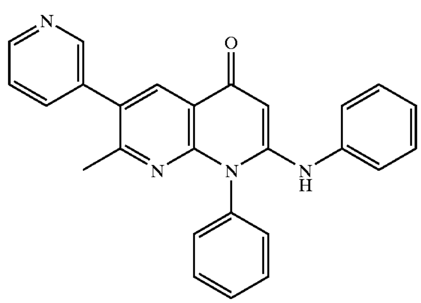 | Intermediate Y, S, T, U, W and Example 15, 4 |
| 333 | 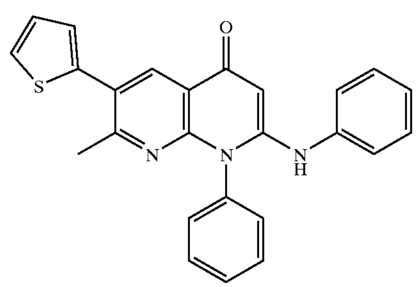 | Intermediate Y, S, T, U, W and Example 15, 4 |
| 334 | 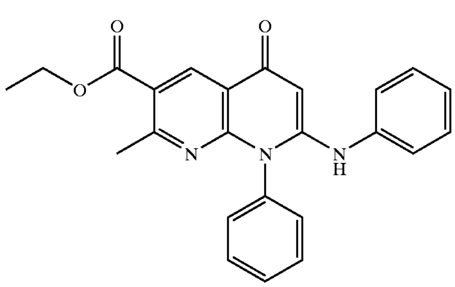 | Intermediate Y, S, T, U, W and Example 15, 34 |

TABLE 1B-continued

| Example | Structure | Representative Procedure |
|---|---|---|
| 335 | 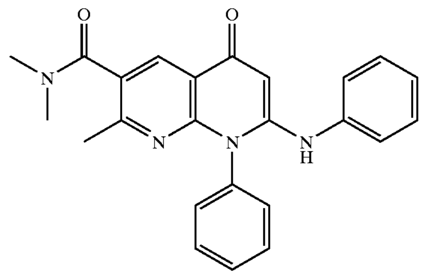 | Intermediate Y, S, T, U, W and Example 15, 34, 13 |
| 336 | 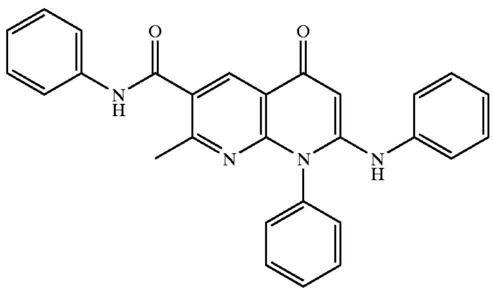 | Intermediate Y, S, T, U, W and Example 15, 34, 13 |
| 337 | 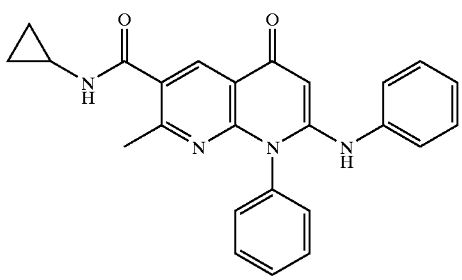 | Intermediate Y, S, T, U, W and Example 15, 34, 13 |
| 338 | 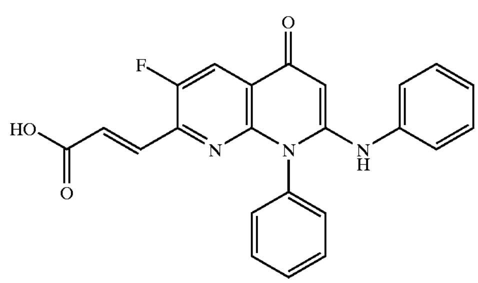 | Intermediate K, L, M, N Example 31, 32 |
| 339 | 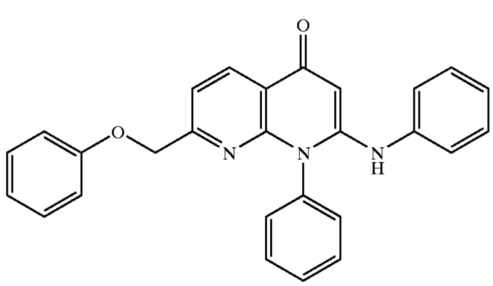 | Intermediate O, P, Q, R and Example 17, 25, 26 |

TABLE 1B-continued
| Example | Structure | Representative Procedure |
|---|---|---|
| 340 | 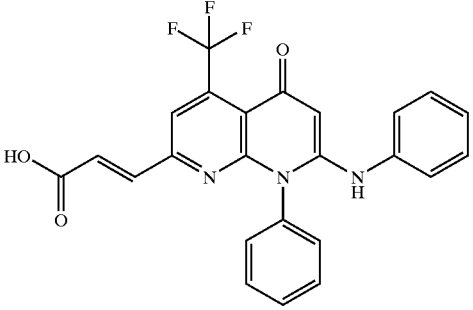 | Intermediate F, G, H, I, J and Example 31, 32 |
| 341 | 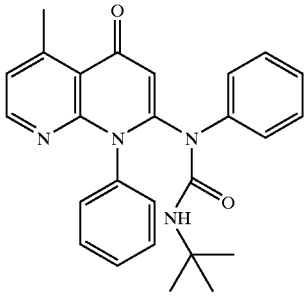 | Intermediate A, B, C, D, E and Example 1 and Intermediate AK |
| 342 | 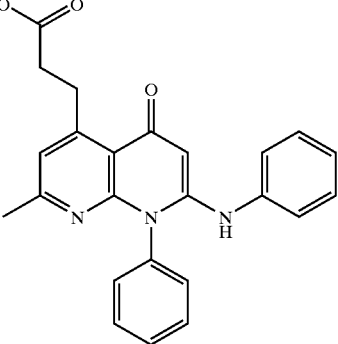 | Intermediate Z, AA, AB and Example 16, 31, 32, 33 |
| 343 | 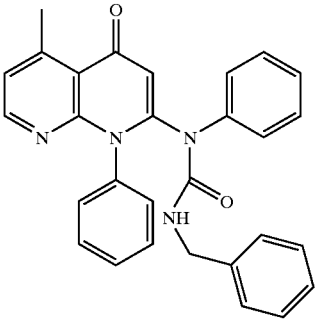 | Intermediate A, B, C, D, E and Example 1 and Intermediate AK |

TABLE 1B-continued
| Example | Structure | Representative Procedure |
|---|---|---|
| 344 | 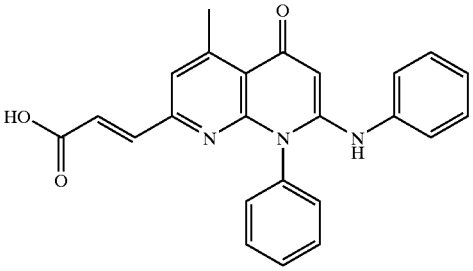 | Intermediate A, B, C, D, E and Example 31, 32 |
| 345 | 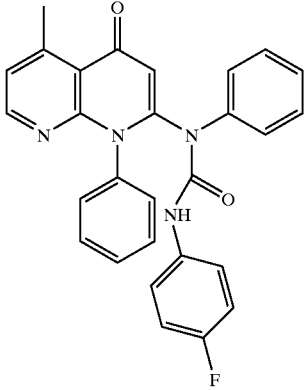 | Intermediate A, B, C, D, E and Example 1 and Intermediate AK |
| 346 | 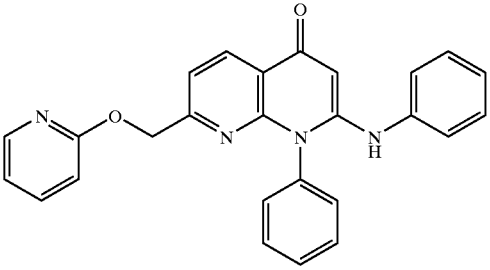 | Intermediate O, P, Q, R and Example 17, 25, 26 |
| 347 | 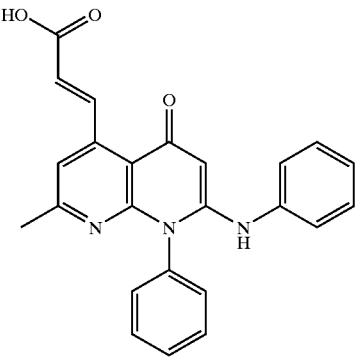 | Intermediate Z, AA, AB, and Example 16, 31, 32 |

TABLE 1B-continued

| Example | Structure | Representative Procedure |
|---|---|---|
| 348 | 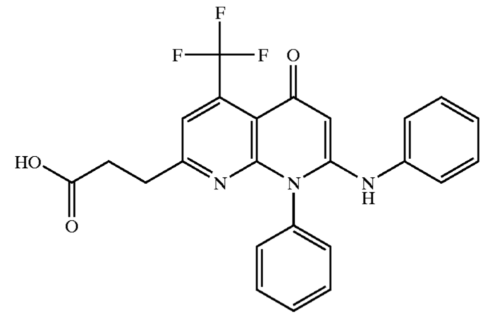 | Intermediate F, G, H, I, J and Example 31, 32, 33 |
| 349 | 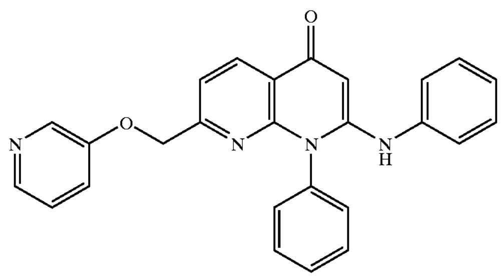 | Intermediate O, P, Q, R and Example 17, 25, 26 |
| 350 | 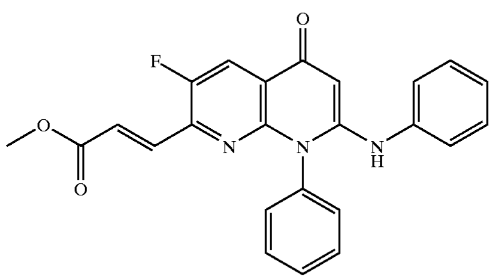 | Intermediate K, L, M, N and Example 31 |
| 351 | 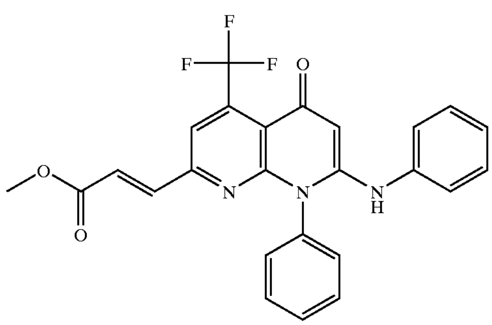 | Intermediate F, G, H, I, J and Example 31 |
| 352 | 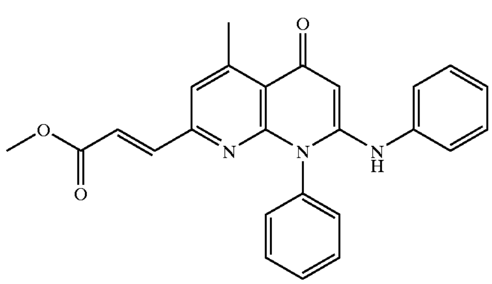 | Intermediate A, B, C, D, E and Example 31 |

TABLE 1B-continued

| Example | Structure | Representative Procedure |
|---------|-----------|--------------------------|
| 353 | 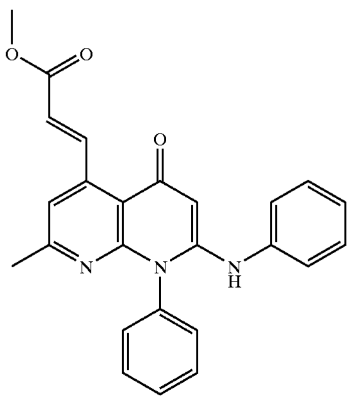 | Intermediate Z, AA, AB and Example 16, 31 |
| 354 | 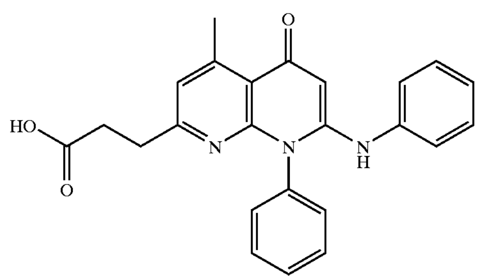 | Intermediate A, B, C, D, E and Example 31, 32, 33 |
| 355 | 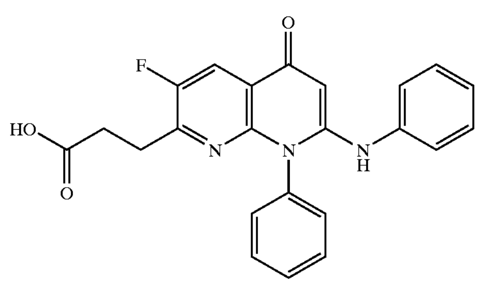 | Intermediate K, L, M, N and Example 31, 32, 33 |
| 356 | 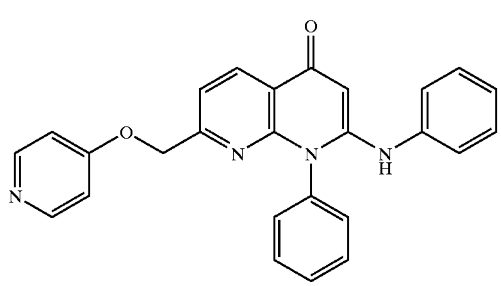 | Intermediate O, P, Q, R and Example 17, 25, 26 |
| 357 | 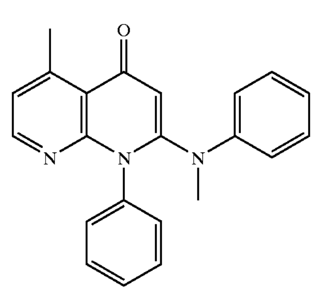 | Intermediate A, B, C, D, E AJ and Example 1 |

TABLE 1B-continued

| Example | Structure | Representative Procedure |
|---|---|---|
| 358 | 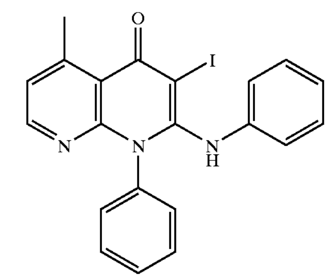 | Intermediate A, B, C, D, E and Example 1 and Intermediate AL |
| 359 | 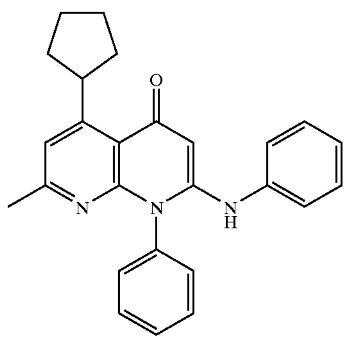 | Intermediate Z, AA, AB, and Example 16, 5 |
| 360 | 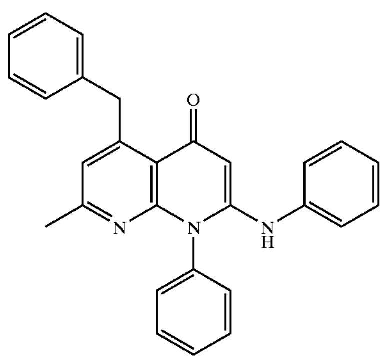 | Intermediate Z, AA, AB, and Example 16, 5 |
| 361 | 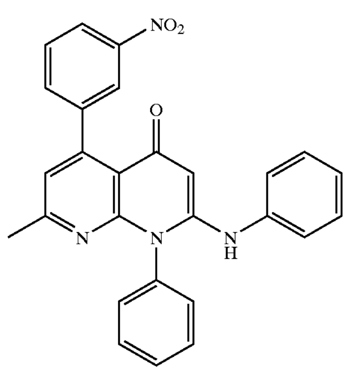 | Intermediate Z, AA, AB, and Example 16, 4 |

TABLE 1B-continued

| Example | Structure | Representative Procedure |
|---------|-----------|--------------------------|
| 362 | 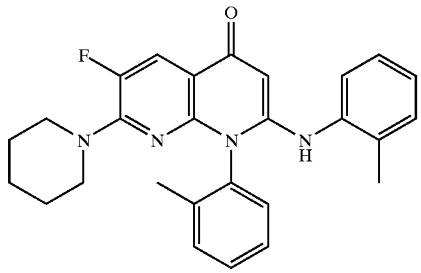 | Intermediate K, L, M, N, and Example 2 |
| 363 | 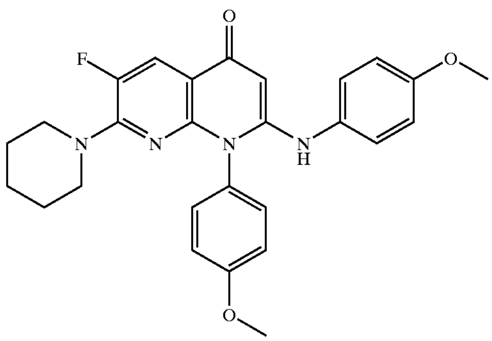 | Intermediate K, L, M, N, and Example 2 |
| 364 | 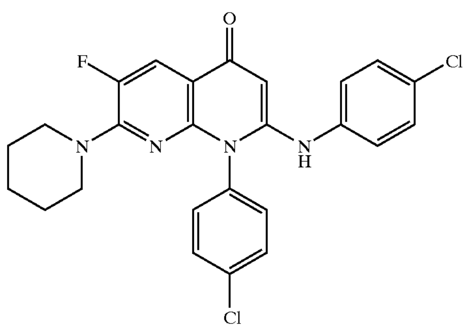 | Intermediate K, L, M, N, and Example 2 |
| 365 | 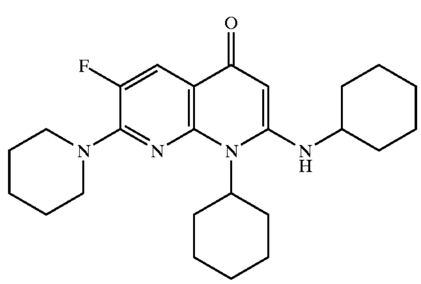 | Intermediate K, L, M, N, and Example 2 |
| 366 | 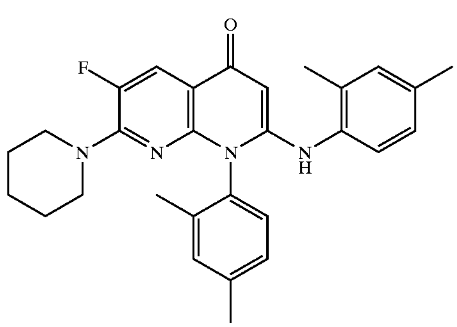 | Intermediate K, L, M, N, and Example 2 |

TABLE 1B-continued
| Example | Structure | Representative Procedure |
|---|---|---|
| 367 | 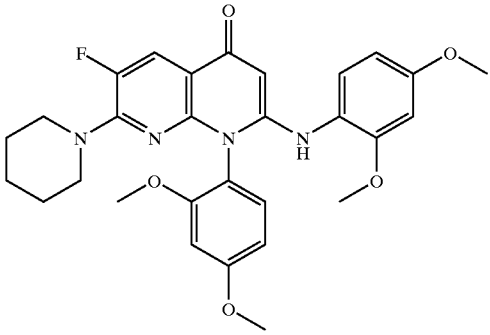 | Intermediate K, L, M, N, and Example 2 |
| 368 | 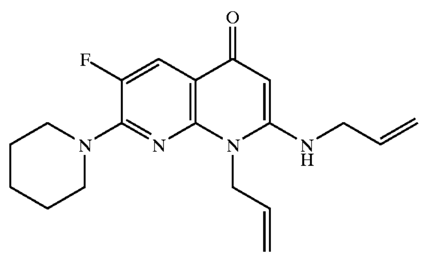 | Intermediate K, L, M, N, and Example 2 |
| 369 | 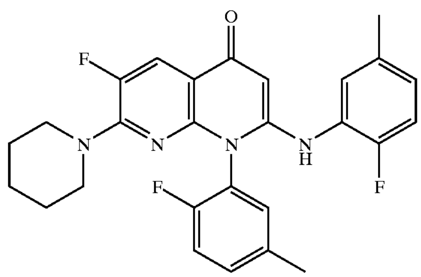 | Intermediate K, L, M, N, and Example 2 |
| 370 | 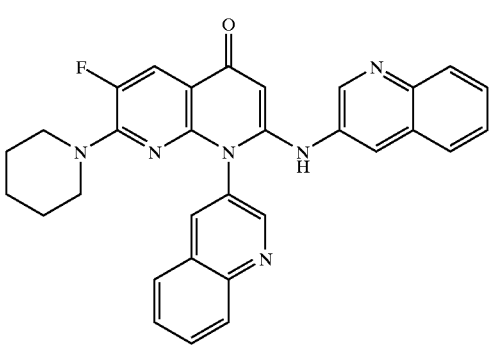 | Intermediate K, L, M, N, and Example 2 |
| 371 | 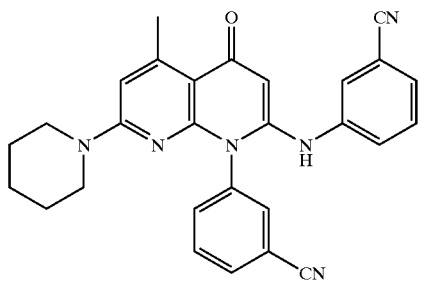 | Intermediate A, B, C, D, E and Example 2 |

TABLE 1B-continued
| Example | Structure | Representative Procedure |
|---|---|---|
| 372 | 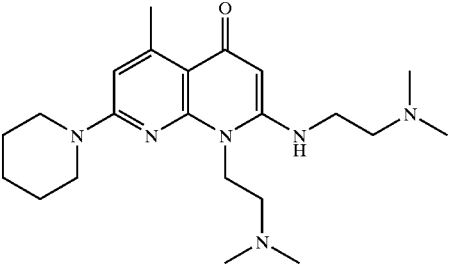 | Intermediate A, B, C, D, E and Example 2 |
| 373 | 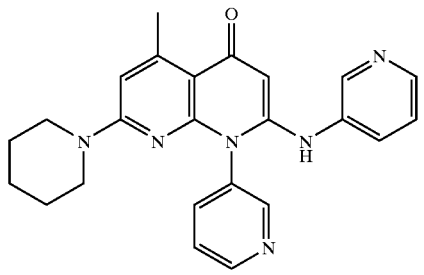 | Intermediate A, B, C, D, E and Example 2 |
| 374 | 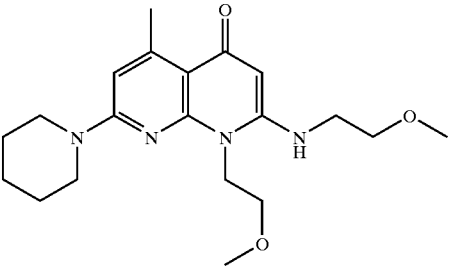 | Intermediate A, B, C, D, E and Example 2 |
| 375 | 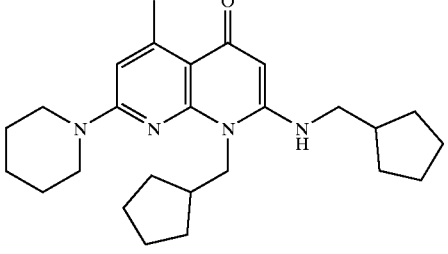 | Intermediate A, B, C, D, E and Example 2 |
| 376 | 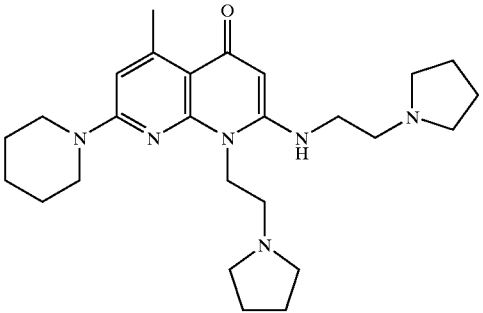 | Intermediate A, B, C, D, E and Example 2 |

TABLE 1B-continued

| Example | Structure | Representative Procedure |
|---|---|---|
| 377 | 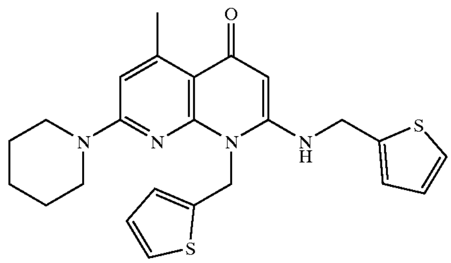 | Intermediate A, B, C, D, E and Example 2 |
| 378 | 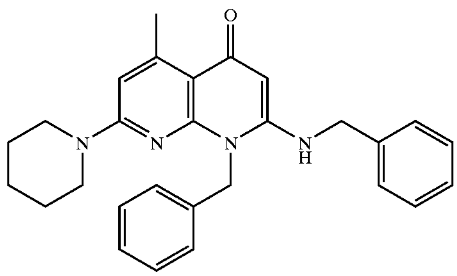 | Intermediate A, B, C, D, E and Example 2 |
| 379 | 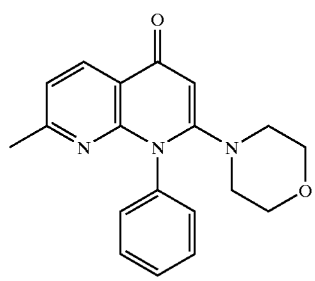 | Intermediate S, T, V, X and Example 15 |
| 380 | 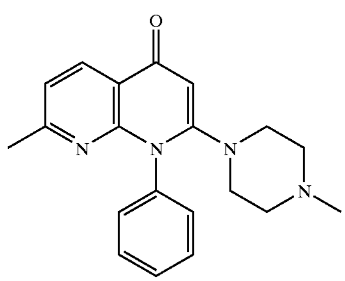 | Intermediate S, T, V, X and Example 15 |
| 381 | 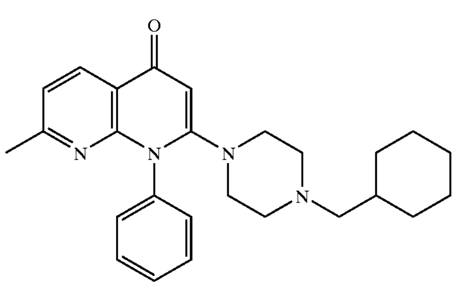 | Intermediate S, T, V, X and Example 15 and Intermediate AJ |

TABLE 1B-continued

| Example | Structure | Representative Procedure |
|---------|-----------|--------------------------|
| 382 | 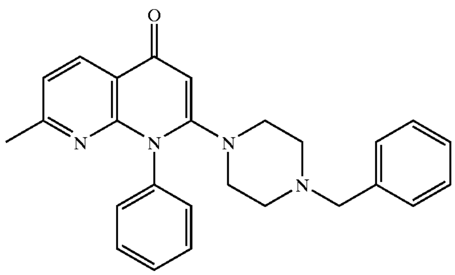 | Intermediate S, T, V, X and Example 15 and Intermediate AJ |
| 383 | 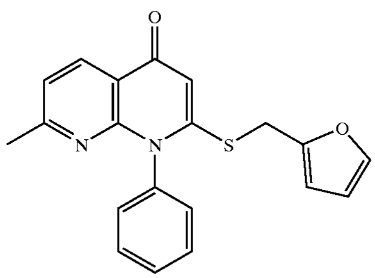 | Intermediate S, T, V and Example 15 |
| 384 | 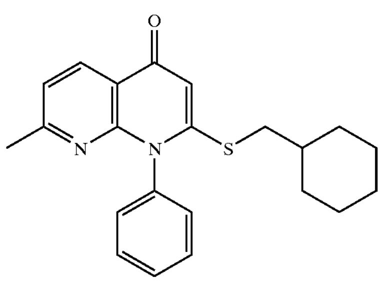 | Intermediate S, T, V and Example 15 |
| 385 | 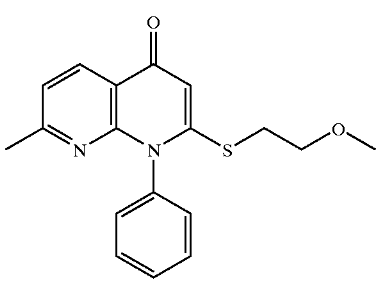 | Intermediate S, T, V and Example 15 |
| 386 | 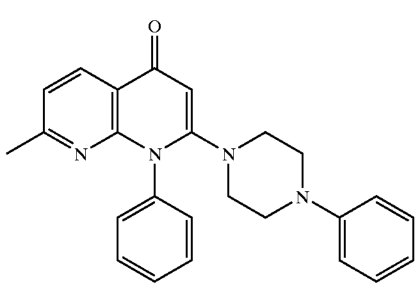 | Intermediate S, T, V, X and Example 15 |

TABLE 1B-continued

| Example | Structure | Representative Procedure |
| --- | --- | --- |
| 387 | 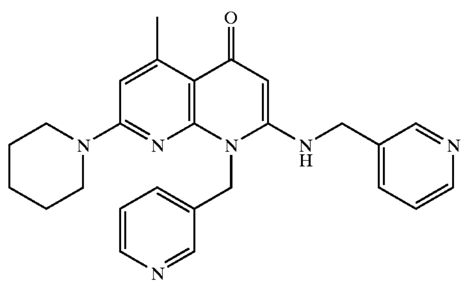 | Intermediate A, B, C, D, E and Example 2 |
| 388 | 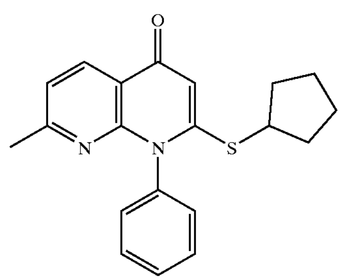 | Intermediate S, T, V and Example 15 |
| 389 | 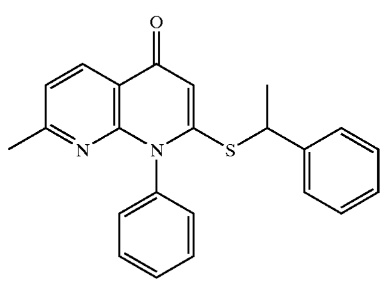 | Intermediate S, T, V and Example 15 |
| 390 | 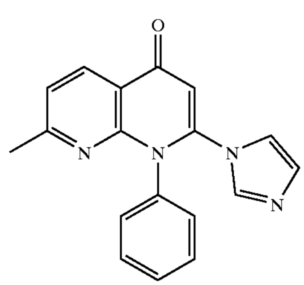 | Intermediate S, T, V, X and Example 15 |
| 391 | 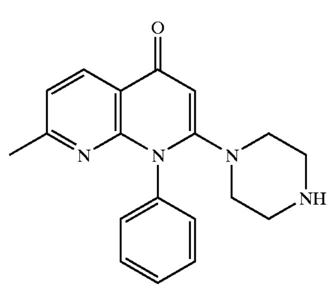 | Intermediate S, T, V, X and Example 15 |

TABLE 1B-continued

| Example | Structure | Representative Procedure |
|---|---|---|
| 392 | 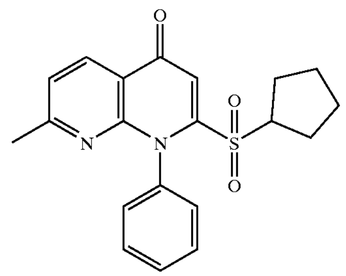 | Intermediate S, T, V and Example 15, 21 |
| 393 | 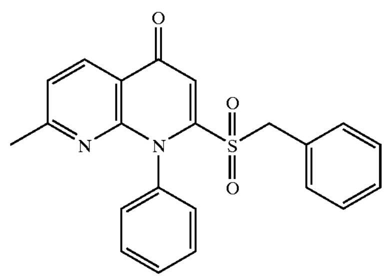 | Intermediate S, T, V and Example 15, 21 |
| 394 | 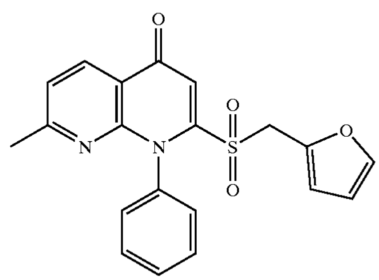 | Intermediate S, T, V and Example 15, 21 |
| 395 | 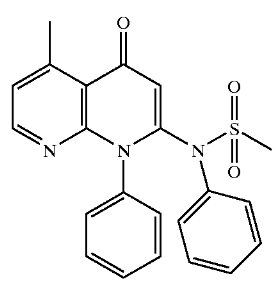 | Intermediate A, B, C, D, E and Example 1, 12 |
| 396 | 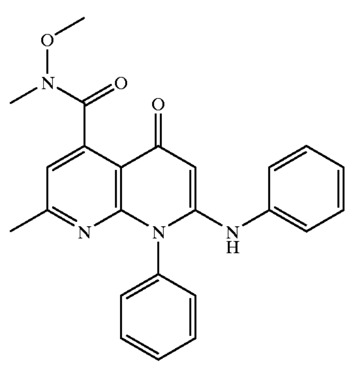 | Intermediate Z, AA, AB and Example 16, 17, 7, 19 |

TABLE 1B-continued
| Example | Structure | Representative Procedure |
|---|---|---|
| 397 | 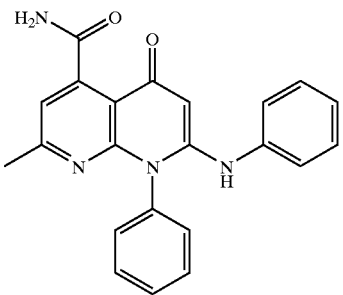 | Intermediate Z, AA, AB and Example 16, 17, 18 |
| 398 | 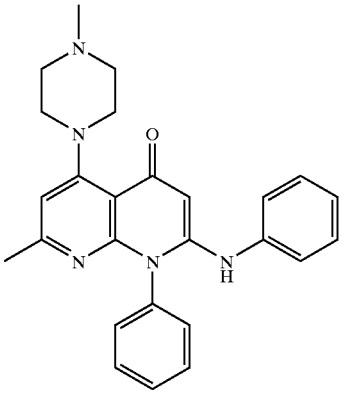 | Intermediate Z, AA, AB and Example 16, 2 |
| 399 | 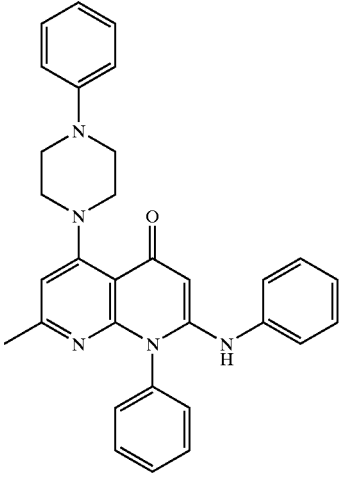 | Intermediate Z, AA, AB and Example 16, 2 |

TABLE 1B-continued

| Example | Structure | Representative Procedure |
|---|---|---|
| 400 | 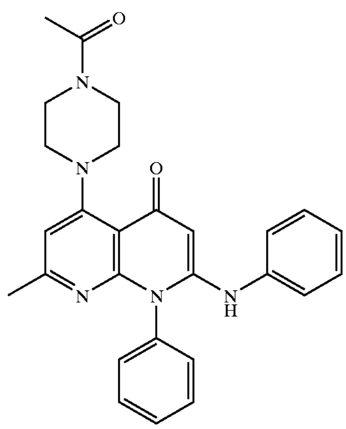 | Intermediate Z, AA, AB and Example 16, 2, 13 |
| 401 | 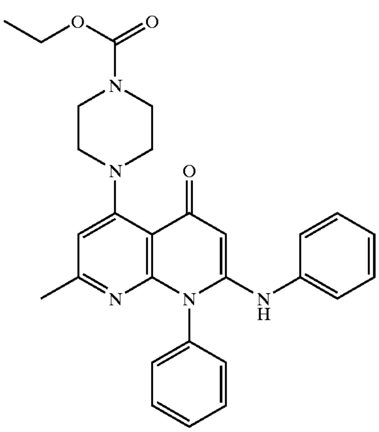 | Intermediate Z, AA, AB and Example 16, 2 |
| 402 | 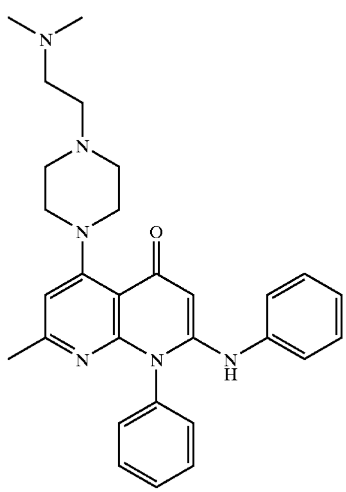 | Intermediate Z, AA, AB and Example 16, 2 |

TABLE 1B-continued

| Example | Structure | Representative Procedure |
|---------|-----------|--------------------------|
| 403 | 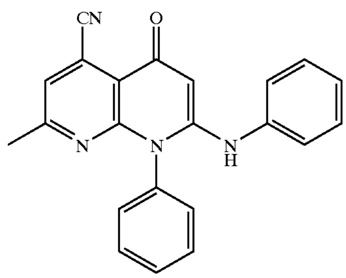 | Intermediate Z, AA, AB and Example 16, 9 |
| 404 | 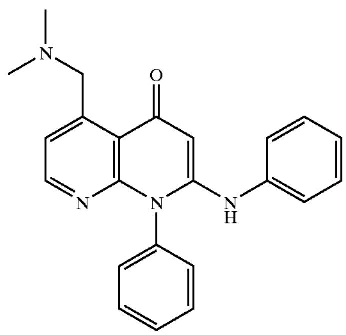 | Intermediate A, B, C, D, E and Example 1, 10, 11 |
| 405 | 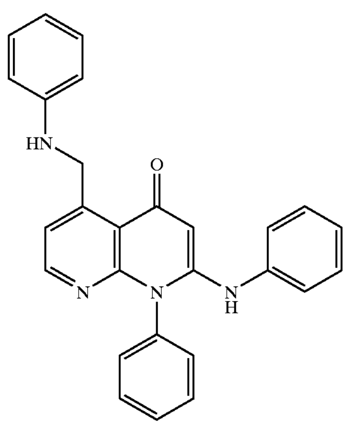 | Intermediate A, B, C, D, E and Example 1, 10, 11 |
| 406 | 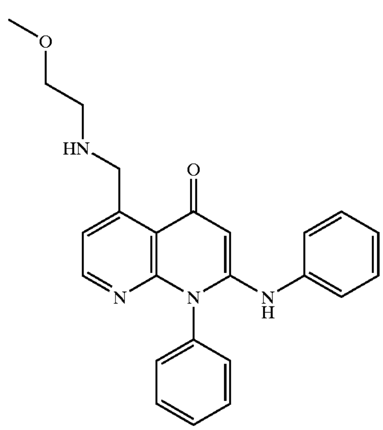 | Intermediate A, B, C, D, E and Example 1, 10, 11 |

TABLE 1B-continued
| Example | Structure | Representative Procedure |
|---|---|---|
| 407 | 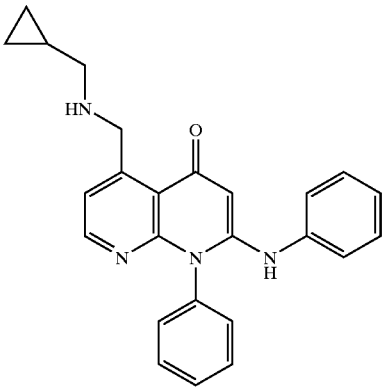 | Intermediate A, B, C, D, E and Example 1, 10, 11 |
| 408 | 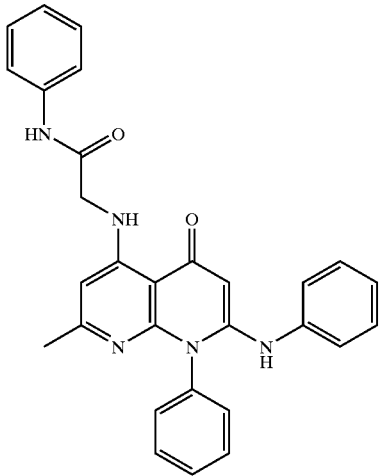 | Intermediate Z, AA, AB and Example 16, 2, 7, 13 |
| 409 | 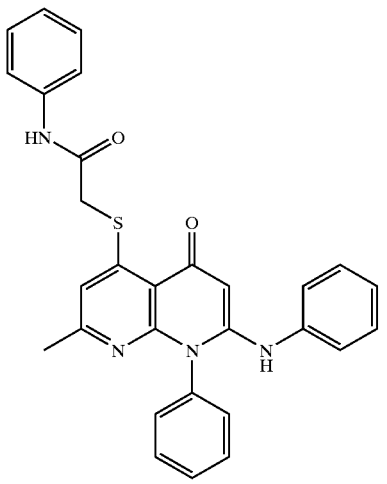 | Intermediate Z, AA, AB and Example 16, 6, 7, 13 |

TABLE 1B-continued
| Example | Structure | Representative Procedure |
|---|---|---|
| 410 | 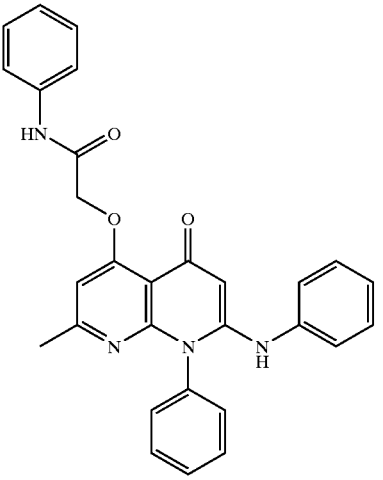 | Intermediate Z, AA, AB and Example 16, 9, 7, 13 |
| 411 | 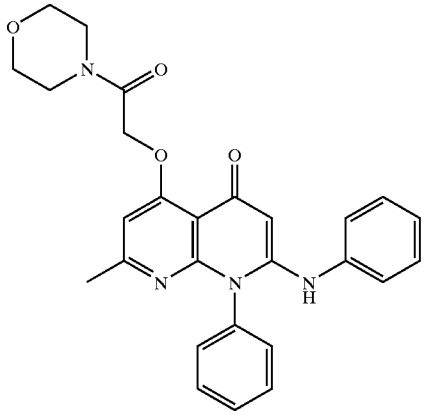 | Intermediate Z, AA, AB and Example 16, 9, 7, 13 |
| 412 | 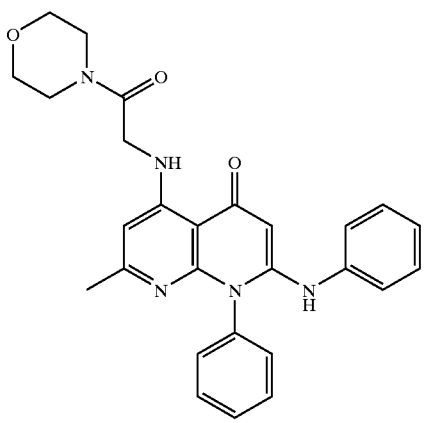 | Intermediate Z, AA, AB and Example 16, 2, 7, 13 |

TABLE 1B-continued
| Example | Structure | Representative Procedure |
|---|---|---|
| 413 | 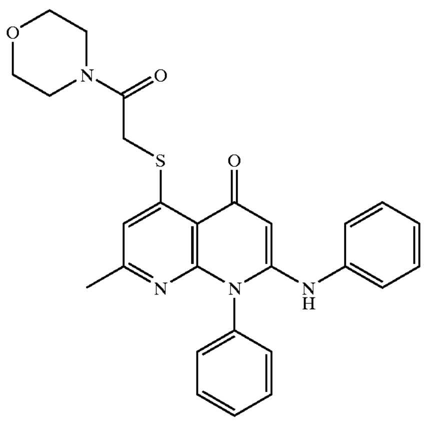 | Intermediate Z, AA, AB and Example 16, 6, 7, 13 |
| 414 | 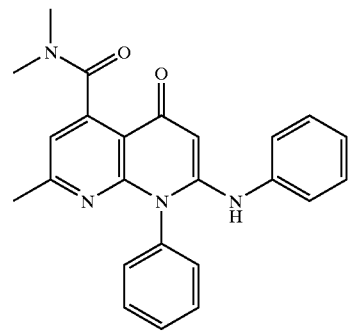 | Intermediate Z, AA, AB and Example 16, 17, 7, 13 |
| 415 | 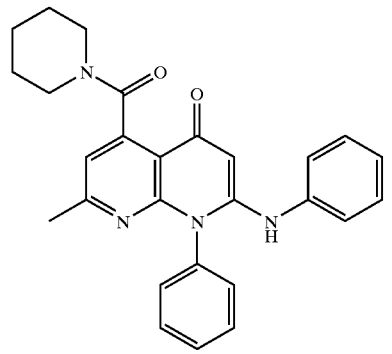 | Intermediate Z, AA, AB and Example 16, 17, 7, 13 |
| 416 | 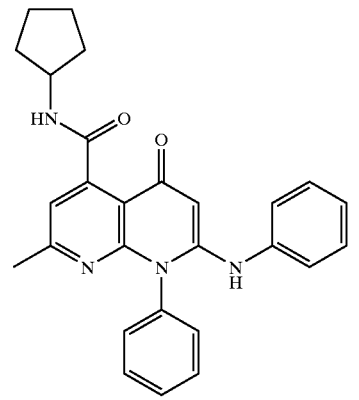 | Intermediate Z, AA, AB and Example 16, 17, 7, 13 |

TABLE 1B-continued
| Example | Structure | Representative Procedure |
|---------|-----------|--------------------------|
| 417 | 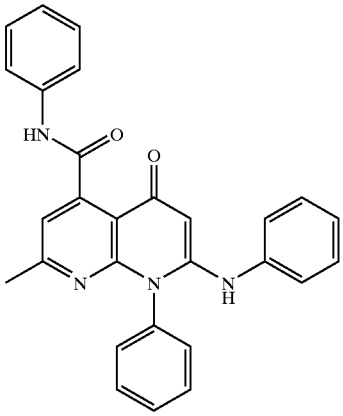 | Intermediate Z, AA, AB and Example 16, 17, 7, 13 |
| 418 | 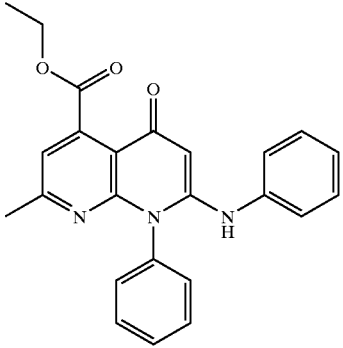 | Intermediate Z, AA, AB and Example 16, 17 |
| 419 | 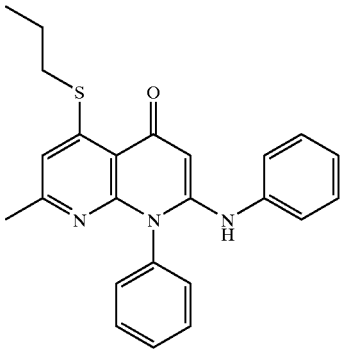 | Intermediate Z, AA, AB and Example 16, 6 |
| 420 | 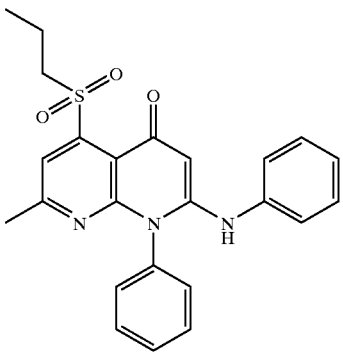 | Intermediate Z, AA, AB and Example 16, 6, 21 |

TABLE 1B-continued

| Example | Structure | Representative Procedure |
|---------|-----------|--------------------------|
| 421 | 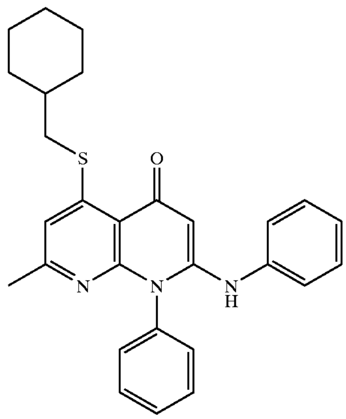 | Intermediate Z, AA, AB and Example 16, 6 |
| 422 | 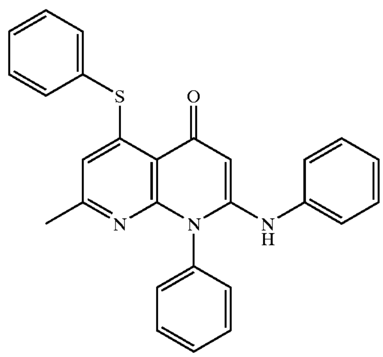 | Intermediate Z, AA, AB and Example 16, 6 |
| 423 | 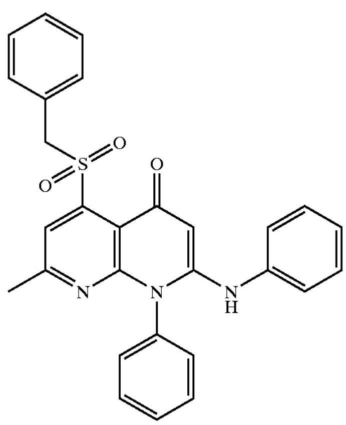 | Intermediate Z, AA, AB and Example 16, 6, 21 |
| 424 | 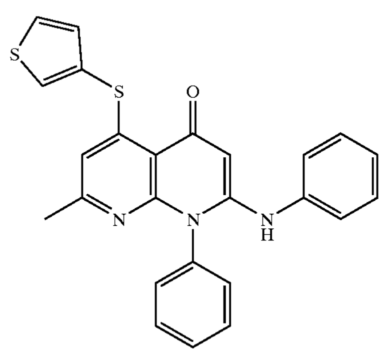 | Intermediate Z, AA, AB and Example 16, 6 |

TABLE 1B-continued

| Example | Structure | Representative Procedure |
|---|---|---|
| 425 | 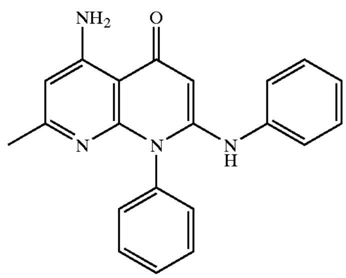 | Intermediate Z, AA, AB and Example 16, 3, 24 |
| 426 | 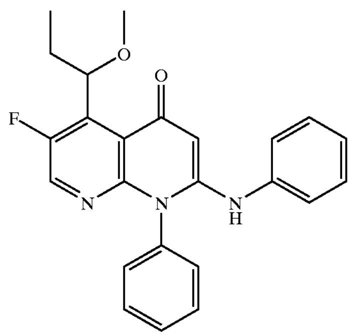 | Intermediate K, L, M, N, AM and Example 1 and Intermediate AJ |
| 427 | 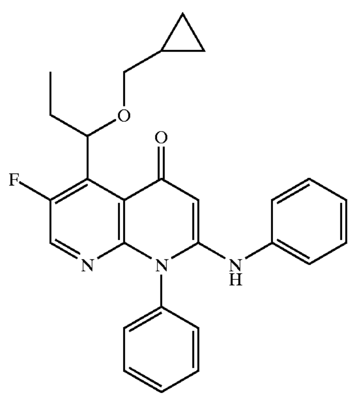 | Intermediate K, L, M, N, AM and Example 1 and Intermediate AJ |
| 428 | 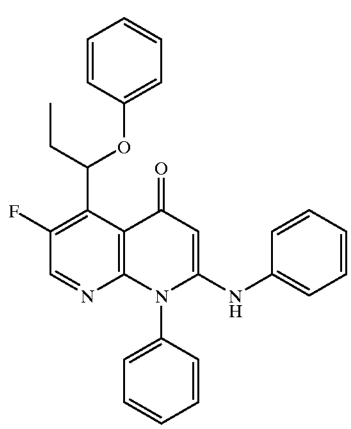 | Intermediate K, L, M, N, AM and Example 1, 26 |

TABLE 1B-continued

| Example | Structure | Representative Procedure |
|---------|-----------|--------------------------|
| 429 | 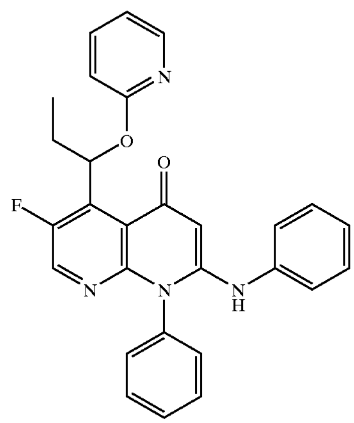 | Intermediate K, L, M, N, AM and Example 1, 26 |
| 430 | 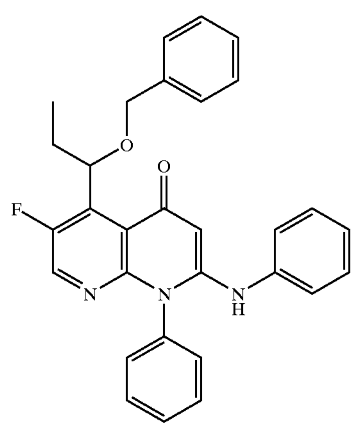 | Intermediate K, L, M, N, AM and Example 1 and Intermediate AJ |
| 431 | 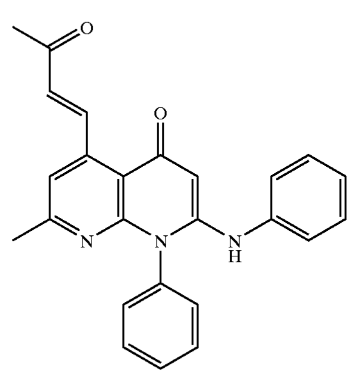 | Intermediate Z, AA, AB and Example 16, 31 |

TABLE 1B-continued

| Example | Structure | Representative Procedure |
|---|---|---|
| 432 | 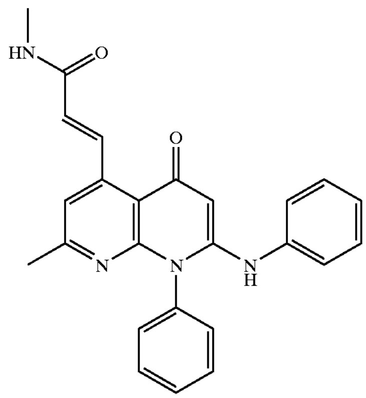 | Intermediate Z, AA, AB and Example 16, 31, 32, 13 |
| 433 | 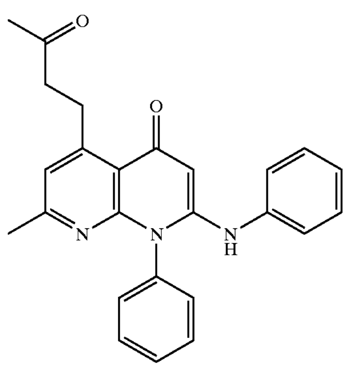 | Intermediate Z, AA, AB and Example 16, 31, 33 |
| 434 | 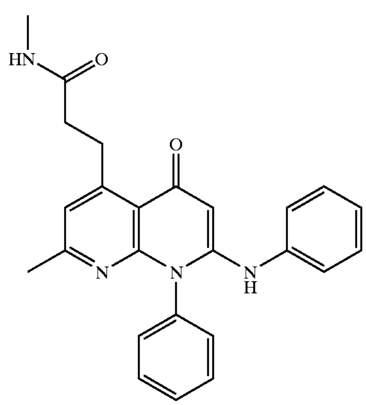 | Intermediate Z, AA, AB and Example 16, 31, 32, 33, 13 |

TABLE 1B-continued
| Example | Structure | Representative Procedure |
|---------|-----------|--------------------------|
| 435 | 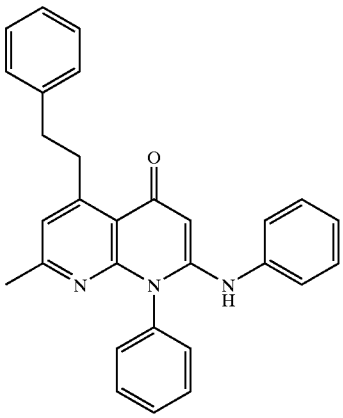 | Intermediate Z, AA, AB and Example 16, 31, 33 |
| 436 | 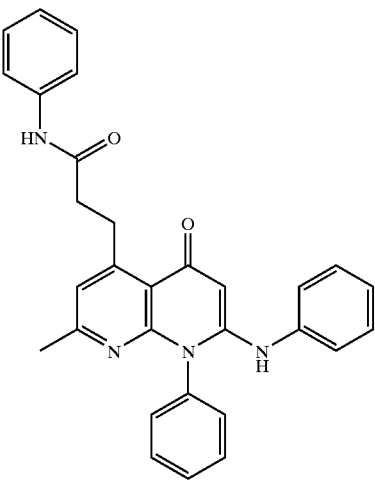 | Intermediate Z, AA, AB and Example 16, 31, 32, 33, 13 |
| 437 | 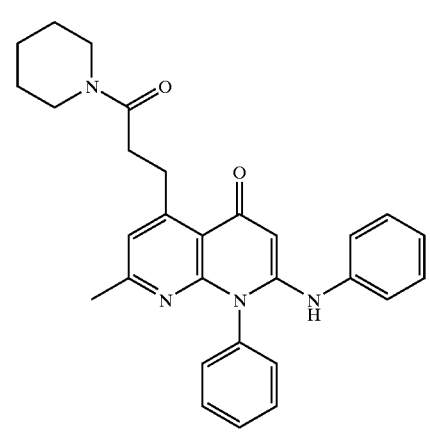 | Intermediate Z, AA, AB and Example 16, 31, 32, 33, 13 |

TABLE 1B-continued
| Example | Structure | Representative Procedure |
|---|---|---|
| 438 | 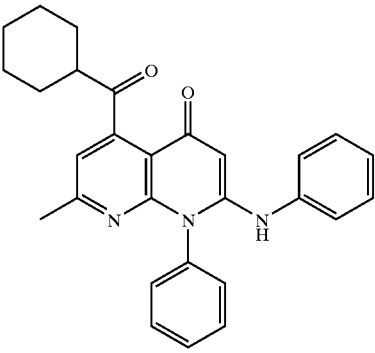 | Intermediate Z, AA, AB and Example 16, 17, 7, 19, 20 |
| 439 | 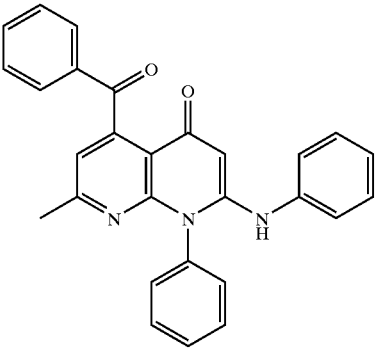 | Intermediate Z, AA, AB and Example 16, 17, 7, 19, 20 |
| 440 | 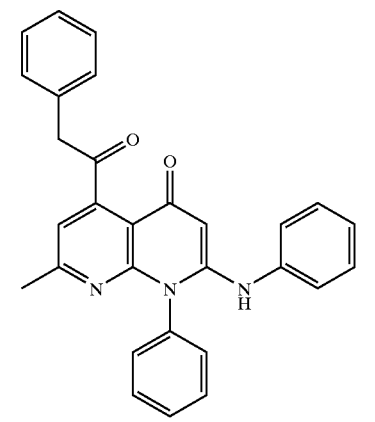 | Intermediate Z, AA, AB and Example 16, 17, 7, 19, 20 |
| 441 | 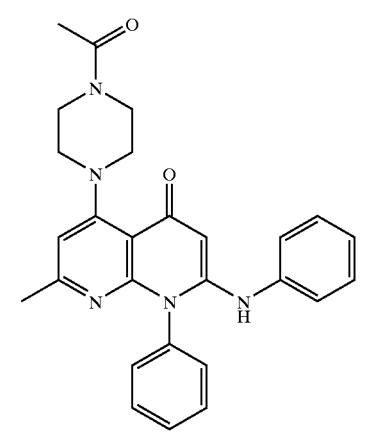 | Intermediate Z, AA, AB and Example 16, 2, 13 |

TABLE 1B-continued
| Example | Structure | Representative Procedure |
|---|---|---|
| 442 | 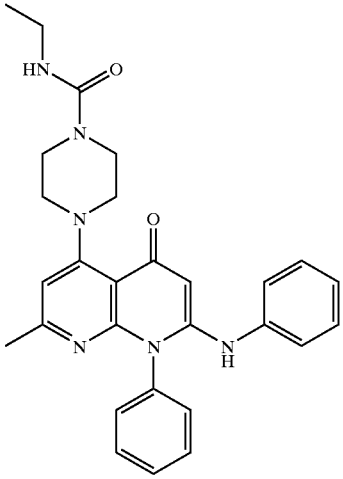 | Intermediate Z, AA, AB and Example 16, 2 and Intermediate AK |
| 443 | 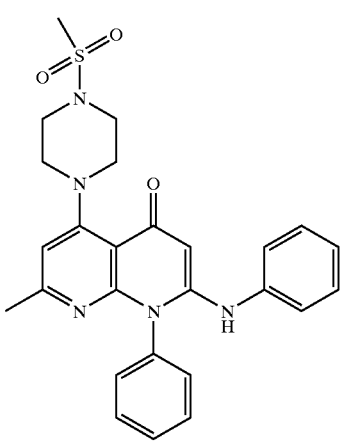 | Intermediate Z, AA, AB and Example 16, 2, 12 |
| 444 | 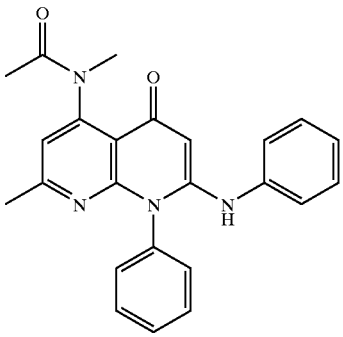 | Intermediate Z, AA, AB and Example 16, 2, 13 |

TABLE 1B-continued

| Example | Structure | Representative Procedure |
|---|---|---|
| 445 | 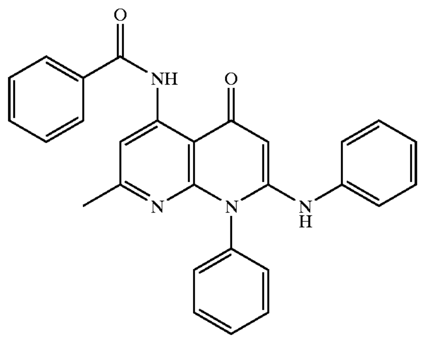 | Intermediate Z, AA, AB and Example 16, 3, 24, 13 |
| 446 | 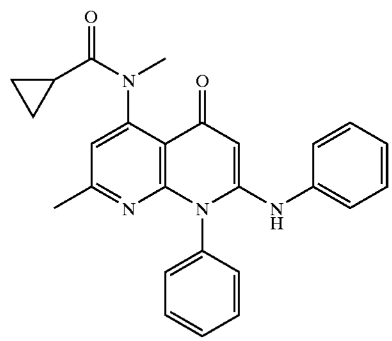 | Intermediate Z, AA, AB and Example 16, 2, 13 |
| 447 | 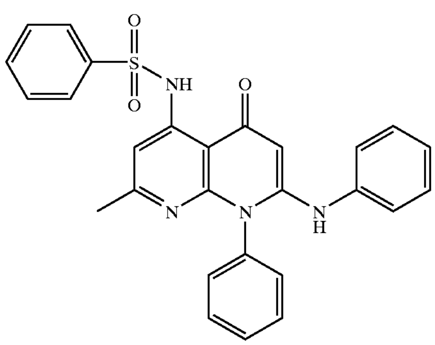 | Intermediate Z, AA, AB and Example 16, 22 |
| 448 | 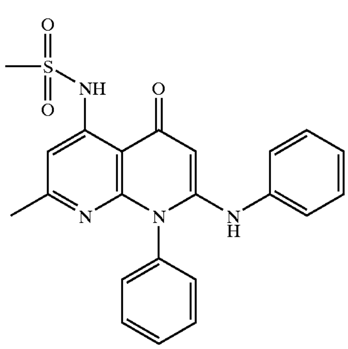 | Intermediate Z, AA, AB and Example 16, 22 |

TABLE 1B-continued

| Example | Structure | Representative Procedure |
|---|---|---|
| 449 | 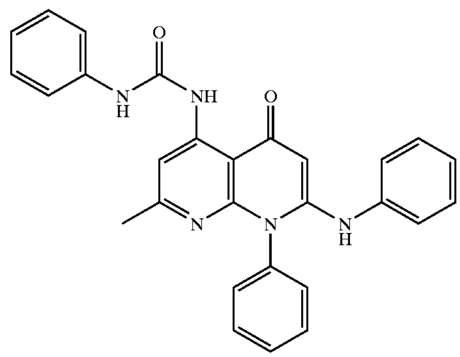 | Intermediate Z, AA, AB and Example 16, 3, 24 and Intermediate AK |
| 450 | 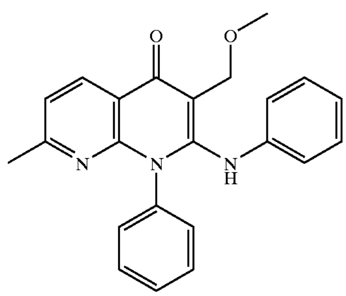 | Intermediate S, T, U, W and Example 25 and Intermediate AJ |
| 451 | 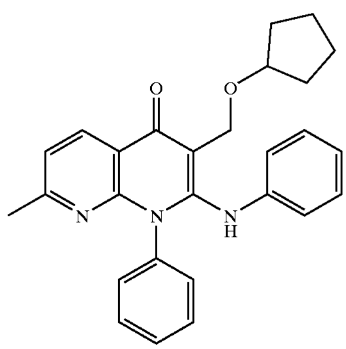 | Intermediate S, T, U, W and Example 25 and Intermediate AJ |
| 452 | 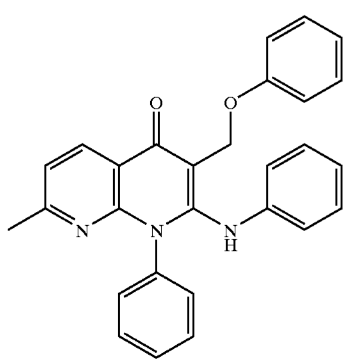 | Intermediate S, T, U, W and Example 25, 26 |

TABLE 1B-continued

| Example | Structure | Representative Procedure |
|---|---|---|
| 453 | 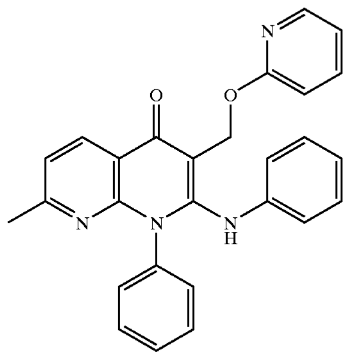 | Intermediate S, T, U, W and Example 25, 26 |
| 454 | 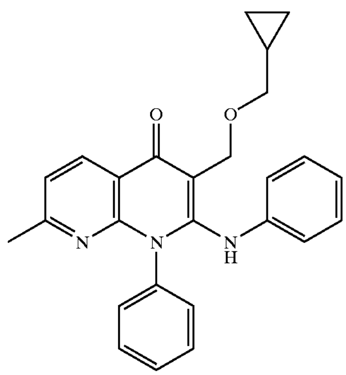 | Intermediate S, T, U, W and Example 25 and Intermediate AJ |
| 455 | 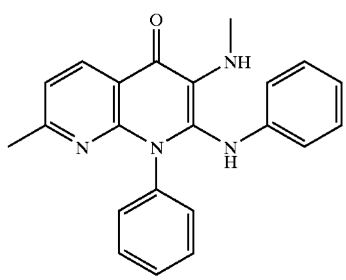 | Intermediate S, T, U, W and Example 15 and Intermediate AL and Example 3 |
| 456 | 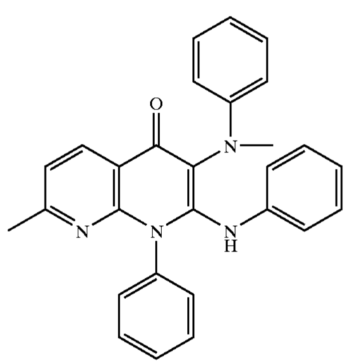 | Intermediate S, T, U, W and Example 15 and Intermediate AL and Example 3 |

TABLE 1B-continued
| Example | Structure | Representative Procedure |
|---|---|---|
| 457 | 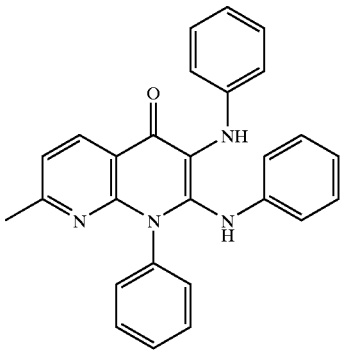 | Intermediate S, T, U, W and Example 15 and Intermediate AL and Example 3 |
| 458 | 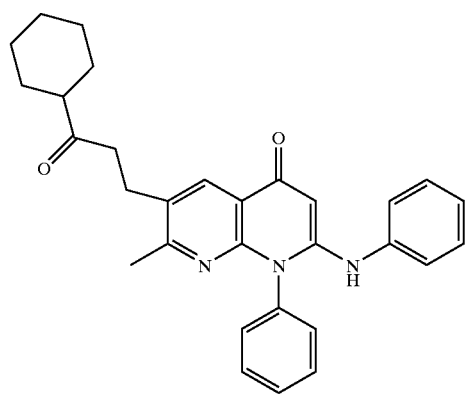 | Intermediate Y, S, T, U, W and Example 15, 31, 32, 33, 19, 20 |
| 459 | 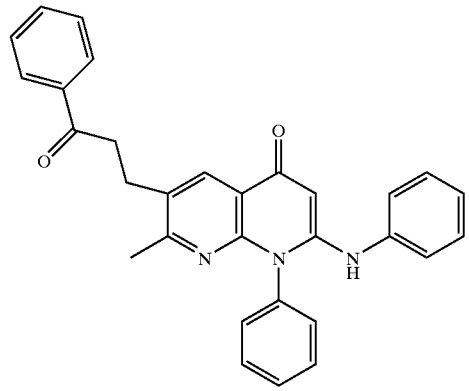 | Intermediate Y, S, T, U, W and Example 15, 31, 33 |
| 460 | 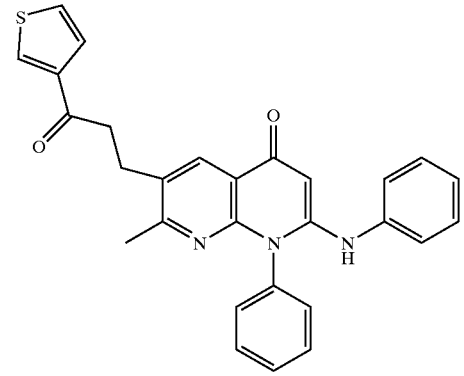 | Intermediate Y, S, T, U, W and Example 15, 31, 32, 33, 19, 20 |

TABLE 1B-continued

| Example | Structure | Representative Procedure |
|---|---|---|
| 461 | 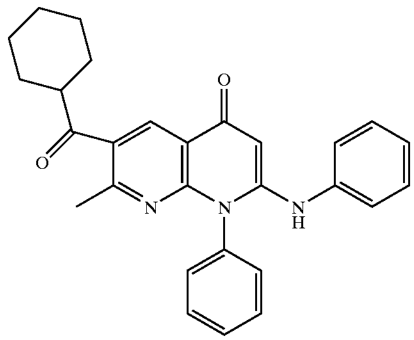 | Intermediate Y, S, T, U, W and Example 15, 17, 7, 19, 20 |
| 462 | 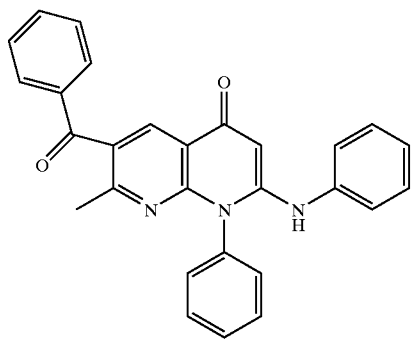 | Intermediate Y, S, T, U, W and Example 15, 17, 7, 19, 20 |
| 463 | 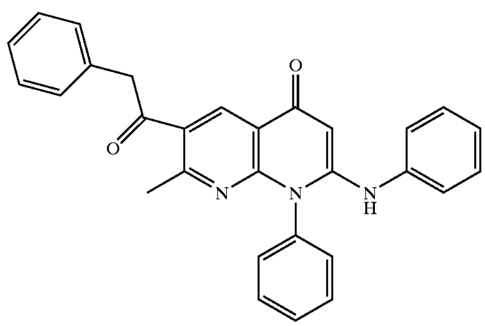 | Intermediate Y, S, T, U, W and Example 15, 17, 7, 19, 20 |
| 464 | 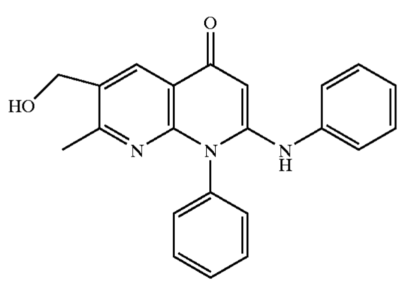 | Intermediate Y, S, T, U, W and Example 15, 17, 25 |
| 465 | 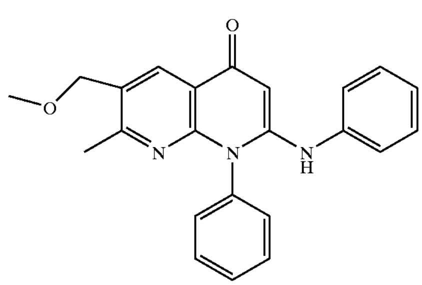 | Intermediate Y, S, T, U, W and Example 15, 17, 25 and Intermediate AJ |

TABLE 1B-continued

| Example | Structure | Representative Procedure |
|---------|-----------|--------------------------|
| 466 | 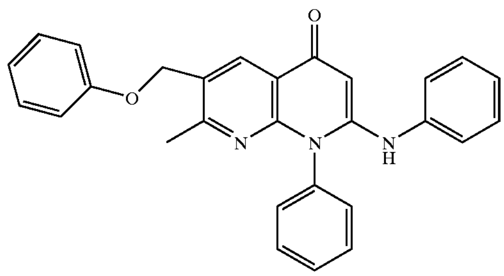 | Intermediate Y, S, T, U, W and Example 15, 17, 25, 26 |
| 467 | 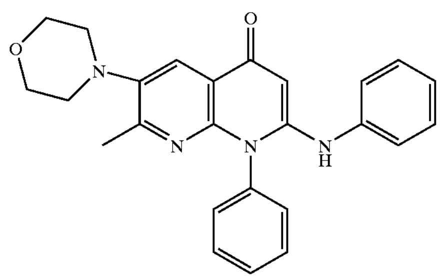 | Intermediate Y, S, T, U, W and Example 15, 3 |
| 468 | 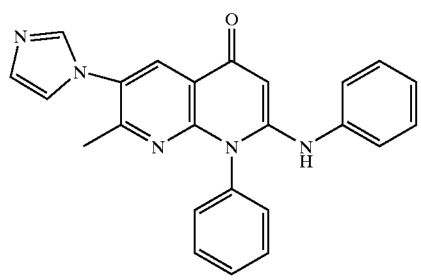 | Intermediate Y, S, T, U, W and Example 15, 3 |
| 469 | 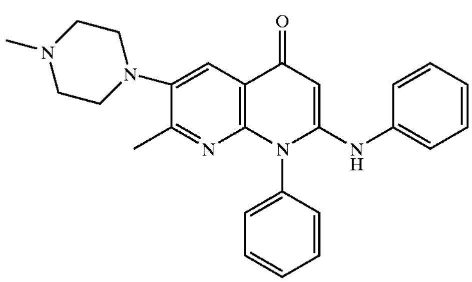 | Intermediate Y, S, T, U, W and Example 15, 3 |
| 470 | 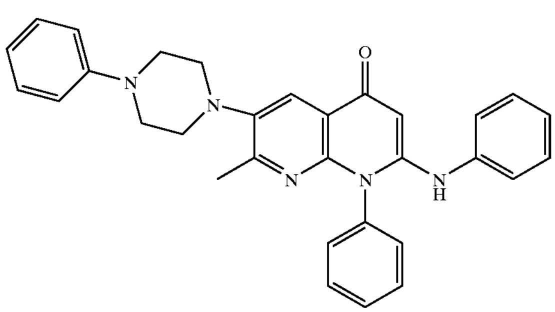 | Intermediate Y, S, T, U, W and Example 15, 3 |

TABLE 1B-continued

| Example | Structure | Representative Procedure |
|---|---|---|
| 471 | 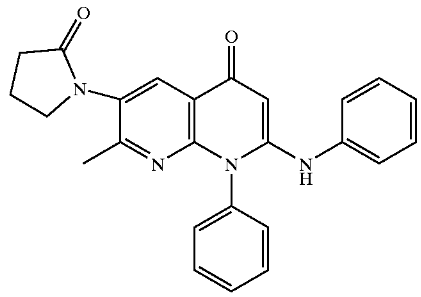 | Intermediate Y, S, T, U, W and Example 15, 3 |
| 472 | 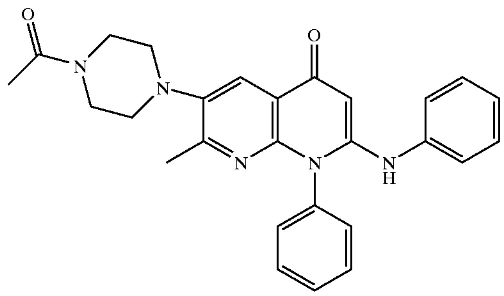 | Intermediate Y, S, T, U, W and Example 15, 3, 13 |
| 473 | 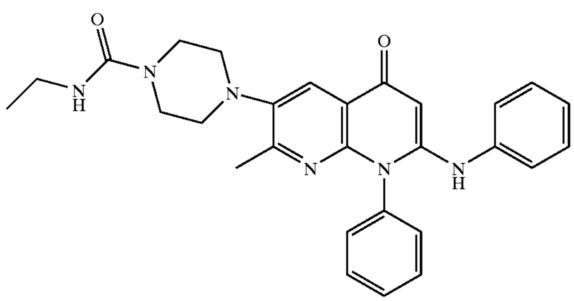 | Intermediate Y, S, T, U, W and Example 15, 3 and Intermediate AK |
| 474 | 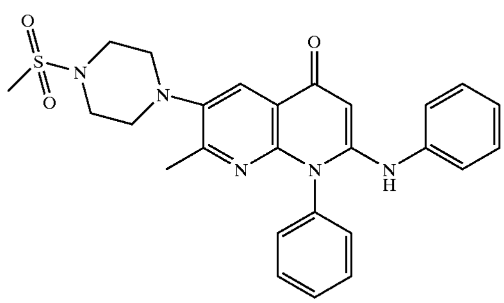 | Intermediate Y, S, T, U, W and Example 15, 3, 12 |
| 475 | 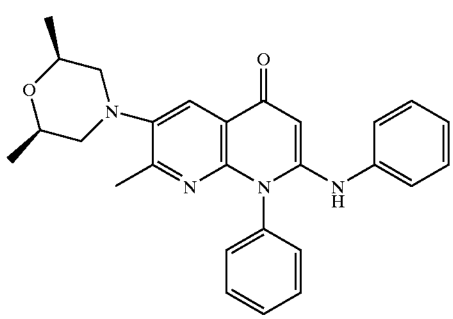 | Intermediate Y, S, T, U, W and Example 15, 3 |

TABLE 1B-continued
| Example | Structure | Representative Procedure |
|---|---|---|
| 476 | 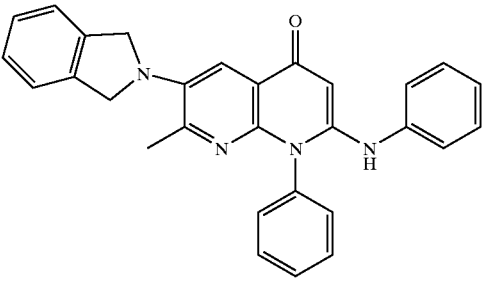 | Intermediate Y, S, T, U, W and Example 15, 3 |
| 477 | 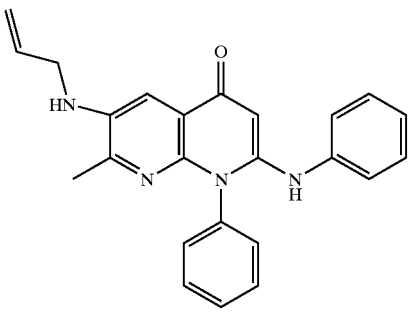 | Intermediate Y, S, T, U, W and Example 15, 3 |
| 478 | 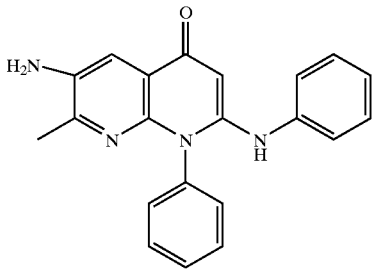 | Intermediate Y, S, T, U, W and Example 15, 3, 24 |
| 479 | 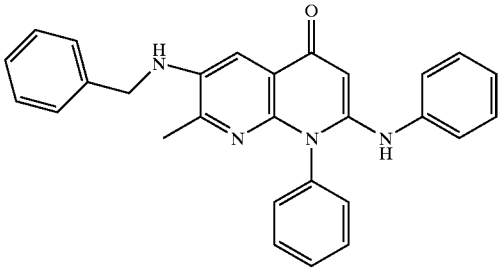 | Intermediate Y, S, T, U, W and Example 15, 3 |
| 480 | 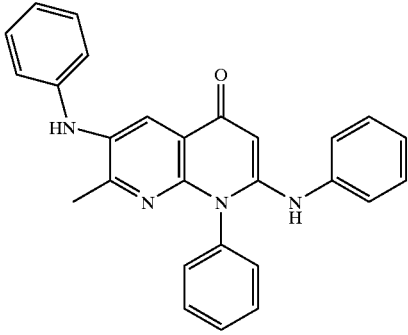 | Intermediate Y, S, T, U, W and Example 15, 3 |

TABLE 1B-continued

| Example | Structure | Representative Procedure |
|---------|-----------|--------------------------|
| 481 | 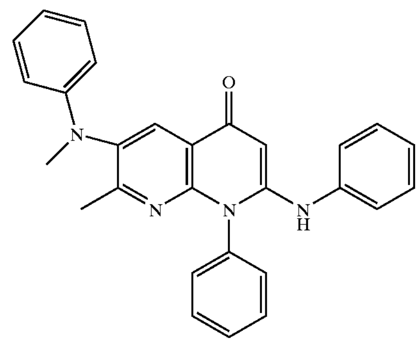 | Intermediate Y, S, T, U, W and Example 15, 3 |
| 482 | 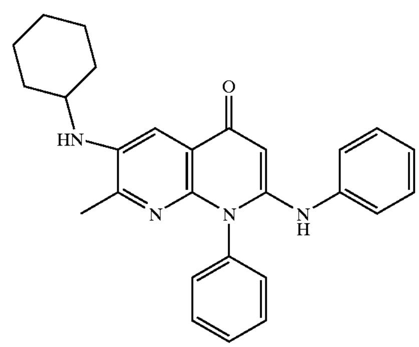 | Intermediate Y, S, T, U, W and Example 15, 3 |
| 483 | 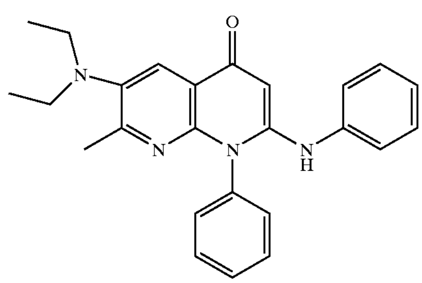 | Intermediate Y, S, T, U, W and Example 15, 3 |
| 484 | 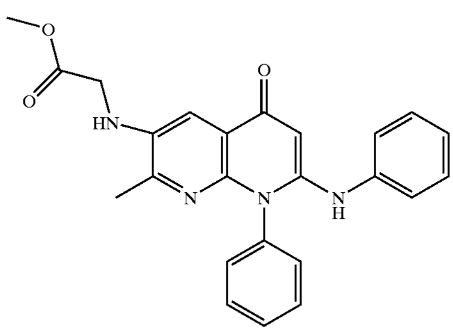 | Intermediate Y, S, T, U, W and Example 15, 3 |

TABLE 1B-continued

| Example | Structure | Representative Procedure |
|---------|-----------|--------------------------|
| 485 | 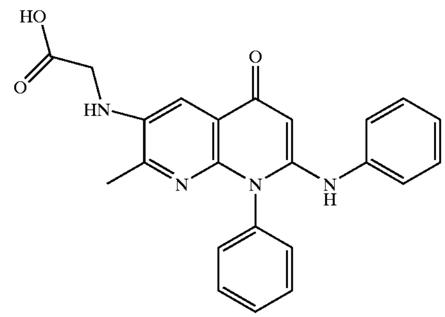 | Intermediate Y, S, T, U, W and Example 15, 3, 7 |
| 486 | 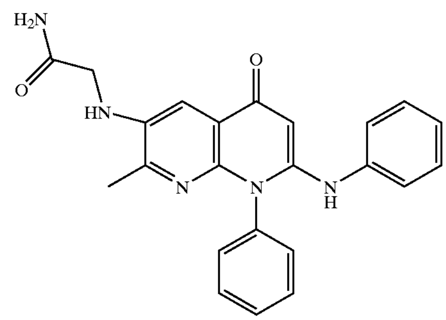 | Intermediate Y, S, T, U, W and Example 15, 3, 18 |
| 487 | 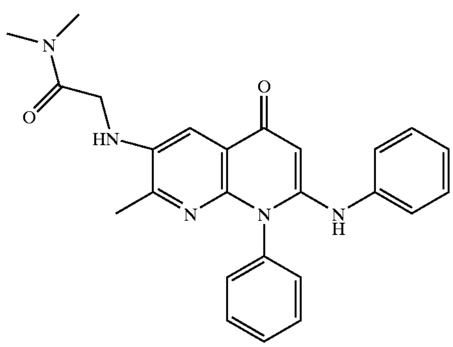 | Intermediate Y, S, T, U, W and Example 15, 3, 7, 13 |
| 488 | 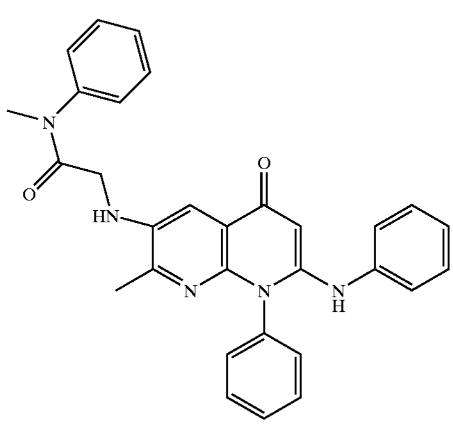 | Intermediate Y, S, T, U, W and Example 15, 3, 7, 13 |

TABLE 1B-continued
| Example | Structure | Representative Procedure |
|---|---|---|
| 489 | 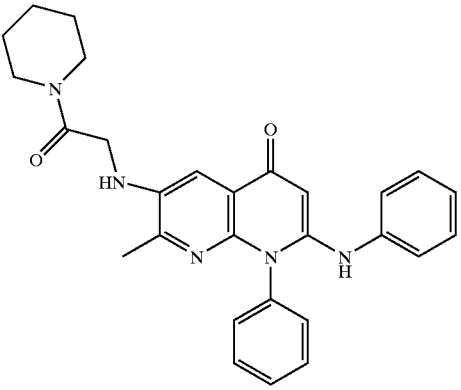 | Intermediate Y, S, T, U, W and Example 15, 3, 7, 13 |
| 490 | 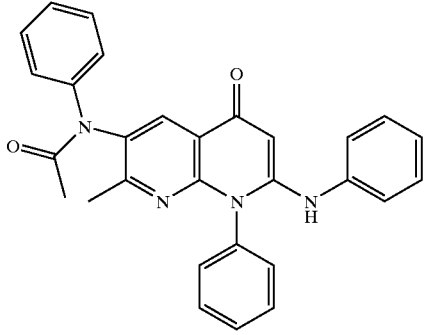 | Intermediate Y, S, T, U, W and Example 15, 3, 13 |
| 491 | 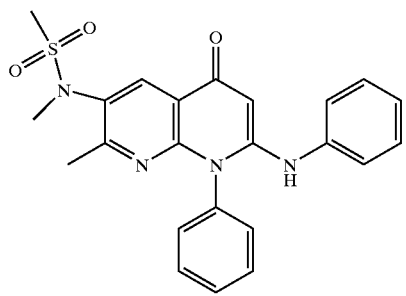 | Intermediate Y, S, T, U, W and Example 15, 3, 12 |
| 492 | 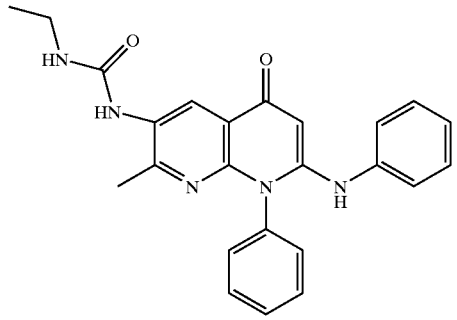 | Intermediate Y, S, T, U, W and Example 15, 3, 24 and Intermediate AK |

TABLE 1B-continued

| Example | Structure | Representative Procedure |
|---------|-----------|--------------------------|
| 493 | 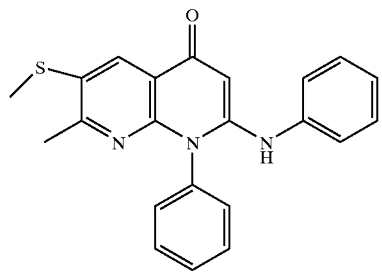 | Intermediate Y, S, T, U, W and Example 15, 34 |
| 494 | 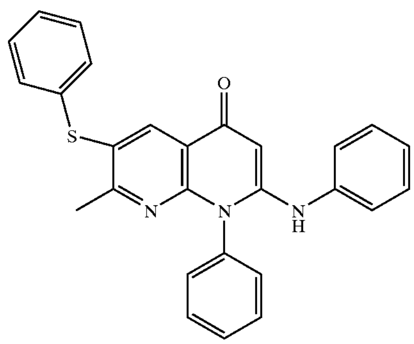 | Intermediate Y, S, T, U, W and Example 15, 34 |
| 495 | 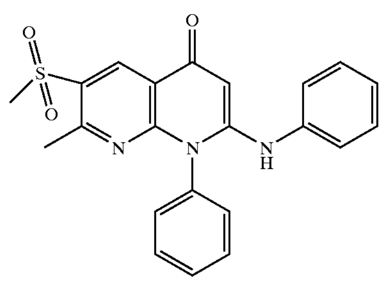 | Intermediate Y, S, T, U, W and Exampe 15, 34, 21 |
| 496 | 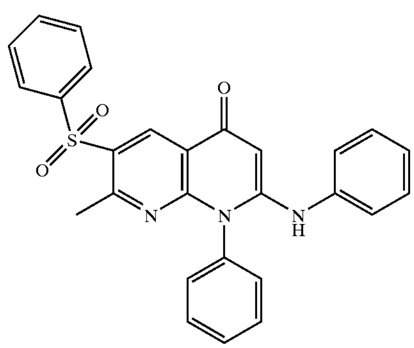 | Intermediate Y, S, T, U, W and Example 15, 34, 21 |

TABLE 1B-continued

| Example | Structure | Representative Procedure |
|---|---|---|
| 497 | 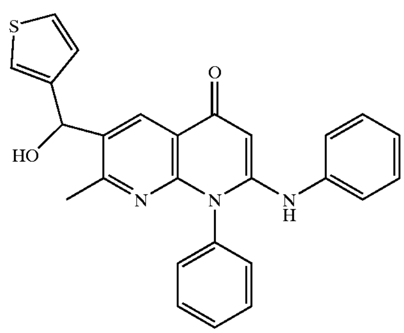 | Intermediate Y, S, T, U, W and Example 15, 34 |
| 498 | 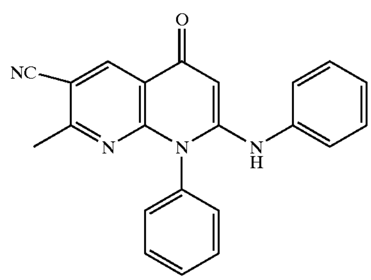 | Intermediate S, T, U, W and Example 15 |
| 499 | 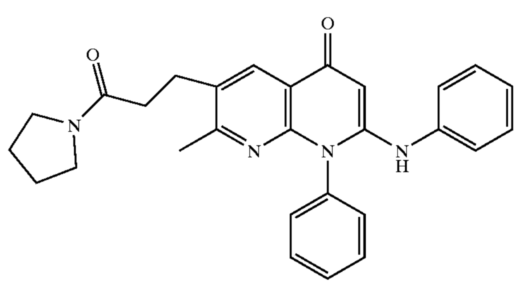 | Intermediate Y, S, T, U, W and Example 15, 31, 32, 33, 13 |
| 500 | 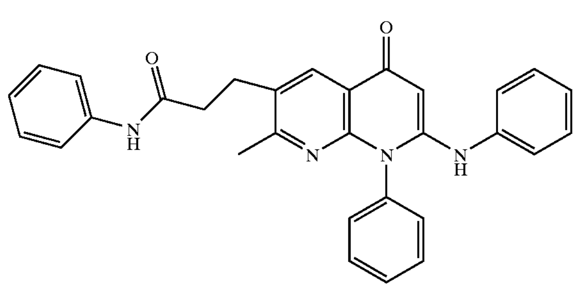 | Intermediate Y, S, T, U, W and Example 15, 31, 32, 33, 13 |
| 501 | 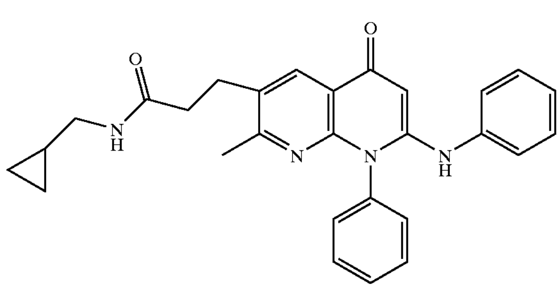 | Intermediate Y, S, T, U, W and Example 15, 31, 32, 33, 13 |

TABLE 1B-continued
| Example | Structure | Representative Procedure |
|---|---|---|
| 502 | 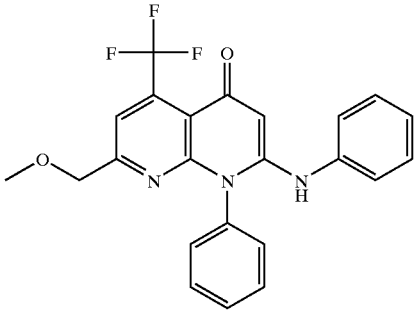 | Intermediate F, G, H, I, J and Example 17, 25 and Intermediate AJ |
| 503 | 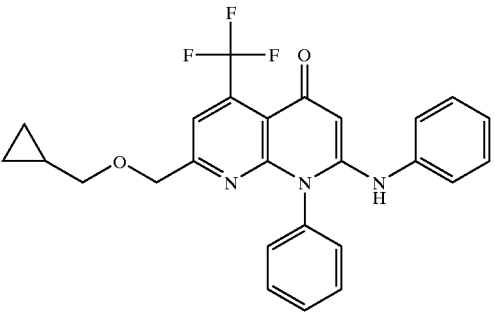 | Intermediate F, G, H, I, J and Example 17, 25 and Intermediate AJ |
| 504 | 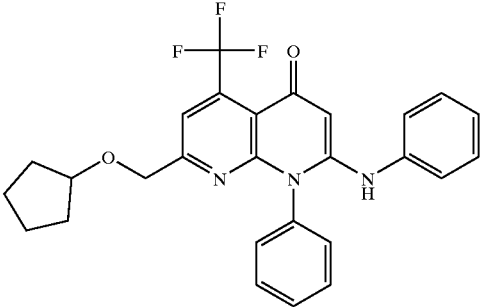 | Intermediate F, G, H, I, J and Example 17, 25 and Intermediate AJ |
| 505 | 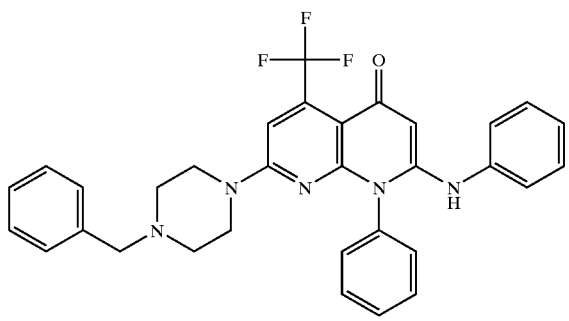 | Intermediate F, G, H, I, J and Example 8 |

TABLE 1B-continued

| Example | Structure | Representative Procedure |
|---------|-----------|--------------------------|
| 506 | 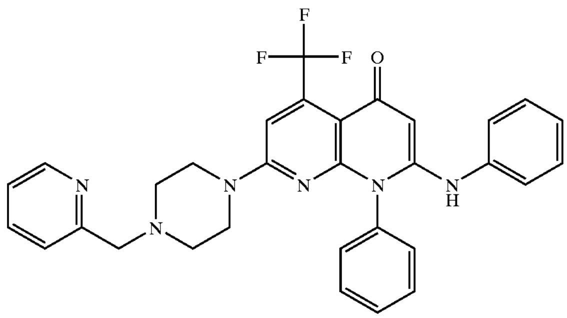 | Intermediate F, G, H, I, J and Example 8 |
| 507 | 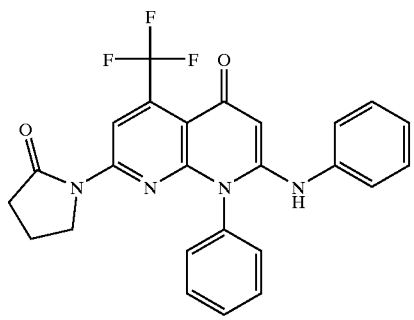 | Intermediate F, G, H, I, J and Example 8 |
| 508 | 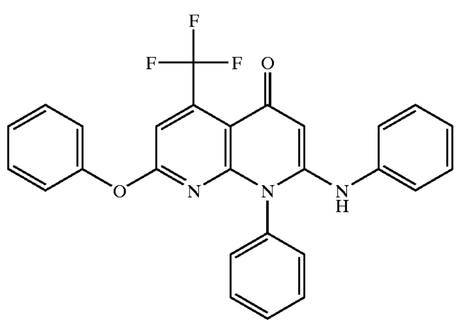 | Intermediate F, G, H, I, J and Example 9 |
| 509 | 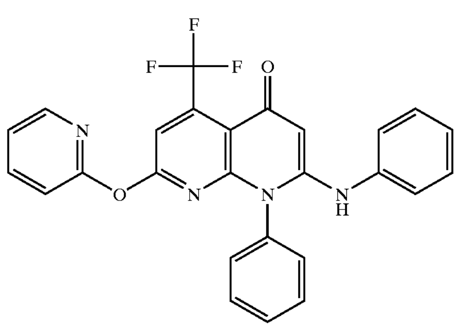 | Intermediate F, G, H, I, J and Example 9 |

TABLE 1B-continued
| Example | Structure | Representative Procedure |
|---|---|---|
| 510 | 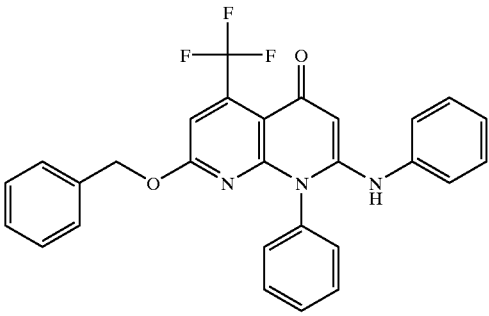 | Intermediate F, G, H, I, J and Example 9 |
| 511 | 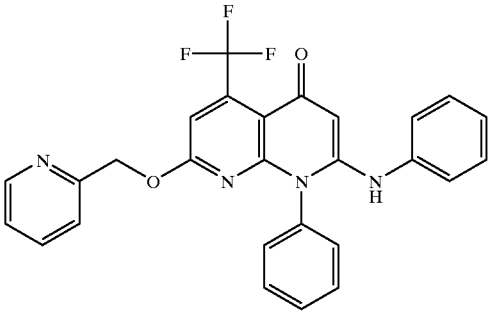 | Intermediate F, G, H, I, J and Example 9 |
| 512 | 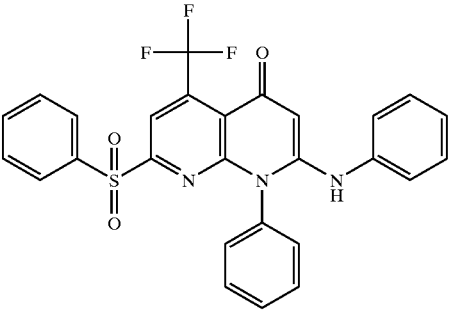 | Intermediate F, G, H, I, J and Example 6, 21 |
| 513 | 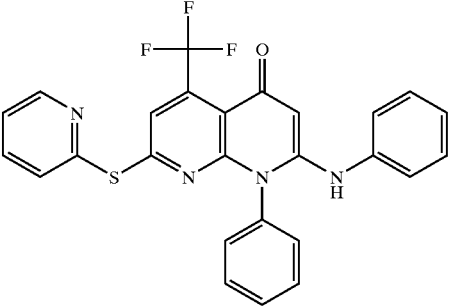 | Intermediate F, G, H, I, J and Example 6 |

TABLE 1B-continued
| Example | Structure | Representative Procedure |
|---|---|---|
| 514 | 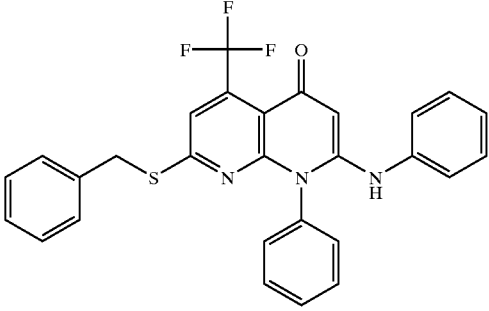 | Intermediate F, G, H, I, J and Example 6 |
| 515 | 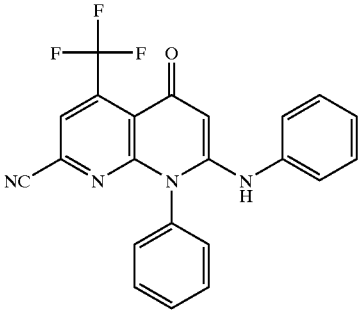 | Intermediate F, G, H, I, J and Example 9 |
| 516 | 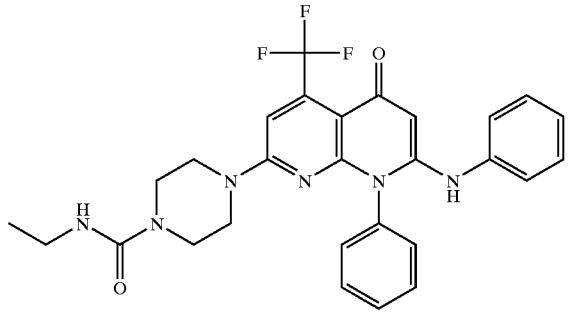 | Intermediate F, G, H, I, J and Example 8 and Intermediate AK |
| 517 | 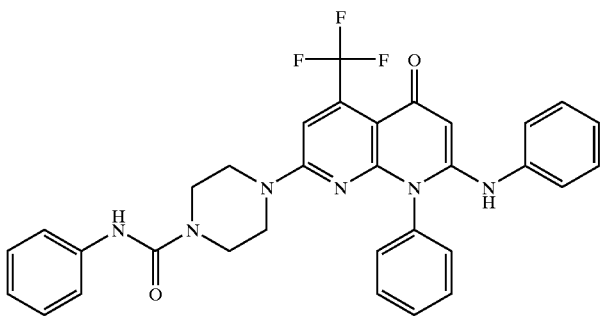 | Intermediate F, G, H, I, J and Example 8 and Intermediate AK |

TABLE 1B-continued

| Example | Structure | Representative Procedure |
|---------|-----------|--------------------------|
| 518 | 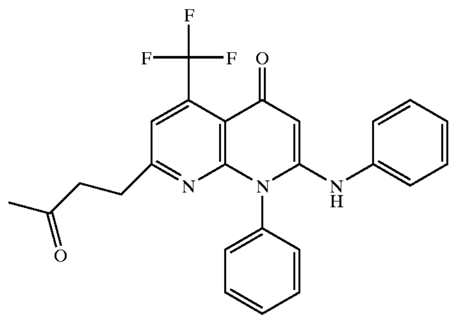 | Intermediate F, G, H, I, J and Example 31, 33 |
| 519 | 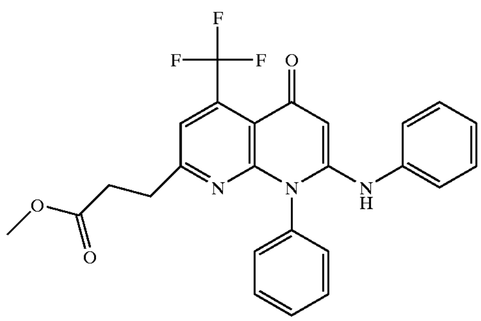 | Intermediate F, G, H, I, J and Example 31, 33 |
| 520 | 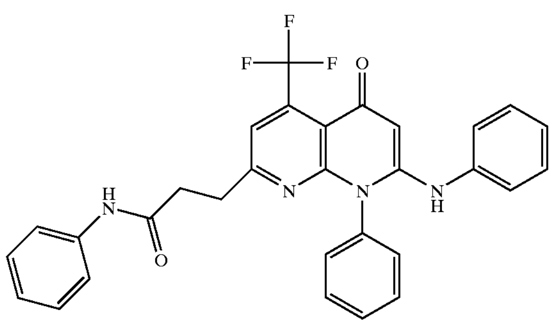 | Intermediate F, G, H, I, J and Example 31, 32, 33, 13 |
| 521 | 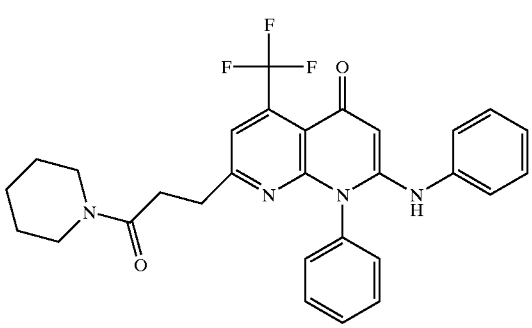 | Intermediate F, G, H, I, J and Example 31, 32, 33, 13 |

TABLE 1B-continued

| Example | Structure | Representative Procedure |
|---|---|---|
| 522 | 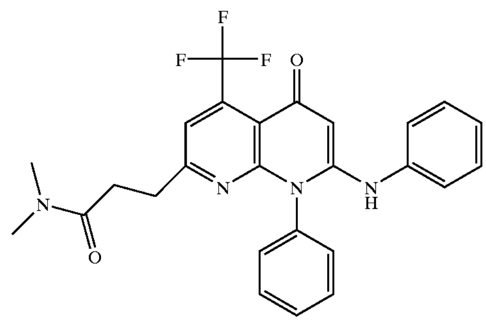 | Intermediate F, G, H, I, J and Example 31, 32, 33, 13 |
| 523 | 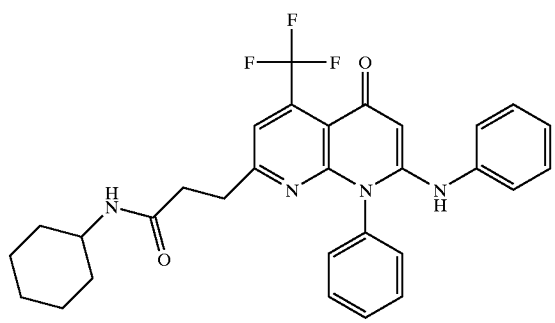 | Intermediate F, G, H, I, J and Example 31, 32, 33, 13 |
| 524 | 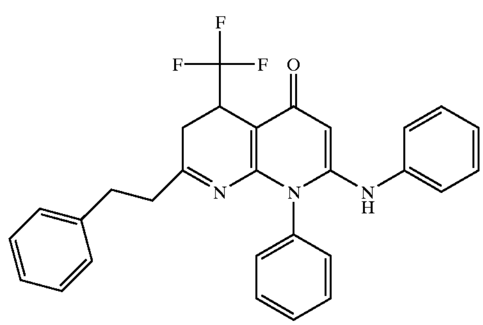 | Intermediate F, G, H, I, J and Example 31, 33 |
| 525 | 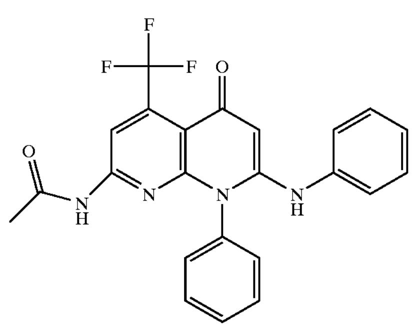 | Intermediate F, G, H, I, J and Example 3, 24, 13 |

TABLE 1B-continued
| Example | Structure | Representative Procedure |
|---|---|---|
| 526 | 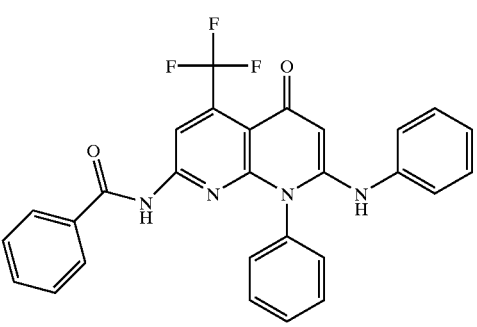 | Intermediate F, G, H, I, J and Example 3, 24, 13 |
| 527 | 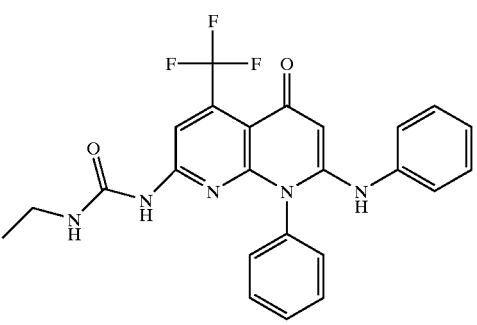 | Intermediate F, G, H, I, J and Example 3, 24 and Intermediate AK |
| 528 | 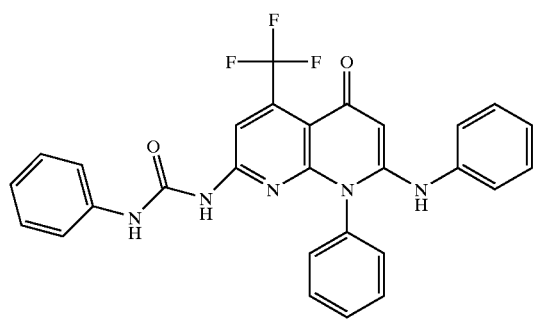 | Intermediate F, G, H, I, J and Example 3, 24 and Intermediate AK |
| 529 | 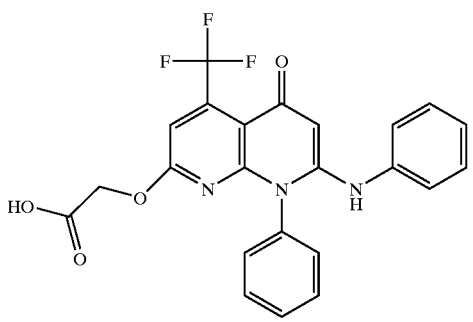 | Intermediate F, G, H, I, J and Example 9, 7 |

TABLE 1B-continued

| Example | Structure | Representative Procedure |
|---------|-----------|--------------------------|
| 530 | 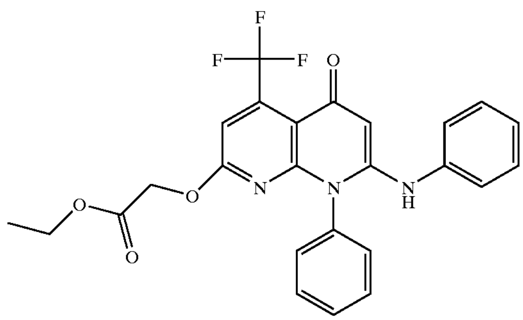 | Intermediate F, G, H, I, J and Example 9 |
| 531 | 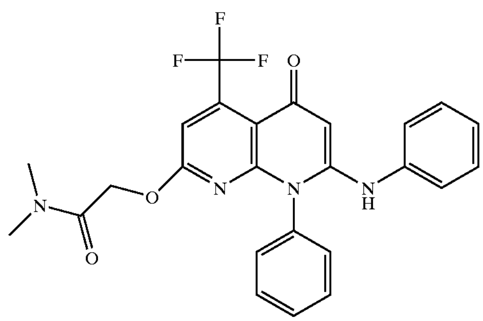 | Intermediate F, G, H, I, J and Example 9, 7, 13 |
| 532 | 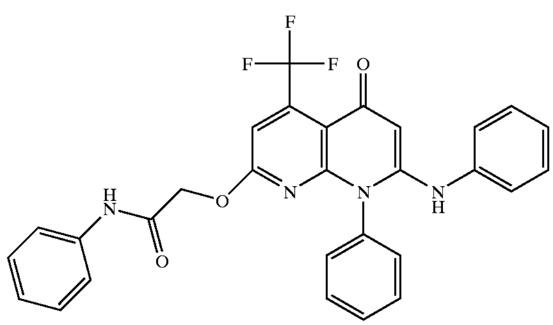 | Intermediate F, G, H, I, J and Example 9, 7, 13 |
| 533 | 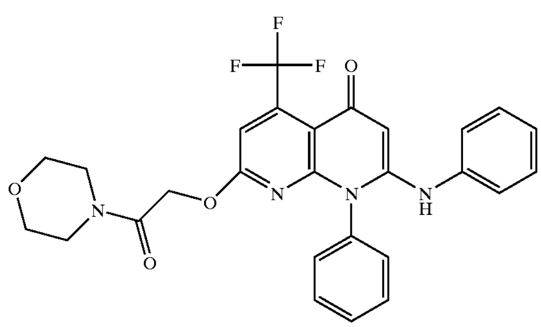 | Intermediate F, G, H, I, J and Example 9, 7, 13 |

Utilizing the above described procedures for intermediates and examples and Flow Diagrams I–XIV alone or in combination, a variety of Formula I compounds can be prepared using the appropriate starting material. These compounds are summarized in Table 1C.

TABLE 1C

| Example | Structure |
|---|---|
| 534 | 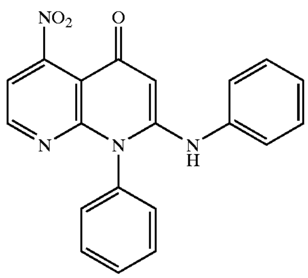 |
| 535 | 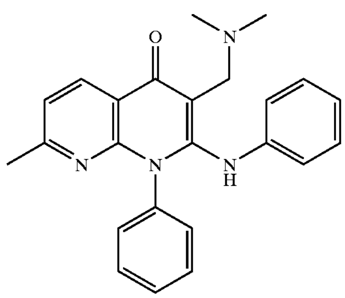 |
| 536 | 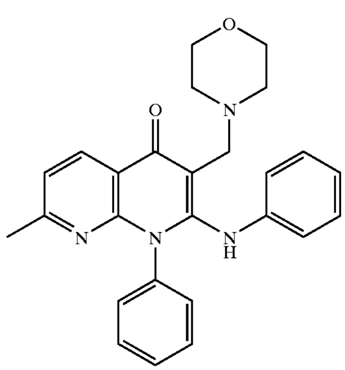 |
| 537 | 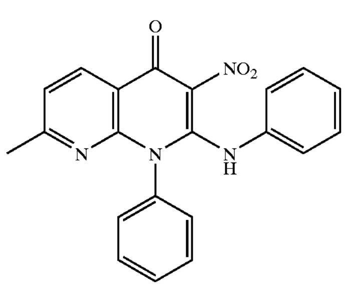 |

TABLE 1C-continued

| Example | Structure |
|---|---|
| 538 | 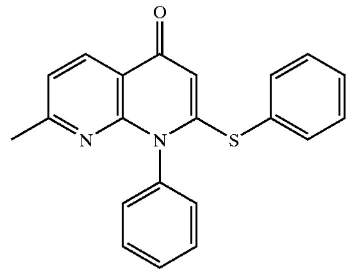 |
| 539 | 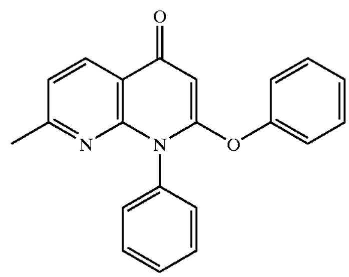 |
| 540 | 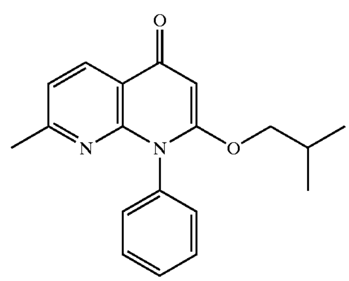 |
| 541 | 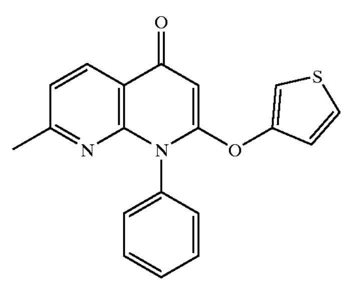 |
| 542 | 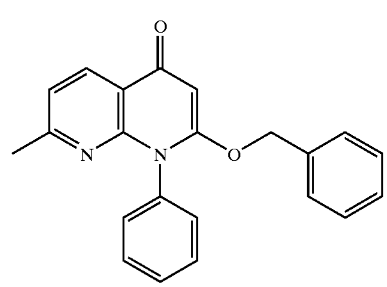 |

TABLE 1C-continued

| Example | Structure |
|---|---|
| 543 | (structure) |
| 544 | (structure) |
| 545 | (structure) |
| 546 | (structure) |
| 547 | (structure) |
| 548 | (structure) |
| 549 | (structure) |
| 550 | (structure) |
| 551 | (structure) |

TABLE 1C-continued

| Example | Structure |
|---|---|
| 552 | 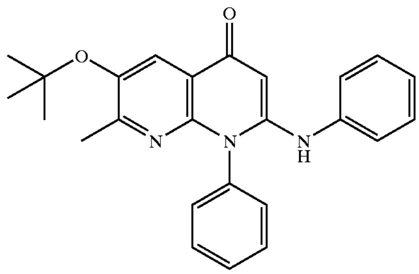 |
| 553 | 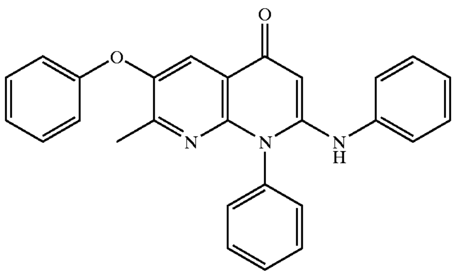 |
| 554 | 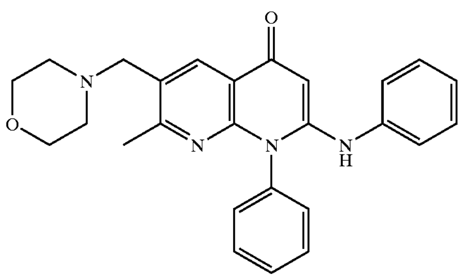 |
| 555 | 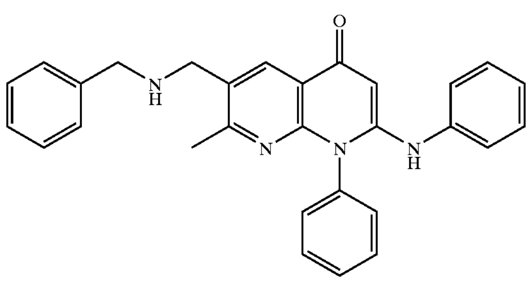 |
| 556 | 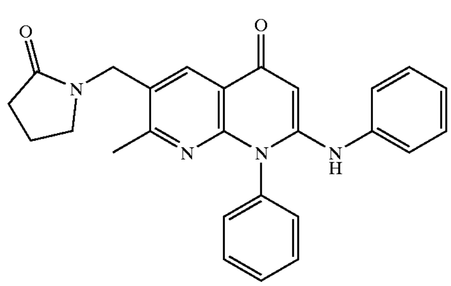 |
| 557 | |
| 558 | |
| 559 | |
| 560 | |
| 561 | |

TABLE 1C-continued

| Example | Structure |
|---|---|
| 562 | 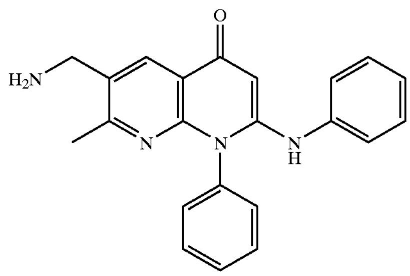 |
| 563 | 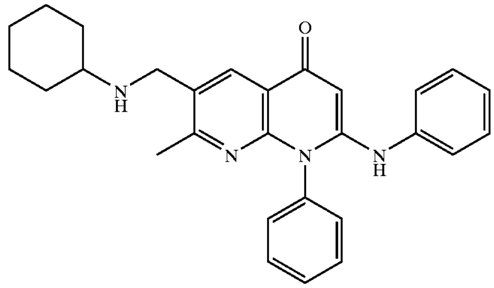 |
| 564 | 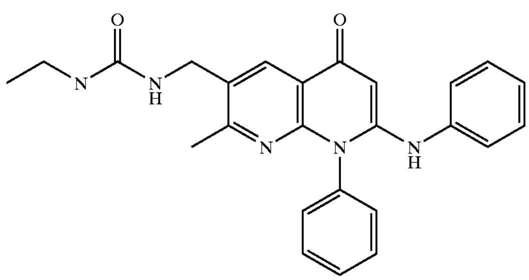 |
| 565 | 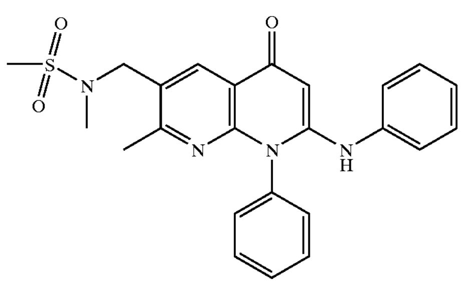 |
| 566 | |用
| 567 | 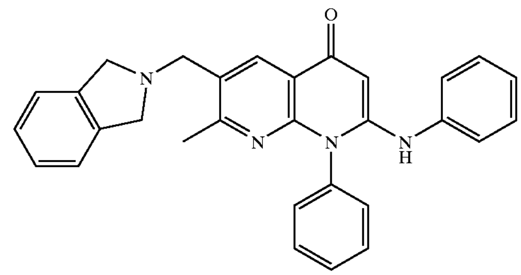 |
| 568 | 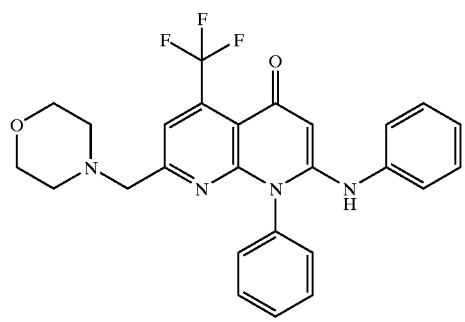 |
| 569 | 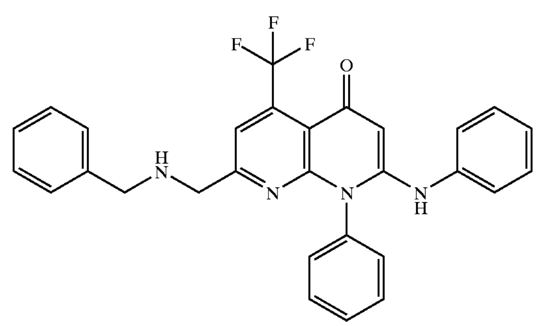 |
| 570 | 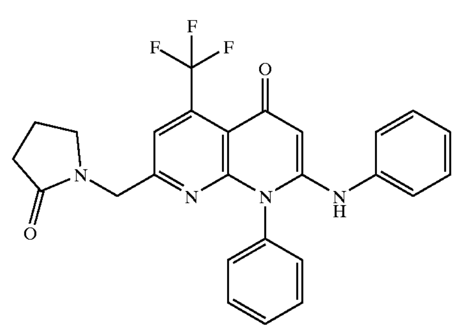 |

TABLE 1C-continued
| Example | Structure |
|---|---|
| 571 | 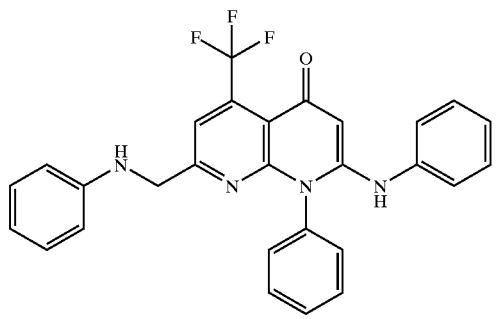 |
| 572 | 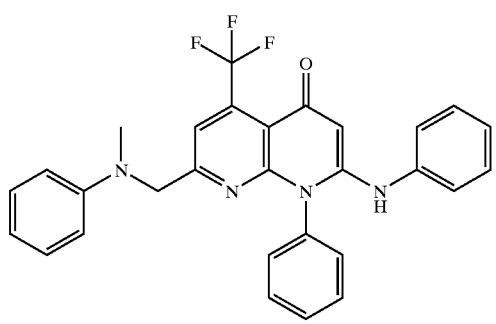 |
| 573 | 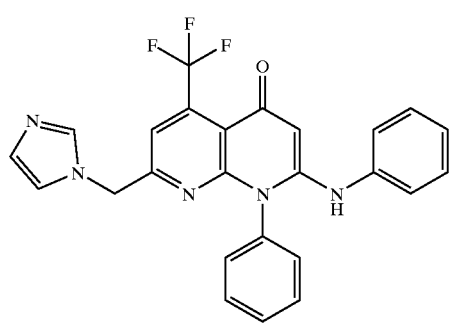 |
| 574 | 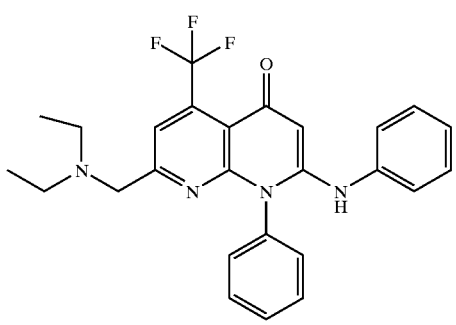 |
| 575 | 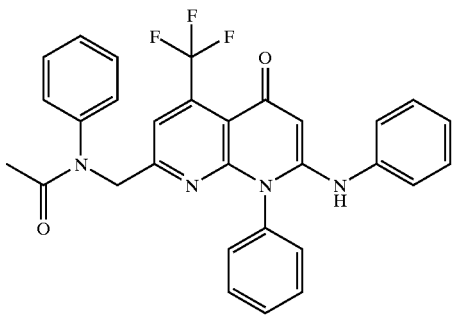 |
| 576 | 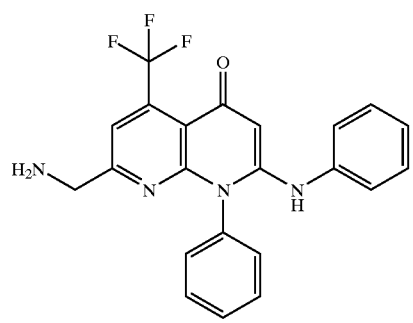 |
| 577 | 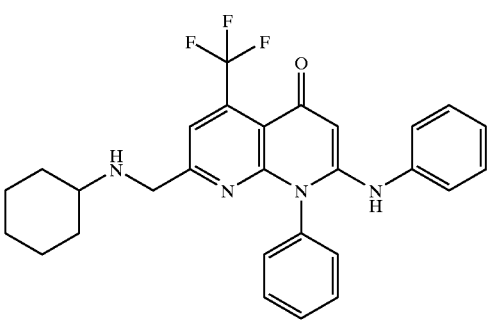 |
| 578 | 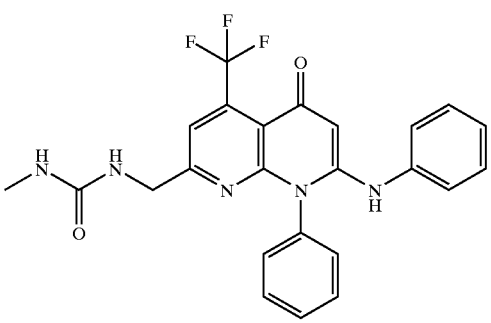 |

TABLE 1C-continued

| Example | Structure |
|---------|-----------|
| 579 | 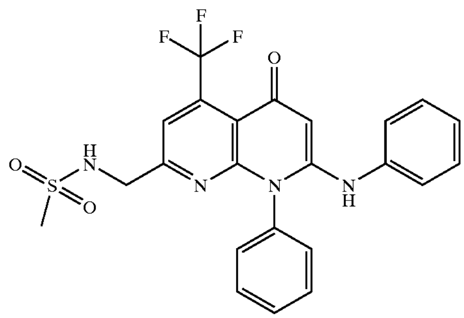 |
| 580 | 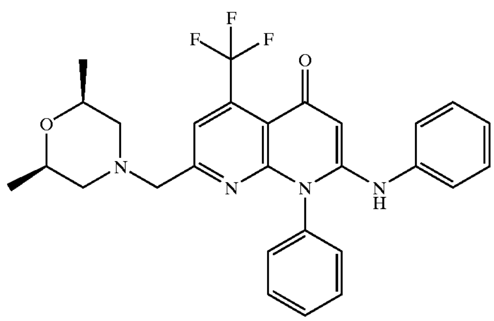 |
| 581 | 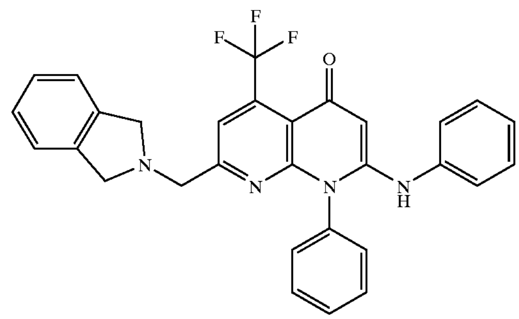 |

Utilizing the above described procedures for intermediates and examples alone or in combination, a variety of Formula II compounds were prepared using the appropriate starting material and the representative procedure described. These results are summarized in Table 2A.

TABLE 2A

| Example | Structure | LCMS RT (min) | [M + H] | Representative Procedure |
|---------|-----------|---------------|---------|--------------------------|
| 582 | 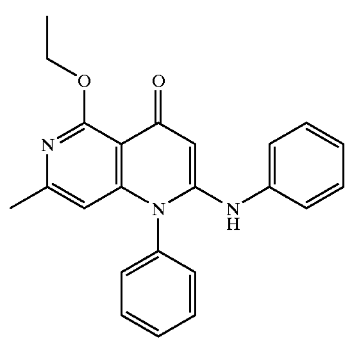 | 2.39 | 372.3 | Intermediate BA, BB, BC and Example 39, 48 |

TABLE 2A-continued

| Example | Structure | LCMS RT (min) | [M + H] | Representative Procedure |
|---------|-----------|---------------|---------|--------------------------|
| 583 | 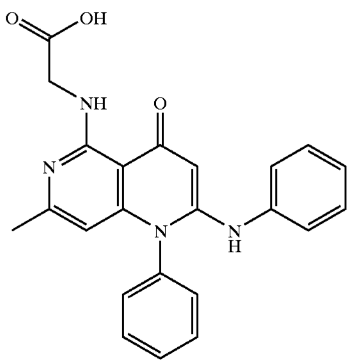 | 2.05 | 401.2 | Intermediate BA, BB, BC and Example 39, 46, 45 |
| 584 | 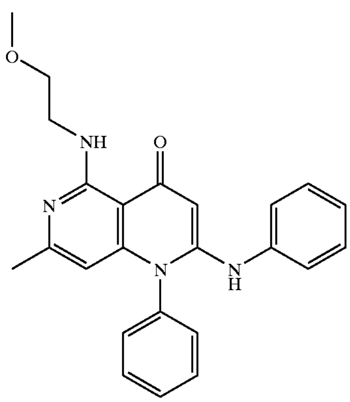 | 1.93 | 401.3 | Intermediate BA, BB, BC and Example 39, 43 |
| 585 | 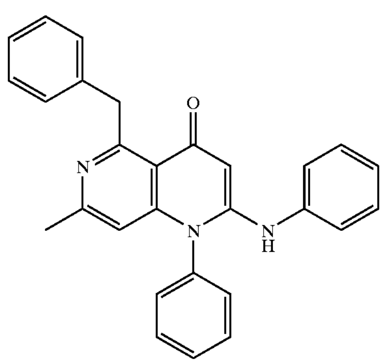 | 2.04 | 418.3 | Intermediate BA, BB, BC and Example 39, 42 |
| 586 | 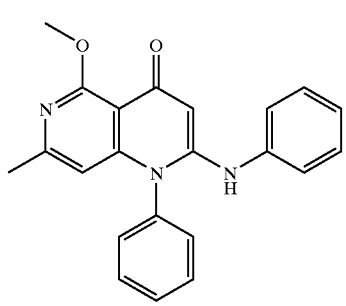 | 2.25 | 358.4 | Intermediate BA, BB, BC and Example 39, 48 |

TABLE 2A-continued
| Example | Structure | LCMS RT (min) | [M + H] | Representative Procedure |
|---|---|---|---|---|
| 587 | 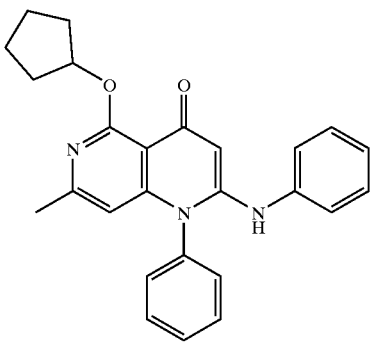 | 2.89 | 412.1 | Intermediate BA, BB, BC and Example 39, 48 |
| 588 | 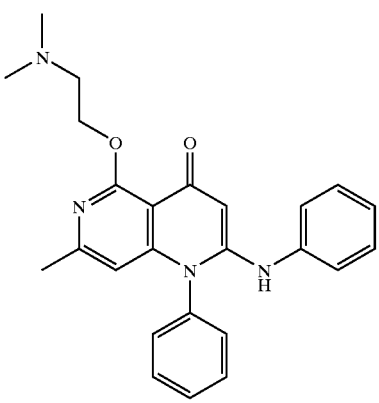 | 1.89 | 415.3 | Intermediate BA, BB, BC and Example 39, 48 |
| 589 | 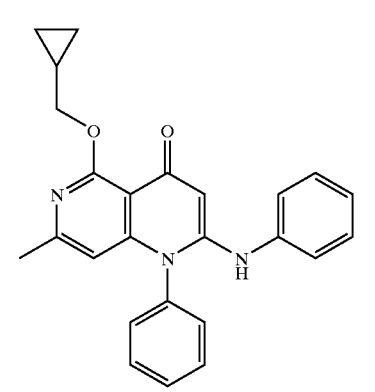 | 2.57 | 398.3 | Intermediate BA, BB, BC and Example 39, 48 |
| 590 | 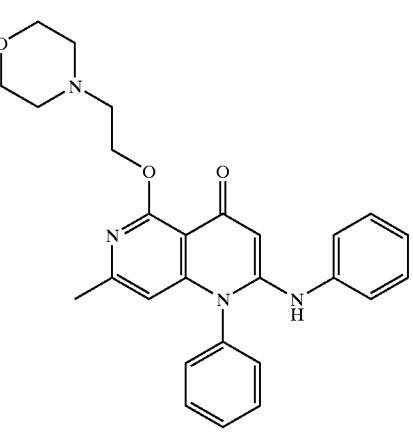 | 1.92 | 457.2 | Intermediate BA, BB, BC and Example 39, 48 |

TABLE 2A-continued
| Example | Structure | LCMS RT (min) | [M + H] | Representative Procedure |
|---|---|---|---|---|
| 591 | 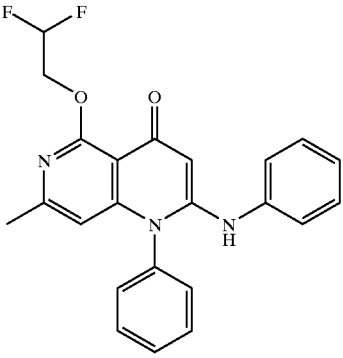 | 2.41 | 408.4 | Intermediate BA, BB, BC and Example 39, 48 |
| 592 | 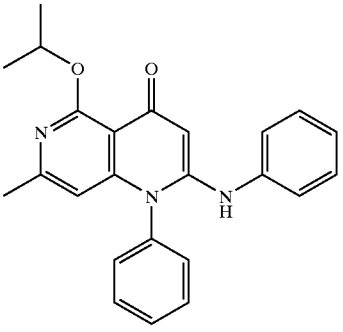 | 2.52 | 386.1 | Intermediate BA, BB, BC and Example 39, 48 |
| 593 | 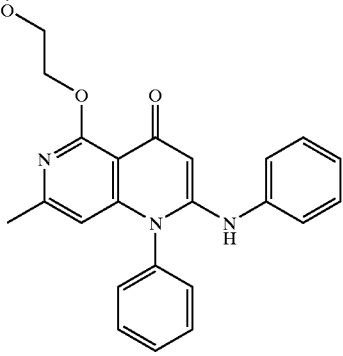 | 2.46 | 402.2 | Intermediate BA, BB, BC and Example 39, 48 |
| 594 | 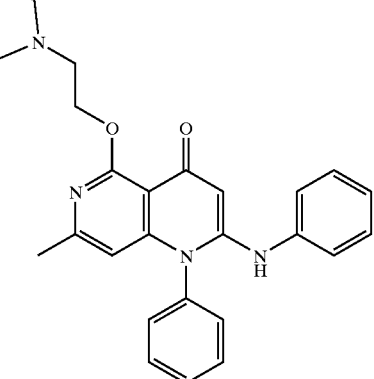 | 2.12 | 441.1 | Intermediate BA, BB, BC and Example 39, 48 |

TABLE 2A-continued

| Example | Structure | LCMS RT (min) | [M + H] | Representative Procedure |
|---------|-----------|---------------|---------|--------------------------|
| 595 | 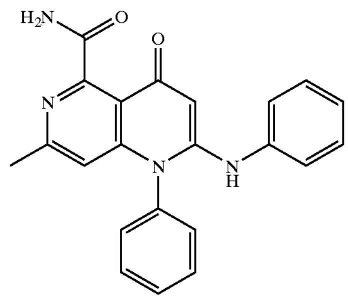 | 1.79 | 371.9 | Intermediate BA, BB, BC and Example 39, 49, 47 |
| 596 | 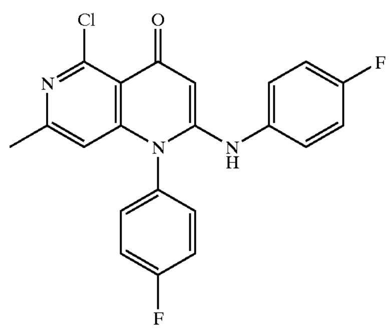 | 2.36 | 398.3 | Intermediate BA, BB, BC and Example 39 |
| 597 | 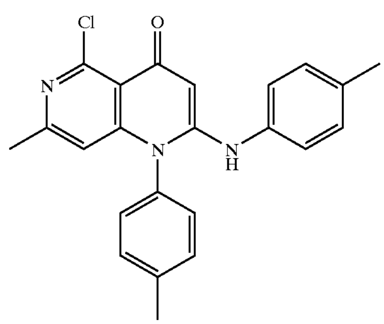 | 2.57 | 390.4 | Intermediate BA, BB, BC and Example 39 |
| 598 | 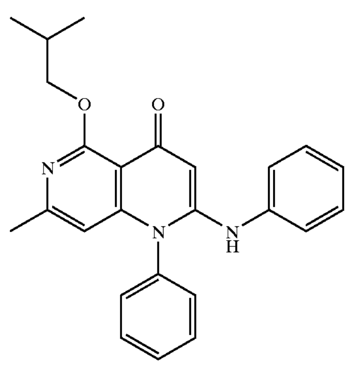 | 3.28 | 400.2 | Intermediate BA, BB, BC and Example 39, 48 |

TABLE 2A-continued

| Example | Structure | LCMS RT (min) | [M + H] | Representative Procedure |
|---------|-----------|---------------|---------|--------------------------|
| 599 | 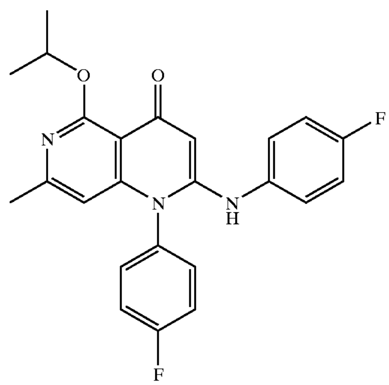 | 2.56 | 422.0 | Intermediate BA, BB, BC and Example 39, 48 |
| 600 | 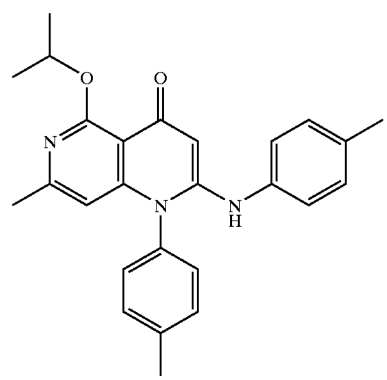 | 2.74 | 414.1 | Intermediate BA, BB, BC and Example 39, 48 |
| 601 | 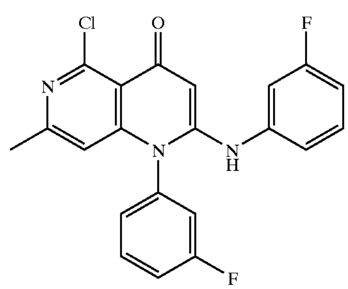 | 2.43 | 398.4 | Intermediate BA, BB, BC and Example 39 |
| 602 | 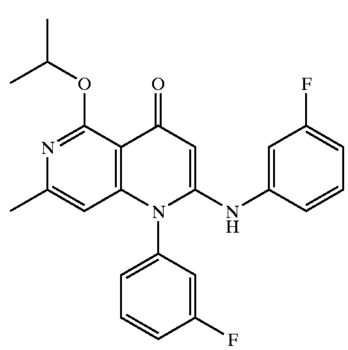 | 2.57 | 422.1 | Intermediate BA, BB, BC and Example 39, 48 |

TABLE 2A-continued
| Example | Structure | LCMS RT (min) | [M + H] | Representative Procedure |
|---|---|---|---|---|
| 603 | 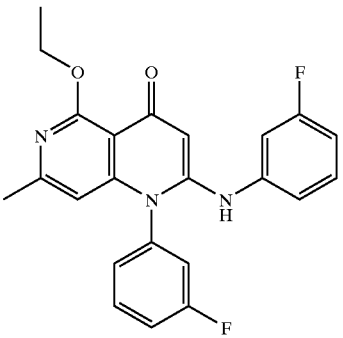 | 2.45 | 408.2 | Intermediate BA, BB, BC and Example 39, 48 |
| 604 | 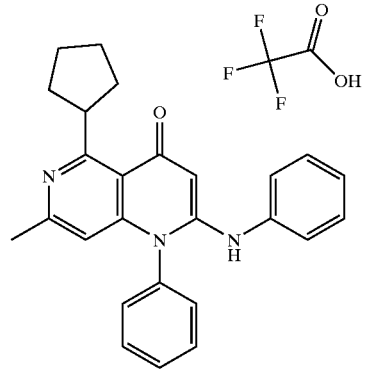 | 2.02 | 396.3 | Intermediate BA, BB, BC and Example 39, 42 |
| 605 | 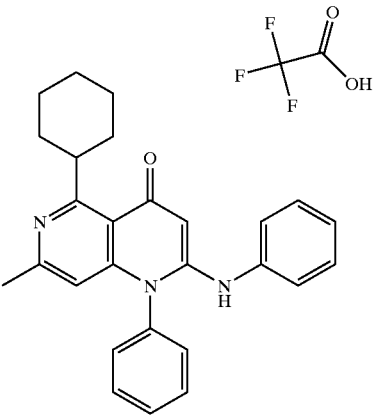 | 2.15 | 410.3 | Intermediate BA, BB, BC and Example 39, 42 |
| 606 | 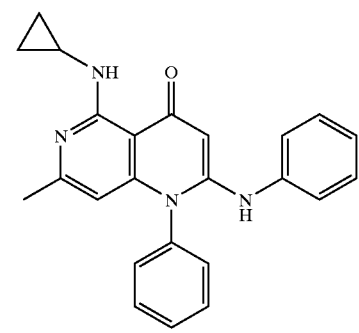 | 1.96 | 383.3 | Intermediate BA, BB, BC and Example 39, 43 |

TABLE 2A-continued

| Example | Structure | LCMS RT (min) | [M + H] | Representative Procedure |
|---------|-----------|---------------|---------|--------------------------|
| 607 | 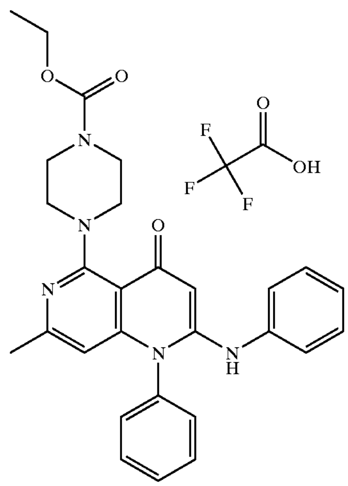 | 2.20 | 484.3 | Intermediate BA, BB, BC and Example 39, 43 |
| 608 | 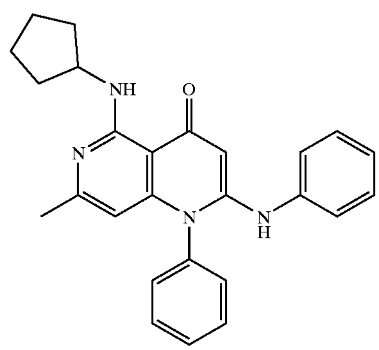 | 2.19 | 411.3 | Intermediate BA, BB, BC and Example 39, 43 |
| 609 | 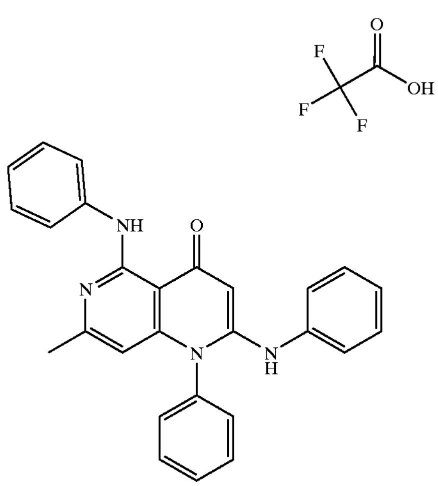 | 2.33 | 419.4 | Intermediate BA, BB, BC and Example 39, 43 |

TABLE 2A-continued
| Example | Structure | LCMS RT (min) | [M + H] | Representative Procedure |
|---------|-----------|---------------|---------|--------------------------|
| 610 | 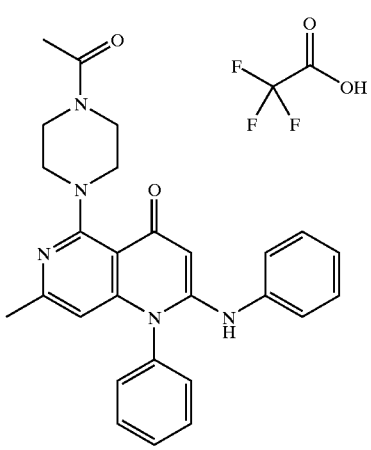 | 1.86 | 454.3 | Intermediate BA, BB, BC and Example 39, 43 |
| 611 | 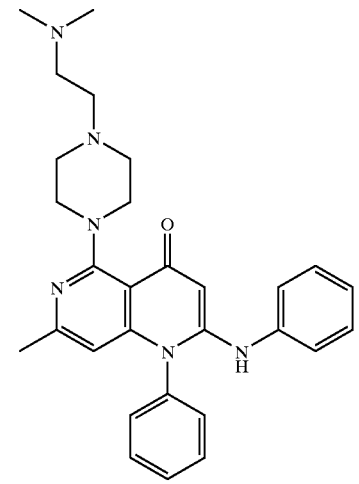 | 1.22 | 483.2 | Intermediate BA, BB, BC and Example 39, 43 |
| 612 | 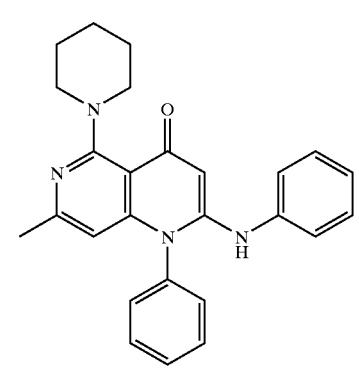 | 2.11 | 411.4 | Intermediate BA, BB, BC and Example 39, 43 |

TABLE 2A-continued

| Example | Structure | LCMS RT (min) | [M + H] | Representative Procedure |
|---------|-----------|---------------|---------|--------------------------|
| 613 | 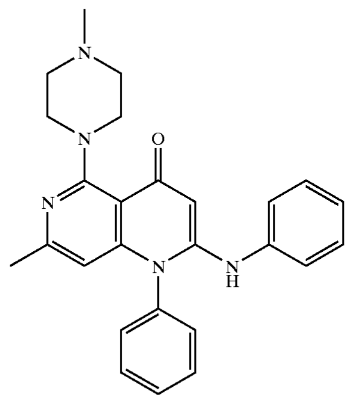 | 1.55 | 426.0 | Intermediate BA, BB, BC and Example 39, 43 |
| 614 | 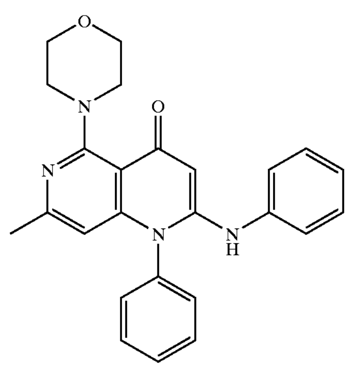 | 1.98 | 413.0 | Intermediate BA, BB, BC and Example 39, 43 |
| 615 | 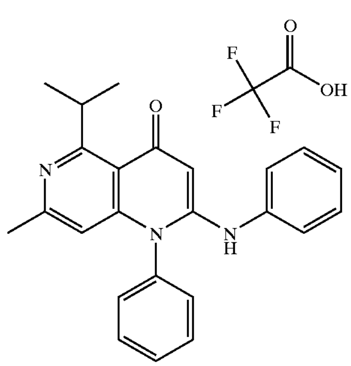 | 1.88 | 370.3 | Intermediate BA, BB, BC and Example 39, 42 |
| 616 | 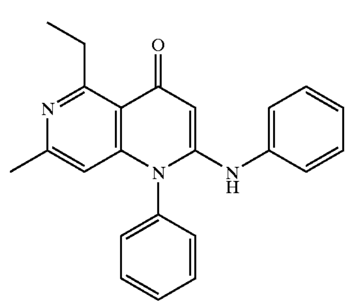 | 1.73 | 356.3 | Intermediate BA, BB, BC and Example 39, 42 |

TABLE 2A-continued
| Example | Structure | LCMS RT (min) | [M + H] | Representative Procedure |
|---|---|---|---|---|
| 617 | 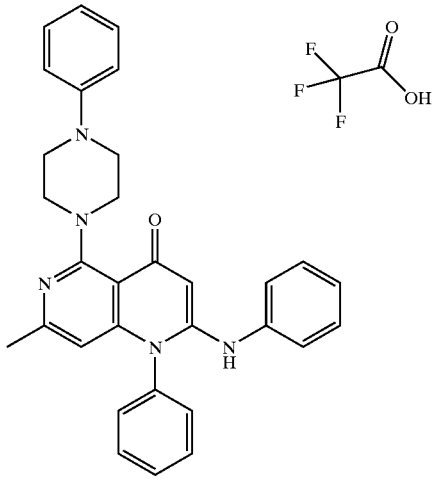 | 2.53 | 488.3 | Intermediate BA, BB, BC and Example 39, 43 |
| 618 | 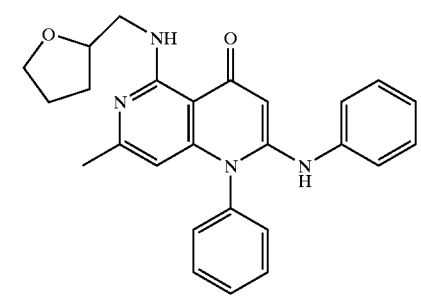 | 2.30 | 427.3 | Intermediate BA, BB, BC and Example 39, 43 |
| 619 | 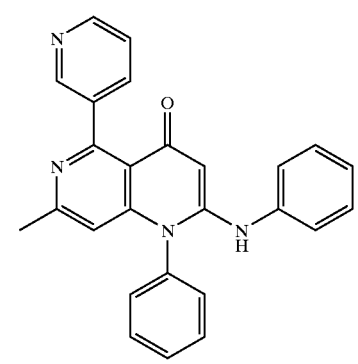 | 1.68 | 405.4 | Intermediate BA, BB, BC and Example 39, 55 |

TABLE 2A-continued

| Example | Structure | LCMS RT (min) | [M + H] | Representative Procedure |
|---------|-----------|---------------|---------|--------------------------|
| 620 | 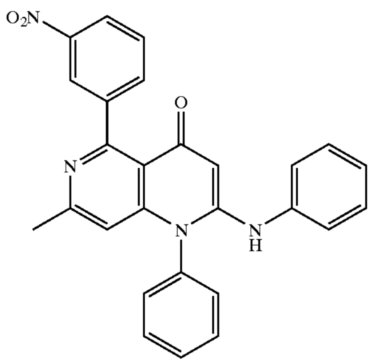 | 2.25 | 449.2 | Intermediate BA, BB, BC and Example 39, 55 |
| 621 | 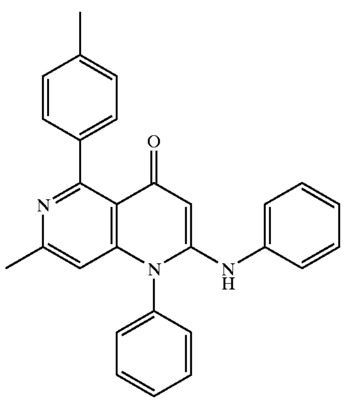 | 2.00 | 418.5 | Intermediate BA, BB, BC and Example 39, 55 |
| 622 | 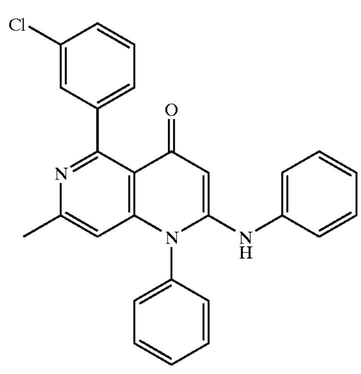 | 2.19 | 438.3 | Intermediate BA, BB, BC and Example 39, 55 |

Utilizing the above described procedures for intermediates and examples alone or in combination, a variety of Formula II compounds can be prepared using the appropriate starting material and the representative procedure described. These compounds are summarized in Table 2B.

TABLE 2B

| Example | Stucture | Representative Procedure |
|---|---|---|
| 623 | | Intermediate BA1, BB1, BC1 and Example 40, 49, 47 |
| 624 | | Intermediate BA1, BB1, BC1 and Example 40, 31, 32 |
| 625 | | Intermediate BA1, BB1, BC1 and Example 40, 43 |
| 626 | | Intermediate BA1, BB1, BC1 and Example 40, 43 and Intermediate AK |
| 627 | | Intermediate BA1, BB1, BC1 and Example 40, 43 and Intermediate AK |

TABLE 2B-continued

| Example | Structure | Representative Procedure |
|---|---|---|
| 628 | | Intermediate BA1, BB1, BC1 and Example 40, 17, 25 and Intermediate AJ |
| 629 | | Intermediate BA1, BB1, BC1 and Example 40, 31, 33 |
| 630 | | Intermediate BA1, BB1, BC1 and Example 40, 31, 33 |
| 631 | | Intermediate BA1, BB1, BC1 and Example 40, 31, 32, 33, 47 |
| 632 | | Intermediate BA1, BB1, BC1 and Example 40, 31, 32, 33, 47 |

TABLE 2B-continued

| Example | Stucture | Representative Procedure |
|---|---|---|
| 633 | | Intermediate BA1, BB1, BC1 and Example 40, 31, 32, 33, 47 |
| 634 | | Intermediate BA1, BB1, BC1 and Example 40, 31, 32, 33, 47 |
| 635 | | Intermediate BA1, BB1, BC1 and Example 40, 31, 33 |
| 636 | | Intermediate BA1, BB1, BC1 and Example 40, 17, 25 and Intermediate AJ |
| 637 | | Intermediate BA1, BB1, BC1 and Example 40, 17, 25 and Intermediate AJ |

TABLE 2B-continued
| Example | Structure | Representative Procedure |
|---|---|---|
| 638 | 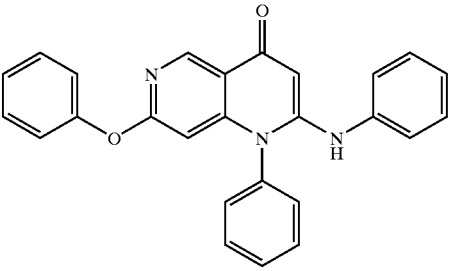 | Intermediate BA1, BB1, BC1 and Example 40, 48 |
| 639 | 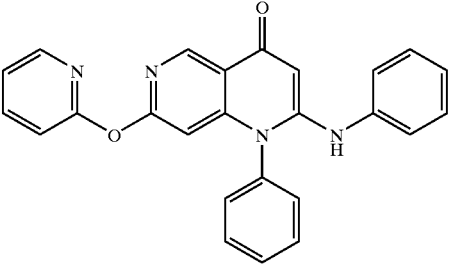 | Intermediate BA1, BB1, BC1 and Example 40, 48 |
| 640 | 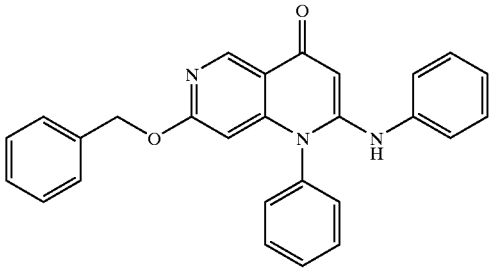 | Intermediate BA1, BB1, BC1 and Example 40, 48 |
| 641 | 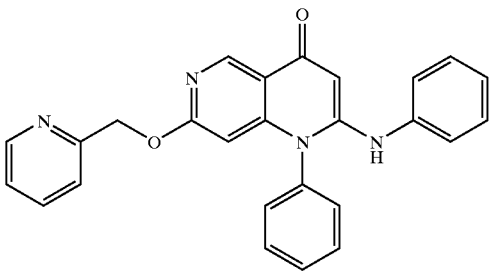 | Intermediate BA1, BB1, BC1 and Example 40, 48 |
| 642 | 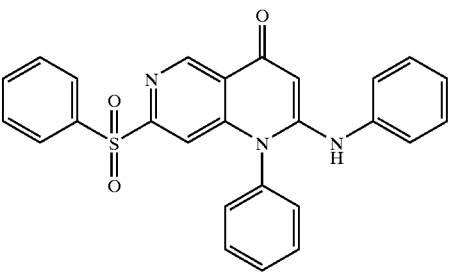 | Intermediate BA1, BB1, BC1 and Example 40, 44, 21 |

TABLE 2B-continued

| Example | Stucture | Representative Procedure |
|---|---|---|
| 643 | | Intermediate BA1, BB1, BC1 and Example 40, 44 |
| 644 | | Intermediate BA1, BB1, BC1 and Example 40, 44 |
| 645 | | Intermediate BA1, BB1, BC1 and Example 40, 43 |
| 646 | | Intermediate BA1, BB1, BC1 and Example 40, 49, 47 |
| 647 | | Intermediate BA1, BB1, BC1 and Example 40, 43 |

TABLE 2B-continued
| Example | Structure | Representative Procedure |
|---|---|---|
| 648 | 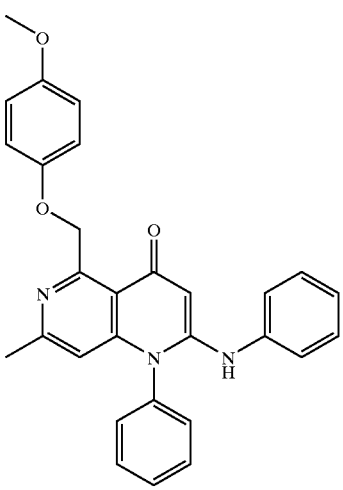 | Intermediate BA, BB, BC and Example 39, 17, 25, 26 |
| 649 | 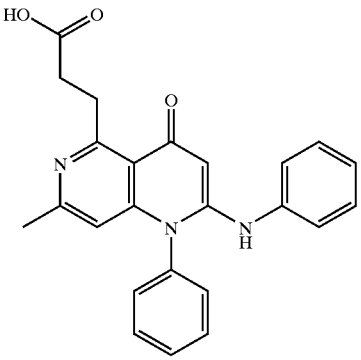 | Intermediate BA, BB, BC and Example 39, 31, 32, 33 |
| 650 | 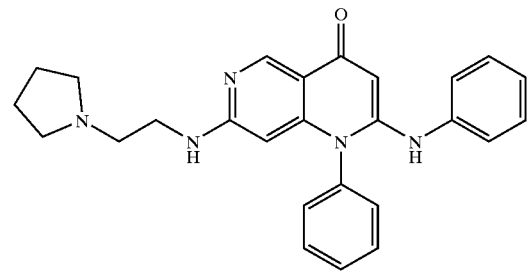 | Intermediate BA1, BB1, BC1 and Example 40, 43 |
| 651 | 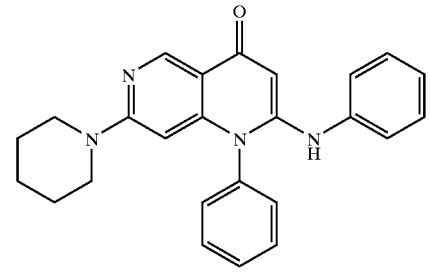 | Intermediate BA1, BB1, BC1 and Example 40, 43 |

TABLE 2B-continued

| Example | Stucture | Representative Procedure |
|---|---|---|
| 652 | | Intermediate BA2, BB2, BC2 and Example 40, 31, 32 |
| 653 | | Intermediate BA1, BB1, BC1 and Example 40, 43 |
| 654 | | Intermediate BA1, BB1, BC1 and Example 40, 49, 47 |
| 655 | | Intermediate BA1, BB1, BC1 and Example 40, 49, 50, 51 |
| 656 | | Intermediate BA1, BB1, BC1 and Example 40, 44 |

TABLE 2B-continued

| Example | Stucture | Representative Procedure |
|---|---|---|
| 657 | | Intermediate BA1, BB1, BC1 and Example 40, 43 |
| 658 | | Intermediate BA1, BB1, BC1 and Example 40, 49, 50, 51 |
| 659 | | Intermediate BA1, BB1, BC1 and Example 40, 43 |
| 660 | | Intermediate BA1, BB1, BC1 and Example 40, 44 |
| 661 | | Intermediate BA1, BB1, BC1 and Example 40, 49, 47 |

TABLE 2B-continued

| Example | Structure | Representative Procedure |
|---|---|---|
| 662 | | Intermediate BA1, BB1, BC1 and Example 40, 44, 21 |
| 663 | | Intermediate BA, BB, BC and Example 39, 31 |
| 664 | | Intermediate BA1, BB1, BC1 and Example 40, 43 |
| 665 | | Intermediate BA, BB, BC and Example 39, 17, 25, 26 |

TABLE 2B-continued

| Example | Stucture | Representative Procedure |
|---|---|---|
| 666 | | Intermediate BA1, BB1, BC1 and Example 40, 44, 21 |
| 667 | | Intermediate BA1, BB1, BC1 and Example 40, 49, 50, 51 |
| 668 | | Intermediate BA1, BB1, BC1 and Example 40, 43, 12 |
| 669 | | Intermediate BA1, BB1, BC1 and Example 40, 3 |
| 670 | | Intermediate BA, BB, BC and Example 39, 3 |

TABLE 2B-continued
| Example | Stucture | Representative Procedure |
|---------|----------|--------------------------|
| 671 | 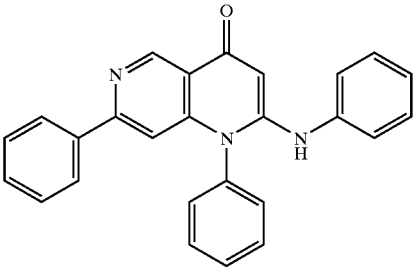 | Intermediate BA1, BB1, BC1 and Example 40, 55 |
| 672 | 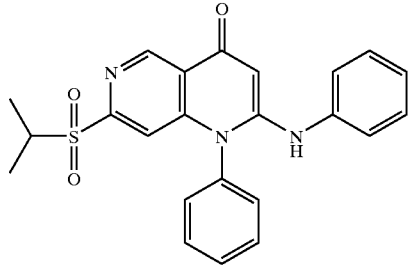 | Intermediate BA1, BB1, BC1 and Example 40, 44, 21 |
| 673 | 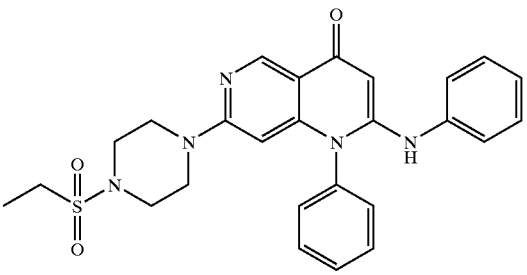 | Intermediate BA1, BB1, BC1 and Example 40, 43, 12 |
| 674 | 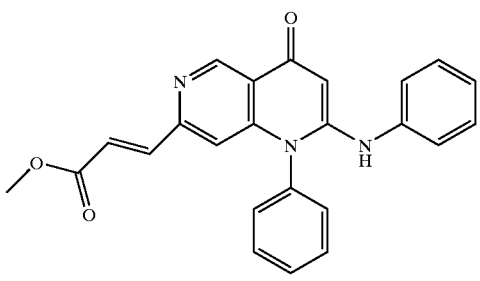 | Intermediate BA1, BB1, BC1 and Example 40, 31 |
| 675 | 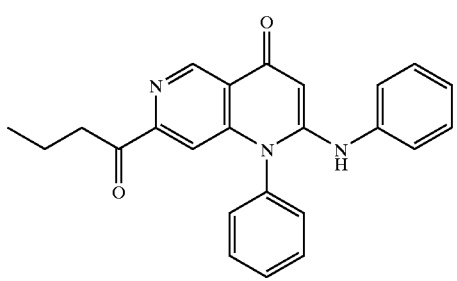 | Intermediate BA1, BB1, BC1 and Example 40, 49, 50, 51 |

TABLE 2B-continued

| Example | Stucture | Representative Procedure |
|---|---|---|
| 676 | | Intermediate BA, BB, BC and Example 39, 17, 25, 26 |
| 677 | | Intermediate BA, BB, BC and Example 39, 54 and Intermediate AL |
| 678 | | Intermediate BA1, BB1, BC1 and Example 40, 3 |
| 679 | | Intermediate BA1, BB1, BC1 and Example 40, 43, 12 |
| 680 | | Intermediate BA1, BB1, BC1 and Example 40, 48 |

TABLE 2B-continued
| Example | Stucture | Representative Procedure |
|---|---|---|
| 681 | 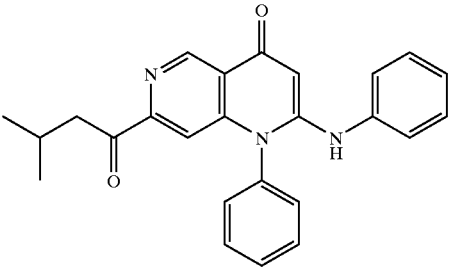 | Intermediate BA1, BB1, BC1 and Example 40, 49, 50, 51 |
| 682 | 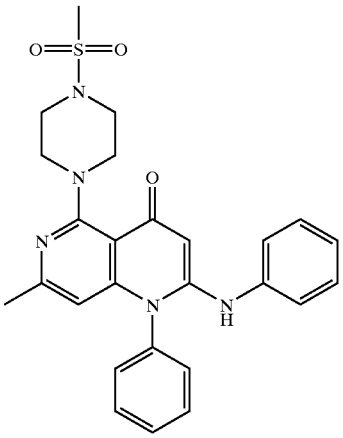 | Intermediate BA, BB, BC and Example 39, 43, 12 |
| 683 | 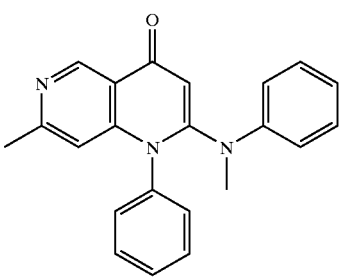 | Intermediate BA, BB, BC and Example 39, 54 and Intermediate AJ |
| 684 | 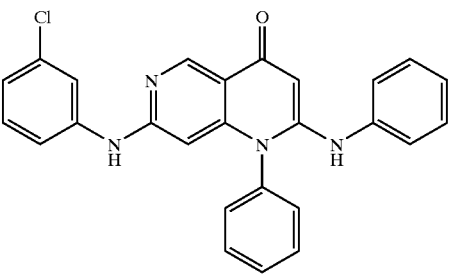 | Intermediate BA1, BB1, BC1 and Example 40, 3 |
| 685 | 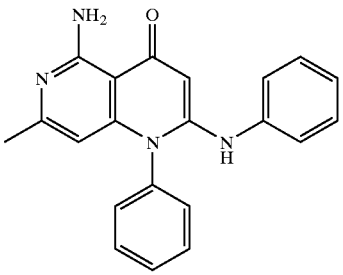 | Intermediate BA, BB, BC and Example 39, 3, 24 |

TABLE 2B-continued

| Example | Stucture | Representative Procedure |
|---------|----------|--------------------------|
| 686 | | Intermediate BA1, BB1, BC1 and Example 40, 17 |
| 687 | | Intermediate BA1, BB1, BC1 and Example 40, 49, 47 |
| 688 | | Intermediate BA2, BB2, BC2 and Example 40, 31, 32, 33 |
| 689 | | Intermediate BA1, BB1, BC1 and Example 40, 22 |
| 690 | | Intermediate BA1, BB1, BC1 and Example 40, 3 |

TABLE 2B-continued

| Example | Stucture | Representative Procedure |
|---------|----------|--------------------------|
| 691 | | Intermediate BA2, BB2, BC2 and Example 41, 55 |
| 692 | | Intermediate BA1, BB1, BC1 and Example 40, 44, 21 |
| 693 | | Intermediate BA1, BB1, BC1 and Example 40, 17, 25, 26 |
| 694 | | Intermediate BA1, BB1, BC1 and Example 40, 17, 25, 23 |
| 695 | | Intermediate BA1, BB1, BC1 and Example 40, 17, 18 |

TABLE 2B-continued

| Example | Stucture | Representative Procedure |
|---|---|---|
| 696 | | Intermediate BA1, BB1, BC1 and Example 40, 3, 24 |
| 697 | | Intermediate BA, BB, BC and Example 39, 17, 25 |
| 698 | | Intermediate BA, BB, BC and Example 39, 17, 25, 26 |
| 699 | | Intermediate BA2, BB2, BC2 and Example 41, 55 |
| 700 | | Intermediate BA1, BB1, BC1 and Example 40, 49, 50 |

TABLE 2B-continued

| Example | Stucture | Representative Procedure |
|---|---|---|
| 701 | | Intermediate BA, BB, BC and Example 39 54, and Intermediate AK |
| 702 | | Intermediate BA1, BB1, BC1 and Example 40, 3 |
| 703 | | Intermediate BA1, BB1, BC1 and Example 40, 49, 50, 51 |
| 704 | | Intermediate BA2, BB2, BC2 and Example 41, 34 |
| 705 | | Intermediate BA2, BB2, BC2 and Example 41, 3 |

TABLE 2B-continued

| Example | Stucture | Representative Procedure |
|---------|----------|--------------------------|
| 706 | | Intermediate BA1, BB1, BC1 and Example 40, 17, 25, 26 |
| 707 | | Intermediate BA1, BB1, BC1 and Example 40, 44 |
| 708 | | Intermediate BA1, BB1, BC1 and Example 40, 43, 47 |
| 709 | | Intermediate BA, BB, BC and Example 39, 17, 25, 26 |
| 710 | | Intermediate BA1, BB1, BC1 and Example 40, 48 |

TABLE 2B-continued

| Example | Stucture | Representative Procedure |
|---------|----------|--------------------------|
| 711 | | Intermediate BA2, BB2, BC2 and Example 41, 31 |
| 712 | | Intermediate BA1, BB1, BC1 and Example 40, 3 |
| 713 | | Intermediate BA, BB, BC and Example 39 54 and Intermediate AK |
| 714 | | Intermediate BA2, BB2, BC2 and Example 41, 34 |
| 715 | | Intermediate BA1, BB1, BC1 and Example 40, 3 |

TABLE 2B-continued

| Example | Structure | Representative Procedure |
|---|---|---|
| 716 | | Intermediate BA1, BB1, BC1 and Example 40, 17, 25, 26 |
| 717 | | Intermediate BA1, BB1, BC1 and Example 40, 48 |
| 718 | | Intermediate BA1, BB1, BC1 and Example 40, 49, 50, 51 |
| 719 | | Intermediate BA2, BB2, BC2 and Example 41, 3 |
| 720 | | Intermediate BA2, BB2, BC2 and Example 41, 34 |

TABLE 2B-continued

| Example | Stucture | Representative Procedure |
|---|---|---|
| 721 | | Intermediate BA1, BB1, BC1 and Example 40, 55 |
| 722 | | Intermediate BA1, BB1, BC1 and Example 40, 44, 45 |
| 723 | | Intermediate BA1, BB1, BC1 and Example 40, 3 |
| 724 | | Intermediate BA1, BB1, BC1 and Example 40, 43, 47 |
| 725 | | Intermediate BA, BB, BC and Example 39, 54 and Intermediate AK |

TABLE 2B-continued

| Example | Stucture | Representative Procedure |
|---|---|---|
| 726 | | Intermediate BA1, BB1, BC1 and Example 40, 17, 25, 26 |
| 727 | | Intermediate BA1, BB1, BC1 and Example 40, 3 |
| 728 | | Intermediate BA2, BB2, BC2 and Example 41, 34 |
| 729 | | Intermediate BA2, BB2, BC2 and Example 41, 3 |
| 730 | | Intermediate BA1, BB1, BC1 and Example 40, 55 |

TABLE 2B-continued

| Example | Stucture | Representative Procedure |
|---|---|---|
| 731 | | Intermediate BA1, BB1, BC1 and Example 40, 3 |
| 732 | | Intermediate BA1, BB1, BC1 and Example 40, 48 |
| 733 | | Intermediate BA1, BB1, BC1 and Example 40, 3 |
| 734 | | Intermediate BA, BB, BC and Example 39, 31, 32 |
| 735 | | Intermediate BA1, BB1, BC1 and Example 40, 3 |

TABLE 2B-continued
| Example | Structure | Representative Procedure |
|---|---|---|
| 736 | 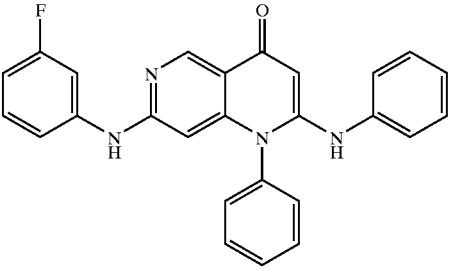 | Intermediate BA1, BB1, BC1 and Example 40, 3 |
| 737 | 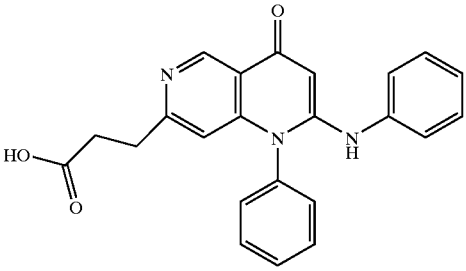 | Intermediate BA1, BB1, BC1 and Example 40, 31, 32, 33 |
| 738 | 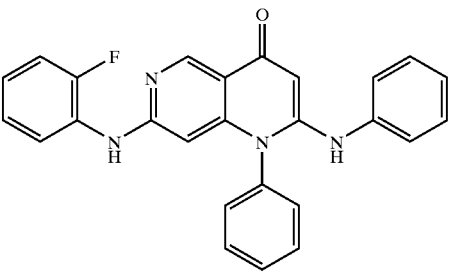 | Intermediate BA1, BB1, BC1 and Example 40, 3 |
| 739 | 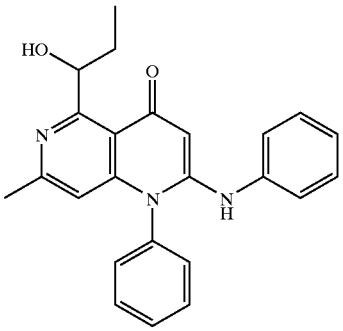 | Intermediate BA, BB, BC and Example 39, 49, 50, 51, 25 |
| 740 | 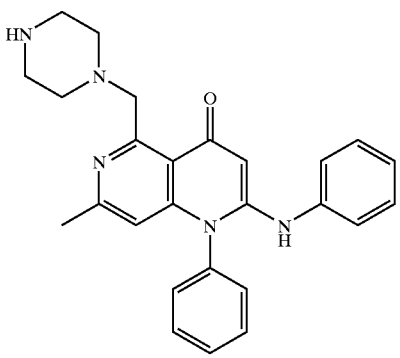 | Intermediate BA, BB, BC and Example 39, 17, 25, 11 |

TABLE 2B-continued

| Example | Stucture | Representative Procedure |
|---|---|---|
| 741 | | Intermediate BA, BB, BC and Example 39, 17, 25, 11 |
| 742 | | Intermediate BA1, BB1, BC1 and Example 40, 42 |
| 743 | | Intermediate BA1, BB1, BC1 and Example 40, 42 |
| 744 | | Intermediate BA1, BB1, BC1 and Example 40, 42 |
| 745 | | Intermediate BA1, BB1, BC1 and Example 40, 42 |

TABLE 2B-continued
| Example | Structure | Representative Procedure |
|---|---|---|
| 746 | 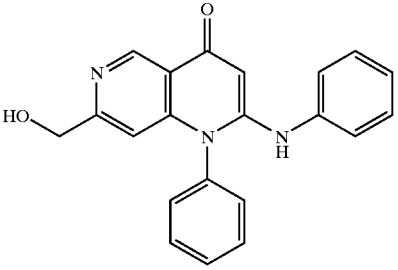 | Intermediate BA1, BB1, BC1 and Example 40, 17, 25 |
| 747 | 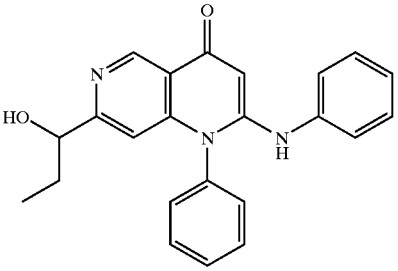 | Intermediate BA1, BB1, BC1 and Example 40, 49, 50, 51, 25 |
| 748 | 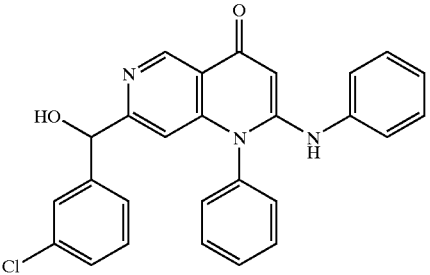 | Intermediate BA1, BB1, BC1 and Example 40, 49, 50, 51, 25 |
| 749 | 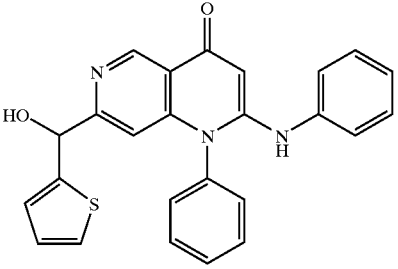 | Intermediate BA1, BB1, BC1 and Example 40, 49, 50, 51, 25 |
| 750 | 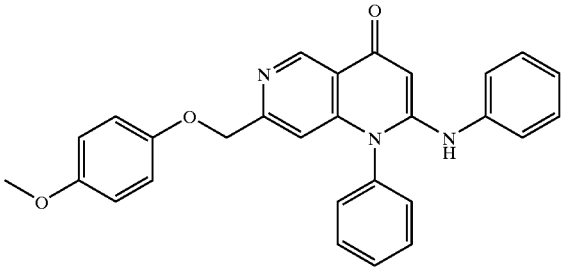 | Intermediate BA1, BB1, BC1 and Example 40, 17, 25, 26 |

TABLE 2B-continued

| Example | Stucture | Representative Procedure |
|---|---|---|
| 751 | | Intermediate BA1, BB1, BC1 and Example 40, 55 |
| 752 | | Intermediate BA1, BB1, BC1 and Example 40, 55 |
| 753 | | Intermediate BA1, BB1, BC1 and Example 40, 55 |
| 754 | | Intermediate BA1, BB1, BC1 and Example 40, 49, 50, 51 |
| 755 | | Intermediate BA1, BB1, BC1 and Example 40, 49, 50, 51 |

TABLE 2B-continued

| Example | Stucture | Representative Procedure |
|---|---|---|
| 756 | | Intermediate BA1, BB1, BC1 and Example 40, 49 |
| 757 | | Intermediate BA1, BB1, BC1 and Example 40, 43 |
| 758 | | Intermediate BA1, BB1, BC1 and Example 40, 43 |
| 759 | | Intermediate BA1, BB1, BC1 and Example 40, 43 |
| 760 | | Intermediate BA1, BB1, BC1 and Example 40, 43 |

TABLE 2B-continued

| Example | Structure | Representative Procedure |
|---|---|---|
| 761 | | Intermediate BA1, BB1, BC1 and Example 40, 43 |
| 762 | | Intermediate BA1, BB1, BC1 and Example 40, 43 |
| 763 | | Intermediate BA1, BB1, BC1 and Example 40, 43, 47 |
| 764 | | Intermediate BA1, BB1, BC1 and Example 40, 43, 12 |
| 765 | | Intermediate BA1, BB1, BC1 and Example 40, 43, 12 |

TABLE 2B-continued

| Example | Stucture | Representative Procedure |
|---|---|---|
| 766 | | Intermediate BA1, BB1, BC1 and Example 40, 43 |
| 767 | | Intermediate BA1, BB1, BC1 and Example 40, 43 |
| 768 | | Intermediate BA1, BB1, BC1 and Example 40, 3 |
| 769 | | Intermediate BA1, BB1, BC1 and Example 40, 43 |
| 770 | | Intermediate BA1, BB1, BC1 and Example 40, 22 |

TABLE 2B-continued
| Example | Structure | Representative Procedure |
|---|---|---|
| 771 | 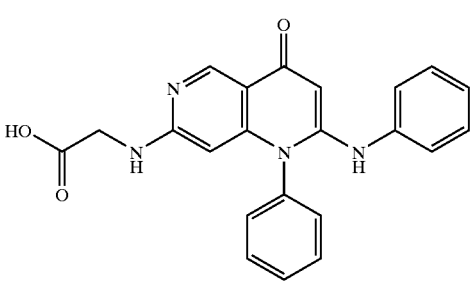 | Intermediate BA1, BB1, BC1 and Example 40, 46, 45 |
| 772 | 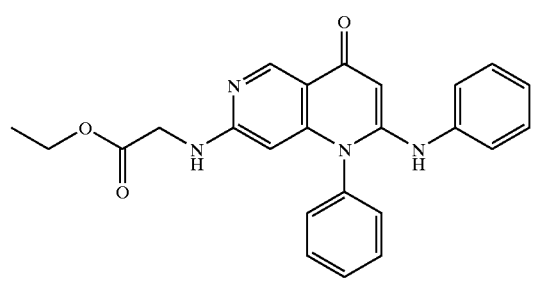 | Intermediate BA1, BB1, BC1 and Example 40, 46 |
| 773 | 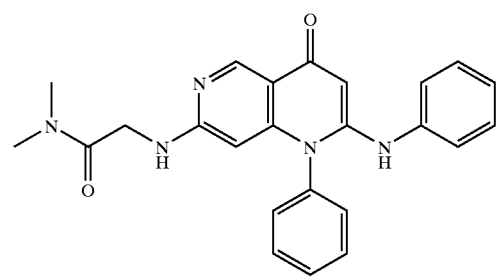 | Intermediate BA1, BB1, BC1 and Example 40, 46, 45, 47 |
| 774 | 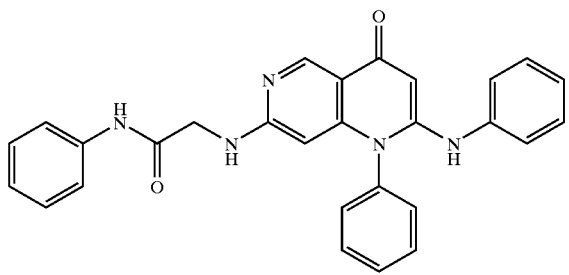 | Intermediate BA1, BB1, BC1 and Example 40, 46, 45, 47 |
| 775 | 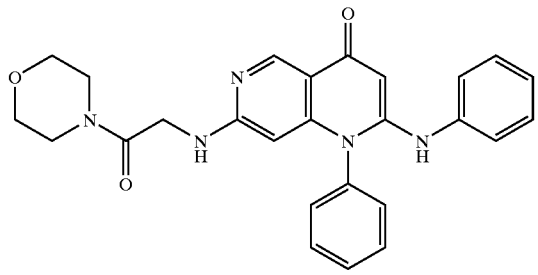 | Intermediate BA1, BB1, BC1 and Example 40, 46, 45, 47 |

TABLE 2B-continued

| Example | Stucture | Representative Procedure |
|---|---|---|
| 776 | | Intermediate BA1, BB1, BC1 and Example 40, 44, 45, 47 |
| 777 | | Intermediate BA1, BB1, BC1 and Example 40, 44, 45, 47 |
| 778 | | Intermediate BA1, BB1, BC1 and Example 40, 44, 45, 47 |
| 779 | | Intermediate BA1, BB1, BC1 and Example 40, 48, 45 |
| 780 | | Intermediate BA1, BB1, BC1 and Example 40, 48 |

TABLE 2B-continued

| Example | Structure | Representative Procedure |
|---|---|---|
| 781 | | Intermediate BA1, BB1, BC1 and Example 40, 48, 45, 47 |
| 782 | | Intermediate BA1, BB1, BC1 and Example 40, 48, 45, 47 |
| 783 | | Intermediate BA1, BB1, BC1 and Example 40, 44 |
| 784 | | Intermediate BA1, BB1, BC1 and Example 40, 44, 21 |
| 785 | | Intermediate BA1, BB1, BC1 and Example 40, 48 |

TABLE 2B-continued

| Example | Stucture | Representative Procedure |
| --- | --- | --- |
| 786 | | Intermediate BA1, BB1, BC1 and Example 40, 48 |
| 787 | | Intermediate BA1, BB1, BC1 and Example 40, 48 |
| 788 | | Intermediate BA1, BB1, BC1 and Example 40, 48 |
| 789 | | Intermediate BA1, BB1, BC1 and Example 40, 48 |
| 790 | | Intermediate BA, BB, BC and Example 39, 48 |

TABLE 2B-continued

| Example | Structure | Representative Procedure |
|---|---|---|
| 791 | | Intermediate BA, BB, BC and Example 39, 48 |
| 792 | | Intermediate BA, BB, BC and Example 39, 48 |
| 793 | | Intermediate BA, BB, BC and Example 39, 48 |
| 794 | | Intermediate BA, BB, BC and Example 39, 48 |

TABLE 2B-continued

| Example | Stucture | Representative Procedure |
|---|---|---|
| 795 | | Intermediate BA, BB, BC and Example 39, 48 |
| 796 | | Intermediate BA, BB, BC and Example 39, 48 |
| 797 | | Intermediate BA, BB, BC and Example 39, 48 |
| 798 | | Intermediate BA, BB, BC and Example 39, 48 |

TABLE 2B-continued

| Example | Structure | Representative Procedure |
|---|---|---|
| 799 | | Intermediate BA, BB, BC and Example 39, 48 |
| 800 | | Intermediate BA, BB, BC and Example 39, 48 |
| 801 | | Intermediate BA, BB, BC and Example 39, 48 |
| 802 | | Intermediate BA, BB, BC and Example 39, 48 |

TABLE 2B-continued

| Example | Stucture | Representative Procedure |
|---|---|---|
| 803 | | Intermediate BA, BB, BC and Example 39, 48 |
| 804 | | Intermediate BA, BB, BC and Example 39, 48 |
| 805 | | Intermediate BA, BB, BC and Example 39, 48 |
| 806 | | Intermediate BA, BB, BC and Example 39, 48 |

TABLE 2B-continued

| Example | Stucture | Representative Procedure |
|---|---|---|
| 807 | | Intermediate BA, BB, BC and Example 39, 48 |
| 808 | | Intermediate BA, BB, BC and Example 39, 48 |
| 809 | | Intermediate BA, BB, BC and Example 39, 48 |
| 810 | | Intermediate BA, BB, BC and Example 39, 48 |

TABLE 2B-continued

| Example | Structure | Representative Procedure |
|---|---|---|
| 811 | | Intermediate BA, BB, BC and Example 39, 54, 47 |
| 812 | | Intermediate BA, BB, BC and Example 39, 54 and Intermediate AJ |
| 813 | | Intermediate BA, BB, BC and Example 39, 54 and Intermediate AK |
| 814 | | Intermediate BA, BB, BC and Example 39, 54, 12 |
| 815 | | Intermediate BA, BB, BC and Example 39, 54, 12 |

TABLE 2B-continued

| Example | Stucture | Representative Procedure |
|---------|----------|--------------------------|
| 816 | | Intermediate BA, BB, BC and Example 39, 54, 12 |
| 817 | | Intermediate BA, BB, BC and Example 39, 54, 12 |
| 818 | | Intermediate BA, BB, BC and Example 39, 54, 12 |
| 819 | | Intermediate BA, BB, BC and Example 39, 54 and Intermediate AL and Example 42 |
| 820 | | Intermediate BA, BB, BC and Example 39, 54 and Intermediate AL |

TABLE 2B-continued

| Example | Structure | Representative Procedure |
|---|---|---|
| 821 | | Intermediate BA, BB, BC and Example 39, 54 and Intermediate AL and Example 17, 25 |
| 822 | | Intermediate BA, BB, BC and Example 39, 54 and Intermediate AL and example 55 |
| 823 | | Intermediate BA, BB, BC and Example 39, 54 and Intermediate AL and Example 55 |
| 824 | | Intermediate BA, BB, BC and Example 39, 54 and Intermediate AL and Example 17, 25 and Intermediate AJ |
| 825 | | Intermediate BA, BB, BC and Example 39, 54 and Intermediate AL and Example 17, 25 and Intermediate AJ |

TABLE 2B-continued
| Example | Structure | Representative Procedure |
|---|---|---|
| 826 | 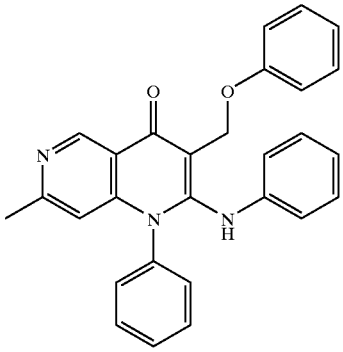 | Intermediate BA, BB, BC and Example 39, 54 and Intermediate AL and Example 17, 25, 26 |
| 827 | 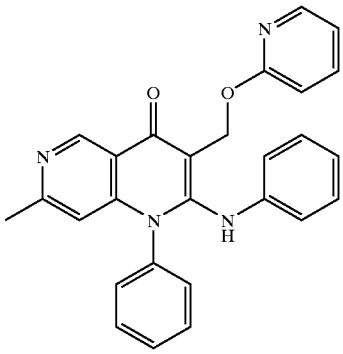 | Intermediate BA, BB, BC and Example 39, 54 and Intermediate AL and Example 17, 25, 26 |
| 828 | 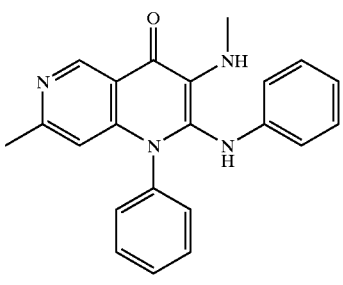 | Intermediate BA, BB, BC and Example 39, 54 and Intermediate AL and Example 3 |
| 829 | 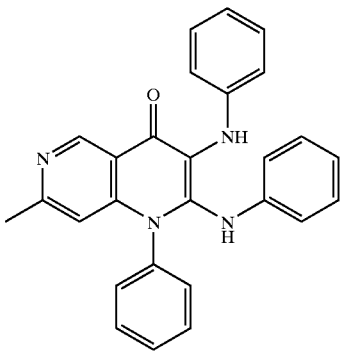 | Intermediate BA, BB, BC and Example 39, 54 and Intermediate AL and Example 3 |

TABLE 2B-continued

| Example | Stucture | Representative Procedure |
|---------|----------|--------------------------|
| 830 | | Intermediate BA, BB, BC and Example 39, 54 and Intermediate AL and Example 3 |
| 831 | | Intermediate BA, BB, BC and Example 39, 43 |
| 832 | | Intermediate BA, BB, BC and Example 39, 43 |
| 833 | | Intermediate BA, BB, BC and Example 39, 46, 45, 47 |

TABLE 2B-continued
| Example | Stucture | Representative Procedure |
|---|---|---|
| 834 | 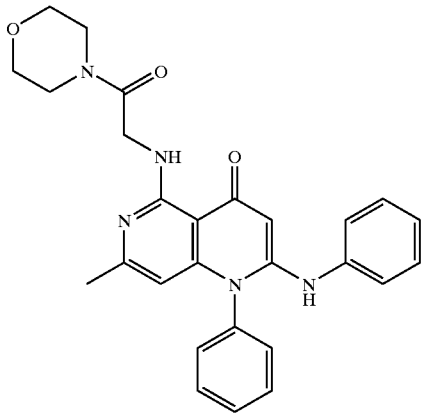 | Intermediate BA, BB, BC and Example 39, 46, 45, 47 |
| 835 | 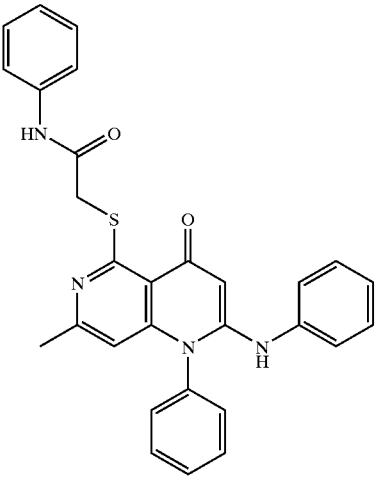 | Intermediate BA, BB, BC and Example 39, 44, 45, 47 |
| 836 | 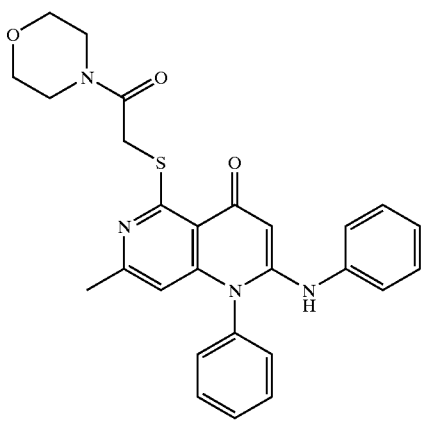 | Intermediate BA, BB, BC and Example 39, 44, 45, 47 |

TABLE 2B-continued
| Example | Stucture | Representative Procedure |
|---|---|---|
| 837 | 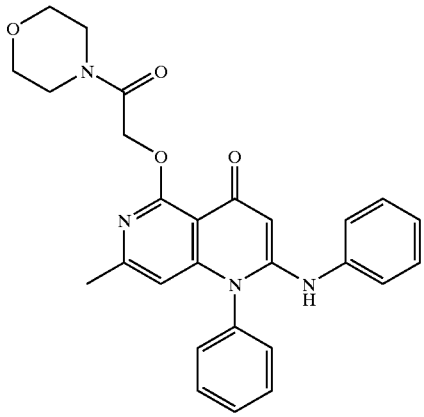 | Intermediate BA, BB, BC and Example 39, 48, 45, 47 |
| 838 | 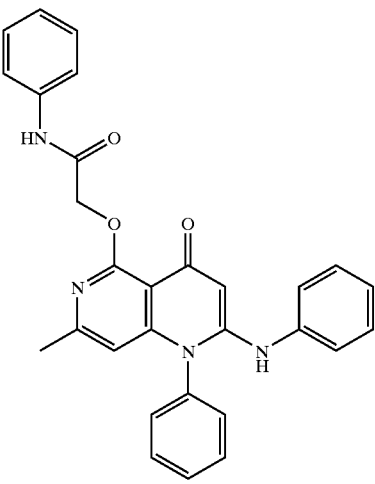 | Intermediate BA, BB, BC and Example 39, 48, 45, 47 |
| 839 | 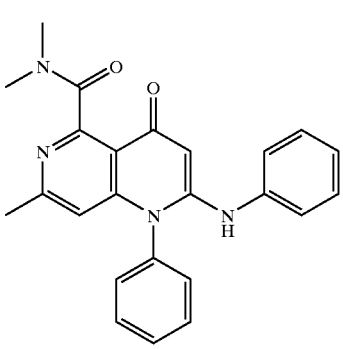 | Intermediate BA, BB, BC and Example 39, 49, 47 |

TABLE 2B-continued
| Example | Stucture | Representative Procedure |
|---|---|---|
| 840 | 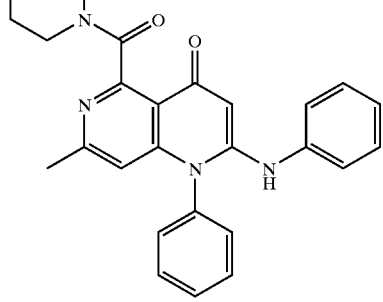 | Intermediate BA, BB, BC and Example 39, 49, 47 |
| 841 | 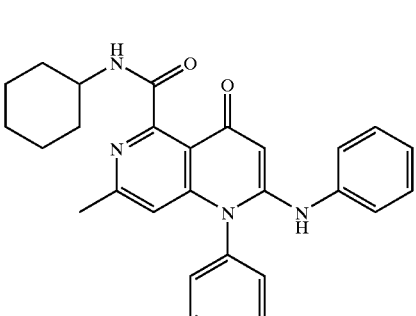 | Intermediate BA, BB, BC and Example 39, 49, 47 |
| 842 | 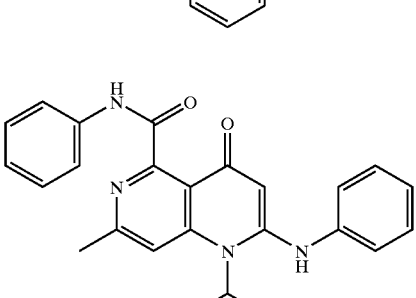 | Intermediate BA, BB, BC and Example 39, 49, 47 |
| 843 | 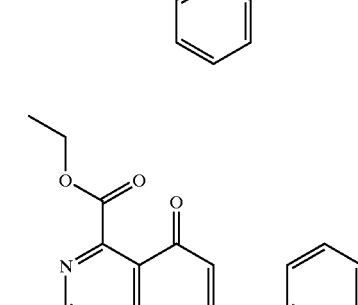 | Intermediate BA, BB, BC and Example 39, 17 |

TABLE 2B-continued

| Example | Stucture | Representative Procedure |
| --- | --- | --- |
| 844 | | Intermediate BA, BB, BC and Example 39, 44 |
| 845 | | Intermediate BA, BB, BC and Example 39, 44 |
| 846 | | Intermediate BA, BB, BC and Example 39, 44 |
| 847 | | Intermediate BA, BB, BC and Example 39, 44 |

TABLE 2B-continued
| Example | Stucture | Representative Procedure |
|---|---|---|
| 848 | 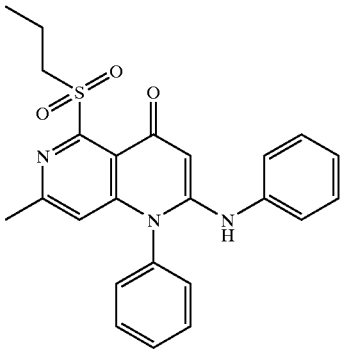 | Intermediate BA, BB, BC and Example 39, 44, 21 |
| 849 | 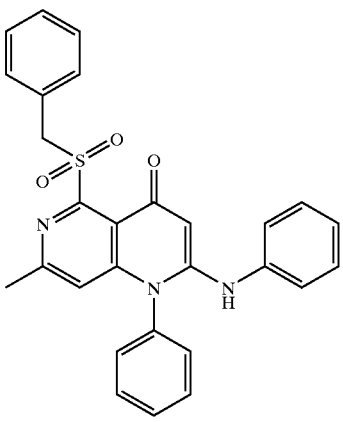 | Intermediate BA, BB, BC and Example 39, 44, 21 |
| 850 | 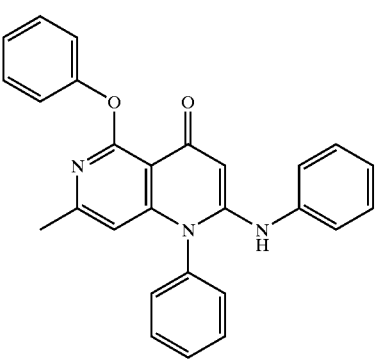 | Intermediate BA, BB, BC and Example 39, 48 |
| 851 | 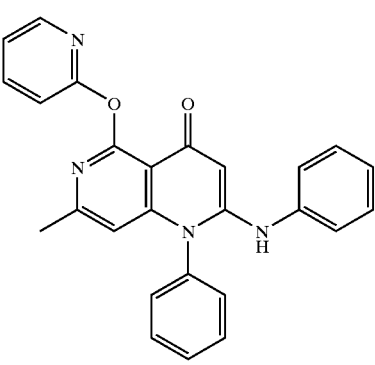 | Intermediate BA, BB, BC and Example 39, 48 |

TABLE 2B-continued

| Example | Stucture | Representative Procedure |
|---|---|---|
| 852 | | Intermediate BA, BB, BC and Example 39, 49, 50, 51, 25 and Intermediate AJ |
| 853 | | Intermediate BA, BB, BC and Example 39, 49, 50, 51, 25 and Intermediate AJ |
| 854 | | Intermediate BA, BB, BC and Example 39, 49, 50, 51, 25, 26 |
| 855 | | Intermediate BA, BB, BC and Example 39, 49, 50, 51, 25, 26 |

TABLE 2B-continued
| Example | Structure | Representative Procedure |
|---|---|---|
| 856 | 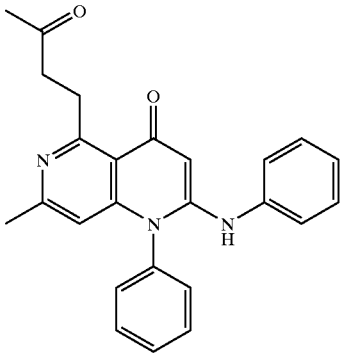 | Intermediate BA, BB, BC and Example 39, 31, 33 |
| 857 | 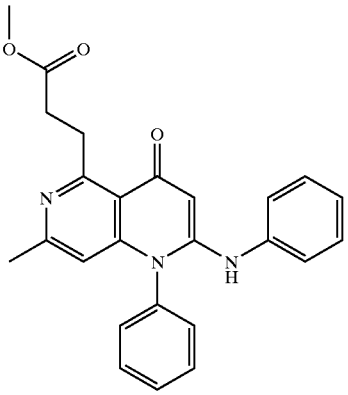 | Intermediate BA, BB, BC and Example 39, 31, 33 |
| 858 | 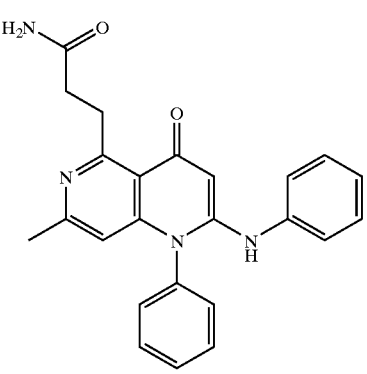 | Intermediate BA, BB, BC and Example 39, 31, 32, 33, 47 |
| 859 | 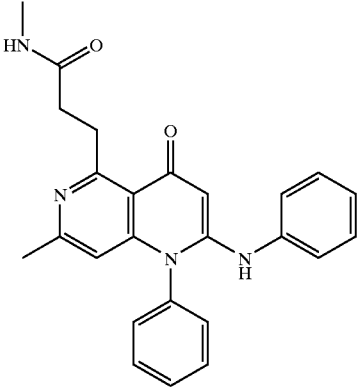 | Intermediate BA, BB, BC and Example 39, 31, 32, 33, 47 |

TABLE 2B-continued
| Example | Stucture | Representative Procedure |
|---|---|---|
| 860 | 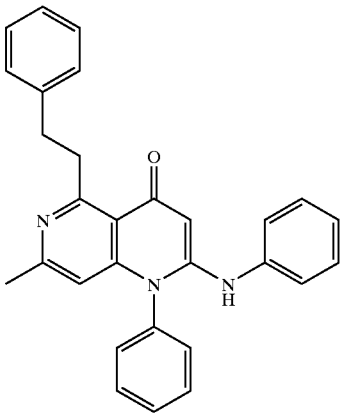 | Intermediate BA, BB, BC and Example 39, 31, 33 |
| 861 | 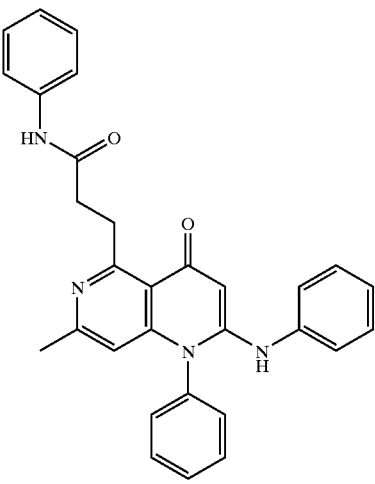 | Intermediate BA, BB, BC and Example 39, 31, 32, 33, 47 |
| 862 | 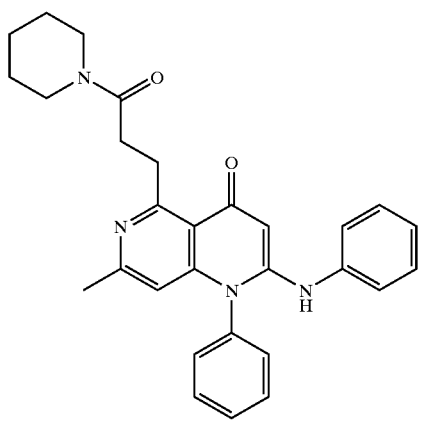 | Intermediate BA, BB, BC and Example 39, 31, 32, 33, 47 |

TABLE 2B-continued

| Example | Structure | Representative Procedure |
|---|---|---|
| 863 | | Intermediate BA, BB, BC and Example 39, 49, 50, 51 |
| 864 | | Intermediate BA, BB, BC and Example 39, 49, 50, 51 |
| 865 | | Intermediate BA, BB, BC and Example 39, 49, 50, 51 |
| 866 | | Intermediate BA, BB, BC and Example 39, 43, 47 |

TABLE 2B-continued
| Example | Stucture | Representative Procedure |
|---|---|---|
| 867 | 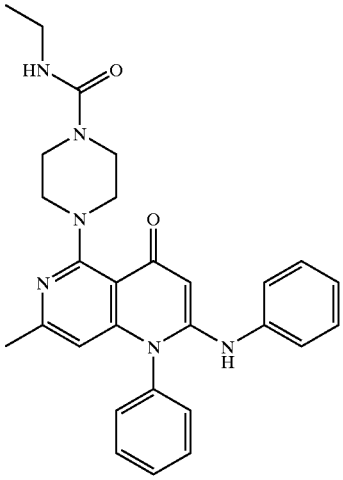 | Intermediate BA, BB, BC and Example 39, 43 and Intermediate AK |
| 868 | 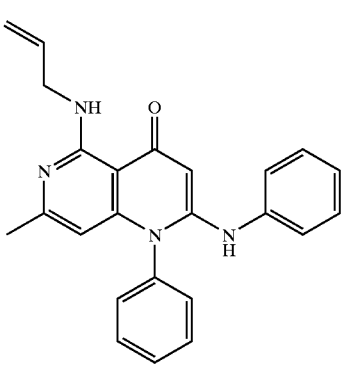 | Intermediate BA, BB, BC and Example 39, 3 |
| 869 | 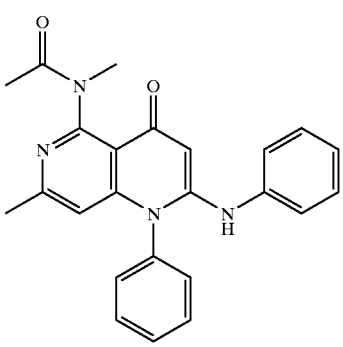 | Intermediate BA, BB, BC and Example 39, 43, 47 |
| 870 | 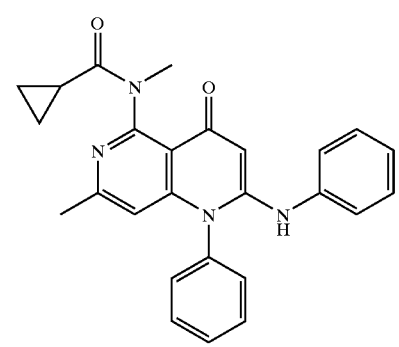 | Intermediate BA, BB, BC and Example 39, 43, 47 |

TABLE 2B-continued

| Example | Stucture | Representative Procedure |
|---|---|---|
| 871 | | Intermediate BA, BB, BC and Example 39, 22 |
| 872 | | Intermediate BA, BB, BC and Example 39, 3, 24, 12 |
| 873 | | Intermediate BA, BB, BC and Example 39, 3, 24 and Intermediate AK |
| 874 | | Intermediate BA2, BB2, BC2 and Example 41, 34 |

TABLE 2B-continued

| Example | Stucture | Representative Procedure |
|---|---|---|
| 875 | | Intermediate BA2, BB2, BC2 and Example 41, 34 |
| 876 | | Intermediate BA2, BB2, BC2 and Example 41, 34 |
| 877 | | Intermediate BA2, BB2, BC2 and Example 41, 34 |
| 878 | | Intermediate BA2, BB2, BC2 and Example 41, 34 |
| 879 | | Intermediate BA2, BB2, BC2 and Example 41, 31, 33 |

TABLE 2B-continued

| Example | Structure | Representative Procedure |
|---|---|---|
| 880 | | Intermediate BA2, BB2, BC2 and Example 41, 31, 33 |
| 881 | | Intermediate BA2, BB2, BC2 and Example 41, 31, 32, 33, 47 |
| 882 | | Intermediate BA2, BB2, BC2 and Example 41, 31, 32, 33, 47 |
| 883 | | Intermediate BA2, BB2, BC2 and Example 41, 31, 32, 33, 47 |

TABLE 2B-continued

| Example | Stucture | Representative Procedure |
|---|---|---|
| 884 | | Intermediate BA2, BB2, BC2 and Example 41, 31, 32, 33, 47 |
| 885 | | Intermediate BA2, BB2, BC2 and Example 41, 31, 32, 33, 47 |
| 886 | | Intermediate BA2, BB2, BC2 and Example 41, 31, 33 |
| 887 | | Intermediate BA2, BB2, BC2 and Example 41, 55 |

TABLE 2B-continued

| Example | Structure | Representative Procedure |
|---------|-----------|--------------------------|
| 888 | | Intermediate BA2, BB2, BC2 and Example 41, 55 |
| 889 | | Intermediate BA2, BB2, BC2 and Example 41, 55 |
| 890 | | Intermediate BA2, BB2, BC2 and Example 41, 49 |
| 891 | | Intermediate BA2, BB2, BC2 and Example 41, 34 |
| 892 | | Intermediate BA2, BB2, BC2 and Example 41, 17 |

TABLE 2B-continued

| Example | Stucture | Representative Procedure |
|---|---|---|
| 893 | | Intermediate BA2, BB2, BC2 and Example 41, 49, 47 |
| 894 | | Intermediate BA2, BB2, BC2 and Example 41, 49, 47 |
| 895 | | Intermediate BA2, BB2, BC2 and Example 41, 49, 47 |
| 896 | | Intermediate BA2, BB2, BC2 and Example 41, 49, 47 |
| 897 | | Intermediate BA2, BB2, BC2 and Example 41, 49, 47 |

TABLE 2B-continued

| Example | Stucture | Representative Procedure |
|---|---|---|
| 898 | | Intermediate BA2, BB2, BC2 and Example 41, 34 |
| 899 | | Intermediate BA2, BB2, BC2 and Example 41, 34 |
| 900 | | Intermediate BA2, BB2, BC2 and Example 41, 34, 21 |
| 901 | | Intermediate BA2, BB2, BC2 and Example 41, 34, 21 |
| 902 | | Intermediate BA2, BB2, BC2 and Example 41, 31, 32, 33, 50, 51 |

TABLE 2B-continued

| Example | Stucture | Representative Procedure |
|---|---|---|
| 903 | | Intermediate BA2, BB2, BC2 and Example 41, 31, 33 |
| 904 | | Intermediate BA2, BB2, BC2 and Example 41, 31, 32, 33, 50, 51 |
| 905 | | Intermediate BA2, BB2, BC2 and Example 41, 49, 50, 51 |
| 906 | | Intermediate BA2, BB2, BC2 and Example 41, 49, 50, 51 |

TABLE 2B-continued

| Example | Stucture | Representative Procedure |
|---|---|---|
| 907 | | Intermediate BA2, BB2, BC2 and Example 41, 49, 50, 51 |
| 908 | | Intermediate BA2, BB2, BC2 and Example 41, 31, 33, 25 |
| 909 | | Intermediate BA2, BB2, BC2 and Example 41, 31, 33, 25 and Intermediate AJ |
| 910 | | Intermediate BA2, BB2, BC2 and Example 41, 17, 25, 26 |

TABLE 2B-continued

| Example | Stucture | Representative Procedure |
|---|---|---|
| 911 | | Intermediate BA2, BB2, BC2 and Example 41, 17, 25 |
| 912 | | Intermediate BA2, BB2, BC2 and Example 41, 17, 25 and Intermediate AJ |
| 913 | | Intermediate BA2, BB2, BC2 and Example 41, 3 |
| 914 | | Intermediate BA2, BB2, BC2 and Example 41, 3 |
| 915 | | Intermediate BA2, BB2, BC2 and Example 41, 3 |

TABLE 2B-continued

| Example | Stucture | Representative Procedure |
|---|---|---|
| 916 | | Intermediate BA2, BB2, BC2 and Example 41, 3 |
| 917 | | Intermediate BA2, BB2, BC2 and Example 41, 3 |
| 918 | | Intermediate BA2, BB2, BC2 and Example 41, 3 |
| 919 | | Intermediate BA2, BB2, BC2 and Example 41, 3 and Intermediate AK |

TABLE 2B-continued

| Example | Structure | Representative Procedure |
|---|---|---|
| 920 | | Intermediate BA2, BB2, BC2 and Example 41, 3, 12 |
| 921 | | Intermediate BA2, BB2, BC2 and Example 41, 3 |
| 922 | | Intermediate BA2, BB2, BC2 and Example 41, 3 |
| 923 | | Intermediate BA2, BB2, BC2 and Example 41, 3 |
| 924 | | Intermediate BA2, BB2, BC2 and Example 41, 3, 24 |

TABLE 2B-continued

| Example | Stucture | Representative Procedure |
|---|---|---|
| 925 | | Intermediate BA2, BB2, BC2 and Example 41, 3 |
| 926 | | Intermediate BA2, BB2, BC2 and Example 41, 3 |
| 927 | | Intermediate BA2, BB2, BC2 and Example 41, 3 |
| 928 | | Intermediate BA2, BB2, BC2 and Example 41, 3 |
| 929 | | Intermediate BA2, BB2, BC2 and Example 41, 3, 45 |

TABLE 2B-continued

| Example | Stucture | Representative Procedure |
|---------|----------|--------------------------|
| 930 | | Intermediate BA2, BB2, BC2 and Example 41, 3, 18 |
| 931 | | Intermediate BA2, BB2, BC2 and Example 41, 3, 45, 47 |
| 932 | | Intermediate BA2, BB2, BC2 and Example 41, 3, 45, 47 |
| 933 | | Intermediate BA2, BB2, BC2 and Example 41, 3, 24, 47 |
| 934 | | Intermediate BA2, BB2, BC2 and Example 41, 3, 47 |

TABLE 2B-continued

| Example | Structure | Representative Procedure |
|---|---|---|
| 935 | | Intermediate BA2, BB2, BC2 and Example 41, 3, 12 |
| 936 | | Intermediate BA2, BB2, BC2 and Example 41, 3, 24 and Intermediate AK |

Utilizing the above described procedures for intermediates and examples, and Flow Diagrams I–XIV alone or in combination, a variety of Formula II compounds can be prepared using the appropriate starting material. These compounds are summarized in Table 2C.

TABLE 2C

| Example | Structure |
|---|---|
| 937 | |
| 938 | |
| 939 | 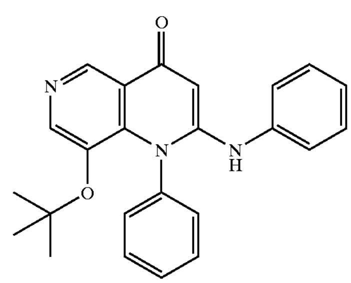 |
| 940 | 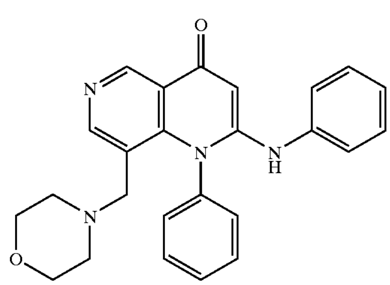 |

TABLE 2C-continued

| Example | Structure |
|---|---|
| 941 | 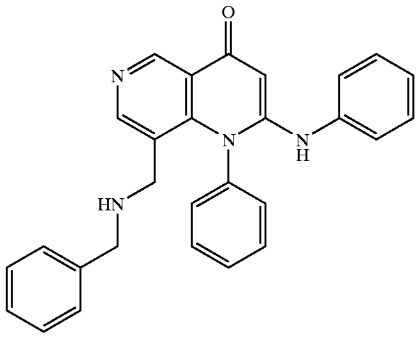 |
| 942 | 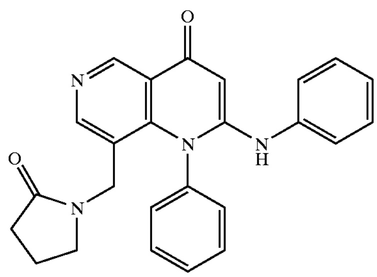 |
| 943 | 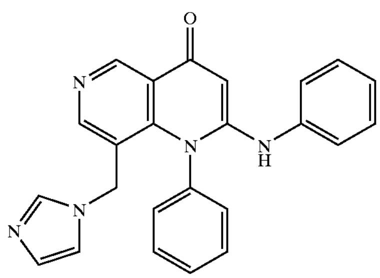 |
| 944 | 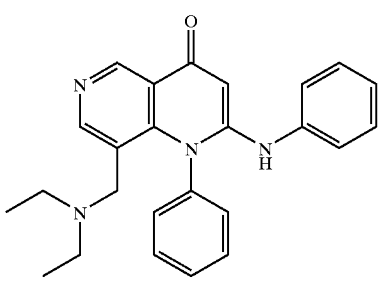 |
| 945 | 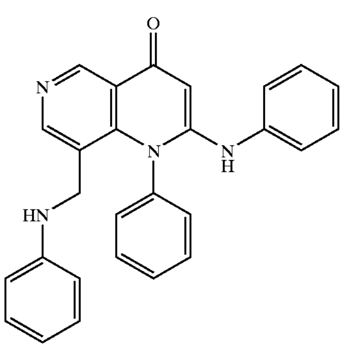 |

TABLE 2C-continued

| Example | Structure |
|---|---|
| 946 | 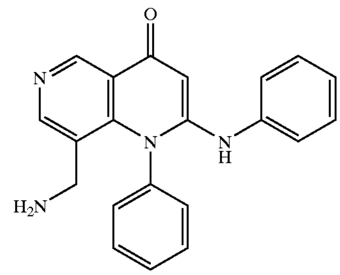 |
| 947 | 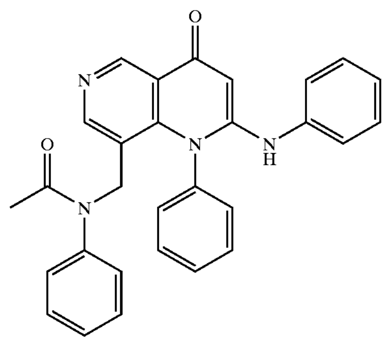 |
| 948 | 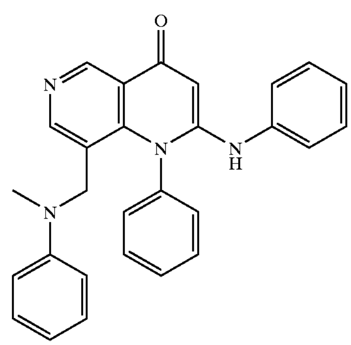 |
| 949 | 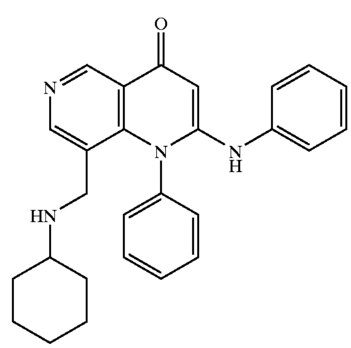 |

TABLE 2C-continued

| Example | Structure |
|---|---|
| 950 | (structure) |
| 951 | (structure) |
| 952 | (structure) |
| 953 | (structure) |
| 954 | (structure) |
| 955 | (structure) |
| 956 | (structure) |
| 957 | (structure) |
| 958 | (structure) |
| 959 | (structure) |

TABLE 2C-continued

| Example | Structure |
|---|---|
| 960 | (structure) |
| 961 | (structure) |
| 962 | (structure) |
| 963 | (structure) |
| 964 | (structure) |

TABLE 2C-continued

| Example | Structure |
|---|---|
| 965 | (structure) |
| 966 | (structure) |
| 967 | (structure) |
| 968 | (structure) |
| 969 | (structure) |

TABLE 2C-continued

| Example | Structure |
|---|---|
| 970 | *structure* |
| 971 | *structure* |
| 972 | *structure* |
| 973 | *structure* |
| 974 | *structure* |
| 975 | *structure* |
| 976 | *structure* |
| 977 | *structure* |
| 978 | *structure* |
| 979 | *structure* |

TABLE 2C-continued

| Example | Structure |
|---|---|
| 980 | 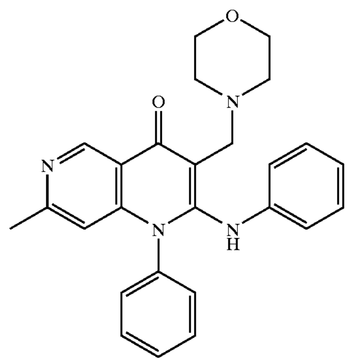 |
| 981 | 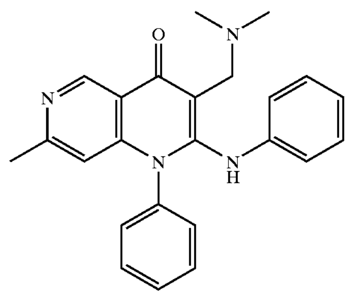 |
| 982 | 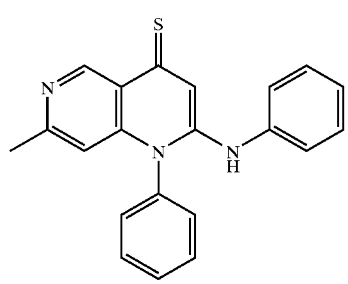 |
| 983 | 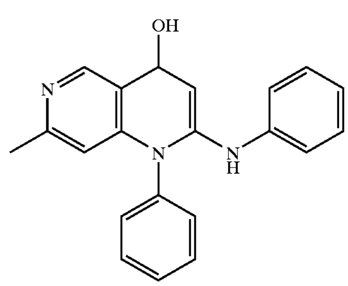 |
| 984 | |–

TABLE 2C-continued

| Example | Structure |
|---|---|
| 985 | 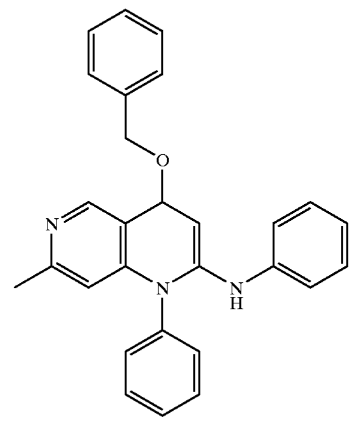 |
| 986 | 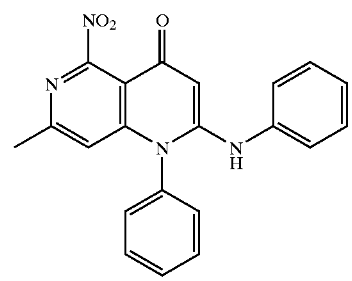 |
| 987 | 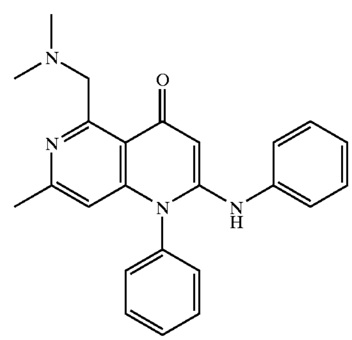 |
| 988 | 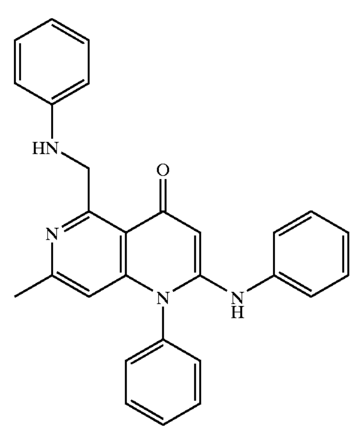 |

TABLE 2C-continued

| Example | Structure |
|---|---|
| 989 | |
| 990 | |
| 991 | |
| 992 | |
| 993 | 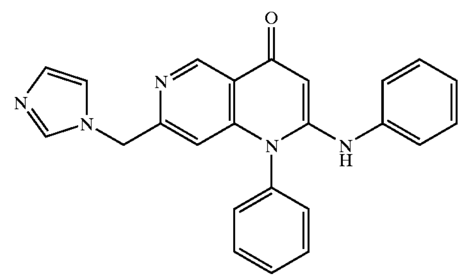 |
| 994 | 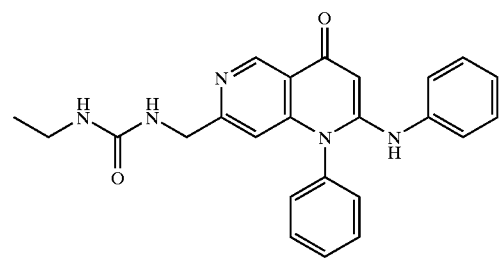 |
| 995 | 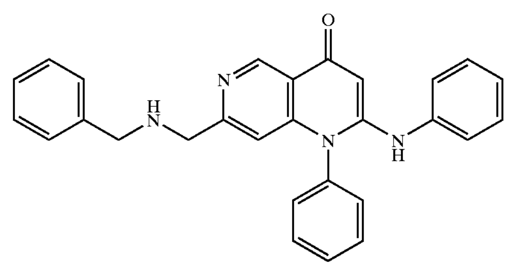 |
| 996 | 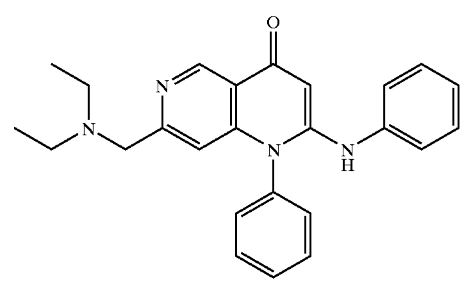 |
| 997 | 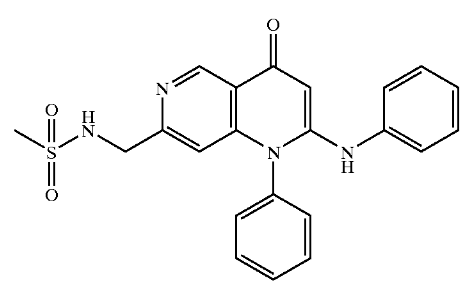 |

TABLE 2C-continued

| Example | Structure |
|---|---|
| 998 | 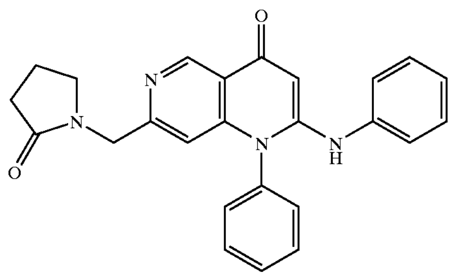 |
| 999 | 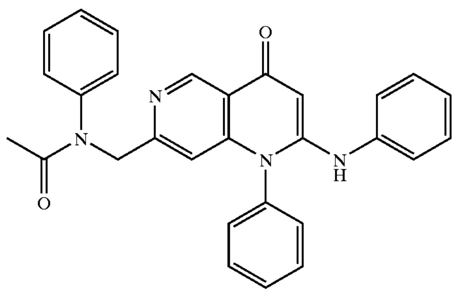 |
| 1000 | 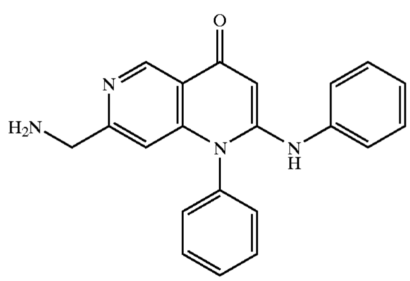 |
| 1001 | 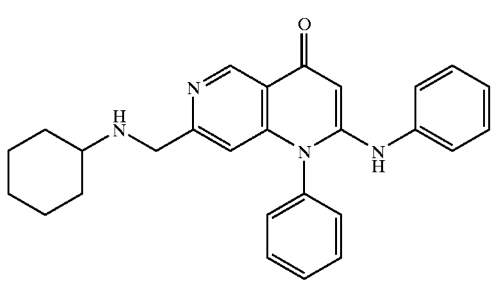 |
| 1002 | 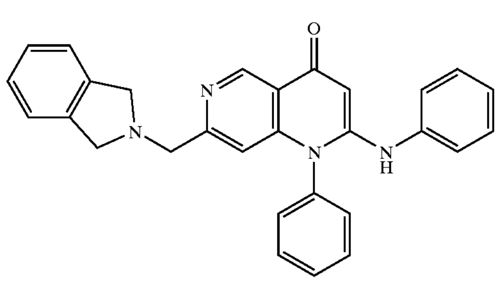 |
| 1003 | |
| 1004 | |

Biological Evaluation

Demonstration of the activity of the compounds of this invention is accomplished through in vitro, ex vivo and in vivo assays that are well known in the art.

In vivo Test Procedure:

Male Wistar rats (270–330 g) were fasted overnight and then given either vehicle or compound by oral gavage. Two or three hours later, the rats were given an intraperitoneal dose of glucose (2 g/kg). The rats were tail-bled for glucose using a Glucometer (Bayer Corporation, Mishawaka, Ind.) just prior to the glucose dose and 15, 30 and 60 minutes afterward. The area under the glucose curve was calculated by the trapezoidal method for both the vehicle and treated animals, and the percent reduction in the glucose AUC by the compound calculated. A typical positive effect of the compound results in a 12–20% reduction in the AUC relative to the AUC of the vehicle-treated group. Compounds of present invention were found to have a blood glucose lowering effect in this in vivo assay.

The invention may be embodied in other specific forms without departing from the spirit or essential characteristics thereof. The foregoing examples are included by way of illustration only. Accordingly, the scope of the invention is limited only by the scope of the appended claims.

What is claimed is:

1. A compound of the formula I

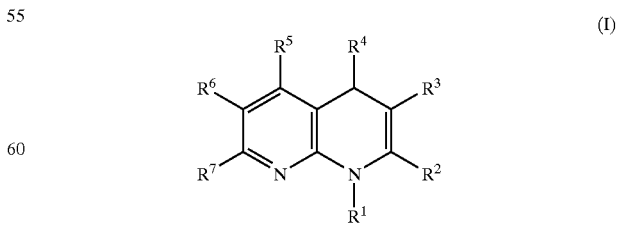

(I)

wherein $R^1$ is selected from alkyl of 1–8 carbon atoms, alkenyl of 2–8 carbon atoms, and alkynyl of 2–8 carbon atoms, or $R^1$ is aryl of 6–10 carbon atoms, which may be substituted with 1–3 of $R^{10}$;

$R^{10}$ is selected from nitro, nitrile, hydroxy, halogen, acyl of 1–6 carbon atoms, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms, cycloalkoxy of 3–6 carbon atoms, aryl of 6–10 carbon atoms, heteroaryl of 2–9 carbon atoms and 1–4 heteroatoms selected from N, $S(=O)_{0-2}$ and O, $NR^{11}R^2$, $C(=O)OR^{11}$, $C(=O)NHR^{11}$, $NHC(=O)R^{13}$, $NHS(=O)_2R^{13}$, $S(=O)O_2R^{13}$, $S(=O)_2NHR^{11}$, cycloalkyl of 3–6 carbon atoms, cycloalkenyl of 3–6 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$;

$R^{13}$ is selected from alkyl of 1–6 carbon atoms, alkenyl of 2–6 carbon atoms, alkynyl of 2–6 carbon atoms, haloalkyl of 1–6 carbon atoms, cycloalkyl of 3–6 carbon atoms, and cycloalkenyl of 4–6 carbon atoms;

$R^{11}$ and $R^{12}$ are independently selected from hydrogen, alkyl of 1–6 carbon atoms, alkenyl of 2–6 carbon atoms, alkynyl of 2–6 carbon atoms, haloalkyl of 1–6 carbon atoms, cycloalkyl of 3–6 carbon atoms, and cycloalkenyl of 4–6 carbon atoms;

A is selected from alkyl of 1–8 carbon atoms, alkenyl of 2–8 carbon atoms, alkynyl of 2–8 carbon atoms, and haloalkyl of 1–8 carbon atoms;

$R^2$ is $NR^{15}R^{16}$;

$R^{15}$ is selected from hydrogen, alkyl of 1–6 carbon atoms, alkenyl of 2–6 carbon atoms, alkynyl of 2–6 carbon atoms, cylcoalkyl of 3–8 carbon atoms, and cycloalkenyl of 4–8 carbon atoms;

$R^{16}$ is selected from alkyl of 1–8 carbon atoms, alkenyl of 2–8 carbon atoms, and alkynyl of 2–8 carbon atoms, or $R^{16}$ is aryl of 6–10 carbon atoms, which may be substituted with 1–3 of $R^{10}$;

$R^3$ is selected from aryl of 6–10 carbon atoms, heteroaryl of 2–9 carbon atoms and 1–4 heteroatoms selected from N, $S(=O)_{0-2}$ and O, cylcoalkyl of 3–8 carbon atoms, heterocycloalkyl of 3–6 carbon atoms and 1–2 heteroatoms selected from N, $S(O)_{0-2}$, and O, cycloalkenyl of 4–8 carbon atoms, and heterocycloalkenyl of 3–6 carbon atoms and 1–2 heteroatoms selected from N, $S(O)_{0-2}$ and O, all of which may be substituted with 1–3 of $R^{10}$, or $R^3$ is selected from alkyl of 1–6 carbon atoms, alkenyl of 2–6 carbon atoms, alkynyl of 2–6 carbon atoms, haloalkyl of 1–6 carbon atoms, hydrogen, nitro, halogen, $NR^{19}R^{20}$, $A-OR^{19}$, $A-NR^{19}R^{20}$, and $A-R^{20}$;

$R^{19}$ and $R^{20}$ are independently selected from hydrogen, alkyl of 1–6 carbon atoms, alkenyl of 2–6 carbon atoms, alkynyl of 2–6 carbon atoms, haloalkyl of 1–6 carbon atoms, and $A-R^9$, or $R^{19}$ and $R^{20}$ are independently selected from aryl of 6–10 carbon atoms, heteroaryl of 2–9 carbon atoms and 1–4 heteroatoms selected from N, $S(O)_{0-2}$ and O, cylcoalkyl of 3–8 carbon atoms, cycloalkenyl of 5–8 carbon atoms, 5–7 membered heterocycloalkyl of 3–6 carbon atoms and 1–2 heteroatoms selected from N, $S(O)_{0-2}$ and O, 5–7 membered heterocycloalkenyl of 3–6 carbon atoms and 1–2 heteroatoms selected from N, $S(O)_{0-2}$ and O, wherein said heterocycloalkyl and said heterocycloakenyl may further be fused with phenyl or a 56 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, all of which may be substituted with 1–3 of $R^{10}$;

$R^4$ is selected from =OH, =S, and $OR^{21}$;

$R^{21}$ is hydrogen, or $R^{21}$ is selected from alkyl of 1–8 carbon atoms, alkenyl of 2–8 carbon atoms, alkynyl of 2–8 carbon atoms, cycloalkyl of 3–8 carbon atoms, cycloalkenyl of 4–8 carbon atoms, 5–7 membered heterocycloalkyl of 3–6 carbon atoms and 1–2 heteroatoms selected from N, $S(=O)_{0-2}$ and O, and 5–7 membered heterocycloalkenyl of 3–6 carbon atoms and 1–2 heteroatoms selected from N, $S(=O)_{0-2}$ and O, all of which may be substituted with 1–3 of $R^{10}$;

$R^5$ and $R^6$ are independently selected from cycloalkyl of 3–8 carbon atoms, cycloalkenyl of 4–8 carbon atoms, aryl of 6–10 carbon atoms, which may be substituted with 1–3 of $R^{10}$, or $R^5$ and $R^6$ are independently selected from hydrogen, halogen, nitrile, nitro, hydroxy, alkyl of 1–8 carbon atoms, alkenyl of 2–8 carbon atoms, alkynyl of 2–8 carbon atoms, haloalkyl of 1–8 carbon atoms, alkoxy of 1–8 carbon atoms, haloalkoxy of 1–8 carbon atoms;

$R^{22}$ is selected from hydrogen, alkyl of 1–8 carbon atoms, haloalkyl of 1–8 carbon atoms, and cycloalkyl of 3–8 carbon atoms;

$R^{23}$ is selected from hydroxy, alkoxy of 1–8 carbon atoms, haloalkoxy of 1–8 carbon atoms, and cycloalkoxy of 3–8 carbon atoms, or $R^{23}$ is selected from cycloalkyl of 3–8 carbon atoms, cycloalkenyl of 4–8 carbon atoms, aryl of 6–10 carbon atoms, and heteroaryl of 2–9 carbon atoms and 1–4 heteroatoms selected from N, $S(=O)_{0-2}$, and O, all of which may be substituted with 1–3 of $R^{10}$, or $R^{23}$ is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

with the proviso for $A(OR^{22})-R^{23}$ that when $R^{23}$ is selected from hydroxy, alkoxy of 1–8 carbon atoms, haloalkoxy of 1–8 carbon atoms, and cycloalkoxy of 3–8 carbon atoms, A is not CH;

$R^{24}$ and $R^{25}$ are independently selected from hydrogen, alkyl of 1–6 carbon atoms, alkenyl of 2–6 carbon atoms, alkynyl of 2–6 carbon atoms, haloalkyl of 1–6 carbon atoms, and $A-R^{23}$, or $R^{24}$ and $R^{25}$ are independently selected from cycloalkyl of 3–6 carbon atoms, cycloalkenyl of 3–6 carbon atoms, aryl of 6–10 carbon atoms, and heteroaryl of 2–9 carbon atoms and 1–4 heteroatoms selected from N, $S(=O)_{0-2}$, and O, all of which may be substituted with 1–3 of $R^{10}$, or $R^{24}$ and $R^{25}$ are independently selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$, or $R^{24}$ and $R^{25}$ combine, together with the nitrogen atom to which they are attached, to form a 5–7 membered heterocycloalkyl of 3–6 carbon atoms and 1–2 heteroatoms selected from N, $S(=O)_{0-2}$, and O, a 5–7 membered heterocycloalkenyl of 3–6 carbon atoms and 1–2 heteroatoms selected from N, $S(=O),2$, and O, or a heteroaryl of 2–9 carbon atoms and 1–4 heteroatoms, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, all of which may be substituted with 1–3 of $R^{10}$;

$R^{26}$ is selected from alkyl of 1–6 carbon atoms, alkenyl of 2–6 carbon atoms, alkynyl of 2–6 carbon atoms, haloalkyl of 1–6 carbon atoms, $A(OR^{22})$-$R^{23}$, and $A$—$R^{23}$, or $R^{26}$ is selected from cycloalkyl of 3–6 carbon atoms, cycloalkenyl of 3–6 carbon atoms, aryl of 6–10 carbon atoms, and heteroaryl of 2–9 carbon atoms and 1–4 heteroatoms selected from N, $S(=O)_{0-2}$, and O, all of which may be substituted with 1–3 of $R^{10}$, or R is selected from 5–7 membered heterocycloalkyl of 3–6 carbon atoms and 1–2 heteroatoms selected from N, O, $S(=O)_{0-2}$, and 5–7 membered heterocycloalkenyl of 3–6 carbon atoms and 1–2 heteroatoms selected from N, O, $S(=O)_{0-2}$, wherein said heterocycloalkyl and said heterocycloakenyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl or heterocycloalkenyl may be oxidized to $C(=O)$, wherein said heterocycloalkyl or said heterocycloalkenyl may be substituted with 1–3 of $R^{10}$;

$R^7$ is selected from cycloalkyl of 3–8 carbon atoms, cycloalkenyl of 4–8 carbon atoms, aryl of 6–10 carbon atoms, all of which may be substituted with 1–3 of $R^{10}$, or $R^7$ is a 6 membered heterocycloalkyl of 4–5 carbon atoms and 1–2 heteroatoms selected from N and O wherein said heterocycloalkyl may further be fused with phenyl or a 5–6 membered heteroaryl of 2–5 carbon atoms and 1–3 heteroatoms selected from N, $S(=O)_{0-2}$ and O, and/or wherein one or more of the carbon atoms in said heterocycloalkyl may be oxidized to $C(=O)$, wherein said heterocycloalkyl may be substituted with 1–3 of $R^{10}$, $A(OR^{22})$—$R^{23}$, $A$—$R^{23}$, $A$—$NR^{24}R^{25}$, $C(=O)R^{24}$, $C(=O)OR^{24}$, $C(=O)NR^{24}R^{25}$, $S(=O)_2R^{26}$, $A$—$C(=O)R^{24}$, $A$—$C(=)OR^{24}$, or $A$—$C(=O)NR^{24}R^{25}$, and pharmaceutically acceptable salts thereof.

2. The compound of claim 1, wherein $R^4$ is $=O$.

3. The compound of claim 1, wherein $R^3$ is selected from cycloalkyl of 3–6 carbon atoms, heterocycloalkyl of 3–6 carbon atoms and 1–2 heteroatoms selected from N, $S(O)_{0-2}$ and O, both of which may be substituted with 1–3 of $R^{10}$, or $R^3$ is selected from alkyl of 1–6 carbon atoms, haloalkyl of 1–6 carbon atoms, hydrogen, nitro, halogen, $NR^{19}R^{20}$, $A$—$OR^{19}$, $A$—$NR^{19}R^{20}$ and $A$—$R^{20}$.

4. The compound of claim 3, wherein $R^{19}$ and $R^{20}$ are independently selected from hydrogen, alkyl of 1–6 carbon atoms, haloalkyl of 1–6 carbon atoms and $A$—$R^9$, or wherein $R^{19}$ and $R^{20}$ are independently selected from phenyl, monocyclic heteroaryl of 2–5 carbon atoms and 1–3 heteroatoms selected from N, $S(O)_{0-2}$ and O, cycloalkyl of 3–6 carbon atoms, 5–7 membered heterocycloalkyl of 3–6 carbon atoms and 1–2 heteroatoms selected from N, $S(O)_{0-2}$ and O, wherein one or more of the carbon atoms in said heterocycloalkyl may be oxidized to $C(=O)$, all of which may be substituted with 1–3 of $R^{10}$.

5. The compound of claim 1, wherein $R^3$ is selected from cycloalkyl of 3–6 carbon atoms, heterocycloalkyl of 3–6 carbon atoms and 1–2 hetcroatoms selected from N, $S(O)_{0-2}$ and O, both of which may be substituted with 1–3 of $R^{10}$, or $R^3$ is selected from alkyl of 1–6 carbon atoms, haloalkyl of 1–6 carbon atoms, hydrogen, nitro, halogen, $NR^{19}R^{20}$, $A$—$OR^{19}$, $A$—$NR^{19}R^{20}$ and $A$—$R^{20}$; and $R^4$ is $=O$.

6. The compound of claim 5, wherein $R^{19}$ and $R^{20}$ are independently selected from hydrogen, alkyl of 1–6 carbon atoms, haloalkyl of 1–6 carbon atoms and $A$—$R^9$, or wherein $R^{19}$ and $R^{20}$ are independently selected from phenyl, monocyclic heteroaryl of 2–5 carbon atoms and 1–3 heteroatoms selected from N, $S(O)_{0-2}$ and O, cycloalkyl of 3–6 carbon atoms, 5–7 membered heterocycloalkyl of 3–6 carbon atoms and 1–2 heteroatoms selected from N, $S(O)_{0-2}$ and O, wherein one or more of the carbon atoms in said heterocycloalkyl may be oxidized to $C(=O)$, all of which may be substituted with 1–3 of $R^{10}$.

7. The compound of claim 1, wherein $R^2$ is $NR^{15}R^{16}$.

8. The compound of claim 7, wherein $R^{15}$ is selected from hydrogen, alkyl of 1–6 carbon atoms, cylcoalkyl of 3–8 carbon atoms; and $R^{16}$ is alkyl of 1–6 carbon atoms, or $R^{16}$ is phenyl, which may be substituted with 1–3 of $R^{10}$.

9. The compound of claim 1, wherein $R^2$ is $NR^{15}R^{16}$;

$R^3$ is selected from cycloalkyl of 3–6 carbon atoms, heterocycloalkyl of 3–6 carbon atoms and 1–2 heteroatoms selected from N, $S(O)_{0-2}$ and O, both of which may be substituted with 1–3 of $R^{10}$, or $R^3$ is selected from alkyl of 1–6 carbon atoms, haloalkyl of 1–6 carbon atoms, hydrogen, nitro, halogen, $NR^{19}R^{20}$, $A$—$OR^{19}$, $A$—$NR^{19}R^{20}$ and $A$—$R^{20}$; and $R^4$ is $=O$.

10. The compound of claim 9, wherein $R^{15}$ is selected from hydrogen, alkyl of 1–6 carbon atoms, cylcoalkyl of 3–8 carbon atoms;

$R^{16}$ is alkyl of 1–6 carbon atoms, or $R^{16}$ is phenyl, which may be substituted with 1–3 of $R^{10}$.

11. The compound of claim 10, selected from the group consisting of:

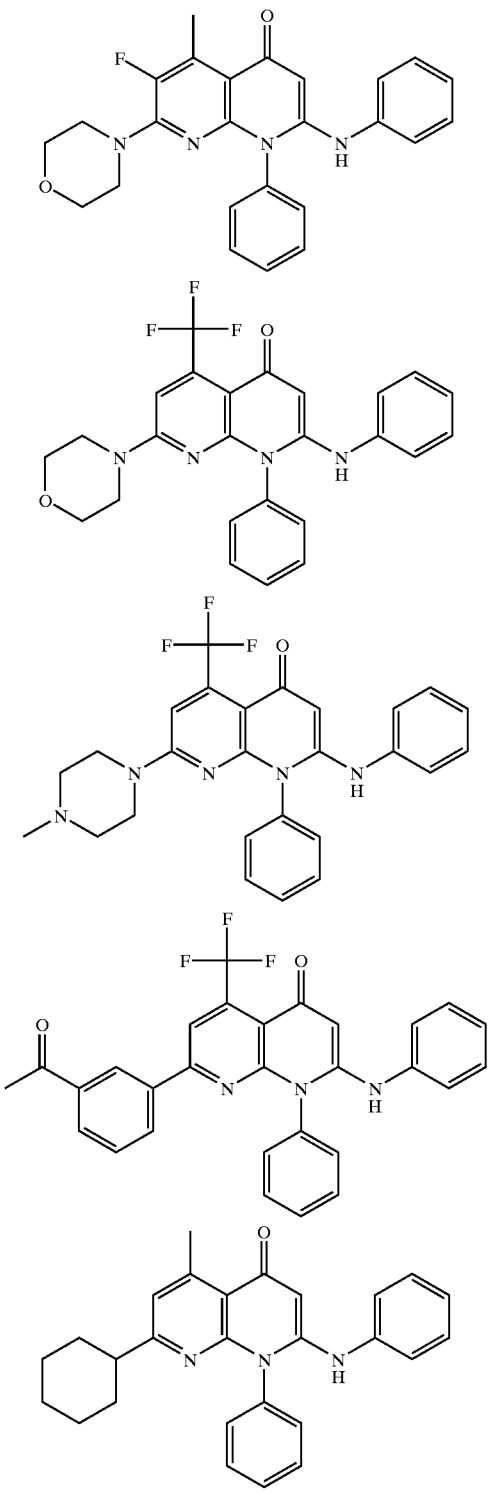

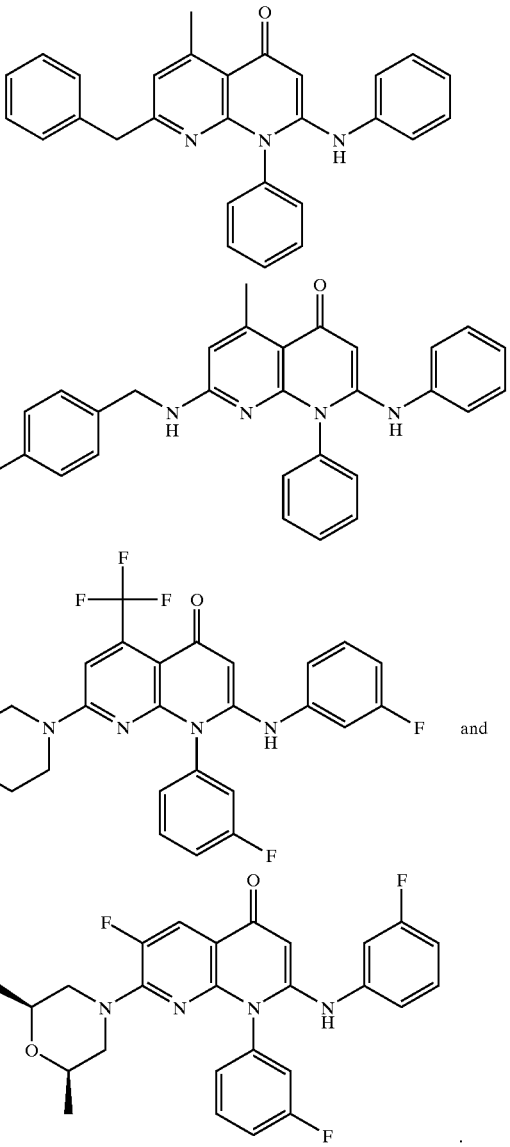

12. The compound of claim 9, wherein $R^{19}$ and $R^{20}$ are independently selected from hydrogen, alkyl of 1–6 carbon atoms, haloalkyl of 1–6 carbon atoms and A—$R^9$, or wherein $R^{19}$ and $R^{20}$ are independently selected from phenyl, monocyclic heteroaryl of 2–5 carbon atoms and 1–3 heteroatoms selected from N, S(O)$_{0-2}$ and O, cycloalkyl of 3–6 carbon atoms, 5–7 membered heterocycloalkyl of 3–6 carbon atoms and 1–2 heteroatoms selected from N, S(O)$_{0-2}$ and O, wherein one or more of the carbon atoms in said heterocycloalkyl may be oxidized to C(=O), all of which may be substituted with 1–3 of $R^{10}$.

13. The compound of claim 1 or 9, wherein $R^5$ is selected from cycloalkyl of 3–6 carbon atoms, cycloalkenyl of 4–6 carbon atoms, phenyl, all of which may be substituted with 1–3 of $R^{10}$, or $R^5$ is selected from hydrogen, halogen, nitrile, nitro, hydroxy, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms.

14. The compound of claim 13, wherein $R^5$ is selected from cycloalkyl of 3–6 carbon atoms, and phenyl, all of which may be substituted with 1–3 of $R^{10}$, or R[5] is selected from hydrogen, halogen, nitrile, nitro, hydroxy, alkyl of 1–6 carbon atoms, haloalkyl of 1–6 carbon atoms, alkoxy of 1–6 carbon atoms, haloalkoxy of 1–6 carbon atoms.
15. The compound of claim 14 selected from the group consisting of:
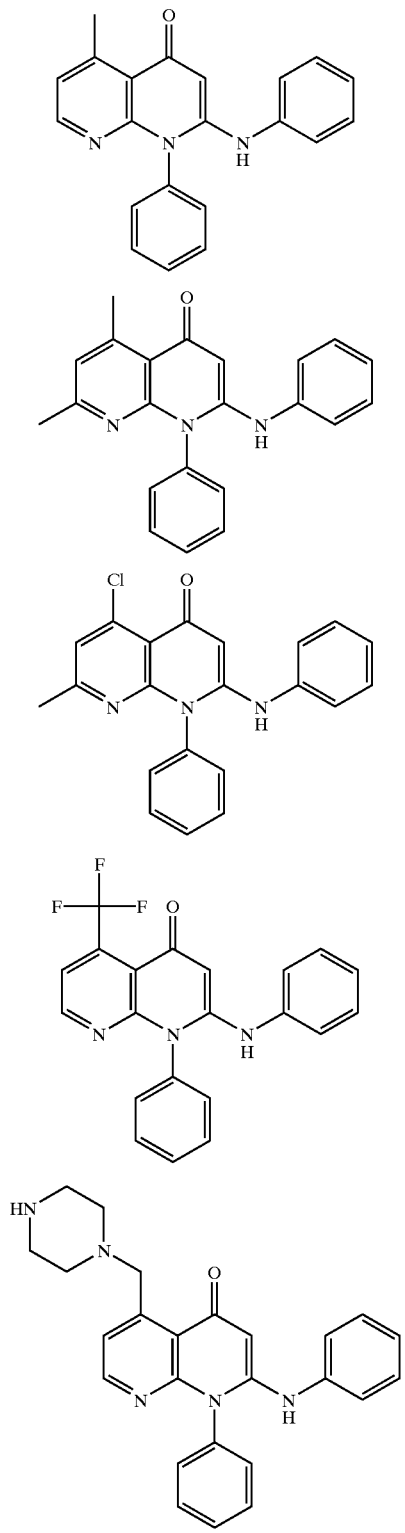
-continued
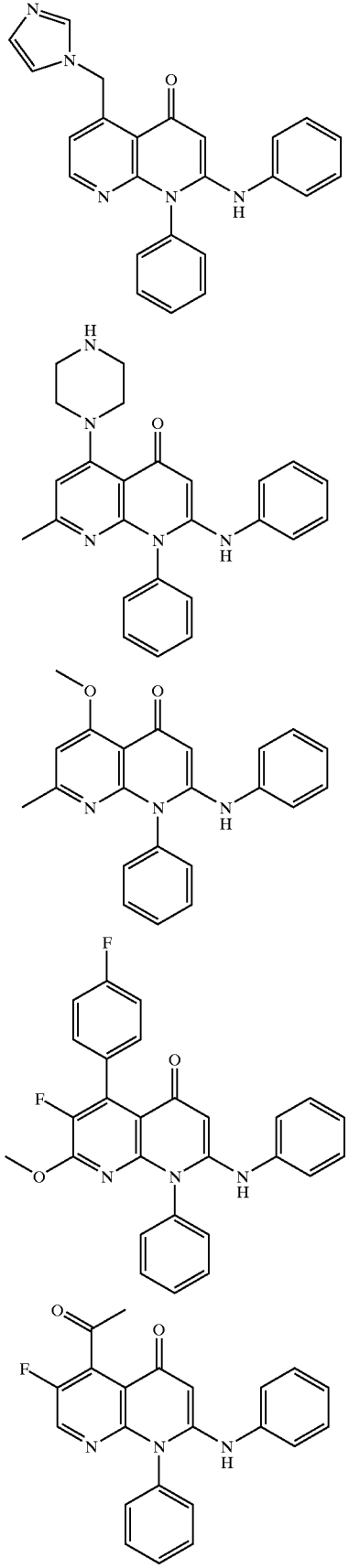

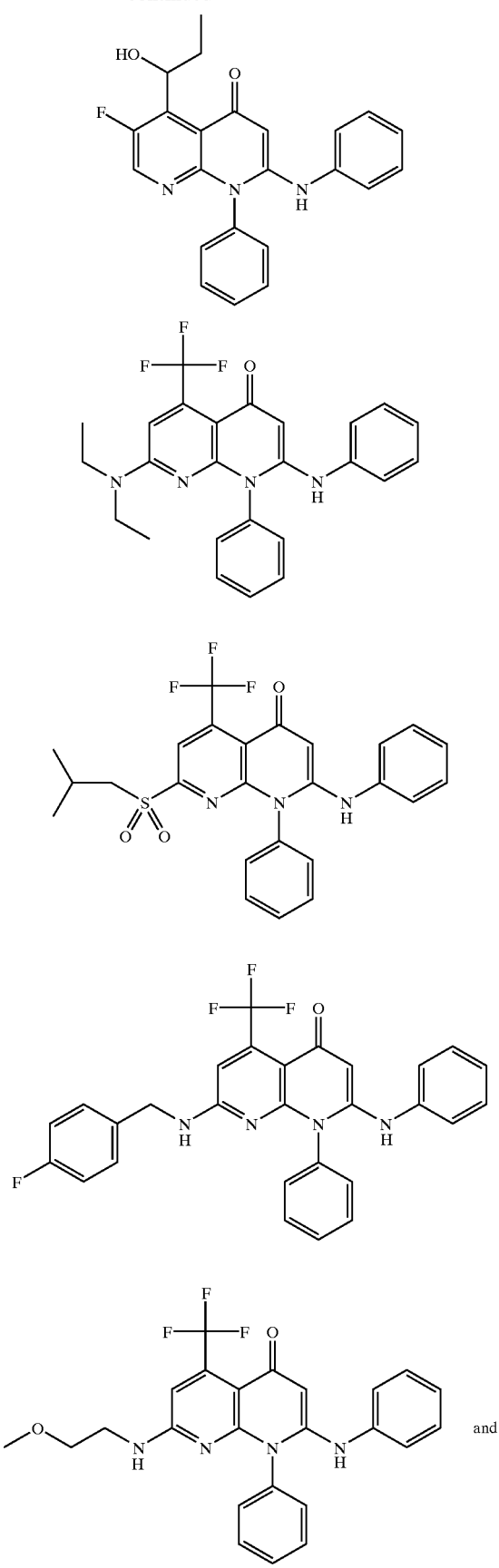

16. The compound of claim 1 or 9, wherein $R^6$ is selected from cycloalkyl of 3–6 carbon atoms, cycloalkenyl of 4–6 carbon atoms, and phenyl, all of which may be substituted with 1–3 of $R^{10}$, or $R^6$ is selected from hydrogen, halogen, nitrile, nitro, hydroxy, alkyl of 1–6 carbon atoms, alkenyl of 2–6 carbon atoms, alkynyl of 2–6 carbon atoms, haloalkyl of 1–6 carbon atoms, alkoxy of 1–6 carbon atoms, haloalkoxy of 1–6 carbon atoms.

17. The compound of claim 16, wherein $R^6$ is selected from cycloalkyl of 3–6 carbon atoms, all of which maybe substituted with 1–3 of $R^{10}$, or $R^6$ is selected from hydrogen, halogen, nitrile, nitro, hydroxy, alkyl of 1–4 carbon atoms, haloalkyl of 1–6 carbon atoms.

18. The compound of claim 17 selected from the group consisting of:

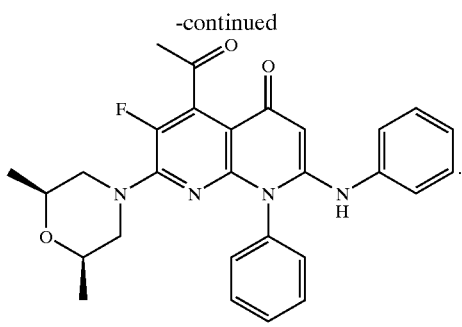

19. The compound of claim 1 or 9, wherein $R^7$ is selected from cycloalkyl of 3–6 carbon atoms, cycloalkenyl of 4–6 carbon atoms, phenyl, all of which may be substituted with 1–3 of $R^{10}$, or $R^7$ is selected from 6 membered heterocycloalkyl of 4–5 carbon atoms and 1–2 heteroatoms selected from N, and O, and/or wherein one or more of the carbon atoms in said heterocycloalkyl may be oxidized to C(=O), wherein said heterocycloalkyl may be substituted with 1–3 of $R^{10}$, A—$R^{23}$, A—$NR^{24}R^{25}$, C(=O)$R^{24}$, C(=O)OR$^{24}$, C(=O)NR$^{24}R^{25}$, S(=O)$_2$R$^{26}$, A—C(=O)R$^{24}$, A—C(=O)OR$^{24}$, or A—C(=O)NR$^{24}R^{25}$, or $R^{22}$ is selected from hydrogen, alkyl of 1–6 carbon atoms, haloalkyl of 1–6 carbon atoms, and cycloalkyl of 3–6 carbon atoms;

$R^{23}$ is selected from hydroxy, alkoxy of 1–6 carbon atoms, haloalkoxy of 1–6 carbon atoms, and cycloalkoxy of 3–6 carbon atoms, or $R^{23}$ is selected from cycloalkyl of 3–6 carbon atoms, cycloalkenyl of 4–6 carbon atoms, phenyl, and monocyclic heteroaryl of 2–5 carbon atoms and 1–3 heteroatoms selected from N, S(=O)$_2$, and O, all of which may be substituted with 1–3 of $R^{10}$, or $R^{23}$ is selected from 5–7 membered heterocycloalkyl of 3–6 carbon atoms and 1–2 heteroatoms selected from N, O, S(=O)s2, and 5–7 membered heterocycloalkenyl of 3–6 carbon atoms and 1–2 heteroatoms selected from N, O, S(=O)$_{0-2}$, and/or wherein one or more of the carbon atoms in said heterocycloalkyl or heterocycloalkenyl may be oxidized to C(=O), wherein said heterocycloalkyl or said heterocycloalkenyl may be substituted with 1–3 of $R^{10}$;

with the proviso for A(OR$^{22}$)—$R^{23}$ that when $R^{23}$ is selected from hydroxy, alkoxy of 1–6 carbon atoms, haloalkoxy of 1–6 carbon atoms, and cycloalkoxy of 3–6 carbon atoms, A is not CH;

$R^{24}$ and $R^{25}$ are independently selected from hydrogen, alkyl of 1–6 carbon atoms, alkenyl of 2–6 carbon atoms, alkynyl of 2–6 carbon atoms, haloalkyl of 1–6 carbon atoms, and A—$R^{23}$, or $R^{24}$ and $R^{25}$ are independently selected from cycloalkyl of 3–6 carbon atoms, cycloalkenyl of 3–6 carbon atoms, phenyl, and monocyclic heteroaryl of 2–5 carbon atoms and 1–3 heteroatoms selected from N, S(=O)$_{0-2}$, and O, all of which may be substituted with 1–3 of $R^{10}$, or $R^{24}$ and $R^{25}$ are independently selected from 5–7 membered heterocycloalkyl of 3–6 carbon atoms and 1–2 heteroatoms selected from N, O, S(=O)2, and 5–7 membered heterocycloalkenyl of 3–6 carbon atoms and 1–2 heteroatoms selected from N, O, S(=O)$_{0-2}$, and/or wherein one or more of the carbon atoms in said heterocycloalkyl or heterocycloalkenyl may be oxidized to C(=O), wherein said heterocycloalkyl or said heterocycloalkenyl may be substituted with 1–3 of $R^{10}$, or $R^{24}$ and $R^{25}$ combine, together with the nitrogen atom to which they are attached, to form a 5–7 membered heterocycloalkyl of 3–6 carbon atoms and 1–2 heteroatoms selected from N, S(=O)$_{0-2}$, and O, a 5–7 membered heterocycloalkenyl of 3–6 carbon atoms and 1–2 heteroatoms selected from N, S(=O)$_{0-2}$, and O, or a monocyclic heteroaryl of 2–5 carbon atoms and 1–3 heteroatoms, and/or wherein one or more of the carbon atoms in said heterocycloalkyl or heterocycloalkenyl may be oxidized to C(=O), all of which may be substituted with 1–3 of $R^{10}$;

$R^{26}$ is selected from alkyl of 1–6 carbon atoms, alkenyl of 2–6 carbon atoms, alkynyl of 2–6 carbon atoms, haloalkyl of 1–6 carbon atoms, A(OR$^{22}$)—$R^{23}$, and A—$R^{23}$, or $R^{26}$ is selected from cycloalkyl of 3–6 carbon atoms, cycloalkenyl of 3–6 carbon atoms, phenyl, and monocyclic heteroaryl of 2–5 carbon atoms and 1–3 heteroatoms selected from N, S(=O)$_{0-2}$, and O, all of which may be substituted with 1–3 of $R^{10}$, or $R^{26}$ is selected from 5–7 membered heterocycloalkyl of 3–6 carbon atoms and 1–2 heteroatoms selected from N, O, S(=O)$_{0-2}$, and 5–7 membered heterocycloalkenyl of 3–6 carbon atoms and 1–2 heteroatoms selected from N, O, S(=O)$_{0-2}$, and/or wherein one or more of the carbon atoms in said heterocycloalkyl or heterocycloalkenyl may be oxidized to C(=O), wherein said heterocycloalkyl or said heterocycloalkenyl may be substituted with 1–3 of $R^{10}$.

20. The compound of claim 19, wherein $R^7$ is selected from cycloalkyl of 3–6 carbon atoms and phenyl, all of which may be substituted with 1–3 of $R^{10}$, or $R^7$ is selected from 6 membered heterocycloalkyl of 4–5 carbon atoms and 1–2 heteroatoms selected from N, and/or wherein one of the carbon atoms in said heterocycloalkyl may be oxidized to C(=O), wherein said heterocycloalkyl may be substituted with 1–3 of $R^{10}$, A—$R^{23}$, A—NR$^{24}R^{25}$, C(=O)R$^{24}$, C(=O)OR$^{24}$, C(O)NR$^{24}R^{25}$, S(=O)$_2$R$^{26}$, A—C(=O)R$^{24}$, A—C(=O)OR$^{24}$, or A—C(=O)NR$^{24}R^{25}$, or $R^{22}$ is selected from hydrogen, alkyl of 1–6 carbon atoms, haloalkyl of 1–6 carbon atoms, and cycloalkyl of 3–6 carbon atoms;

$R^{23}$ is selected from hydroxy, alkoxy of 1–6 carbon atoms, haloalkoxy of 1–6 carbon atoms, and cycloalkoxy of 3–6 carbon atoms, or $R^{23}$ is selected from cycloalkyl of 3–6 carbon atoms, phenyl, and monocyclic heteroaryl of 2–5 carbon atoms and 1–3 heteroatoms selected from N, S(=O)$_{0-2}$, and O, all of which may be substituted with 1–3 of $R^{10}$, or $R^{23}$ is selected from 5–7 membered heterocycloalkyl of 3–6 carbon atoms and 1–2 heteroatoms selected from N, O, S(=O)$_{0-2}$, and/or wherein one of the carbon atoms in said heterocycloalkyl may be oxidized to C(=O), wherein said heterocycloalkyl may be substituted with 1–3 of $R^{10}$;

with the proviso for A(OR$^{22}$)—$R^{23}$ that when $R^{23}$ is selected from hydroxy, alkoxy of 1–6 carbon atoms, haloalkoxy of 1–6 carbon atoms, and cycloalkoxy of 3–6 carbon atoms, A is not CH;

$R^{24}$ and $R^{25}$ are independently selected from hydrogen, alkyl of 1–6 carbon atoms, haloalkyl of 1–6 carbon atoms, and A—$R^{23}$, or $R^{24}$ and $R^{25}$ are independently selected from cycloalkyl of 3–6 carbon atoms, phenyl, and monocyclic heteroaryl of 2–5 carbon atoms and 1–3 heteroatoms selected from N, S(=O)$_{0-2}$, and O, all of which may be substituted with 1–3 of $R^{10}$, or $R^{24}$ and $R^{25}$ are independently selected from 5–7 membered heterocycloalkyl of 3–6 carbon atoms and 1–2 heteroatoms selected from N, O, S(=O)$_{0-2}$, and/or wherein one of the carbon atoms in said heterocycloalkyl may be oxidized to C(=O), wherein said heterocycloalkyl may be substituted with 1–3 of $R^{10}$, or $R^{24}$ and $R^{25}$ combine, together with the nitrogen atom to which they are attached, to form a 5–7 membered heterocycloalkyl of 3–6 carbon atoms and 1–2 heteroatoms selected from N, S(=O)$_{0-2}$, or a monocyclic heteroaryl of 2-S carbon atoms and 1–3 heteroatoms, and/or wherein one of the carbon atoms in said heterocycloalkyl may be oxidized to C(=O), all of which may be substituted with 1–3 of $R^{10}$;

$R^{26}$ is selected from alkyl of 1–6 carbon atoms, haloalkyl of 1–6 carbon atoms, A(OR$^{22}$)—$R^{23}$, and A—$R^{23}$, or $R^{26}$ is selected from cycloalkyl of 3–6 carbon atoms, phenyl, and monocyclic heteroaryl of 2–5 carbon atoms and 1–3 heteroatoms selected from N, S(=O)$_{0-2}$, and O, all of which may be substituted with 1–3 of $R^{10}$, or $R^{26}$ is selected from 5–7 membered heterocycloalkyl of 3–6 carbon atoms and 1–2 heteroatoms selected from N, O, S(=O)$_{0-2}$, and/or wherein one of the carbon atoms in said heterocycloalkyl may be oxidized to C(=O), wherein said heterocycloalkyl may be substituted with 1–3 of $R^{10}$.

21. The compound of claim 20 selected from the group consisting of:

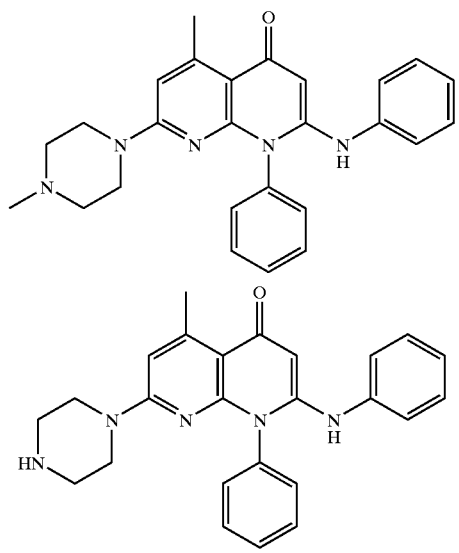

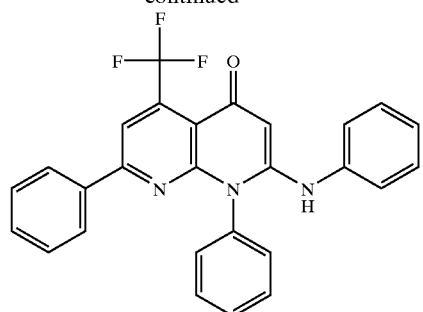

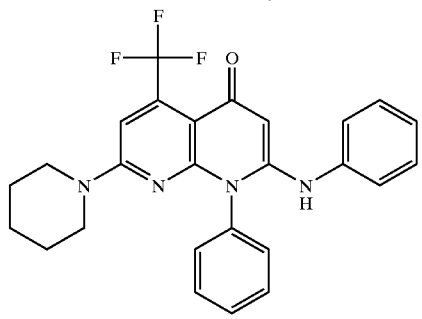

and

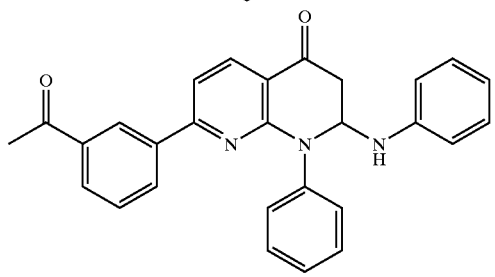

22. A method of treating a disease or condition selected from the group consisting of diabetes (Type 1 or Type 2), maturity-onset diabetes of the young (MODY), latent autoimmune diabetes adult (LADA), impaired glucose tolerance (IGT), impaired fasting glucose (IFG), gestational diabetes, and metabolic syndrome X, comprising administering to a mammal an effective amount of a compound of claim 1.

23. The method of claim 22, wherein said disease or condition is diabetes (Type 1 or Type 2).

24. The method of claim 23, wherein said disease or condition is Type 2 diabetes.

25. The method of claim 22, further comprising administering a PPAR-agonist, an insulin sensitizer, a sulfonylurea, an insulin secretagogue, a hepatic glucose output lowering compound, an α-glucosidase inhibitor or insulin in combination with said compound of claim 1.

26. The method of claim 25, wherein said PPAR-agonist is selected from rosiglitazone and pioglitazone.

27. The method of claim 25, wherein said sulfonylurea is selected from glibenclamide, glimepiride, chlorpropamide, and glipizide.

28. The method of claim 25, wherein said insulin secretagogue is selected from GLP-1, GIP, PAC/VPAC receptor agonists, secretin, nateglinide, meglitinide, repaglinide, glibenclamide, glimepiride, chlorpropamide, and glipizide.

29. The method of claim 25, wherein said α-glucosidase inhibitor is selected from acarbose, miglitol and voglibose.

30. The method of claim 25, wherein said hepatic glucose output lowering compound is metformin.

31. The method of claim 22, further comprising administering an HMG-CoA reductase inhibitor, nicotinic acid, a bile acid sequestrant, a fibric acid derivative, antihypertensive drug, or an anti-obesity drug in combination with said compound of claim 1.

32. The method of claim 31, wherein said anti-obesity drug is selected from a β-3 agonist, a CB-1 antagonist, and a lipase inhibitor.

33. A method of treating secondary causes of diabetes selected from glucocorticoid excess, growth hormone excess, pheochromocytoma, and drug-induced diabetes, comprising administering to a mammal an effective amount of a compound of claim 1.

34. A method of increasing the sensitivity of pancreatic beta cells to an insulin secretagogue, comprising administering to a mammal an effective amount of a compound of claim 1.

35. The method of claim 34, wherein said insulin secretagogue is selected from GLP-1, GIP, PAC/VPAC receptor agonists, secretin, nateglinide, meglitinide, repaglinide, glibenclamide, glimepiride, chlorpropamide, and glipizide.

36. A pharmaceutical composition, comprising a compound according to claim 1 and a pharmaceutically acceptable carrier.

* * * * *